(12) United States Patent
Jun et al.

(10) Patent No.: US 10,428,090 B2
(45) Date of Patent: Oct. 1, 2019

(54) CONDENSED-CYCLIC COMPOUND AND ORGANIC LIGHT-EMITTING DEVICE COMPRISING THE SAME

(71) Applicant: Samsung Display Co., Ltd., Yongin-si, Gyeonggi-do (KR)

(72) Inventors: Mieun Jun, Yongin-si (KR); Soobyung Ko, Yongin-si (KR); Haejin Kim, Yongin-si (KR); Youngkook Kim, Yongin-si (KR); Seokhwan Hwang, Yongin-si (KR)

(73) Assignee: Samsung Display Co., Ltd. (KR)

( * ) Notice: Subject to any disclaimer, the term of this patent is extended or adjusted under 35 U.S.C. 154(b) by 0 days.

(21) Appl. No.: 16/054,976

(22) Filed: Aug. 3, 2018

(65) Prior Publication Data
US 2019/0071458 A1  Mar. 7, 2019

(30) Foreign Application Priority Data

Aug. 4, 2017  (KR) .................. 10-2017-0099000

(51) Int. Cl.
*H01L 29/08*    (2006.01)
*H01L 35/24*    (2006.01)
(Continued)

(52) U.S. Cl.
CPC .......... *C07F 7/0816* (2013.01); *H01L 51/006* (2013.01); *H01L 51/0061* (2013.01);
(Continued)

(58) Field of Classification Search
USPC ...... 428/690, 917, 411.1, 336; 313/502–509; 257/88, 104, 40; 548/61.1, 27, 440
See application file for complete search history.

(56) References Cited

U.S. PATENT DOCUMENTS 7,053,255 B2    5/2006    Ikeda et al.
7,233,019 B2    6/2007    Ionkin et al.
(Continued)

FOREIGN PATENT DOCUMENTS

KR    10-2006-0006760 A    1/2006
KR    10-2008-0108329 A    12/2008
(Continued)

*Primary Examiner* — Niki H Nguyen
(74) *Attorney, Agent, or Firm* — Innovation Counsel LLP

(57) ABSTRACT

A condensed-cyclic compound and an organic light-emitting device including the same are provided. The compound is represented by the formula

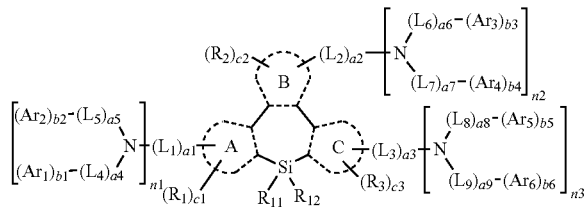

wherein ring A, ring B, and ring C are each independently selected from a $C_5$-$C_{30}$ carbocyclic group and a $C_1$-$C_{30}$ heterocyclic group, each of $L_1$ to $L_9$ is independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, and each of $Ar_1$ to $Ar_6$, (Continued)

10

| 190 |
|-----|
| 150 |
| 110 |

R1 to R3, $R_{11}$, and $R_{12}$ are further defined. The compound may be incorporated into one or more layers of an organic light-emitting diode device.

20 Claims, 4 Drawing Sheets

(51) Int. Cl.
*H01L 51/00* (2006.01)
*C07F 7/08* (2006.01)
*H01L 51/50* (2006.01)

(52) U.S. Cl.
CPC ...... *H01L 51/0094* (2013.01); *H01L 51/0058* (2013.01); *H01L 51/0072* (2013.01); *H01L 51/0073* (2013.01); *H01L 51/5012* (2013.01); *H01L 51/5056* (2013.01); *H01L 51/5072* (2013.01)

(56) References Cited

U.S. PATENT DOCUMENTS

| | | | |
|---|---|---|---|
| 8,039,126 B2 | 10/2011 | Stossel et al. | |
| 8,647,754 B2 | 2/2014 | Mizuki et al. | |
| 9,324,953 B2 * | 4/2016 | Kim | H01L 51/0072 |
| 10,249,824 B2 * | 4/2019 | Park | C07D 221/08 |
| 2004/0126616 A1 * | 7/2004 | Iwasaki | C08G 63/685 |
| | | | 428/690 |
| 2013/0069523 A1 | 3/2013 | Matsuura et al. | |
| 2015/0171337 A1 | 6/2015 | Jung et al. | |
| 2016/0351825 A1 | 12/2016 | Kim et al. | |
| 2019/0088877 A1 * | 3/2019 | Xie | H01L 51/005 |

FOREIGN PATENT DOCUMENTS

| | | |
|---|---|---|
| KR | 10-2010-0097182 A | 9/2010 |
| KR | 10-1031463 B1 | 4/2011 |
| KR | 10-2011-0049244 A | 5/2011 |
| KR | 10-2015-0068893 A | 6/2015 |
| KR | 10-2015-0070897 A | 6/2015 |

\* cited by examiner

| 190 |
|---|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

CONDENSED-CYCLIC COMPOUND AND ORGANIC LIGHT-EMITTING DEVICE COMPRISING THE SAME

CROSS-REFERENCE TO RELATED APPLICATION

This application claims the benefit of Korean Patent Application No. 10-2017-0099000 filed on Aug. 4, 2017 in the Korean Intellectual Property Office, the disclosure of which is incorporated herein in its entirety by reference.

BACKGROUND

1. Field

One or more embodiments relate to a condensed-cyclic compound and an organic light-emitting device including the same.

2. Description of the Related Art

Organic light-emitting devices (OLEDs) are self-emission devices that have wide viewing angles, high contrast ratios, and short response times, compared to conventional devices. In addition, OLEDs exhibit excellent luminance, driving voltage, and response speed characteristics.

OLEDs may include a first electrode disposed on a substrate, and may include a hole transport region, an emission layer, an electron transport region, and a second electrode sequentially disposed on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. These excitons transition from an excited state to a ground state to thereby generate light.

SUMMARY

One or more embodiments include a condensed-cyclic compound and an organic light-emitting device including the same.

Additional aspects will be set forth in part in the description which follows and, in part, will be apparent from the description, or may be learned by practice of the presented embodiments.

According to one or more embodiments, a condensed-cyclic compound is represented by Formula 1:

wherein, in Formula 1, each of ring A, ring B, and ring C is independently selected from a $C_5$-$C_{30}$ carbocyclic group and a $C_1$-$C_{30}$ heterocyclic group, each of $L_1$ to $L_9$ is independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a9 are each independently an integer from 0 to 5, each of $Ar_1$ to $Ar_6$, $R_{11}$, and $R_{12}$ is independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, each of b1 to b6 is independently an integer from 1 to 5, each of n1 to n3 is independently selected from 0, 1, 2, and 3, provided that the sum of n1, n2, and n3 is 2 or greater, each of $R_1$ to $R_3$ is independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_{3-10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)$

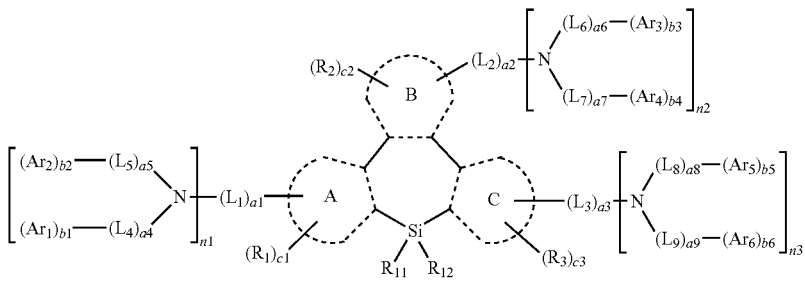

Formula 1

($Q_3$), —$N(Q_1)(Q_2)$, —$B(Q_1)(Q_2)$, —$C(=O)(Q_1)$, —$S(=O)_2(Q_1)$, and —$P(=O)(Q_1)(Q_2)$, each of c1 to c3 is independently an integer from 0 to 8, and at least one substituent of the substituted $C_{3-10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a phenyl group, a biphenyl group, and a terphenyl group.

According to one or more embodiments, an organic light-emitting device includes a first electrode; a second electrode facing the first electrode; and an organic layer between the first electrode and the second electrode, the organic layer including an emission layer and at least one of the condensed-cyclic compound represented by Formula 1.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional view illustrating an organic light-emitting device according to an embodiment;

FIG. 2 is a schematic cross-sectional view illustrating an organic light-emitting device according to an embodiment;

FIG. 3 is a schematic cross-sectional view illustrating an organic light-emitting device according to an embodiment; and FIG. 4 is a schematic cross-sectional view illustrating an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of", when preceding a list of elements, modify the entire list of elements and do not modify the individual elements of the list.

A condensed-cyclic compound may be represented by Formula 1:

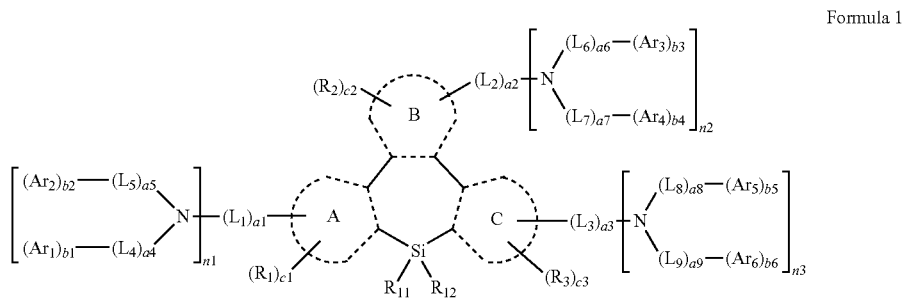

Formula 1

In Formula 1, ring A, ring B, and ring C may each independently be selected from a $C_5$-$C_{30}$ carbocyclic group and a $C_1$-$C_{30}$ heterocyclic group.

For example, ring A, ring B, and ring C may each independently be selected from a benzene group, a naphthalene group, an anthracene group, a phenanthrene group, a naphthacene group, a benzoanthracene group, a pyrene group, a chrysene group, a triphenylene group, an indene group, a fluorene group, a benzofluorene group, a spirobifluorene group, a carbazole group, a dibenzofuran group, a dibenzothiophene group, a pyridine group, a pyrazine group, a pyrimidine group, a pyridazine group, a pyrrole group, an imidazole group, a quinoline group, an isoquinoline group, a quinoxaline group, a quinazoline group, a naphthyridine group, a triazine group, an indenopyrazine group, an indenopyridine group, a phenanthroline group, and a phenanthridine group.

In some embodiments, ring A, ring B, and ring C may each independently be selected from a benzene group, a naphthalene group, an anthracene group, a phenanthrene group, a naphthacene group, a benzoanthracene group, a chrysene group, a pyridine group, a pyridazine group, a pyrimidine group, a pyrazine group, a quinoline group, an isoquinoline group, a quinazoline group, a quinoxaline group, and a naphthyridine group.

In one or more embodiments, ring A, ring B, and ring C may each independently be a benzene group or a naphthalene group, but embodiments are not limited thereto.

In Formula 1, $L_1$ to $L_9$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, $L_1$ to $L_9$ may each independently be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

In some embodiments, $L_1$ to $L_9$ may each independently be selected from groups represented by Formulae 3-1 to 3-33:

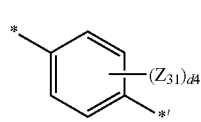

3-1

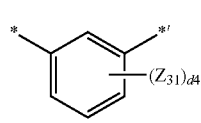

3-2

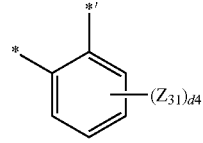

3-3

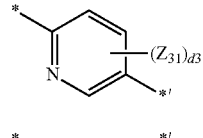

3-4

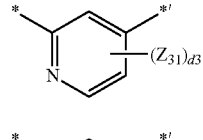

3-5

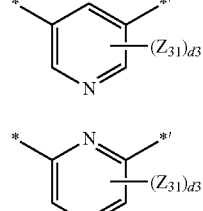

3-6

3-7

3-8

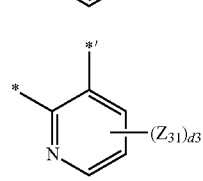

3-9

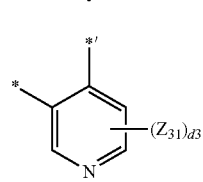

3-10

3-11

3-12

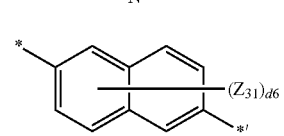

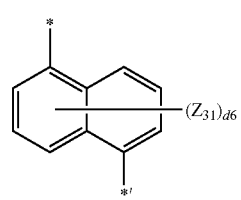

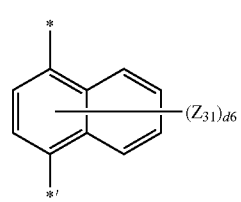

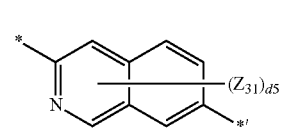

3-13

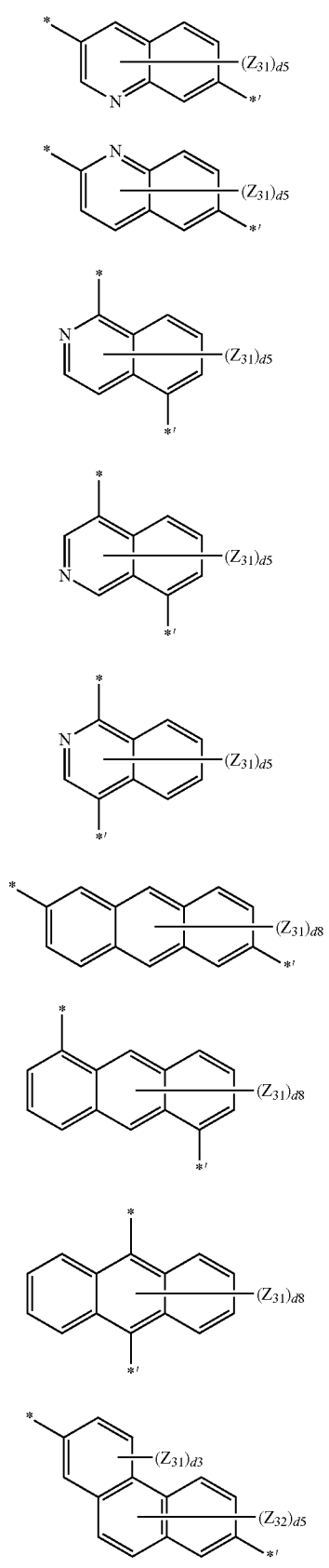
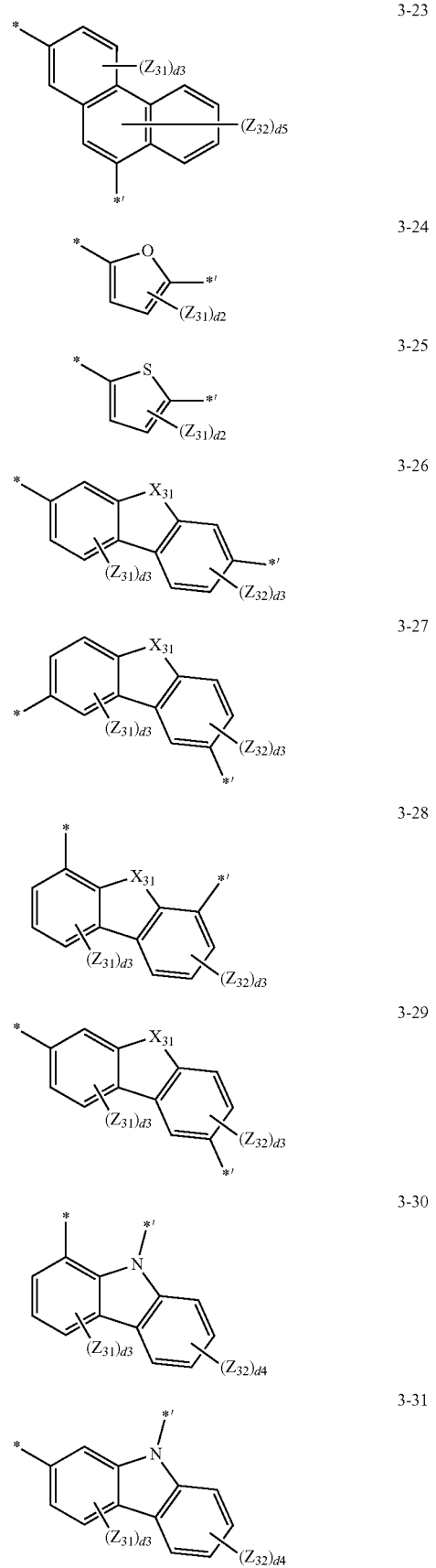

3-32

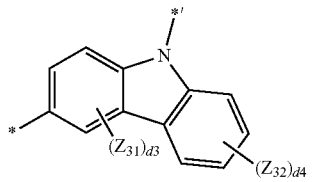

3-33

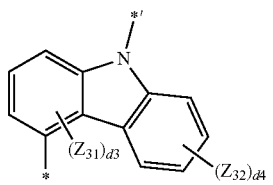

wherein, in Formulae 3-1 to 3-33, $X_{31}$ may be selected from O, S, $C(Z_{33})(Z_{34})$, $N(Z_{33})$, and $Si(Z_{33})(Z_{34})$, $Z_{31}$ to $Z_{34}$ may each independently be selected from hydrogen, deuterium, —F, —$CF_3$, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d2 may be an integer selected from 1 and 2,
d3 may be an integer from 1 to 3,
d4 may be an integer from 1 to 4,
d5 may be an integer from 1 to 5,
d6 may be an integer from 1 to 6,
d8 may be an integer from 1 to 8, and
* and *' each indicate a binding site to an adjacent atom. $Z_{33}$ and $Z_{34}$ may optionally be bound to each other to form a saturated or unsaturated ring.

In one or more embodiments, $L_1$ to $L_9$ may each independently be selected from Formulae 4-1 to 4-35, but embodiments are not limited thereto:

4-1

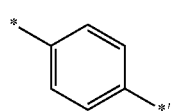

4-2

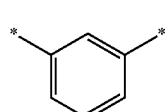

4-3

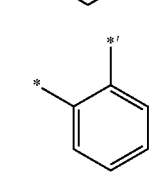

4-4

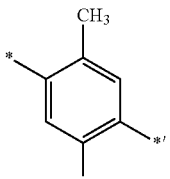

4-5

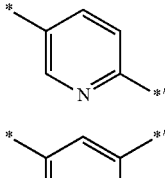

4-6

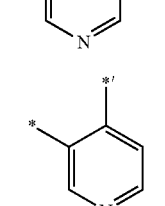

4-7

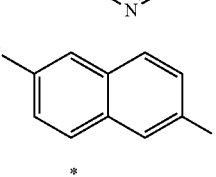

4-8

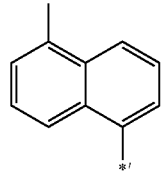

4-9

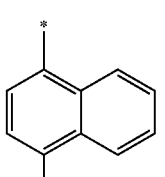

4-10

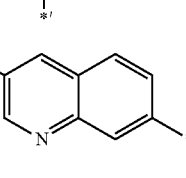

4-11

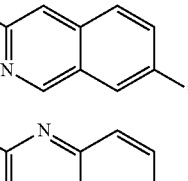

4-12

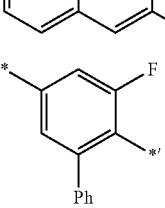

4-13

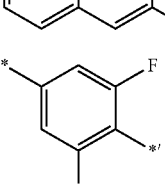

4-14

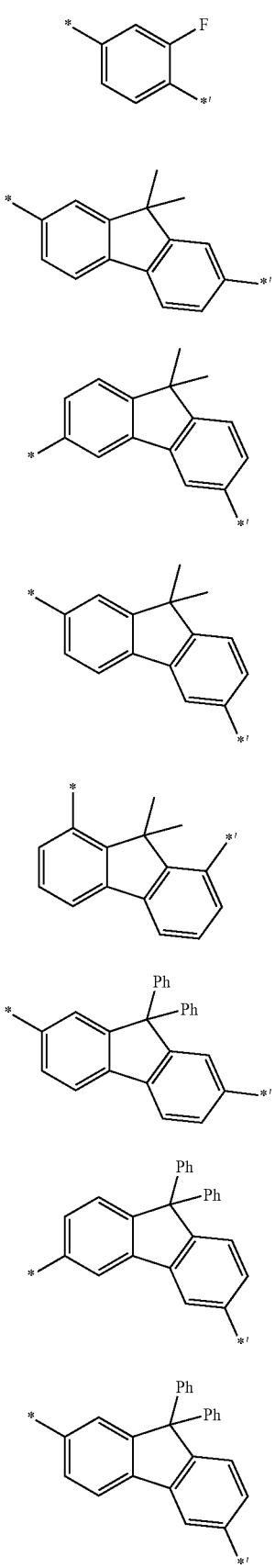
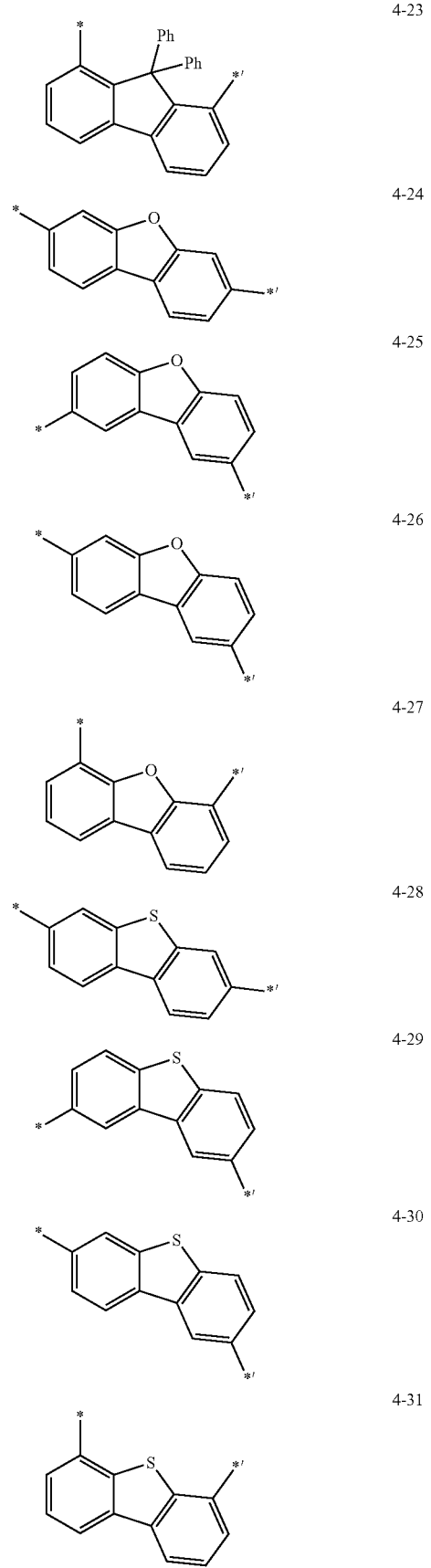

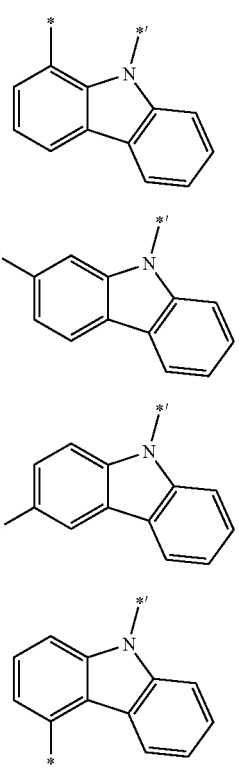

wherein, in Formulae 4-1 to 4-35,
"Ph" represents a phenyl group, and
* and *' each indicate a binding site to an adjacent atom.

In Formula 1, a1 to a9 may each independently be an integer from 0 to 5. a1 indicates the number of $L_1$ groups. When a1 is 0, *-$(L_1)_{a1}$-*' may be a single bond. When a1 is two or greater, at least two $L_1$ groups may be identical to or different from each other. a2 to a9 may be substantially the same as a1 and be understood by referring to the structure of Formula 1.

In one embodiment, a1 to a9 may each independently be 0, 1, 2, or 3.

In one or more embodiments, a1 to a9 may each independently be 0 or 1, but embodiments are not limited thereto.

In Formula 1, $Ar_1$ to $Ar_6$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, $Ar_1$ to $Ar_6$ may each independently be selected from
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzosilolyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si(Q$_{31}$)(Q$_{32}$)(Q$_{33}$), —N(Q$_{31}$)(Q$_{32}$), —C(=O)(Q$_{31}$), —S(=O)$_2$(Q$_{31}$), and —P(=O)(Q$_{31}$)(Q$_{32}$), wherein Q$_{31}$ to Q$_{33}$ may each independently be selected from a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

In one embodiment, Ar$_1$ to Ar$_6$ may each independently be selected from groups represented by Formulae 5-1 to 5-37:

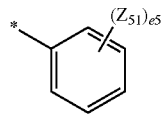

5-1

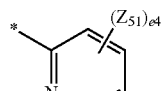

5-2

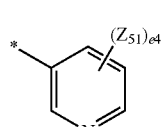

5-3

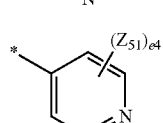

5-4

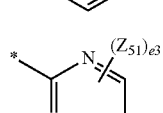

5-5

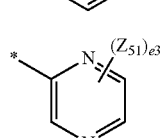

5-6

-continued

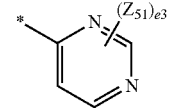

5-7

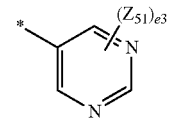

5-8

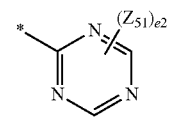

5-9

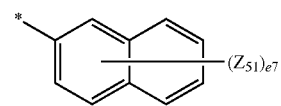

5-10

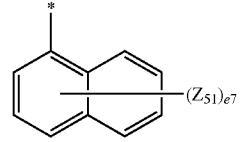

5-11

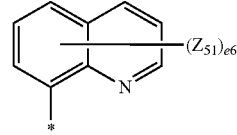

5-12

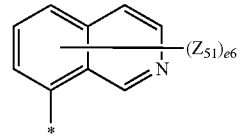

5-13

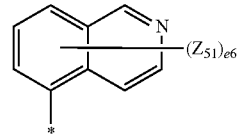

5-14

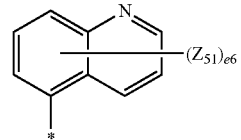

5-15

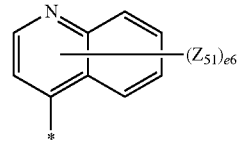

5-16

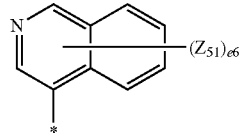

5-17

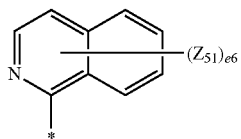 5-18
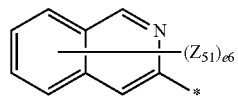 5-19
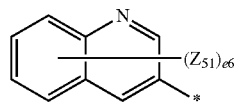 5-20
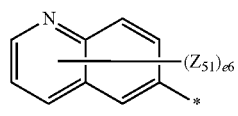 5-21
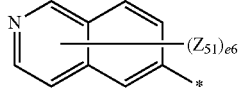 5-22
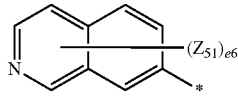 5-23
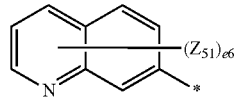 5-24
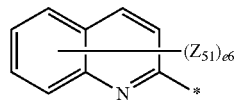 5-25
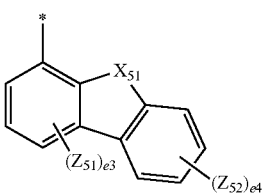 5-26
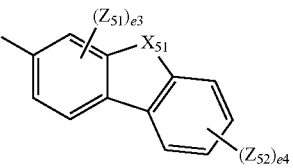 5-27
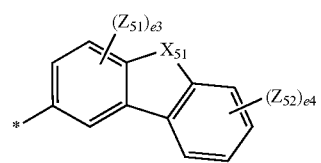 5-28
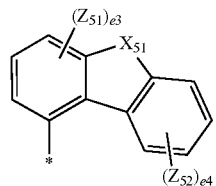 5-29
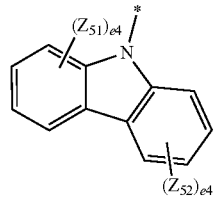 5-30
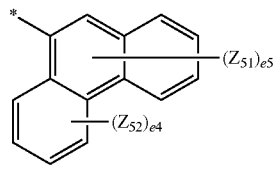 5-31
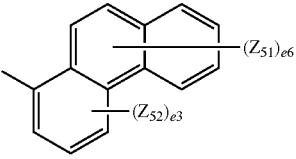 5-32
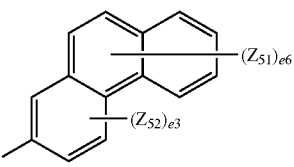 5-33
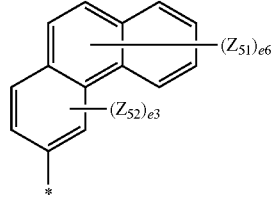 5-34
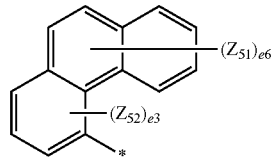 5-35
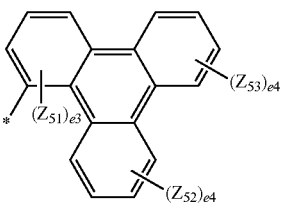 5-36

-continued

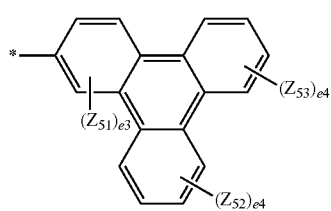

5-37 wherein, in Formulae 5-1 to 5-37, $X_{51}$ may be selected from O, S, $C(Z_{54})(Z_{55})$, $N(Z_{54})$, and $Si(Z_{54})(Z_{55})$, $Z_{51}$ to $Z_{55}$ may each independently be selected from hydrogen, deuterium, —F, —$CF_3$, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, e2 may be an integer selected from 1 and 2,
e3 may be an integer from 1 to 3,
e4 may be an integer from 1 to 4,
e5 may be an integer from 1 to 5,
e6 may be an integer from 1 to 6,
e7 may be an integer from 1 to 7, and
* indicates a binding site to an adjacent atom. $Z_{54}$ and $Z_{55}$ may optionally be bound to each other to form a saturated or unsaturated ring.

In one or more embodiments, $Ar_1$ to $Ar_6$ may each independently be selected from groups represented by Formulae 6-1 to 6-40, but embodiments are not limited thereto:

6-1

6-2

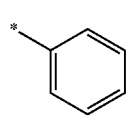

6-3

6-4

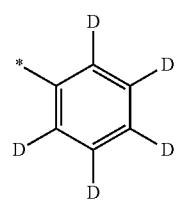

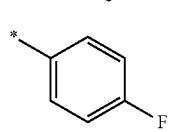

6-5

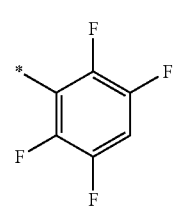

6-6

6-7

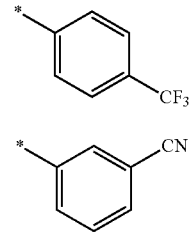

6-8

6-9

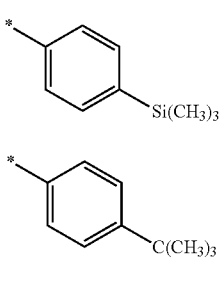

6-10

6-11

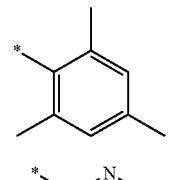

6-12

6-13

6-14

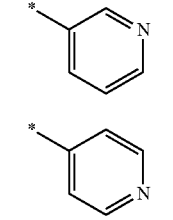

6-15

6-16

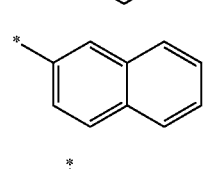

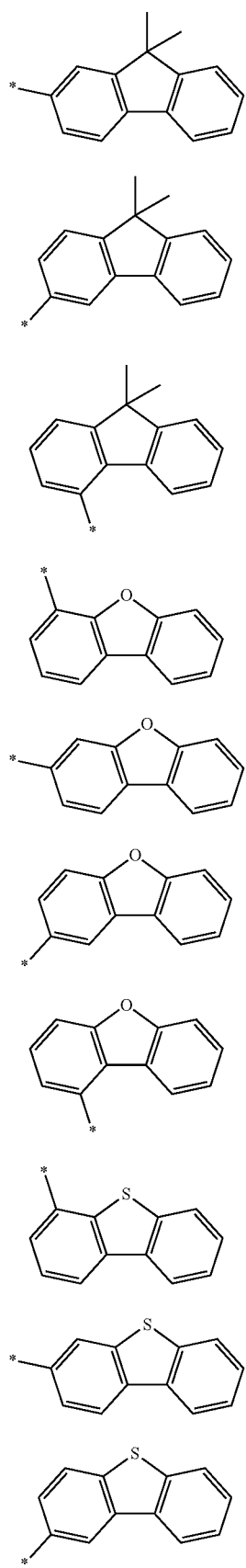
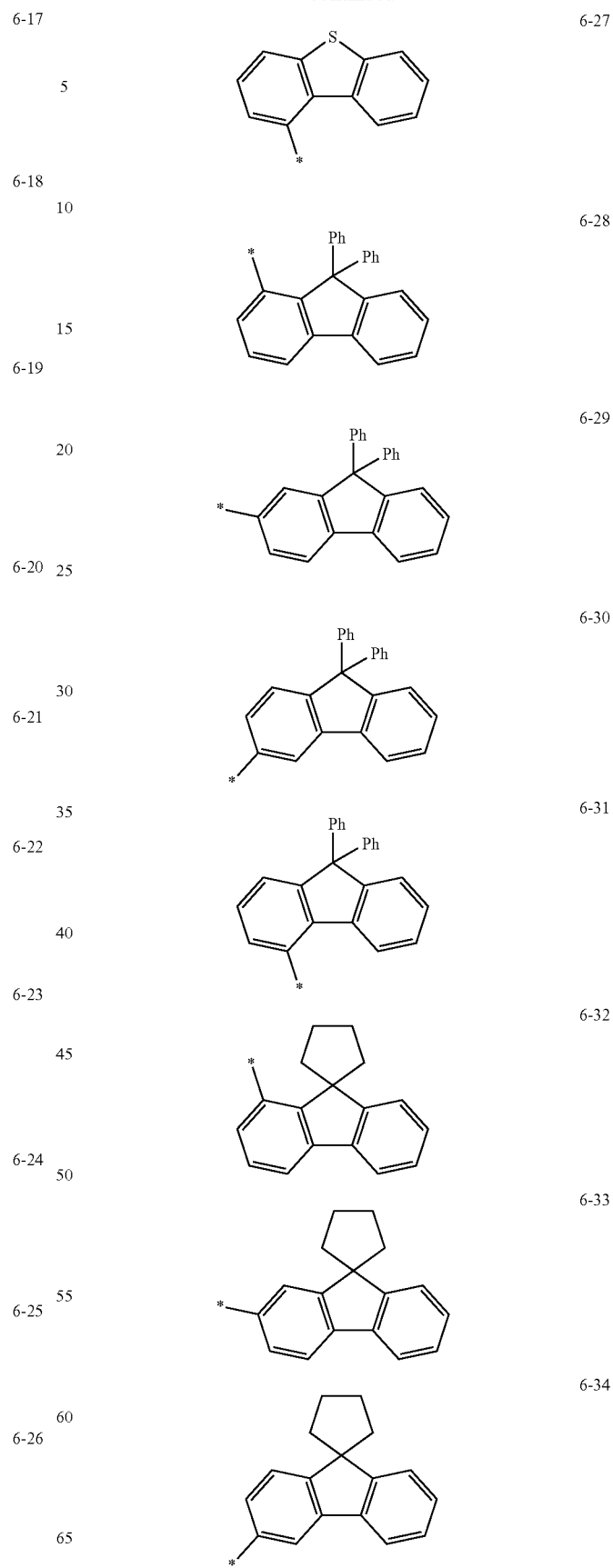

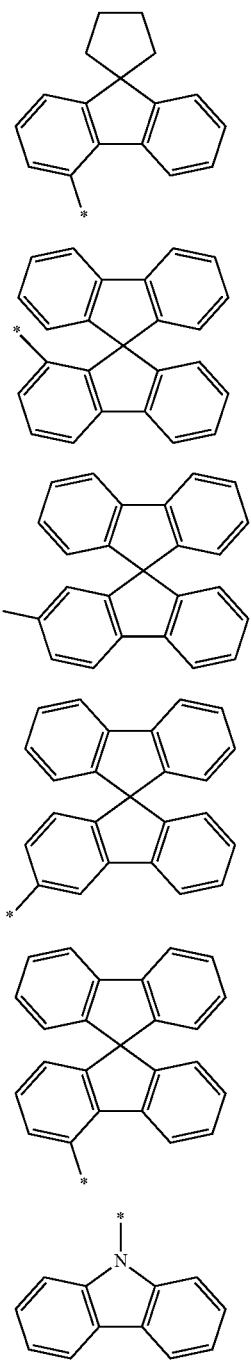

6-35
6-36
6-37
6-38
6-39
6-40 wherein, in Formulae 6-1 to 6-40, "Ph" represents a phenyl group, and * indicates a binding site to an adjacent atom.

In Formula 1, b1 to b6 may each independently be an integer from 1 to 5. b1 indicates the number of $Ar_1$ groups. When b1 is two or greater, at least two $Ar_1$ groups may be identical to or different from each other. b2 to b6 may be substantially the same as b1 and be understood by referring to the structure of Formula 1.

In some embodiments, b1 to b6 may each independently be 1, 2, or 3.

In some embodiments, b1 to b6 may each be 1, but embodiments are not limited thereto.

In Formula 1, n1 to n3 may each independently be selected from 0, 1, 2, and 3, provided that the sum of n1, n2, and n3 may be 2 or greater.

In one embodiment, n1 to n3 may each independently be 0, 1, or 2.

In one or more embodiments,
n1 may be 1, n2 may be 1, and n3 may be 0;
n1 may be 1, n2 may be 0, and n3 may be 1;
n1 may be 0, n2 may be 1, and n3 may be 1; or
n1 may be 1, n2 may be 1, and n3 may be 1, but embodiments are not limited thereto.

In Formula 1, $R_1$ to $R_3$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, wherein $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a phenyl group, a biphenyl group, and a terphenyl group.

In some embodiments, $R_1$ to $R_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In some embodiments, $R_1$ to $R_3$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, and —Si($Q_1$)($Q_2$)($Q_3$), wherein $Q_1$ to $Q_3$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

In one or more embodiments, $R_1$ to $R_3$ may each be hydrogen, but embodiments are not limited thereto.

In Formula 1, c1 to c3 may each independently be an integer from 0 to 8. c1 indicates the number of $R_1$ groups. When c1 is two or greater, at least two $R_1$ groups may be identical to or different from each other. c2 and c3 may be substantially the same as c1 and be understood by referring to the structure of Formula 1.

In one embodiment, c1 to c3 may each independently an integer from 0 to 6.

In one or more embodiments, c1 to c3 may each independently be 0, 1, 2, or 3.

In one or more embodiments, c1 to c3 may each independently be 0 or 1, but embodiments are not limited thereto.

In Formula 1, $R_{11}$ and $R_{12}$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_{3-10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, $R_{11}$ and $R_{12}$ may each independently be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and —Si($Q_{31}$)($Q_{32}$)($Q_{33}$);

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, and a chrysenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one embodiment, $R_{11}$ and $R_{12}$ may each independently be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a biphenyl group, a terphenyl group, a naphthyl group, a fluorenyl group, and a spiro-bifluorenyl group;

a phenyl group, a biphenyl group, a terphenyl group, a naphthyl group, a fluorenyl group, and a spiro-bifluorenyl group; and a phenyl group, a biphenyl group, a terphenyl group, a naphthyl group, a fluorenyl group, and a spiro-bifluorenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, and a spiro-bifluorenyl group.

In one or more embodiments, $R_{11}$ and $R_{12}$ may each independently be selected from a $C_1$-$C_{20}$ alkyl group, a $C_1$-$C_{20}$ alkoxy group, a phenyl group, a biphenyl group, a terphenyl group, and a naphthyl group, but embodiments are not limited thereto.

In some embodiments, the condensed-cyclic compound may be represented by one of Formulae 1-1 to 1-18:

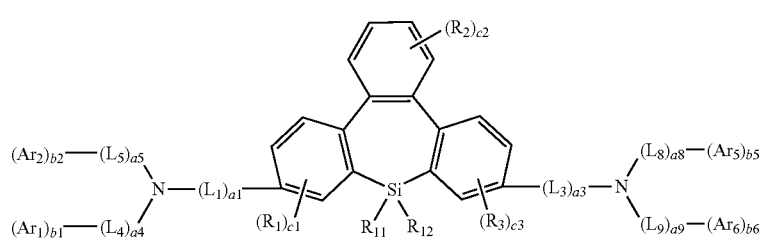

1-1

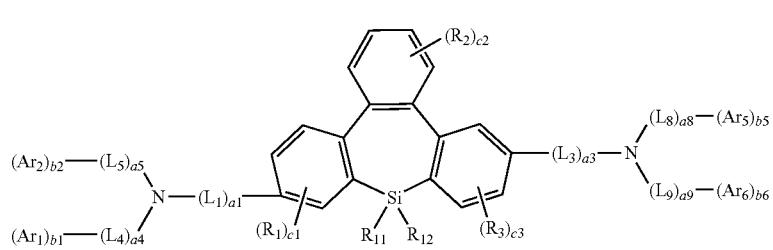

1-2

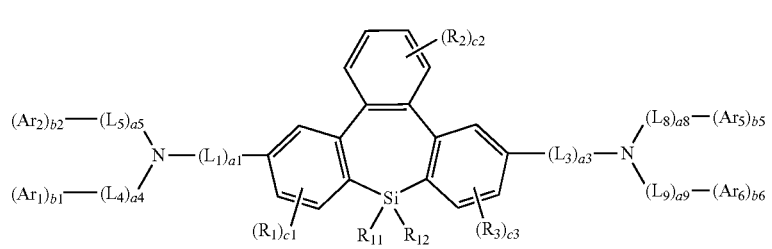

1-3

-continued
1-4
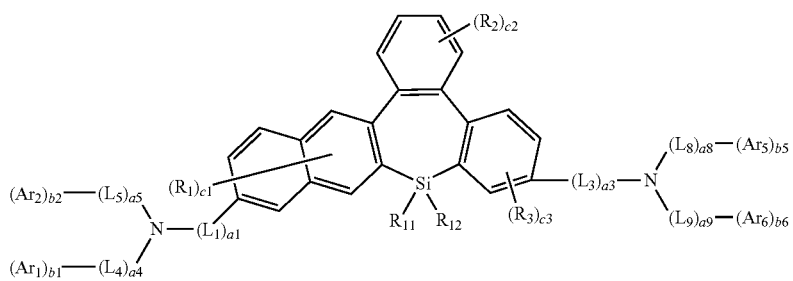
1-5
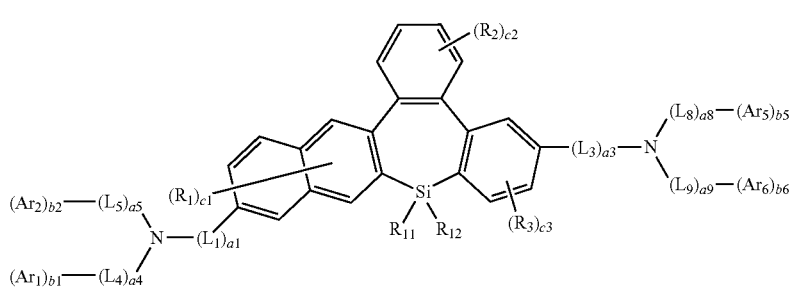
1-6
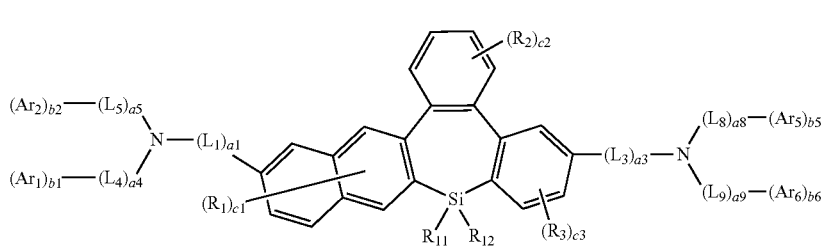
1-7
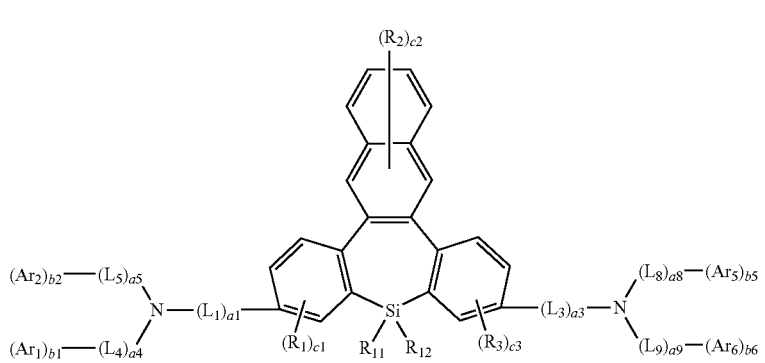
1-8
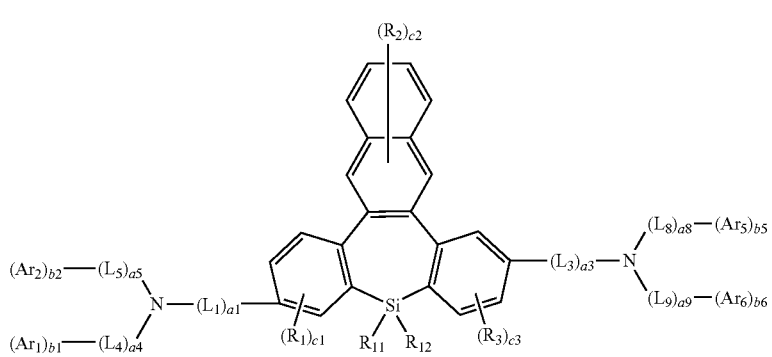

-continued
1-9
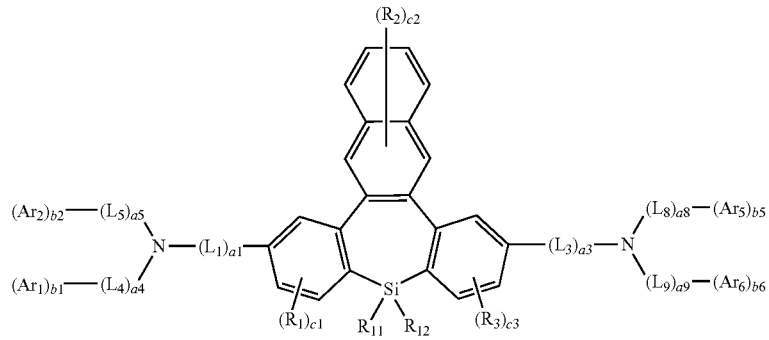
1-10
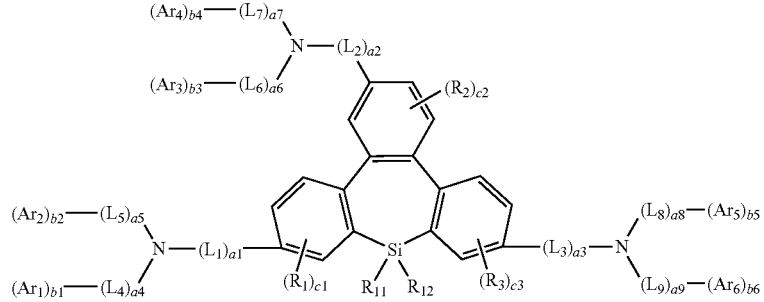
1-11
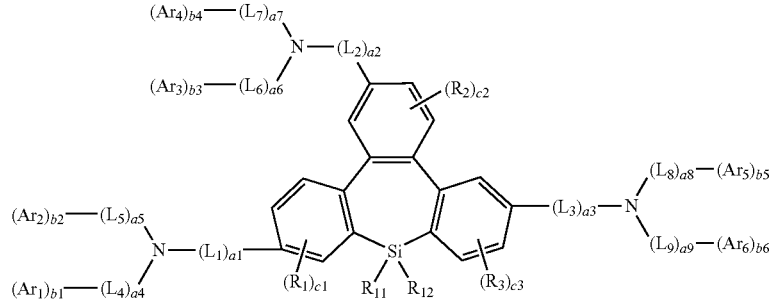
1-12
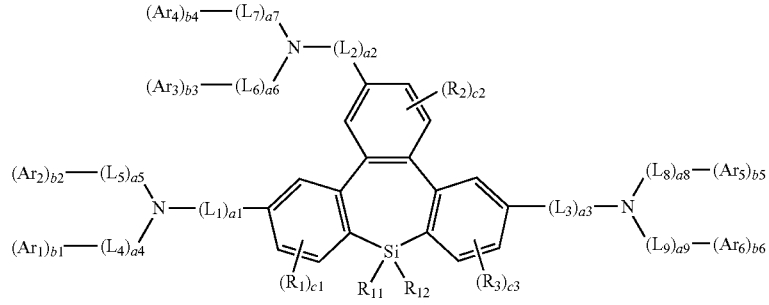
1-13
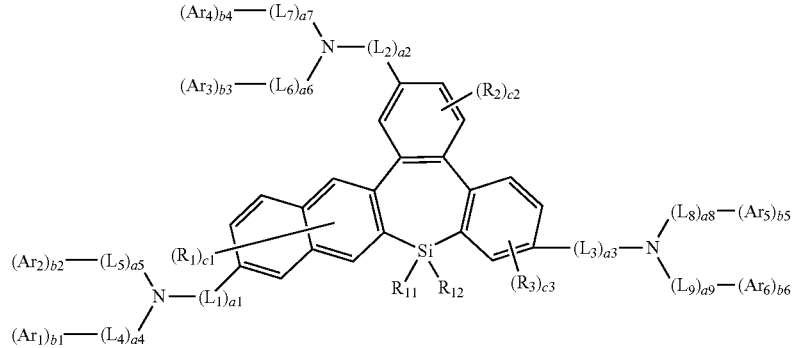

1-14
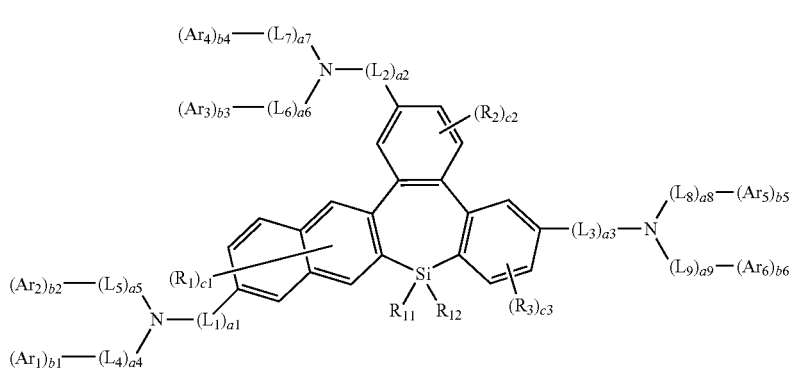
1-15
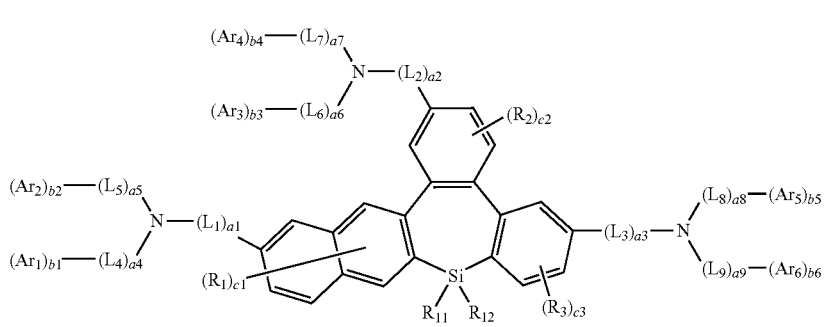
1-16
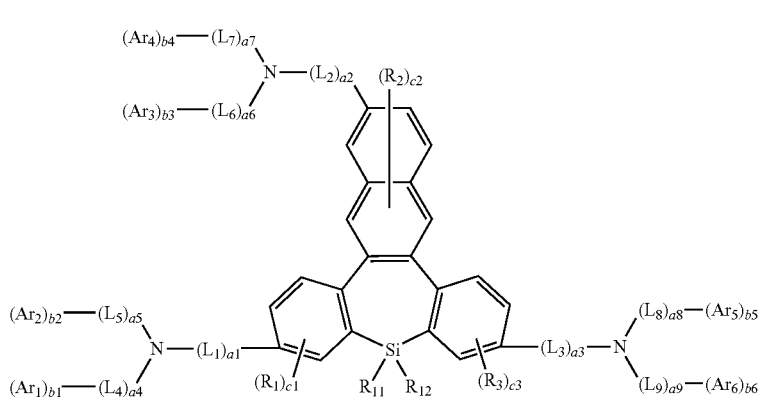
1-17
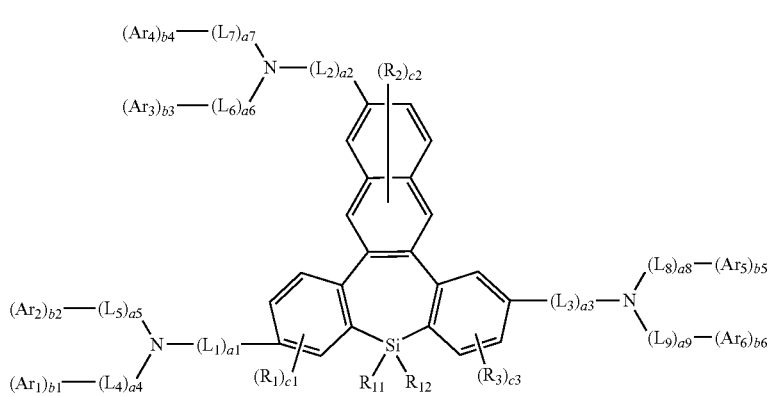

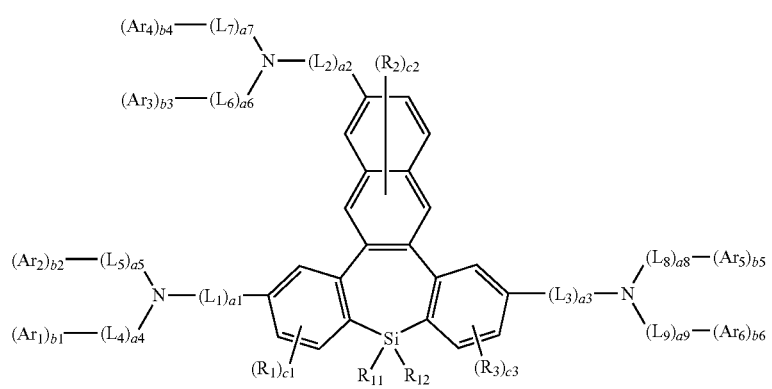
1-18
wherein, in Formulae 1-1 and 1-18,
L₁ to L₉, a1 to a9, Ar₁ to Ar₆, b1 to b6, R₁ to R₃, c1 to c3, R₁₁, and R₁₂ may be the same as those described herein.
In some embodiments, in Formulae 1-1 and 1-9, R₁ to R₃ may each be hydrogen.
In one embodiment, in Formulae 1-1 and 1-9, c1 to c3 may each independently be 0 or 1.
In some embodiments the condensed-cyclic compound may be represented by one of Formulae 1A to 1R:
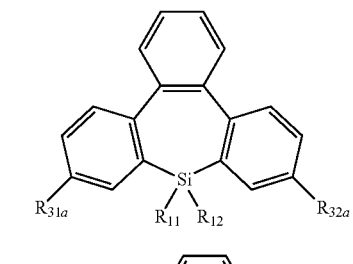
1A
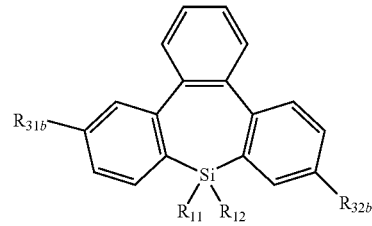
1B
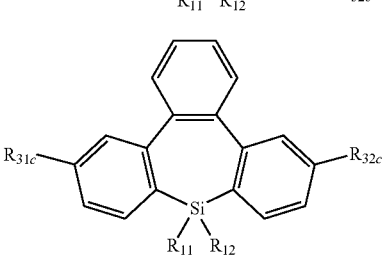
1C
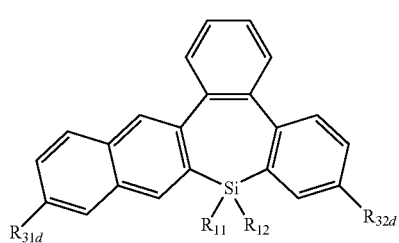
1D
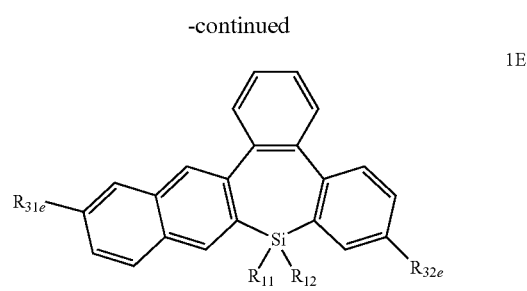
1E
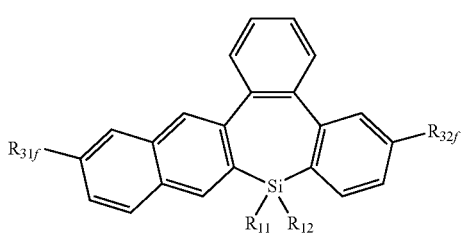
1F
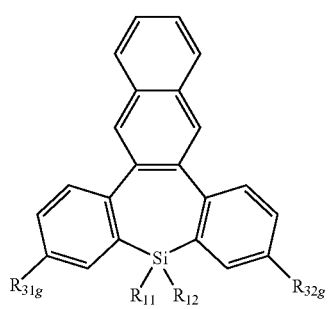
1G
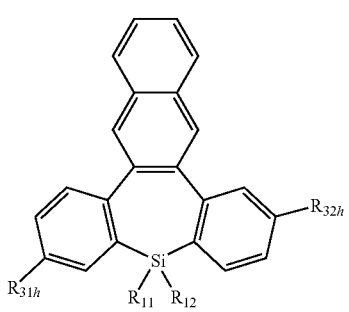
1H

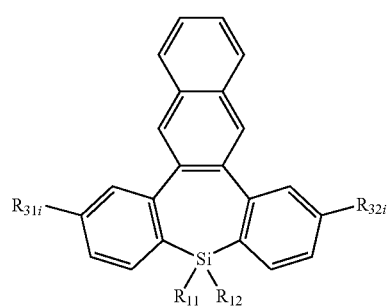
1I
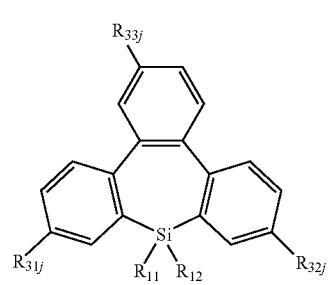
1J
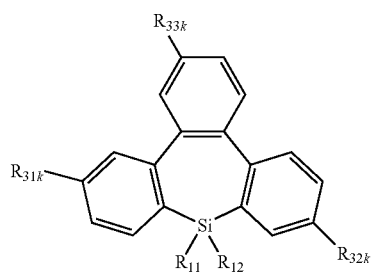
1K
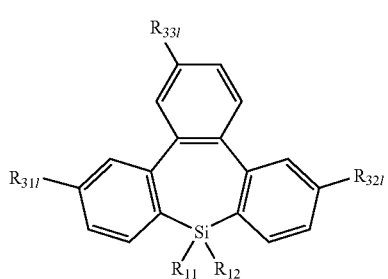
1L
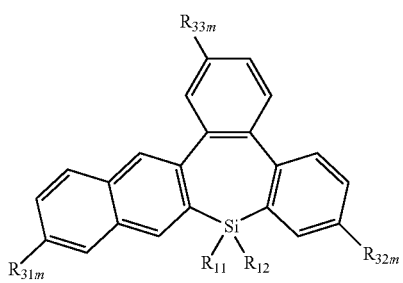
1M
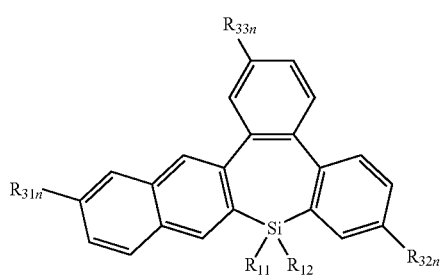
1N
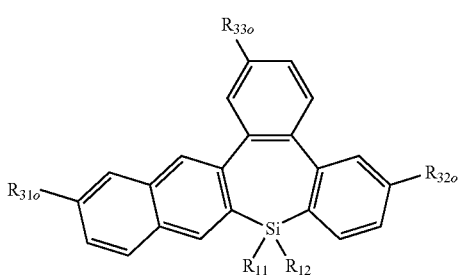
1O
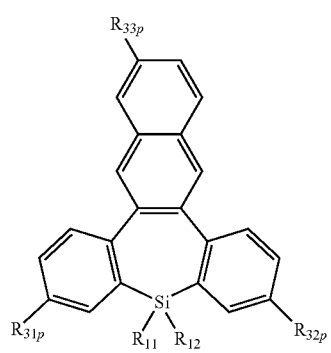
1P
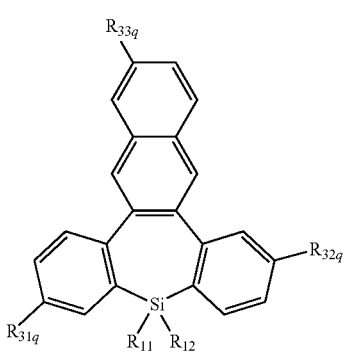
1Q -continued
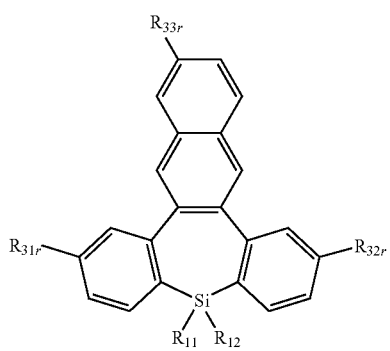
1R
wherein, in Formulae 1A to 1R,
$R_{11}$ and $R_{12}$ may each be the same as those described herein, and
$R_{31a}$ to $R_{31r}$, $R_{32a}$ to $R_{32r}$, and $R_{33j}$ to $R_{33r}$ may each independently be selected from groups represented by Formulae N-1 to N-38:
N-1
N-2
N-3
N-4
N-5
-continued
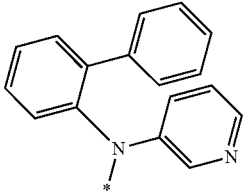
N-6
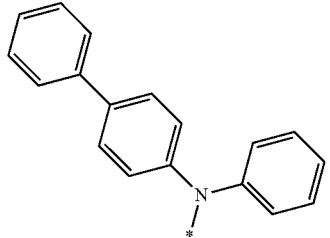
N-7
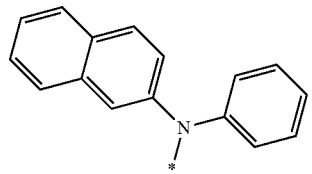
N-8
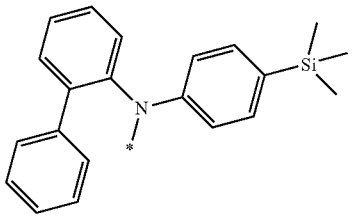
N-9
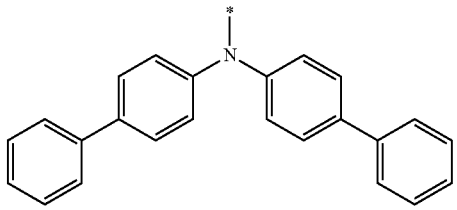
N-10
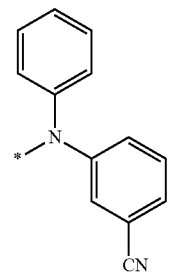
N-11

N-12
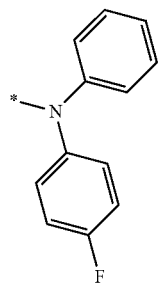
N-13
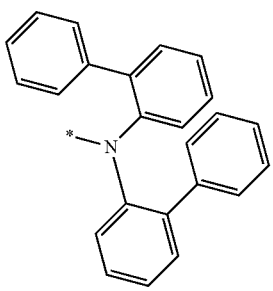
N-14
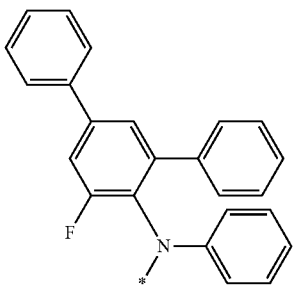
N-15
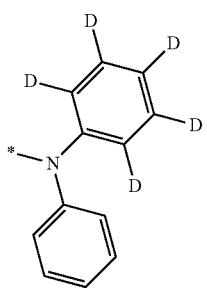
N-16
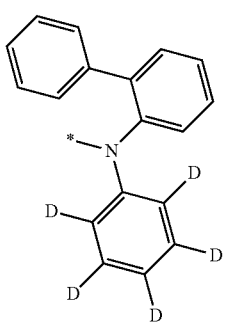
N-17
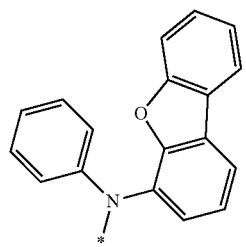
N-18
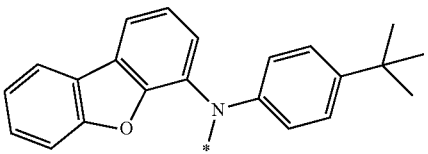
N-19
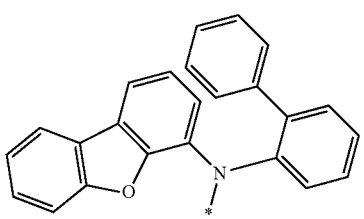
N-20
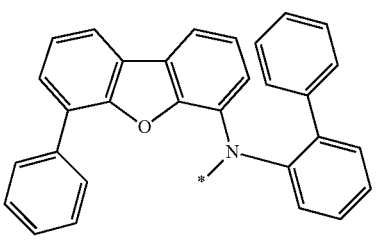
N-21
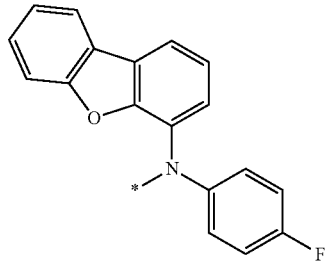
N-22
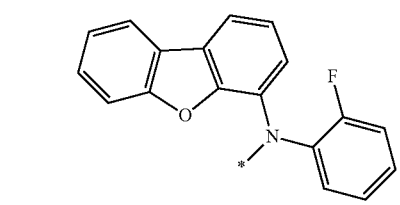
N-23
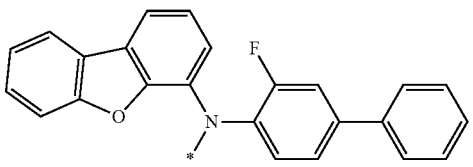

N-24
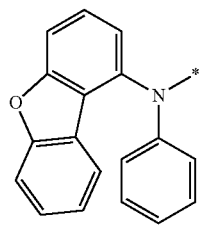
N-25
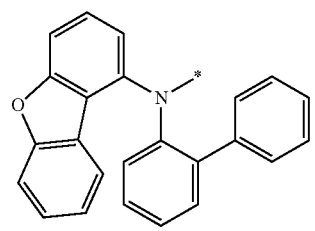
N-26
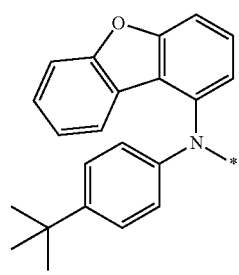
N-27
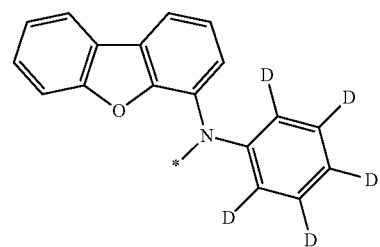
N-28
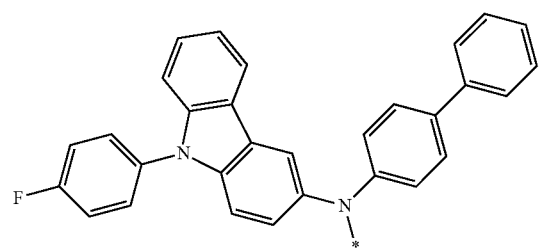
N-29
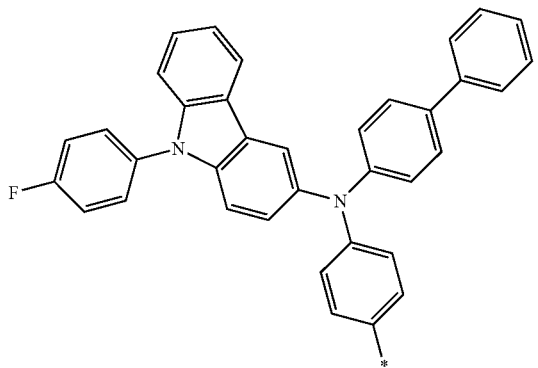
N-30
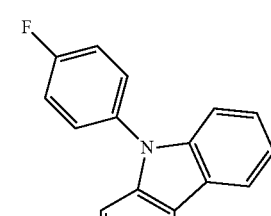
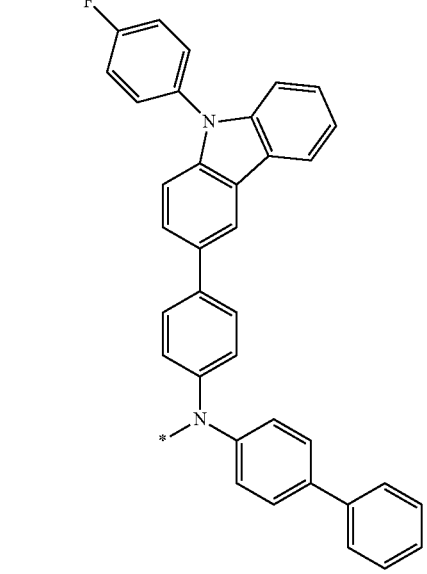
N-31
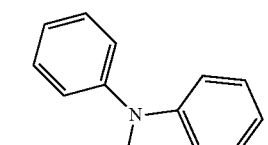
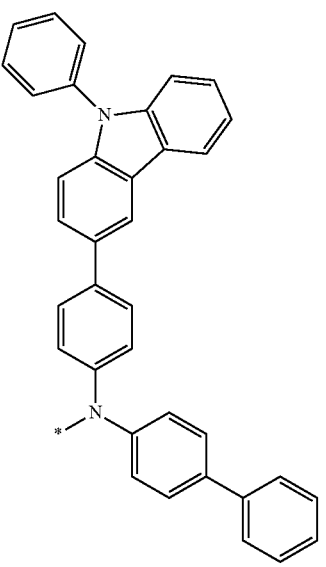

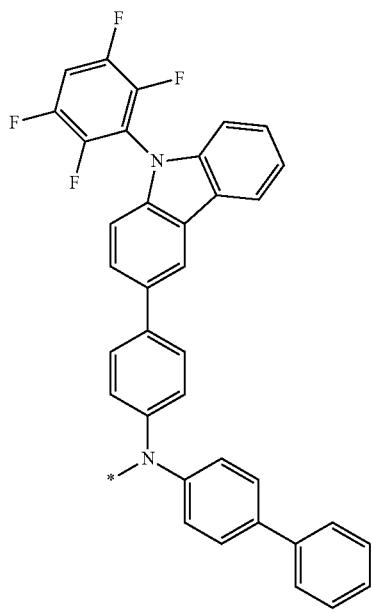

N-32

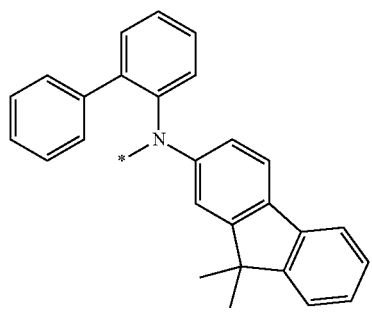

N-33

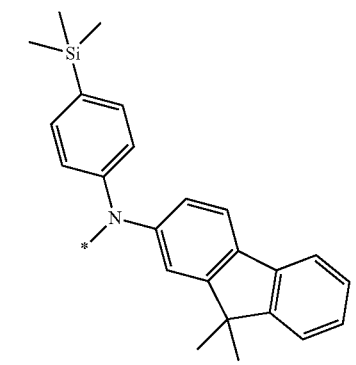

N-34

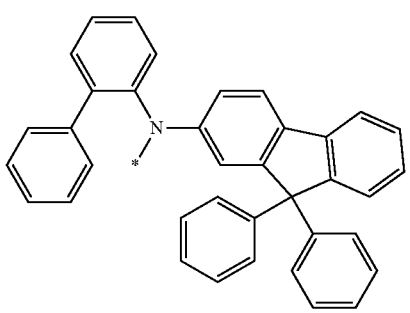

N-35

N-36

N-37

N-38 wherein, in Formulae N-1 to N-38, * indicates a binding site to an adjacent atom.

In one or more embodiments, the condensed-cyclic compound may be represented by one of Formulae 1A to 1R, and in Formulae 1A to 1R, $R_{11}$, $R_{12}$, $R_{31a}$ to $R_{31r}$, $R_{32a}$ to $R_{32r}$, and $R_{33j}$ to $R_{33r}$ may each independently be selected from Compounds 1 to 1416 in Table 1, but embodiments are not limited thereto:

TABLE 1

| Compound No. | Formula | $R_{11}$ | $R_{12}$ | $R_{31a}$ | $R_{32a}$ |
|---|---|---|---|---|---|
| 1 | 1A | Me | Me | N-1 | N-1 |
| 2 | 1A | Me | Me | N-2 | N-2 |
| 3 | 1A | Me | Me | N-3 | N-3 |
| 4 | 1A | Me | Me | N-4 | N-4 |
| 5 | 1A | Me | Me | N-5 | N-5 |
| 6 | 1A | Me | Me | N-6 | N-6 |
| 7 | 1A | Me | Me | N-7 | N-7 |
| 8 | 1A | Me | Me | N-8 | N-8 |
| 9 | 1A | Me | Me | N-9 | N-9 |
| 10 | 1A | Me | Me | N-10 | N-10 |
| 11 | 1A | Me | Me | N-11 | N-11 |
| 12 | 1A | Me | Me | N-12 | N-12 |
| 13 | 1A | Me | Me | N-13 | N-13 |
| 14 | 1A | Me | Me | N-14 | N-14 |
| 15 | 1A | Me | Me | N-15 | N-15 |
| 16 | 1A | Me | Me | N-16 | N-16 |
| 17 | 1A | Me | Me | N-17 | N-17 |

TABLE 1-continued

| Compound No. | Formula | $R_{11}$ | $R_{12}$ | $R_{31a}$ | $R_{32a}$ |
|---|---|---|---|---|---|
| 18 | 1A | Me | Me | N-18 | N-18 |
| 19 | 1A | Me | Me | N-19 | N-19 |
| 20 | 1A | Me | Me | N-20 | N-20 |
| 21 | 1A | Me | Me | N-21 | N-21 |
| 22 | 1A | Me | Me | N-22 | N-22 |
| 23 | 1A | Me | Me | N-23 | N-23 |
| 24 | 1A | Me | Me | N-24 | N-24 |
| 25 | 1A | Me | Me | N-25 | N-25 |
| 26 | 1A | Me | Me | N-26 | N-26 |
| 27 | 1A | Me | Me | N-27 | N-27 |
| 28 | 1A | Me | Me | N-28 | N-28 |
| 29 | 1A | Me | Me | N-29 | N-29 |
| 30 | 1A | Me | Me | N-30 | N-30 |
| 31 | 1A | Me | Me | N-31 | N-31 |
| 32 | 1A | Me | Me | N-32 | N-32 |
| 33 | 1A | Me | Me | N-33 | N-33 |
| 34 | 1A | Me | Me | N-34 | N-34 |
| 35 | 1A | Me | Me | N-35 | N-35 |
| 36 | 1A | Me | Me | N-36 | N-36 |
| 37 | 1A | Me | Me | N-37 | N-37 |
| 38 | 1A | Me | Me | N-38 | N-38 |
| 39 | 1A | Ph | Ph | N-1 | N-1 |
| 40 | 1A | Ph | Ph | N-2 | N-2 |
| 41 | 1A | Ph | Ph | N-3 | N-3 |
| 42 | 1A | Ph | Ph | N-4 | N-4 |
| 43 | 1A | Ph | Ph | N-5 | N-5 |
| 44 | 1A | Ph | Ph | N-6 | N-6 |
| 45 | 1A | Ph | Ph | N-7 | N-7 |
| 46 | 1A | Ph | Ph | N-8 | N-8 |
| 47 | 1A | Ph | Ph | N-9 | N-9 |
| 48 | 1A | Ph | Ph | N-10 | N-10 |
| 49 | 1A | Ph | Ph | N-11 | N-11 |
| 50 | 1A | Ph | Ph | N-12 | N-12 |
| 51 | 1A | Ph | Ph | N-13 | N-13 |
| 52 | 1A | Ph | Ph | N-14 | N-14 |
| 53 | 1A | Ph | Ph | N-15 | N-15 |
| 54 | 1A | Ph | Ph | N-16 | N-16 |
| 55 | 1A | Ph | Ph | N-17 | N-17 |
| 56 | 1A | Ph | Ph | N-18 | N-18 |
| 57 | 1A | Ph | Ph | N-19 | N-19 |
| 58 | 1A | Ph | Ph | N-20 | N-20 |
| 59 | 1A | Ph | Ph | N-21 | N-21 |
| 60 | 1A | Ph | Ph | N-22 | N-22 |
| 61 | 1A | Ph | Ph | N-23 | N-23 |
| 62 | 1A | Ph | Ph | N-24 | N-24 |
| 63 | 1A | Ph | Ph | N-25 | N-25 |
| 64 | 1A | Ph | Ph | N-26 | N-26 |
| 65 | 1A | Ph | Ph | N-27 | N-27 |
| 66 | 1A | Ph | Ph | N-28 | N-28 |
| 67 | 1A | Ph | Ph | N-29 | N-29 |
| 68 | 1A | Ph | Ph | N-30 | N-30 |
| 69 | 1A | Ph | Ph | N-31 | N-31 |
| 70 | 1A | Ph | Ph | N-32 | N-32 |
| 71 | 1A | Ph | Ph | N-33 | N-33 |
| 72 | 1A | Ph | Ph | N-34 | N-34 |
| 73 | 1A | Ph | Ph | N-35 | N-35 |
| 74 | 1A | Ph | Ph | N-36 | N-36 |
| 75 | 1A | Ph | Ph | N-37 | N-37 |
| 76 | 1A | Ph | Ph | N-38 | N-38 |
| 77 | 1A | Me | Me | N-1 | N-15 |
| 78 | 1A | Me | Me | N-5 | N-30 |
| 79 | 1A | Ph | Ph | N-1 | N-15 |
| 80 | 1A | Ph | Ph | N-5 | N-30 |

| Compound No. | Formula | $R_{11}$ | $R_{12}$ | $R_{31b}$ | $R_{32b}$ |
|---|---|---|---|---|---|
| 81 | 1B | Me | Me | N-1 | N-1 |
| 82 | 1B | Me | Me | N-2 | N-2 |
| 83 | 1B | Me | Me | N-3 | N-3 |
| 84 | 1B | Me | Me | N-4 | N-4 |
| 85 | 1B | Me | Me | N-5 | N-5 |
| 86 | 1B | Me | Me | N-6 | N-6 |
| 87 | 1B | Me | Me | N-7 | N-7 |
| 88 | 1B | Me | Me | N-8 | N-8 |
| 89 | 1B | Me | Me | N-9 | N-9 |
| 90 | 1B | Me | Me | N-10 | N-10 |
| 91 | 1B | Me | Me | N-11 | N-11 |
| 92 | 1B | Me | Me | N-12 | N-12 |
| 93 | 1B | Me | Me | N-13 | N-13 |
| 94 | 1B | Me | Me | N-14 | N-14 |
| 95 | 1B | Me | Me | N-15 | N-15 |
| 96 | 1B | Me | Me | N-16 | N-16 |
| 97 | 1B | Me | Me | N-17 | N-17 |
| 98 | 1B | Me | Me | N-18 | N-18 |
| 99 | 1B | Me | Me | N-19 | N-19 |
| 100 | 1B | Me | Me | N-20 | N-20 |
| 101 | 1B | Me | Me | N-21 | N-21 |
| 102 | 1B | Me | Me | N-22 | N-22 |
| 103 | 1B | Me | Me | N-23 | N-23 |
| 104 | 1B | Me | Me | N-24 | N-24 |
| 105 | 1B | Me | Me | N-25 | N-25 |
| 106 | 1B | Me | Me | N-26 | N-26 |
| 107 | 1B | Me | Me | N-27 | N-27 |
| 108 | 1B | Me | Me | N-28 | N-28 |
| 109 | 1B | Me | Me | N-29 | N-29 |
| 110 | 1B | Me | Me | N-30 | N-30 |
| 111 | 1B | Me | Me | N-31 | N-31 |
| 112 | 1B | Me | Me | N-32 | N-32 |
| 113 | 1B | Me | Me | N-33 | N-33 |
| 114 | 1B | Me | Me | N-34 | N-34 |
| 115 | 1B | Me | Me | N-35 | N-35 |
| 116 | 1B | Me | Me | N-36 | N-36 |
| 117 | 1B | Me | Me | N-37 | N-37 |
| 118 | 1B | Me | Me | N-38 | N-38 |
| 119 | 1B | Ph | Ph | N-1 | N-1 |
| 120 | 1B | Ph | Ph | N-2 | N-2 |
| 121 | 1B | Ph | Ph | N-3 | N-3 |
| 122 | 1B | Ph | Ph | N-4 | N-4 |
| 123 | 1B | Ph | Ph | N-5 | N-5 |
| 124 | 1B | Ph | Ph | N-6 | N-6 |
| 125 | 1B | Ph | Ph | N-7 | N-7 |
| 126 | 1B | Ph | Ph | N-8 | N-8 |
| 127 | 1B | Ph | Ph | N-9 | N-9 |
| 128 | 1B | Ph | Ph | N-10 | N-10 |
| 129 | 1B | Ph | Ph | N-11 | N-11 |
| 130 | 1B | Ph | Ph | N-12 | N-12 |
| 131 | 1B | Ph | Ph | N-13 | N-13 |
| 132 | 1B | Ph | Ph | N-14 | N-14 |
| 133 | 1B | Ph | Ph | N-15 | N-15 |
| 134 | 1B | Ph | Ph | N-16 | N-16 |
| 135 | 1B | Ph | Ph | N-17 | N-17 |
| 136 | 1B | Ph | Ph | N-18 | N-18 |
| 137 | 1B | Ph | Ph | N-19 | N-19 |
| 138 | 1B | Ph | Ph | N-20 | N-20 |
| 139 | 1B | Ph | Ph | N-21 | N-21 |
| 140 | 1B | Ph | Ph | N-22 | N-22 |
| 141 | 1B | Ph | Ph | N-23 | N-23 |
| 142 | 1B | Ph | Ph | N-24 | N-24 |
| 143 | 1B | Ph | Ph | N-25 | N-25 |
| 144 | 1B | Ph | Ph | N-26 | N-26 |
| 145 | 1B | Ph | Ph | N-27 | N-27 |
| 146 | 1B | Ph | Ph | N-28 | N-28 |
| 147 | 1B | Ph | Ph | N-29 | N-29 |
| 148 | 1B | Ph | Ph | N-30 | N-30 |
| 149 | 1B | Ph | Ph | N-31 | N-31 |
| 150 | 1B | Ph | Ph | N-32 | N-32 |
| 151 | 1B | Ph | Ph | N-33 | N-33 |
| 152 | 1B | Ph | Ph | N-34 | N-34 |
| 153 | 1B | Ph | Ph | N-35 | N-35 |
| 154 | 1B | Ph | Ph | N-36 | N-36 |
| 155 | 1B | Ph | Ph | N-37 | N-37 |
| 156 | 1B | Ph | Ph | N-38 | N-38 |
| 157 | 1B | Me | Me | N-38 | N-11 |
| 158 | 1B | Me | Me | N-9 | N-10 |
| 159 | 1B | Ph | Ph | N-38 | N-11 |
| 160 | 1B | Ph | Ph | N-9 | N-10 |

| Compound No. | Formula | $R_{11}$ | $R_{12}$ | $R_{31c}$ | $R_{32c}$ |
|---|---|---|---|---|---|
| 161 | 1C | Me | Me | N-1 | N-1 |
| 162 | 1C | Me | Me | N-2 | N-2 |
| 163 | 1C | Me | Me | N-3 | N-3 |
| 164 | 1C | Me | Me | N-4 | N-4 |
| 165 | 1C | Me | Me | N-5 | N-5 |
| 166 | 1C | Me | Me | N-6 | N-6 |
| 167 | 1C | Me | Me | N-7 | N-7 |
| 168 | 1C | Me | Me | N-8 | N-8 |
| 169 | 1C | Me | Me | N-9 | N-9 |
| 170 | 1C | Me | Me | N-10 | N-10 |
| 171 | 1C | Me | Me | N-11 | N-11 |

TABLE 1-continued

| | | | | | |
|---|---|---|---|---|---|
| 172 | 1C | Me | Me | N-12 | N-12 |
| 173 | 1C | Me | Me | N-13 | N-13 |
| 174 | 1C | Me | Me | N-14 | N-14 |
| 175 | 1C | Me | Me | N-15 | N-15 |
| 176 | 1C | Me | Me | N-16 | N-16 |
| 177 | 1C | Me | Me | N-17 | N-17 |
| 178 | 1C | Me | Me | N-18 | N-18 |
| 179 | 1C | Me | Me | N-19 | N-19 |
| 180 | 1C | Me | Me | N-20 | N-20 |
| 181 | 1C | Me | Me | N-21 | N-21 |
| 182 | 1C | Me | Me | N-22 | N-22 |
| 183 | 1C | Me | Me | N-23 | N-23 |
| 184 | 1C | Me | Me | N-24 | N-24 |
| 185 | 1C | Me | Me | N-25 | N-25 |
| 186 | 1C | Me | Me | N-26 | N-26 |
| 187 | 1C | Me | Me | N-27 | N-27 |
| 188 | 1C | Me | Me | N-28 | N-28 |
| 189 | 1C | Me | Me | N-29 | N-29 |
| 190 | 1C | Me | Me | N-30 | N-30 |
| 191 | 1C | Me | Me | N-31 | N-31 |
| 192 | 1C | Me | Me | N-32 | N-32 |
| 193 | 1C | Me | Me | N-33 | N-33 |
| 194 | 1C | Me | Me | N-34 | N-34 |
| 195 | 1C | Me | Me | N-35 | N-35 |
| 196 | 1C | Me | Me | N-36 | N-36 |
| 197 | 1C | Me | Me | N-37 | N-37 |
| 198 | 1C | Me | Me | N-38 | N-38 |
| 199 | 1C | Ph | Ph | N-1 | N-1 |
| 200 | 1C | Ph | Ph | N-2 | N-2 |
| 201 | 1C | Ph | Ph | N-3 | N-3 |
| 202 | 1C | Ph | Ph | N-4 | N-4 |
| 203 | 1C | Ph | Ph | N-5 | N-5 |
| 204 | 1C | Ph | Ph | N-6 | N-6 |
| 205 | 1C | Ph | Ph | N-7 | N-7 |
| 206 | 1C | Ph | Ph | N-8 | N-8 |
| 207 | 1C | Ph | Ph | N-9 | N-9 |
| 208 | 1C | Ph | Ph | N-10 | N-10 |
| 209 | 1C | Ph | Ph | N-11 | N-11 |
| 210 | 1C | Ph | Ph | N-12 | N-12 |
| 211 | 1C | Ph | Ph | N-13 | N-13 |
| 212 | 1C | Ph | Ph | N-14 | N-14 |
| 213 | 1C | Ph | Ph | N-15 | N-15 |
| 214 | 1C | Ph | Ph | N-16 | N-16 |
| 215 | 1C | Ph | Ph | N-17 | N-17 |
| 216 | 1C | Ph | Ph | N-18 | N-18 |
| 217 | 1C | Ph | Ph | N-19 | N-19 |
| 218 | 1C | Ph | Ph | N-20 | N-20 |
| 219 | 1C | Ph | Ph | N-21 | N-21 |
| 220 | 1C | Ph | Ph | N-22 | N-22 |
| 221 | 1C | Ph | Ph | N-23 | N-23 |
| 222 | 1C | Ph | Ph | N-24 | N-24 |
| 223 | 1C | Ph | Ph | N-25 | N-25 |
| 224 | 1C | Ph | Ph | N-26 | N-26 |
| 225 | 1C | Ph | Ph | N-27 | N-27 |
| 226 | 1C | Ph | Ph | N-28 | N-28 |
| 227 | 1C | Ph | Ph | N-29 | N-29 |
| 228 | 1C | Ph | Ph | N-30 | N-30 |
| 229 | 1C | Ph | Ph | N-31 | N-31 |
| 230 | 1C | Ph | Ph | N-32 | N-32 |
| 231 | 1C | Ph | Ph | N-33 | N-33 |
| 232 | 1C | Ph | Ph | N-34 | N-34 |
| 233 | 1C | Ph | Ph | N-35 | N-35 |
| 234 | 1C | Ph | Ph | N-36 | N-36 |
| 235 | 1C | Ph | Ph | N-37 | N-37 |
| 236 | 1C | Ph | Ph | N-38 | N-38 |

| Compound No. | Formula | $R_{11}$ | $R_{12}$ | $R_{31d}$ | $R_{32d}$ |
|---|---|---|---|---|---|
| 237 | 1D | Me | Me | N-1 | N-1 |
| 238 | 1D | Me | Me | N-2 | N-2 |
| 239 | 1D | Me | Me | N-3 | N-3 |
| 240 | 1D | Me | Me | N-4 | N-4 |
| 241 | 1D | Me | Me | N-5 | N-5 |
| 242 | 1D | Me | Me | N-6 | N-6 |
| 243 | 1D | Me | Me | N-7 | N-7 |
| 244 | 1D | Me | Me | N-8 | N-8 |
| 245 | 1D | Me | Me | N-9 | N-9 |
| 246 | 1D | Me | Me | N-10 | N-10 |
| 247 | 1D | Me | Me | N-11 | N-11 |
| 248 | 1D | Me | Me | N-12 | N-12 |
| 249 | 1D | Me | Me | N-13 | N-13 |
| 250 | 1D | Me | Me | N-14 | N-14 |
| 251 | 1D | Me | Me | N-15 | N-15 |
| 252 | 1D | Me | Me | N-16 | N-16 |
| 253 | 1D | Me | Me | N-17 | N-17 |
| 254 | 1D | Me | Me | N-18 | N-18 |
| 255 | 1D | Me | Me | N-19 | N-19 |
| 256 | 1D | Me | Me | N-20 | N-20 |
| 257 | 1D | Me | Me | N-21 | N-21 |
| 258 | 1D | Me | Me | N-22 | N-22 |
| 259 | 1D | Me | Me | N-23 | N-23 |
| 260 | 1D | Me | Me | N-24 | N-24 |
| 261 | 1D | Me | Me | N-25 | N-25 |
| 262 | 1D | Me | Me | N-26 | N-26 |
| 263 | 1D | Me | Me | N-27 | N-27 |
| 264 | 1D | Me | Me | N-28 | N-28 |
| 265 | 1D | Me | Me | N-29 | N-29 |
| 266 | 1D | Me | Me | N-30 | N-30 |
| 267 | 1D | Me | Me | N-31 | N-31 |
| 268 | 1D | Me | Me | N-32 | N-32 |
| 269 | 1D | Me | Me | N-33 | N-33 |
| 270 | 1D | Me | Me | N-34 | N-34 |
| 271 | 1D | Me | Me | N-35 | N-35 |
| 272 | 1D | Me | Me | N-36 | N-36 |
| 273 | 1D | Me | Me | N-37 | N-37 |
| 274 | 1D | Me | Me | N-38 | N-38 |
| 275 | 1D | Ph | Ph | N-1 | N-1 |
| 276 | 1D | Ph | Ph | N-2 | N-2 |
| 277 | 1D | Ph | Ph | N-3 | N-3 |
| 278 | 1D | Ph | Ph | N-4 | N-4 |
| 279 | 1D | Ph | Ph | N-5 | N-5 |
| 280 | 1D | Ph | Ph | N-6 | N-6 |
| 281 | 1D | Ph | Ph | N-7 | N-7 |
| 282 | 1D | Ph | Ph | N-8 | N-8 |
| 283 | 1D | Ph | Ph | N-9 | N-9 |
| 284 | 1D | Ph | Ph | N-10 | N-10 |
| 285 | 1D | Ph | Ph | N-11 | N-11 |
| 286 | 1D | Ph | Ph | N-12 | N-12 |
| 287 | 1D | Ph | Ph | N-13 | N-13 |
| 288 | 1D | Ph | Ph | N-14 | N-14 |
| 289 | 1D | Ph | Ph | N-15 | N-15 |
| 290 | 1D | Ph | Ph | N-16 | N-16 |
| 291 | 1D | Ph | Ph | N-17 | N-17 |
| 292 | 1D | Ph | Ph | N-18 | N-18 |
| 293 | 1D | Ph | Ph | N-19 | N-19 |
| 294 | 1D | Ph | Ph | N-20 | N-20 |
| 295 | 1D | Ph | Ph | N-21 | N-21 |
| 296 | 1D | Ph | Ph | N-22 | N-22 |
| 297 | 1D | Ph | Ph | N-23 | N-23 |
| 298 | 1D | Ph | Ph | N-24 | N-24 |
| 299 | 1D | Ph | Ph | N-25 | N-25 |
| 300 | 1D | Ph | Ph | N-26 | N-26 |
| 301 | 1D | Ph | Ph | N-27 | N-27 |
| 302 | 1D | Ph | Ph | N-28 | N-28 |
| 303 | 1D | Ph | Ph | N-29 | N-29 |
| 304 | 1D | Ph | Ph | N-30 | N-30 |
| 305 | 1D | Ph | Ph | N-31 | N-31 |
| 306 | 1D | Ph | Ph | N-32 | N-32 |
| 307 | 1D | Ph | Ph | N-33 | N-33 |
| 308 | 1D | Ph | Ph | N-34 | N-34 |
| 309 | 1D | Ph | Ph | N-35 | N-35 |
| 310 | 1D | Ph | Ph | N-36 | N-36 |
| 311 | 1D | Ph | Ph | N-37 | N-37 |
| 312 | 1D | Ph | Ph | N-38 | N-38 |
| 313 | 1D | Me | Me | N-1 | N-15 |
| 314 | 1D | Me | Me | N-5 | N-30 |
| 315 | 1D | Ph | Ph | N-1 | N-15 |
| 316 | 1D | Ph | Ph | N-5 | N-30 |

| Compound No. | Formula | $R_{11}$ | $R_{12}$ | $R_{31e}$ | $R_{32e}$ |
|---|---|---|---|---|---|
| 317 | 1E | Me | Me | N-1 | N-1 |
| 318 | 1E | Me | Me | N-2 | N-2 |
| 319 | 1E | Me | Me | N-3 | N-3 |
| 320 | 1E | Me | Me | N-4 | N-4 |
| 321 | 1E | Me | Me | N-5 | N-5 |
| 322 | 1E | Me | Me | N-6 | N-6 |
| 323 | 1E | Me | Me | N-7 | N-7 |
| 324 | 1E | Me | Me | N-8 | N-8 |
| 325 | 1E | Me | Me | N-9 | N-9 |

TABLE 1-continued

| | | | | | |
|---|---|---|---|---|---|
| 326 | 1E | Me | Me | N-10 | N-10 |
| 327 | 1E | Me | Me | N-11 | N-11 |
| 328 | 1E | Me | Me | N-12 | N-12 |
| 329 | 1E | Me | Me | N-13 | N-13 |
| 330 | 1E | Me | Me | N-14 | N-14 |
| 331 | 1E | Me | Me | N-15 | N-15 |
| 332 | 1E | Me | Me | N-16 | N-16 |
| 333 | 1E | Me | Me | N-17 | N-17 |
| 334 | 1E | Me | Me | N-18 | N-18 |
| 335 | 1E | Me | Me | N-19 | N-19 |
| 336 | 1E | Me | Me | N-20 | N-20 |
| 337 | 1E | Me | Me | N-21 | N-21 |
| 338 | 1E | Me | Me | N-22 | N-22 |
| 339 | 1E | Me | Me | N-23 | N-23 |
| 340 | 1E | Me | Me | N-24 | N-24 |
| 341 | 1E | Me | Me | N-25 | N-25 |
| 342 | 1E | Me | Me | N-26 | N-26 |
| 343 | 1E | Me | Me | N-27 | N-27 |
| 344 | 1E | Me | Me | N-28 | N-28 |
| 345 | 1E | Me | Me | N-29 | N-29 |
| 346 | 1E | Me | Me | N-30 | N-30 |
| 347 | 1E | Me | Me | N-31 | N-31 |
| 348 | 1E | Me | Me | N-32 | N-32 |
| 349 | 1E | Me | Me | N-33 | N-33 |
| 350 | 1E | Me | Me | N-34 | N-34 |
| 351 | 1E | Me | Me | N-35 | N-35 |
| 352 | 1E | Me | Me | N-36 | N-36 |
| 353 | 1E | Me | Me | N-37 | N-37 |
| 354 | 1E | Me | Me | N-38 | N-38 |
| 355 | 1E | Ph | Ph | N-1 | N-1 |
| 356 | 1E | Ph | Ph | N-2 | N-2 |
| 357 | 1E | Ph | Ph | N-3 | N-3 |
| 358 | 1E | Ph | Ph | N-4 | N-4 |
| 359 | 1E | Ph | Ph | N-5 | N-5 |
| 360 | 1E | Ph | Ph | N-6 | N-6 |
| 361 | 1E | Ph | Ph | N-7 | N-7 |
| 362 | 1E | Ph | Ph | N-8 | N-8 |
| 363 | 1E | Ph | Ph | N-9 | N-9 |
| 364 | 1E | Ph | Ph | N-10 | N-10 |
| 365 | 1E | Ph | Ph | N-11 | N-11 |
| 366 | 1E | Ph | Ph | N-12 | N-12 |
| 367 | 1E | Ph | Ph | N-13 | N-13 |
| 368 | 1E | Ph | Ph | N-14 | N-14 |
| 369 | 1E | Ph | Ph | N-15 | N-15 |
| 370 | 1E | Ph | Ph | N-16 | N-16 |
| 371 | 1E | Ph | Ph | N-17 | N-17 |
| 372 | 1E | Ph | Ph | N-18 | N-18 |
| 373 | 1E | Ph | Ph | N-19 | N-19 |
| 374 | 1E | Ph | Ph | N-20 | N-20 |
| 375 | 1E | Ph | Ph | N-21 | N-21 |
| 376 | 1E | Ph | Ph | N-22 | N-22 |
| 377 | 1E | Ph | Ph | N-23 | N-23 |
| 378 | 1E | Ph | Ph | N-24 | N-24 |
| 379 | 1E | Ph | Ph | N-25 | N-25 |
| 380 | 1E | Ph | Ph | N-26 | N-26 |
| 381 | 1E | Ph | Ph | N-27 | N-27 |
| 382 | 1E | Ph | Ph | N-28 | N-28 |
| 383 | 1E | Ph | Ph | N-29 | N-29 |
| 384 | 1E | Ph | Ph | N-30 | N-30 |
| 385 | 1E | Ph | Ph | N-31 | N-31 |
| 386 | 1E | Ph | Ph | N-32 | N-32 |
| 387 | 1E | Ph | Ph | N-33 | N-33 |
| 388 | 1E | Ph | Ph | N-34 | N-34 |
| 389 | 1E | Ph | Ph | N-35 | N-35 |
| 390 | 1E | Ph | Ph | N-36 | N-36 |
| 391 | 1E | Ph | Ph | N-37 | N-37 |
| 392 | 1E | Ph | Ph | N-38 | N-38 |
| 393 | 1E | Me | Me | N-38 | N-11 |
| 394 | 1E | Me | Me | N-9 | N-10 |
| 395 | 1E | Ph | Ph | N-38 | N-11 |
| 396 | 1E | Ph | Ph | N-9 | N-10 |

| Compound No. | Formula | $R_{11}$ | $R_{12}$ | $R_{31f}$ | $R_{32f}$ |
|---|---|---|---|---|---|
| 397 | 1F | Me | Me | N-1 | N-1 |
| 398 | 1F | Me | Me | N-2 | N-2 |
| 399 | 1F | Me | Me | N-3 | N-3 |
| 400 | 1F | Me | Me | N-4 | N-4 |
| 401 | 1F | Me | Me | N-5 | N-5 |
| 402 | 1F | Me | Me | N-6 | N-6 |
| 403 | 1F | Me | Me | N-7 | N-7 |
| 404 | 1F | Me | Me | N-8 | N-8 |
| 405 | 1F | Me | Me | N-9 | N-9 |
| 406 | 1F | Me | Me | N-10 | N-10 |
| 407 | 1F | Me | Me | N-11 | N-11 |
| 408 | 1F | Me | Me | N-12 | N-12 |
| 409 | 1F | Me | Me | N-13 | N-13 |
| 410 | 1F | Me | Me | N-14 | N-14 |
| 411 | 1F | Me | Me | N-15 | N-15 |
| 412 | 1F | Me | Me | N-16 | N-16 |
| 413 | 1F | Me | Me | N-17 | N-17 |
| 414 | 1F | Me | Me | N-18 | N-18 |
| 415 | 1F | Me | Me | N-19 | N-19 |
| 416 | 1F | Me | Me | N-20 | N-20 |
| 417 | 1F | Me | Me | N-21 | N-21 |
| 418 | 1F | Me | Me | N-22 | N-22 |
| 419 | 1F | Me | Me | N-23 | N-23 |
| 420 | 1F | Me | Me | N-24 | N-24 |
| 421 | 1F | Me | Me | N-25 | N-25 |
| 422 | 1F | Me | Me | N-26 | N-26 |
| 423 | 1F | Me | Me | N-27 | N-27 |
| 424 | 1F | Me | Me | N-28 | N-28 |
| 425 | 1F | Me | Me | N-29 | N-29 |
| 426 | 1F | Me | Me | N-30 | N-30 |
| 427 | 1F | Me | Me | N-31 | N-31 |
| 428 | 1F | Me | Me | N-32 | N-32 |
| 429 | 1F | Me | Me | N-33 | N-33 |
| 430 | 1F | Me | Me | N-34 | N-34 |
| 431 | 1F | Me | Me | N-35 | N-35 |
| 432 | 1F | Me | Me | N-36 | N-36 |
| 433 | 1F | Me | Me | N-37 | N-37 |
| 434 | 1F | Me | Me | N-38 | N-38 |
| 435 | 1F | Ph | Ph | N-1 | N-1 |
| 436 | 1F | Ph | Ph | N-2 | N-2 |
| 437 | 1F | Ph | Ph | N-3 | N-3 |
| 438 | 1F | Ph | Ph | N-4 | N-4 |
| 439 | 1F | Ph | Ph | N-5 | N-5 |
| 440 | 1F | Ph | Ph | N-6 | N-6 |
| 441 | 1F | Ph | Ph | N-7 | N-7 |
| 442 | 1F | Ph | Ph | N-8 | N-8 |
| 443 | 1F | Ph | Ph | N-9 | N-9 |
| 444 | 1F | Ph | Ph | N-10 | N-10 |
| 445 | 1F | Ph | Ph | N-11 | N-11 |
| 446 | 1F | Ph | Ph | N-12 | N-12 |
| 447 | 1F | Ph | Ph | N-13 | N-13 |
| 448 | 1F | Ph | Ph | N-14 | N-14 |
| 449 | 1F | Ph | Ph | N-15 | N-15 |
| 450 | 1F | Ph | Ph | N-16 | N-16 |
| 451 | 1F | Ph | Ph | N-17 | N-17 |
| 452 | 1F | Ph | Ph | N-18 | N-18 |
| 453 | 1F | Ph | Ph | N-19 | N-19 |
| 454 | 1F | Ph | Ph | N-20 | N-20 |
| 455 | 1F | Ph | Ph | N-21 | N-21 |
| 456 | 1F | Ph | Ph | N-22 | N-22 |
| 457 | 1F | Ph | Ph | N-23 | N-23 |
| 458 | 1F | Ph | Ph | N-24 | N-24 |
| 459 | 1F | Ph | Ph | N-25 | N-25 |
| 460 | 1F | Ph | Ph | N-26 | N-26 |
| 461 | 1F | Ph | Ph | N-27 | N-27 |
| 462 | 1F | Ph | Ph | N-28 | N-28 |
| 463 | 1F | Ph | Ph | N-29 | N-29 |
| 464 | 1F | Ph | Ph | N-30 | N-30 |
| 465 | 1F | Ph | Ph | N-31 | N-31 |
| 466 | 1F | Ph | Ph | N-32 | N-32 |
| 467 | 1F | Ph | Ph | N-33 | N-33 |
| 468 | 1F | Ph | Ph | N-34 | N-34 |
| 469 | 1F | Ph | Ph | N-35 | N-35 |
| 470 | 1F | Ph | Ph | N-36 | N-36 |
| 471 | 1F | Ph | Ph | N-37 | N-37 |
| 472 | 1F | Ph | Ph | N-38 | N-38 |

| Compound No. | Formula | $R_{11}$ | $R_{12}$ | $R_{31g}$ | $R_{32g}$ |
|---|---|---|---|---|---|
| 473 | 1G | Me | Me | N-1 | N-1 |
| 474 | 1G | Me | Me | N-2 | N-2 |
| 475 | 1G | Me | Me | N-3 | N-3 |
| 476 | 1G | Me | Me | N-4 | N-4 |
| 477 | 1G | Me | Me | N-5 | N-5 |
| 478 | 1G | Me | Me | N-6 | N-6 |
| 479 | 1G | Me | Me | N-7 | N-7 |

TABLE 1-continued

| Compound No. | Formula | $R_{11}$ | $R_{12}$ | $R_{31h}$ | $R_{32h}$ |
|---|---|---|---|---|---|
| 480 | 1G | Me | Me | N-8 | N-8 |
| 481 | 1G | Me | Me | N-9 | N-9 |
| 482 | 1G | Me | Me | N-10 | N-10 |
| 483 | 1G | Me | Me | N-11 | N-11 |
| 484 | 1G | Me | Me | N-12 | N-12 |
| 485 | 1G | Me | Me | N-13 | N-13 |
| 486 | 1G | Me | Me | N-14 | N-14 |
| 487 | 1G | Me | Me | N-15 | N-15 |
| 488 | 1G | Me | Me | N-16 | N-16 |
| 489 | 1G | Me | Me | N-17 | N-17 |
| 490 | 1G | Me | Me | N-18 | N-18 |
| 491 | 1G | Me | Me | N-19 | N-19 |
| 492 | 1G | Me | Me | N-20 | N-20 |
| 493 | 1G | Me | Me | N-21 | N-21 |
| 494 | 1G | Me | Me | N-22 | N-22 |
| 495 | 1G | Me | Me | N-23 | N-23 |
| 496 | 1G | Me | Me | N-24 | N-24 |
| 497 | 1G | Me | Me | N-25 | N-25 |
| 498 | 1G | Me | Me | N-26 | N-26 |
| 499 | 1G | Me | Me | N-27 | N-27 |
| 500 | 1G | Me | Me | N-28 | N-28 |
| 501 | 1G | Me | Me | N-29 | N-29 |
| 502 | 1G | Me | Me | N-30 | N-30 |
| 503 | 1G | Me | Me | N-31 | N-31 |
| 504 | 1G | Me | Me | N-32 | N-32 |
| 505 | 1G | Me | Me | N-33 | N-33 |
| 506 | 1G | Me | Me | N-34 | N-34 |
| 507 | 1G | Me | Me | N-35 | N-35 |
| 508 | 1G | Me | Me | N-36 | N-36 |
| 509 | 1G | Me | Me | N-37 | N-37 |
| 510 | 1G | Me | Me | N-38 | N-38 |
| 511 | 1G | Ph | Ph | N-1 | N-1 |
| 512 | 1G | Ph | Ph | N-2 | N-2 |
| 513 | 1G | Ph | Ph | N-3 | N-3 |
| 514 | 1G | Ph | Ph | N-4 | N-4 |
| 515 | 1G | Ph | Ph | N-5 | N-5 |
| 516 | 1G | Ph | Ph | N-6 | N-6 |
| 517 | 1G | Ph | Ph | N-7 | N-7 |
| 518 | 1G | Ph | Ph | N-8 | N-8 |
| 519 | 1G | Ph | Ph | N-9 | N-9 |
| 520 | 1G | Ph | Ph | N-10 | N-10 |
| 521 | 1G | Ph | Ph | N-11 | N-11 |
| 522 | 1G | Ph | Ph | N-12 | N-12 |
| 523 | 1G | Ph | Ph | N-13 | N-13 |
| 524 | 1G | Ph | Ph | N-14 | N-14 |
| 525 | 1G | Ph | Ph | N-15 | N-15 |
| 526 | 1G | Ph | Ph | N-16 | N-16 |
| 527 | 1G | Ph | Ph | N-17 | N-17 |
| 528 | 1G | Ph | Ph | N-18 | N-18 |
| 529 | 1G | Ph | Ph | N-19 | N-19 |
| 530 | 1G | Ph | Ph | N-20 | N-20 |
| 531 | 1G | Ph | Ph | N-21 | N-21 |
| 532 | 1G | Ph | Ph | N-22 | N-22 |
| 533 | 1G | Ph | Ph | N-23 | N-23 |
| 534 | 1G | Ph | Ph | N-24 | N-24 |
| 535 | 1G | Ph | Ph | N-25 | N-25 |
| 536 | 1G | Ph | Ph | N-26 | N-26 |
| 537 | 1G | Ph | Ph | N-27 | N-27 |
| 538 | 1G | Ph | Ph | N-28 | N-28 |
| 539 | 1G | Ph | Ph | N-29 | N-29 |
| 540 | 1G | Ph | Ph | N-30 | N-30 |
| 541 | 1G | Ph | Ph | N-31 | N-31 |
| 542 | 1G | Ph | Ph | N-32 | N-32 |
| 543 | 1G | Ph | Ph | N-33 | N-33 |
| 544 | 1G | Ph | Ph | N-34 | N-34 |
| 545 | 1G | Ph | Ph | N-35 | N-35 |
| 546 | 1G | Ph | Ph | N-36 | N-36 |
| 547 | 1G | Ph | Ph | N-37 | N-37 |
| 548 | 1G | Ph | Ph | N-38 | N-38 |
| 549 | 1G | Me | Me | N-1 | N-15 |
| 550 | 1G | Me | Me | N-5 | N-30 |
| 551 | 1G | Ph | Ph | N-1 | N-15 |
| 552 | 1G | Ph | Ph | N-5 | N-30 |

| Compound No. | Formula | $R_{11}$ | $R_{12}$ | $R_{31h}$ | $R_{32h}$ |
|---|---|---|---|---|---|
| 553 | 1H | Me | Me | N-1 | N-1 |
| 554 | 1H | Me | Me | N-2 | N-2 |
| 555 | 1H | Me | Me | N-3 | N-3 |
| 556 | 1H | Me | Me | N-4 | N-4 |
| 557 | 1H | Me | Me | N-5 | N-5 |
| 558 | 1H | Me | Me | N-6 | N-6 |
| 559 | 1H | Me | Me | N-7 | N-7 |
| 560 | 1H | Me | Me | N-8 | N-8 |
| 561 | 1H | Me | Me | N-9 | N-9 |
| 562 | 1H | Me | Me | N-10 | N-10 |
| 563 | 1H | Me | Me | N-11 | N-11 |
| 564 | 1H | Me | Me | N-12 | N-12 |
| 565 | 1H | Me | Me | N-13 | N-13 |
| 566 | 1H | Me | Me | N-14 | N-14 |
| 567 | 1H | Me | Me | N-15 | N-15 |
| 568 | 1H | Me | Me | N-16 | N-16 |
| 569 | 1H | Me | Me | N-17 | N-17 |
| 570 | 1H | Me | Me | N-18 | N-18 |
| 571 | 1H | Me | Me | N-19 | N-19 |
| 572 | 1H | Me | Me | N-20 | N-20 |
| 573 | 1H | Me | Me | N-21 | N-21 |
| 574 | 1H | Me | Me | N-22 | N-22 |
| 575 | 1H | Me | Me | N-23 | N-23 |
| 576 | 1H | Me | Me | N-24 | N-24 |
| 577 | 1H | Me | Me | N-25 | N-25 |
| 578 | 1H | Me | Me | N-26 | N-26 |
| 579 | 1H | Me | Me | N-27 | N-27 |
| 580 | 1H | Me | Me | N-28 | N-28 |
| 581 | 1H | Me | Me | N-29 | N-29 |
| 582 | 1H | Me | Me | N-30 | N-30 |
| 583 | 1H | Me | Me | N-31 | N-31 |
| 584 | 1H | Me | Me | N-32 | N-32 |
| 585 | 1H | Me | Me | N-33 | N-33 |
| 586 | 1H | Me | Me | N-34 | N-34 |
| 587 | 1H | Me | Me | N-35 | N-35 |
| 588 | 1H | Me | Me | N-36 | N-36 |
| 589 | 1H | Me | Me | N-37 | N-37 |
| 590 | 1H | Me | Me | N-38 | N-38 |
| 591 | 1H | Ph | Ph | N-1 | N-1 |
| 592 | 1H | Ph | Ph | N-2 | N-2 |
| 593 | 1H | Ph | Ph | N-3 | N-3 |
| 594 | 1H | Ph | Ph | N-4 | N-4 |
| 595 | 1H | Ph | Ph | N-5 | N-5 |
| 596 | 1H | Ph | Ph | N-6 | N-6 |
| 597 | 1H | Ph | Ph | N-7 | N-7 |
| 598 | 1H | Ph | Ph | N-8 | N-8 |
| 599 | 1H | Ph | Ph | N-9 | N-9 |
| 600 | 1H | Ph | Ph | N-10 | N-10 |
| 601 | 1H | Ph | Ph | N-11 | N-11 |
| 602 | 1H | Ph | Ph | N-12 | N-12 |
| 603 | 1H | Ph | Ph | N-13 | N-13 |
| 604 | 1H | Ph | Ph | N-14 | N-14 |
| 605 | 1H | Ph | Ph | N-15 | N-15 |
| 606 | 1H | Ph | Ph | N-16 | N-16 |
| 607 | 1H | Ph | Ph | N-17 | N-17 |
| 608 | 1H | Ph | Ph | N-18 | N-18 |
| 609 | 1H | Ph | Ph | N-19 | N-19 |
| 610 | 1H | Ph | Ph | N-20 | N-20 |
| 611 | 1H | Ph | Ph | N-21 | N-21 |
| 612 | 1H | Ph | Ph | N-22 | N-22 |
| 613 | 1H | Ph | Ph | N-23 | N-23 |
| 614 | 1H | Ph | Ph | N-24 | N-24 |
| 615 | 1H | Ph | Ph | N-25 | N-25 |
| 616 | 1H | Ph | Ph | N-26 | N-26 |
| 617 | 1H | Ph | Ph | N-27 | N-27 |
| 618 | 1H | Ph | Ph | N-28 | N-28 |
| 619 | 1H | Ph | Ph | N-29 | N-29 |
| 620 | 1H | Ph | Ph | N-30 | N-30 |
| 621 | 1H | Ph | Ph | N-31 | N-31 |
| 622 | 1H | Ph | Ph | N-32 | N-32 |
| 623 | 1H | Ph | Ph | N-33 | N-33 |
| 624 | 1H | Ph | Ph | N-34 | N-34 |
| 625 | 1H | Ph | Ph | N-35 | N-35 |
| 626 | 1H | Ph | Ph | N-36 | N-36 |
| 627 | 1H | Ph | Ph | N-37 | N-37 |
| 628 | 1H | Ph | Ph | N-38 | N-38 |
| 629 | 1H | Me | Me | N-38 | N-11 |
| 630 | 1H | Me | Me | N-9 | N-10 |
| 631 | 1H | Ph | Ph | N-38 | N-11 |
| 632 | 1H | Ph | Ph | N-9 | N-10 |

TABLE 1-continued

| Compound No. | Formula | $R_{11}$ | $R_{12}$ | $R_{31i}$ | $R_{32i}$ |
|---|---|---|---|---|---|
| 633 | 1I | Me | Me | N-1 | N-1 |
| 634 | 1I | Me | Me | N-2 | N-2 |
| 635 | 1I | Me | Me | N-3 | N-3 |
| 636 | 1I | Me | Me | N-4 | N-4 |
| 637 | 1I | Me | Me | N-5 | N-5 |
| 638 | 1I | Me | Me | N-6 | N-6 |
| 639 | 1I | Me | Me | N-7 | N-7 |
| 640 | 1I | Me | Me | N-8 | N-8 |
| 641 | 1I | Me | Me | N-9 | N-9 |
| 642 | 1I | Me | Me | N-10 | N-10 |
| 643 | 1I | Me | Me | N-11 | N-11 |
| 644 | 1I | Me | Me | N-12 | N-12 |
| 645 | 1I | Me | Me | N-13 | N-13 |
| 646 | 1I | Me | Me | N-14 | N-14 |
| 647 | 1I | Me | Me | N-15 | N-15 |
| 648 | 1I | Me | Me | N-16 | N-16 |
| 649 | 1I | Me | Me | N-17 | N-17 |
| 650 | 1I | Me | Me | N-18 | N-18 |
| 651 | 1I | Me | Me | N-19 | N-19 |
| 652 | 1I | Me | Me | N-20 | N-20 |
| 653 | 1I | Me | Me | N-21 | N-21 |
| 654 | 1I | Me | Me | N-22 | N-22 |
| 655 | 1I | Me | Me | N-23 | N-23 |
| 656 | 1I | Me | Me | N-24 | N-24 |
| 657 | 1I | Me | Me | N-25 | N-25 |
| 658 | 1I | Me | Me | N-26 | N-26 |
| 659 | 1I | Me | Me | N-27 | N-27 |
| 660 | 1I | Me | Me | N-28 | N-28 |
| 661 | 1I | Me | Me | N-29 | N-29 |
| 662 | 1I | Me | Me | N-30 | N-30 |
| 663 | 1I | Me | Me | N-31 | N-31 |
| 664 | 1I | Me | Me | N-32 | N-32 |
| 665 | 1I | Me | Me | N-33 | N-33 |
| 666 | 1I | Me | Me | N-34 | N-34 |
| 667 | 1I | Me | Me | N-35 | N-35 |
| 668 | 1I | Me | Me | N-36 | N-36 |
| 669 | 1I | Me | Me | N-37 | N-37 |
| 670 | 1I | Me | Me | N-38 | N-38 |
| 671 | 1I | Ph | Ph | N-1 | N-1 |
| 672 | 1I | Ph | Ph | N-2 | N-2 |
| 673 | 1I | Ph | Ph | N-3 | N-3 |
| 674 | 1I | Ph | Ph | N-4 | N-4 |
| 675 | 1I | Ph | Ph | N-5 | N-5 |
| 676 | 1I | Ph | Ph | N-6 | N-6 |
| 677 | 1I | Ph | Ph | N-7 | N-7 |
| 678 | 1I | Ph | Ph | N-8 | N-8 |
| 679 | 1I | Ph | Ph | N-9 | N-9 |
| 680 | 1I | Ph | Ph | N-10 | N-10 |
| 681 | 1I | Ph | Ph | N-11 | N-11 |
| 682 | 1I | Ph | Ph | N-12 | N-12 |
| 683 | 1I | Ph | Ph | N-13 | N-13 |
| 684 | 1I | Ph | Ph | N-14 | N-14 |
| 685 | 1I | Ph | Ph | N-15 | N-15 |
| 686 | 1I | Ph | Ph | N-16 | N-16 |
| 687 | 1I | Ph | Ph | N-17 | N-17 |
| 688 | 1I | Ph | Ph | N-18 | N-18 |
| 689 | 1I | Ph | Ph | N-19 | N-19 |
| 690 | 1I | Ph | Ph | N-20 | N-20 |
| 691 | 1I | Ph | Ph | N-21 | N-21 |
| 692 | 1I | Ph | Ph | N-22 | N-22 |
| 693 | 1I | Ph | Ph | N-23 | N-23 |
| 694 | 1I | Ph | Ph | N-24 | N-24 |
| 695 | 1I | Ph | Ph | N-25 | N-25 |
| 696 | 1I | Ph | Ph | N-26 | N-26 |
| 697 | 1I | Ph | Ph | N-27 | N-27 |
| 698 | 1I | Ph | Ph | N-28 | N-28 |
| 699 | 1I | Ph | Ph | N-29 | N-29 |
| 700 | 1I | Ph | Ph | N-30 | N-30 |
| 701 | 1I | Ph | Ph | N-31 | N-31 |
| 702 | 1I | Ph | Ph | N-32 | N-32 |
| 703 | 1I | Ph | Ph | N-33 | N-33 |
| 704 | 1I | Ph | Ph | N-34 | N-34 |
| 705 | 1I | Ph | Ph | N-35 | N-35 |
| 706 | 1I | Ph | Ph | N-36 | N-36 |
| 707 | 1I | Ph | Ph | N-37 | N-37 |
| 708 | 1I | Ph | Ph | N-38 | N-38 |

TABLE 1-continued

| Compound No. | Formula | $R_{11}$ | $R_{12}$ | $R_{31j}$ | $R_{32j}$ | $R_{33j}$ |
|---|---|---|---|---|---|---|
| 709 | 1J | Me | Me | N-1 | N-1 | N-1 |
| 710 | 1J | Me | Me | N-2 | N-2 | N-2 |
| 711 | 1J | Me | Me | N-3 | N-3 | N-3 |
| 712 | 1J | Me | Me | N-4 | N-4 | N-4 |
| 713 | 1J | Me | Me | N-5 | N-5 | N-5 |
| 714 | 1J | Me | Me | N-6 | N-6 | N-6 |
| 715 | 1J | Me | Me | N-7 | N-7 | N-7 |
| 716 | 1J | Me | Me | N-8 | N-8 | N-8 |
| 717 | 1J | Me | Me | N-9 | N-9 | N-9 |
| 718 | 1J | Me | Me | N-10 | N-10 | N-10 |
| 719 | 1J | Me | Me | N-11 | N-11 | N-11 |
| 720 | 1J | Me | Me | N-12 | N-12 | N-12 |
| 721 | 1J | Me | Me | N-13 | N-13 | N-13 |
| 722 | 1J | Me | Me | N-14 | N-14 | N-14 |
| 723 | 1J | Me | Me | N-15 | N-15 | N-15 |
| 724 | 1J | Me | Me | N-16 | N-16 | N-16 |
| 725 | 1J | Me | Me | N-17 | N-17 | N-17 |
| 726 | 1J | Me | Me | N-18 | N-18 | N-18 |
| 727 | 1J | Me | Me | N-19 | N-19 | N-19 |
| 728 | 1J | Me | Me | N-20 | N-20 | N-20 |
| 729 | 1J | Me | Me | N-21 | N-21 | N-21 |
| 730 | 1J | Me | Me | N-22 | N-22 | N-22 |
| 731 | 1J | Me | Me | N-23 | N-23 | N-23 |
| 732 | 1J | Me | Me | N-24 | N-24 | N-24 |
| 733 | 1J | Me | Me | N-25 | N-25 | N-25 |
| 734 | 1J | Me | Me | N-26 | N-26 | N-26 |
| 735 | 1J | Me | Me | N-27 | N-27 | N-27 |
| 736 | 1J | Me | Me | N-28 | N-28 | N-28 |
| 737 | 1J | Me | Me | N-29 | N-29 | N-29 |
| 738 | 1J | Me | Me | N-30 | N-30 | N-30 |
| 739 | 1J | Me | Me | N-31 | N-31 | N-31 |
| 740 | 1J | Me | Me | N-32 | N-32 | N-32 |
| 741 | 1J | Me | Me | N-33 | N-33 | N-33 |
| 742 | 1J | Me | Me | N-34 | N-34 | N-34 |
| 743 | 1J | Me | Me | N-35 | N-35 | N-35 |
| 744 | 1J | Me | Me | N-36 | N-36 | N-36 |
| 745 | 1J | Me | Me | N-37 | N-37 | N-37 |
| 746 | 1J | Me | Me | N-38 | N-38 | N-38 |
| 747 | 1J | Ph | Ph | N-1 | N-1 | N-1 |
| 748 | 1J | Ph | Ph | N-2 | N-2 | N-2 |
| 749 | 1J | Ph | Ph | N-3 | N-3 | N-3 |
| 750 | 1J | Ph | Ph | N-4 | N-4 | N-4 |
| 751 | 1J | Ph | Ph | N-5 | N-5 | N-5 |
| 752 | 1J | Ph | Ph | N-6 | N-6 | N-6 |
| 753 | 1J | Ph | Ph | N-7 | N-7 | N-7 |
| 754 | 1J | Ph | Ph | N-8 | N-8 | N-8 |
| 755 | 1J | Ph | Ph | N-9 | N-9 | N-9 |
| 756 | 1J | Ph | Ph | N-10 | N-10 | N-10 |
| 757 | 1J | Ph | Ph | N-11 | N-11 | N-11 |
| 758 | 1J | Ph | Ph | N-12 | N-12 | N-12 |
| 759 | 1J | Ph | Ph | N-13 | N-13 | N-13 |
| 760 | 1J | Ph | Ph | N-14 | N-14 | N-14 |
| 761 | 1J | Ph | Ph | N-15 | N-15 | N-15 |
| 762 | 1J | Ph | Ph | N-16 | N-16 | N-16 |
| 763 | 1J | Ph | Ph | N-17 | N-17 | N-17 |
| 764 | 1J | Ph | Ph | N-18 | N-18 | N-18 |
| 765 | 1J | Ph | Ph | N-19 | N-19 | N-19 |
| 766 | 1J | Ph | Ph | N-20 | N-20 | N-20 |
| 767 | 1J | Ph | Ph | N-21 | N-21 | N-21 |
| 768 | 1J | Ph | Ph | N-22 | N-22 | N-22 |
| 769 | 1J | Ph | Ph | N-23 | N-23 | N-23 |
| 770 | 1J | Ph | Ph | N-24 | N-24 | N-24 |
| 771 | 1J | Ph | Ph | N-25 | N-25 | N-25 |
| 772 | 1J | Ph | Ph | N-26 | N-26 | N-26 |
| 773 | 1J | Ph | Ph | N-27 | N-27 | N-27 |
| 774 | 1J | Ph | Ph | N-28 | N-28 | N-28 |
| 775 | 1J | Ph | Ph | N-29 | N-29 | N-29 |
| 776 | 1J | Ph | Ph | N-30 | N-30 | N-30 |
| 777 | 1J | Ph | Ph | N-31 | N-31 | N-31 |
| 778 | 1J | Ph | Ph | N-32 | N-32 | N-32 |
| 779 | 1J | Ph | Ph | N-33 | N-33 | N-33 |
| 780 | 1J | Ph | Ph | N-34 | N-34 | N-34 |
| 781 | 1J | Ph | Ph | N-35 | N-35 | N-35 |
| 782 | 1J | Ph | Ph | N-36 | N-36 | N-36 |
| 783 | 1J | Ph | Ph | N-37 | N-37 | N-37 |
| 784 | 1J | Ph | Ph | N-38 | N-38 | N-38 |
| 785 | 1J | Me | Me | N-1 | N-15 | N-29 |
| 786 | 1J | Me | Me | N-5 | N-30 | N-15 |

TABLE 1-continued

| | | | | | |
|---|---|---|---|---|---|
| 787 | 1J | Ph | Ph | N-1 | N-15 | N-29 |
| 788 | 1J | Ph | Ph | N-5 | N-30 | N-15 |

| Compound No. | Formula | $R_{11}$ | $R_{12}$ | $R_{31k}$ | $R_{32k}$ | $R_{33k}$ |
|---|---|---|---|---|---|---|
| 789 | 1K | Me | Me | N-1 | N-1 | N-1 |
| 790 | 1K | Me | Me | N-2 | N-2 | N-2 |
| 791 | 1K | Me | Me | N-3 | N-3 | N-3 |
| 792 | 1K | Me | Me | N-4 | N-4 | N-4 |
| 793 | 1K | Me | Me | N-5 | N-5 | N-5 |
| 794 | 1K | Me | Me | N-6 | N-6 | N-6 |
| 795 | 1K | Me | Me | N-7 | N-7 | N-7 |
| 796 | 1K | Me | Me | N-8 | N-8 | N-8 |
| 797 | 1K | Me | Me | N-9 | N-9 | N-9 |
| 798 | 1K | Me | Me | N-10 | N-10 | N-10 |
| 799 | 1K | Me | Me | N-11 | N-11 | N-11 |
| 800 | 1K | Me | Me | N-12 | N-12 | N-12 |
| 801 | 1K | Me | Me | N-13 | N-13 | N-13 |
| 802 | 1K | Me | Me | N-14 | N-14 | N-14 |
| 803 | 1K | Me | Me | N-15 | N-15 | N-15 |
| 804 | 1K | Me | Me | N-16 | N-16 | N-16 |
| 805 | 1K | Me | Me | N-17 | N-17 | N-17 |
| 806 | 1K | Me | Me | N-18 | N-18 | N-18 |
| 807 | 1K | Me | Me | N-19 | N-19 | N-19 |
| 808 | 1K | Me | Me | N-20 | N-20 | N-20 |
| 809 | 1K | Me | Me | N-21 | N-21 | N-21 |
| 810 | 1K | Me | Me | N-22 | N-22 | N-22 |
| 811 | 1K | Me | Me | N-23 | N-23 | N-23 |
| 812 | 1K | Me | Me | N-24 | N-24 | N-24 |
| 813 | 1K | Me | Me | N-25 | N-25 | N-25 |
| 814 | 1K | Me | Me | N-26 | N-26 | N-26 |
| 815 | 1K | Me | Me | N-27 | N-27 | N-27 |
| 816 | 1K | Me | Me | N-28 | N-28 | N-28 |
| 817 | 1K | Me | Me | N-29 | N-29 | N-29 |
| 818 | 1K | Me | Me | N-30 | N-30 | N-30 |
| 819 | 1K | Me | Me | N-31 | N-31 | N-31 |
| 820 | 1K | Me | Me | N-32 | N-32 | N-32 |
| 821 | 1K | Me | Me | N-33 | N-33 | N-33 |
| 822 | 1K | Me | Me | N-34 | N-34 | N-34 |
| 823 | 1K | Me | Me | N-35 | N-35 | N-35 |
| 824 | 1K | Me | Me | N-36 | N-36 | N-36 |
| 825 | 1K | Me | Me | N-37 | N-37 | N-37 |
| 826 | 1K | Me | Me | N-38 | N-38 | N-38 |
| 827 | 1K | Ph | Ph | N-1 | N-1 | N-1 |
| 828 | 1K | Ph | Ph | N-2 | N-2 | N-2 |
| 829 | 1K | Ph | Ph | N-3 | N-3 | N-3 |
| 830 | 1K | Ph | Ph | N-4 | N-4 | N-4 |
| 831 | 1K | Ph | Ph | N-5 | N-5 | N-5 |
| 832 | 1K | Ph | Ph | N-6 | N-6 | N-6 |
| 833 | 1K | Ph | Ph | N-7 | N-7 | N-7 |
| 834 | 1K | Ph | Ph | N-8 | N-8 | N-8 |
| 835 | 1K | Ph | Ph | N-9 | N-9 | N-9 |
| 836 | 1K | Ph | Ph | N-10 | N-10 | N-10 |
| 837 | 1K | Ph | Ph | N-11 | N-11 | N-11 |
| 838 | 1K | Ph | Ph | N-12 | N-12 | N-12 |
| 839 | 1K | Ph | Ph | N-13 | N-13 | N-13 |
| 840 | 1K | Ph | Ph | N-14 | N-14 | N-14 |
| 841 | 1K | Ph | Ph | N-15 | N-15 | N-15 |
| 842 | 1K | Ph | Ph | N-16 | N-16 | N-16 |
| 843 | 1K | Ph | Ph | N-17 | N-17 | N-17 |
| 844 | 1K | Ph | Ph | N-18 | N-18 | N-18 |
| 845 | 1K | Ph | Ph | N-19 | N-19 | N-19 |
| 846 | 1K | Ph | Ph | N-20 | N-20 | N-20 |
| 847 | 1K | Ph | Ph | N-21 | N-21 | N-21 |
| 848 | 1K | Ph | Ph | N-22 | N-22 | N-22 |
| 849 | 1K | Ph | Ph | N-23 | N-23 | N-23 |
| 850 | 1K | Ph | Ph | N-24 | N-24 | N-24 |
| 851 | 1K | Ph | Ph | N-25 | N-25 | N-25 |
| 852 | 1K | Ph | Ph | N-26 | N-26 | N-26 |
| 853 | 1K | Ph | Ph | N-27 | N-27 | N-27 |
| 854 | 1K | Ph | Ph | N-28 | N-28 | N-28 |
| 855 | 1K | Ph | Ph | N-29 | N-29 | N-29 |
| 856 | 1K | Ph | Ph | N-30 | N-30 | N-30 |
| 857 | 1K | Ph | Ph | N-31 | N-31 | N-31 |
| 858 | 1K | Ph | Ph | N-32 | N-32 | N-32 |
| 859 | 1K | Ph | Ph | N-33 | N-33 | N-33 |
| 860 | 1K | Ph | Ph | N-34 | N-34 | N-34 |
| 861 | 1K | Ph | Ph | N-35 | N-35 | N-35 |
| 862 | 1K | Ph | Ph | N-36 | N-36 | N-36 |
| 863 | 1K | Ph | Ph | N-37 | N-37 | N-37 |
| 864 | 1K | Ph | Ph | N-38 | N-38 | N-38 |
| 865 | 1K | Me | Me | N-38 | N-11 | N-31 |
| 866 | 1K | Me | Me | N-9 | N-10 | N-14 |
| 867 | 1K | Ph | Ph | N-38 | N-11 | N-31 |
| 868 | 1K | Ph | Ph | N-9 | N-10 | N-14 |

| Compound No. | Formula | $R_{11}$ | $R_{12}$ | $R_{31l}$ | $R_{32l}$ | $R_{33l}$ |
|---|---|---|---|---|---|---|
| 869 | 1L | Me | Me | N-1 | N-1 | N-1 |
| 870 | 1L | Me | Me | N-2 | N-2 | N-2 |
| 871 | 1L | Me | Me | N-3 | N-3 | N-3 |
| 872 | 1L | Me | Me | N-4 | N-4 | N-4 |
| 873 | 1L | Me | Me | N-5 | N-5 | N-5 |
| 874 | 1L | Me | Me | N-6 | N-6 | N-6 |
| 875 | 1L | Me | Me | N-7 | N-7 | N-7 |
| 876 | 1L | Me | Me | N-8 | N-8 | N-8 |
| 877 | 1L | Me | Me | N-9 | N-9 | N-9 |
| 878 | 1L | Me | Me | N-10 | N-10 | N-10 |
| 879 | 1L | Me | Me | N-11 | N-11 | N-11 |
| 880 | 1L | Me | Me | N-12 | N-12 | N-12 |
| 881 | 1L | Me | Me | N-13 | N-13 | N-13 |
| 882 | 1L | Me | Me | N-14 | N-14 | N-14 |
| 883 | 1L | Me | Me | N-15 | N-15 | N-15 |
| 884 | 1L | Me | Me | N-16 | N-16 | N-16 |
| 885 | 1L | Me | Me | N-17 | N-17 | N-17 |
| 886 | 1L | Me | Me | N-18 | N-18 | N-18 |
| 887 | 1L | Me | Me | N-19 | N-19 | N-19 |
| 888 | 1L | Me | Me | N-20 | N-20 | N-20 |
| 889 | 1L | Me | Me | N-21 | N-21 | N-21 |
| 890 | 1L | Me | Me | N-22 | N-22 | N-22 |
| 891 | 1L | Me | Me | N-23 | N-23 | N-23 |
| 892 | 1L | Me | Me | N-24 | N-24 | N-24 |
| 893 | 1L | Me | Me | N-25 | N-25 | N-25 |
| 894 | 1L | Me | Me | N-26 | N-26 | N-26 |
| 895 | 1L | Me | Me | N-27 | N-27 | N-27 |
| 896 | 1L | Me | Me | N-28 | N-28 | N-28 |
| 897 | 1L | Me | Me | N-29 | N-29 | N-29 |
| 898 | 1L | Me | Me | N-30 | N-30 | N-30 |
| 899 | 1L | Me | Me | N-31 | N-31 | N-31 |
| 900 | 1L | Me | Me | N-32 | N-32 | N-32 |
| 901 | 1L | Me | Me | N-33 | N-33 | N-33 |
| 902 | 1L | Me | Me | N-34 | N-34 | N-34 |
| 903 | 1L | Me | Me | N-35 | N-35 | N-35 |
| 904 | 1L | Me | Me | N-36 | N-36 | N-36 |
| 905 | 1L | Me | Me | N-37 | N-37 | N-37 |
| 906 | 1L | Me | Me | N-38 | N-38 | N-38 |
| 907 | 1L | Ph | Ph | N-1 | N-1 | N-1 |
| 908 | 1L | Ph | Ph | N-2 | N-2 | N-2 |
| 909 | 1L | Ph | Ph | N-3 | N-3 | N-3 |
| 910 | 1L | Ph | Ph | N-4 | N-4 | N-4 |
| 911 | 1L | Ph | Ph | N-5 | N-5 | N-5 |
| 912 | 1L | Ph | Ph | N-6 | N-6 | N-6 |
| 913 | 1L | Ph | Ph | N-7 | N-7 | N-7 |
| 914 | 1L | Ph | Ph | N-8 | N-8 | N-8 |
| 915 | 1L | Ph | Ph | N-9 | N-9 | N-9 |
| 916 | 1L | Ph | Ph | N-10 | N-10 | N-10 |
| 917 | 1L | Ph | Ph | N-11 | N-11 | N-11 |
| 918 | 1L | Ph | Ph | N-12 | N-12 | N-12 |
| 919 | 1L | Ph | Ph | N-13 | N-13 | N-13 |
| 920 | 1L | Ph | Ph | N-14 | N-14 | N-14 |
| 921 | 1L | Ph | Ph | N-15 | N-15 | N-15 |
| 922 | 1L | Ph | Ph | N-16 | N-16 | N-16 |
| 923 | 1L | Ph | Ph | N-17 | N-17 | N-17 |
| 924 | 1L | Ph | Ph | N-18 | N-18 | N-18 |
| 925 | 1L | Ph | Ph | N-19 | N-19 | N-19 |
| 926 | 1L | Ph | Ph | N-20 | N-20 | N-20 |
| 927 | 1L | Ph | Ph | N-21 | N-21 | N-21 |
| 928 | 1L | Ph | Ph | N-22 | N-22 | N-22 |
| 929 | 1L | Ph | Ph | N-23 | N-23 | N-23 |
| 930 | 1L | Ph | Ph | N-24 | N-24 | N-24 |
| 931 | 1L | Ph | Ph | N-25 | N-25 | N-25 |
| 932 | 1L | Ph | Ph | N-26 | N-26 | N-26 |
| 933 | 1L | Ph | Ph | N-27 | N-27 | N-27 |
| 934 | 1L | Ph | Ph | N-28 | N-28 | N-28 |
| 935 | 1L | Ph | Ph | N-29 | N-29 | N-29 |
| 936 | 1L | Ph | Ph | N-30 | N-30 | N-30 |
| 937 | 1L | Ph | Ph | N-31 | N-31 | N-31 |
| 938 | 1L | Ph | Ph | N-32 | N-32 | N-32 |
| 939 | 1L | Ph | Ph | N-33 | N-33 | N-33 |
| 940 | 1L | Ph | Ph | N-34 | N-34 | N-34 |

TABLE 1-continued

| Compound No. | Formula | $R_{11}$ | $R_{12}$ | $R_{31m}$ | $R_{32m}$ | $R_{33m}$ |
|---|---|---|---|---|---|---|
| 941 | 1L | Ph | Ph | N-35 | N-35 | N-35 |
| 942 | 1L | Ph | Ph | N-36 | N-36 | N-36 |
| 943 | 1L | Ph | Ph | N-37 | N-37 | N-37 |
| 944 | 1L | Ph | Ph | N-38 | N-38 | N-38 |
| 945 | 1M | Me | Me | N-1 | N-1 | N-1 |
| 946 | 1M | Me | Me | N-2 | N-2 | N-2 |
| 947 | 1M | Me | Me | N-3 | N-3 | N-3 |
| 948 | 1M | Me | Me | N-4 | N-4 | N-4 |
| 949 | 1M | Me | Me | N-5 | N-5 | N-5 |
| 950 | 1M | Me | Me | N-6 | N-6 | N-6 |
| 951 | 1M | Me | Me | N-7 | N-7 | N-7 |
| 952 | 1M | Me | Me | N-8 | N-8 | N-8 |
| 953 | 1M | Me | Me | N-9 | N-9 | N-9 |
| 954 | 1M | Me | Me | N-10 | N-10 | N-10 |
| 955 | 1M | Me | Me | N-11 | N-11 | N-11 |
| 956 | 1M | Me | Me | N-12 | N-12 | N-12 |
| 957 | 1M | Me | Me | N-13 | N-13 | N-13 |
| 958 | 1M | Me | Me | N-14 | N-14 | N-14 |
| 959 | 1M | Me | Me | N-15 | N-15 | N-15 |
| 960 | 1M | Me | Me | N-16 | N-16 | N-16 |
| 961 | 1M | Me | Me | N-17 | N-17 | N-17 |
| 962 | 1M | Me | Me | N-18 | N-18 | N-18 |
| 963 | 1M | Me | Me | N-19 | N-19 | N-19 |
| 964 | 1M | Me | Me | N-20 | N-20 | N-20 |
| 965 | 1M | Me | Me | N-21 | N-21 | N-21 |
| 966 | 1M | Me | Me | N-22 | N-22 | N-22 |
| 967 | 1M | Me | Me | N-23 | N-23 | N-23 |
| 968 | 1M | Me | Me | N-24 | N-24 | N-24 |
| 969 | 1M | Me | Me | N-25 | N-25 | N-25 |
| 970 | 1M | Me | Me | N-26 | N-26 | N-26 |
| 971 | 1M | Me | Me | N-27 | N-27 | N-27 |
| 972 | 1M | Me | Me | N-28 | N-28 | N-28 |
| 973 | 1M | Me | Me | N-29 | N-29 | N-29 |
| 974 | 1M | Me | Me | N-30 | N-30 | N-30 |
| 975 | 1M | Me | Me | N-31 | N-31 | N-31 |
| 976 | 1M | Me | Me | N-32 | N-32 | N-32 |
| 977 | 1M | Me | Me | N-33 | N-33 | N-33 |
| 978 | 1M | Me | Me | N-34 | N-34 | N-34 |
| 979 | 1M | Me | Me | N-35 | N-35 | N-35 |
| 980 | 1M | Me | Me | N-36 | N-36 | N-36 |
| 981 | 1M | Me | Me | N-37 | N-37 | N-37 |
| 982 | 1M | Me | Me | N-38 | N-38 | N-38 |
| 983 | 1M | Ph | Ph | N-1 | N-1 | N-1 |
| 984 | 1M | Ph | Ph | N-2 | N-2 | N-2 |
| 985 | 1M | Ph | Ph | N-3 | N-3 | N-3 |
| 986 | 1M | Ph | Ph | N-4 | N-4 | N-4 |
| 987 | 1M | Ph | Ph | N-5 | N-5 | N-5 |
| 988 | 1M | Ph | Ph | N-6 | N-6 | N-6 |
| 989 | 1M | Ph | Ph | N-7 | N-7 | N-7 |
| 990 | 1M | Ph | Ph | N-8 | N-8 | N-8 |
| 991 | 1M | Ph | Ph | N-9 | N-9 | N-9 |
| 992 | 1M | Ph | Ph | N-10 | N-10 | N-10 |
| 993 | 1M | Ph | Ph | N-11 | N-11 | N-11 |
| 994 | 1M | Ph | Ph | N-12 | N-12 | N-12 |
| 995 | 1M | Ph | Ph | N-13 | N-13 | N-13 |
| 996 | 1M | Ph | Ph | N-14 | N-14 | N-14 |
| 997 | 1M | Ph | Ph | N-15 | N-15 | N-15 |
| 998 | 1M | Ph | Ph | N-16 | N-16 | N-16 |
| 999 | 1M | Ph | Ph | N-17 | N-17 | N-17 |
| 1000 | 1M | Ph | Ph | N-18 | N-18 | N-18 |
| 1001 | 1M | Ph | Ph | N-19 | N-19 | N-19 |
| 1002 | 1M | Ph | Ph | N-20 | N-20 | N-20 |
| 1003 | 1M | Ph | Ph | N-21 | N-21 | N-21 |
| 1004 | 1M | Ph | Ph | N-22 | N-22 | N-22 |
| 1005 | 1M | Ph | Ph | N-23 | N-23 | N-23 |
| 1006 | 1M | Ph | Ph | N-24 | N-24 | N-24 |
| 1007 | 1M | Ph | Ph | N-25 | N-25 | N-25 |
| 1008 | 1M | Ph | Ph | N-26 | N-26 | N-26 |
| 1009 | 1M | Ph | Ph | N-27 | N-27 | N-27 |
| 1010 | 1M | Ph | Ph | N-28 | N-28 | N-28 |
| 1011 | 1M | Ph | Ph | N-29 | N-29 | N-29 |
| 1012 | 1M | Ph | Ph | N-30 | N-30 | N-30 |
| 1013 | 1M | Ph | Ph | N-31 | N-31 | N-31 |
| 1014 | 1M | Ph | Ph | N-32 | N-32 | N-32 |
| 1015 | 1M | Ph | Ph | N-33 | N-33 | N-33 |
| 1016 | 1M | Ph | Ph | N-34 | N-34 | N-34 |
| 1017 | 1M | Ph | Ph | N-35 | N-35 | N-35 |
| 1018 | 1M | Ph | Ph | N-36 | N-36 | N-36 |
| 1019 | 1M | Ph | Ph | N-37 | N-37 | N-37 |
| 1020 | 1M | Ph | Ph | N-38 | N-38 | N-38 |
| 1021 | 1M | Me | Me | N-1 | N-15 | N-29 |
| 1022 | 1M | Me | Me | N-5 | N-30 | N-15 |
| 1023 | 1M | Ph | Ph | N-1 | N-15 | N-29 |
| 1024 | 1M | Ph | Ph | N-5 | N-30 | N-15 |

| Compound No. | Formula | $R_{11}$ | $R_{12}$ | $R_{31n}$ | $R_{32n}$ | $R_{33n}$ |
|---|---|---|---|---|---|---|
| 1025 | 1N | Me | Me | N-1 | N-1 | N-1 |
| 1026 | 1N | Me | Me | N-2 | N-2 | N-2 |
| 1027 | 1N | Me | Me | N-3 | N-3 | N-3 |
| 1028 | 1N | Me | Me | N-4 | N-4 | N-4 |
| 1029 | 1N | Me | Me | N-5 | N-5 | N-5 |
| 1030 | 1N | Me | Me | N-6 | N-6 | N-6 |
| 1031 | 1N | Me | Me | N-7 | N-7 | N-7 |
| 1032 | 1N | Me | Me | N-8 | N-8 | N-8 |
| 1033 | 1N | Me | Me | N-9 | N-9 | N-9 |
| 1034 | 1N | Me | Me | N-10 | N-10 | N-10 |
| 1035 | 1N | Me | Me | N-11 | N-11 | N-11 |
| 1036 | 1N | Me | Me | N-12 | N-12 | N-12 |
| 1037 | 1N | Me | Me | N-13 | N-13 | N-13 |
| 1038 | 1N | Me | Me | N-14 | N-14 | N-14 |
| 1039 | 1N | Me | Me | N-15 | N-15 | N-15 |
| 1040 | 1N | Me | Me | N-16 | N-16 | N-16 |
| 1041 | 1N | Me | Me | N-17 | N-17 | N-17 |
| 1042 | 1N | Me | Me | N-18 | N-18 | N-18 |
| 1043 | 1N | Me | Me | N-19 | N-19 | N-19 |
| 1044 | 1N | Me | Me | N-20 | N-20 | N-20 |
| 1045 | 1N | Me | Me | N-21 | N-21 | N-21 |
| 1046 | 1N | Me | Me | N-22 | N-22 | N-22 |
| 1047 | 1N | Me | Me | N-23 | N-23 | N-23 |
| 1048 | 1N | Me | Me | N-24 | N-24 | N-24 |
| 1049 | 1N | Me | Me | N-25 | N-25 | N-25 |
| 1050 | 1N | Me | Me | N-26 | N-26 | N-26 |
| 1051 | 1N | Me | Me | N-27 | N-27 | N-27 |
| 1052 | 1N | Me | Me | N-28 | N-28 | N-28 |
| 1053 | 1N | Me | Me | N-29 | N-29 | N-29 |
| 1054 | 1N | Me | Me | N-30 | N-30 | N-30 |
| 1055 | 1N | Me | Me | N-31 | N-31 | N-31 |
| 1056 | 1N | Me | Me | N-32 | N-32 | N-32 |
| 1057 | 1N | Me | Me | N-33 | N-33 | N-33 |
| 1058 | 1N | Me | Me | N-34 | N-34 | N-34 |
| 1059 | 1N | Me | Me | N-35 | N-35 | N-35 |
| 1060 | 1N | Me | Me | N-36 | N-36 | N-36 |
| 1061 | 1N | Me | Me | N-37 | N-37 | N-37 |
| 1062 | 1N | Me | Me | N-38 | N-38 | N-38 |
| 1063 | 1N | Ph | Ph | N-1 | N-1 | N-1 |
| 1064 | 1N | Ph | Ph | N-2 | N-2 | N-2 |
| 1065 | 1N | Ph | Ph | N-3 | N-3 | N-3 |
| 1066 | 1N | Ph | Ph | N-4 | N-4 | N-4 |
| 1067 | 1N | Ph | Ph | N-5 | N-5 | N-5 |
| 1068 | 1N | Ph | Ph | N-6 | N-6 | N-6 |
| 1069 | 1N | Ph | Ph | N-7 | N-7 | N-7 |
| 1070 | 1N | Ph | Ph | N-8 | N-8 | N-8 |
| 1071 | 1N | Ph | Ph | N-9 | N-9 | N-9 |
| 1072 | 1N | Ph | Ph | N-10 | N-10 | N-10 |
| 1073 | 1N | Ph | Ph | N-11 | N-11 | N-11 |
| 1074 | 1N | Ph | Ph | N-12 | N-12 | N-12 |
| 1075 | 1N | Ph | Ph | N-13 | N-13 | N-13 |
| 1076 | 1N | Ph | Ph | N-14 | N-14 | N-14 |
| 1077 | 1N | Ph | Ph | N-15 | N-15 | N-15 |
| 1078 | 1N | Ph | Ph | N-16 | N-16 | N-16 |
| 1079 | 1N | Ph | Ph | N-17 | N-17 | N-17 |
| 1080 | 1N | Ph | Ph | N-18 | N-18 | N-18 |
| 1081 | 1N | Ph | Ph | N-19 | N-19 | N-19 |
| 1082 | 1N | Ph | Ph | N-20 | N-20 | N-20 |
| 1083 | 1N | Ph | Ph | N-21 | N-21 | N-21 |
| 1084 | 1N | Ph | Ph | N-22 | N-22 | N-22 |
| 1085 | 1N | Ph | Ph | N-23 | N-23 | N-23 |
| 1086 | 1N | Ph | Ph | N-24 | N-24 | N-24 |
| 1087 | 1N | Ph | Ph | N-25 | N-25 | N-25 |
| 1088 | 1N | Ph | Ph | N-26 | N-26 | N-26 |
| 1089 | 1N | Ph | Ph | N-27 | N-27 | N-27 |
| 1090 | 1N | Ph | Ph | N-28 | N-28 | N-28 |
| 1091 | 1N | Ph | Ph | N-29 | N-29 | N-29 |
| 1092 | 1N | Ph | Ph | N-30 | N-30 | N-30 |
| 1093 | 1N | Ph | Ph | N-31 | N-31 | N-31 |
| 1094 | 1N | Ph | Ph | N-32 | N-32 | N-32 |

TABLE 1-continued

| Compound No. | Formula | $R_{11}$ | $R_{12}$ | $R_{31o}$ | $R_{32o}$ | $R_{33o}$ |
|---|---|---|---|---|---|---|
| 1095 | 1N | Ph | Ph | N-33 | N-33 | N-33 |
| 1096 | 1N | Ph | Ph | N-34 | N-34 | N-34 |
| 1097 | 1N | Ph | Ph | N-35 | N-35 | N-35 |
| 1098 | 1N | Ph | Ph | N-36 | N-36 | N-36 |
| 1099 | 1N | Ph | Ph | N-37 | N-37 | N-37 |
| 1100 | 1N | Ph | Ph | N-38 | N-38 | N-38 |
| 1101 | 1N | Me | Me | N-38 | N-11 | N-31 |
| 1102 | 1N | Me | Me | N-9 | N-10 | N-14 |
| 1103 | 1N | Ph | Ph | N-38 | N-11 | N-31 |
| 1104 | 1N | Ph | Ph | N-9 | N-10 | N-14 |

| Compound No. | Formula | $R_{11}$ | $R_{12}$ | $R_{31o}$ | $R_{32o}$ | $R_{33o}$ |
|---|---|---|---|---|---|---|
| 1105 | 1O | Me | Me | N-1 | N-1 | N-1 |
| 1106 | 1O | Me | Me | N-2 | N-2 | N-2 |
| 1107 | 1O | Me | Me | N-3 | N-3 | N-3 |
| 1108 | 1O | Me | Me | N-4 | N-4 | N-4 |
| 1109 | 1O | Me | Me | N-5 | N-5 | N-5 |
| 1110 | 1O | Me | Me | N-6 | N-6 | N-6 |
| 1111 | 1O | Me | Me | N-7 | N-7 | N-7 |
| 1112 | 1O | Me | Me | N-8 | N-8 | N-8 |
| 1113 | 1O | Me | Me | N-9 | N-9 | N-9 |
| 1114 | 1O | Me | Me | N-10 | N-10 | N-10 |
| 1115 | 1O | Me | Me | N-11 | N-11 | N-11 |
| 1116 | 1O | Me | Me | N-12 | N-12 | N-12 |
| 1117 | 1O | Me | Me | N-13 | N-13 | N-13 |
| 1118 | 1O | Me | Me | N-14 | N-14 | N-14 |
| 1119 | 1O | Me | Me | N-15 | N-15 | N-15 |
| 1120 | 1O | Me | Me | N-16 | N-16 | N-16 |
| 1121 | 1O | Me | Me | N-17 | N-17 | N-17 |
| 1122 | 1O | Me | Me | N-18 | N-18 | N-18 |
| 1123 | 1O | Me | Me | N-19 | N-19 | N-19 |
| 1124 | 1O | Me | Me | N-20 | N-20 | N-20 |
| 1125 | 1O | Me | Me | N-21 | N-21 | N-21 |
| 1126 | 1O | Me | Me | N-22 | N-22 | N-22 |
| 1127 | 1O | Me | Me | N-23 | N-23 | N-23 |
| 1128 | 1O | Me | Me | N-24 | N-24 | N-24 |
| 1129 | 1O | Me | Me | N-25 | N-25 | N-25 |
| 1130 | 1O | Me | Me | N-26 | N-26 | N-26 |
| 1131 | 1O | Me | Me | N-27 | N-27 | N-27 |
| 1132 | 1O | Me | Me | N-28 | N-28 | N-28 |
| 1133 | 1O | Me | Me | N-29 | N-29 | N-29 |
| 1134 | 1O | Me | Me | N-30 | N-30 | N-30 |
| 1135 | 1O | Me | Me | N-31 | N-31 | N-31 |
| 1136 | 1O | Me | Me | N-32 | N-32 | N-32 |
| 1137 | 1O | Me | Me | N-33 | N-33 | N-33 |
| 1138 | 1O | Me | Me | N-34 | N-34 | N-34 |
| 1139 | 1O | Me | Me | N-35 | N-35 | N-35 |
| 1140 | 1O | Me | Me | N-36 | N-36 | N-36 |
| 1141 | 1O | Me | Me | N-37 | N-37 | N-37 |
| 1142 | 1O | Me | Me | N-38 | N-38 | N-38 |
| 1143 | 1O | Ph | Ph | N-1 | N-1 | N-1 |
| 1144 | 1O | Ph | Ph | N-2 | N-2 | N-2 |
| 1145 | 1O | Ph | Ph | N-3 | N-3 | N-3 |
| 1146 | 1O | Ph | Ph | N-4 | N-4 | N-4 |
| 1147 | 1O | Ph | Ph | N-5 | N-5 | N-5 |
| 1148 | 1O | Ph | Ph | N-6 | N-6 | N-6 |
| 1149 | 1O | Ph | Ph | N-7 | N-7 | N-7 |
| 1150 | 1O | Ph | Ph | N-8 | N-8 | N-8 |
| 1151 | 1O | Ph | Ph | N-9 | N-9 | N-9 |
| 1152 | 1O | Ph | Ph | N-10 | N-10 | N-10 |
| 1153 | 1O | Ph | Ph | N-11 | N-11 | N-11 |
| 1154 | 1O | Ph | Ph | N-12 | N-12 | N-12 |
| 1155 | 1O | Ph | Ph | N-13 | N-13 | N-13 |
| 1156 | 1O | Ph | Ph | N-14 | N-14 | N-14 |
| 1157 | 1O | Ph | Ph | N-15 | N-15 | N-15 |
| 1158 | 1O | Ph | Ph | N-16 | N-16 | N-16 |
| 1159 | 1O | Ph | Ph | N-17 | N-17 | N-17 |
| 1160 | 1O | Ph | Ph | N-18 | N-18 | N-18 |
| 1161 | 1O | Ph | Ph | N-19 | N-19 | N-19 |
| 1162 | 1O | Ph | Ph | N-20 | N-20 | N-20 |
| 1163 | 1O | Ph | Ph | N-21 | N-21 | N-21 |
| 1164 | 1O | Ph | Ph | N-22 | N-22 | N-22 |
| 1165 | 1O | Ph | Ph | N-23 | N-23 | N-23 |
| 1166 | 1O | Ph | Ph | N-24 | N-24 | N-24 |
| 1167 | 1O | Ph | Ph | N-25 | N-25 | N-25 |
| 1168 | 1O | Ph | Ph | N-26 | N-26 | N-26 |
| 1169 | 1O | Ph | Ph | N-27 | N-27 | N-27 |
| 1170 | 1O | Ph | Ph | N-28 | N-28 | N-28 |
| 1171 | 1O | Ph | Ph | N-29 | N-29 | N-29 |
| 1172 | 1O | Ph | Ph | N-30 | N-30 | N-30 |
| 1173 | 1O | Ph | Ph | N-31 | N-31 | N-31 |
| 1174 | 1O | Ph | Ph | N-32 | N-32 | N-32 |
| 1175 | 1O | Ph | Ph | N-33 | N-33 | N-33 |
| 1176 | 1O | Ph | Ph | N-34 | N-34 | N-34 |
| 1177 | 1O | Ph | Ph | N-35 | N-35 | N-35 |
| 1178 | 1O | Ph | Ph | N-36 | N-36 | N-36 |
| 1179 | 1O | Ph | Ph | N-37 | N-37 | N-37 |
| 1180 | 1O | Ph | Ph | N-38 | N-38 | N-38 |

| Compound No. | Formula | $R_{11}$ | $R_{12}$ | $R_{31p}$ | $R_{32p}$ | $R_{33p}$ |
|---|---|---|---|---|---|---|
| 1181 | 1P | Me | Me | N-1 | N-1 | N-1 |
| 1182 | 1P | Me | Me | N-2 | N-2 | N-2 |
| 1183 | 1P | Me | Me | N-3 | N-3 | N-3 |
| 1184 | 1P | Me | Me | N-4 | N-4 | N-4 |
| 1185 | 1P | Me | Me | N-9 | N-9 | N-9 |
| 1186 | 1P | Me | Me | N-10 | N-10 | N-10 |
| 1187 | 1P | Me | Me | N-11 | N-11 | N-11 |
| 1188 | 1P | Me | Me | N-12 | N-12 | N-12 |
| 1189 | 1P | Me | Me | N-13 | N-13 | N-13 |
| 1190 | 1P | Me | Me | N-14 | N-14 | N-14 |
| 1191 | 1P | Me | Me | N-15 | N-15 | N-15 |
| 1192 | 1P | Me | Me | N-16 | N-16 | N-16 |
| 1193 | 1P | Me | Me | N-17 | N-17 | N-17 |
| 1194 | 1P | Me | Me | N-18 | N-18 | N-18 |
| 1195 | 1P | Me | Me | N-19 | N-19 | N-19 |
| 1196 | 1P | Me | Me | N-20 | N-20 | N-20 |
| 1197 | 1P | Me | Me | N-21 | N-21 | N-21 |
| 1198 | 1P | Me | Me | N-22 | N-22 | N-22 |
| 1199 | 1P | Me | Me | N-23 | N-23 | N-23 |
| 1200 | 1P | Me | Me | N-24 | N-24 | N-24 |
| 1201 | 1P | Me | Me | N-25 | N-25 | N-25 |
| 1202 | 1P | Me | Me | N-26 | N-26 | N-26 |
| 1203 | 1P | Me | Me | N-27 | N-27 | N-27 |
| 1204 | 1P | Me | Me | N-28 | N-28 | N-28 |
| 1205 | 1P | Me | Me | N-29 | N-29 | N-29 |
| 1206 | 1P | Me | Me | N-30 | N-30 | N-30 |
| 1207 | 1P | Me | Me | N-31 | N-31 | N-31 |
| 1208 | 1P | Me | Me | N-32 | N-32 | N-32 |
| 1209 | 1P | Me | Me | N-33 | N-33 | N-33 |
| 1210 | 1P | Me | Me | N-34 | N-34 | N-34 |
| 1211 | 1P | Me | Me | N-35 | N-35 | N-35 |
| 1212 | 1P | Me | Me | N-36 | N-36 | N-36 |
| 1213 | 1P | Me | Me | N-37 | N-37 | N-37 |
| 1214 | 1P | Me | Me | N-38 | N-38 | N-38 |
| 1215 | 1P | Ph | Ph | N-1 | N-1 | N-1 |
| 1216 | 1P | Ph | Ph | N-2 | N-2 | N-2 |
| 1217 | 1P | Ph | Ph | N-3 | N-3 | N-3 |
| 1218 | 1P | Ph | Ph | N-4 | N-4 | N-4 |
| 1219 | 1P | Ph | Ph | N-5 | N-5 | N-5 |
| 1220 | 1P | Ph | Ph | N-6 | N-6 | N-6 |
| 1221 | 1P | Ph | Ph | N-7 | N-7 | N-7 |
| 1222 | 1P | Ph | Ph | N-8 | N-8 | N-8 |
| 1223 | 1P | Ph | Ph | N-9 | N-9 | N-9 |
| 1224 | 1P | Ph | Ph | N-10 | N-10 | N-10 |
| 1225 | 1P | Ph | Ph | N-11 | N-11 | N-11 |
| 1226 | 1P | Ph | Ph | N-12 | N-12 | N-12 |
| 1227 | 1P | Ph | Ph | N-13 | N-13 | N-13 |
| 1228 | 1P | Ph | Ph | N-14 | N-14 | N-14 |
| 1229 | 1P | Ph | Ph | N-15 | N-15 | N-15 |
| 1230 | 1P | Ph | Ph | N-16 | N-16 | N-16 |
| 1231 | 1P | Ph | Ph | N-17 | N-17 | N-17 |
| 1232 | 1P | Ph | Ph | N-18 | N-18 | N-18 |
| 1233 | 1P | Ph | Ph | N-19 | N-19 | N-19 |
| 1234 | 1P | Ph | Ph | N-20 | N-20 | N-20 |
| 1235 | 1P | Ph | Ph | N-21 | N-21 | N-21 |
| 1236 | 1P | Ph | Ph | N-22 | N-22 | N-22 |
| 1237 | 1P | Ph | Ph | N-23 | N-23 | N-23 |
| 1238 | 1P | Ph | Ph | N-24 | N-24 | N-24 |
| 1239 | 1P | Ph | Ph | N-25 | N-25 | N-25 |
| 1240 | 1P | Ph | Ph | N-26 | N-26 | N-26 |
| 1241 | 1P | Ph | Ph | N-27 | N-27 | N-27 |
| 1242 | 1P | Ph | Ph | N-28 | N-28 | N-28 |
| 1243 | 1P | Ph | Ph | N-29 | N-29 | N-29 |
| 1244 | 1P | Ph | Ph | N-30 | N-30 | N-30 |
| 1245 | 1P | Ph | Ph | N-31 | N-31 | N-31 |
| 1246 | 1P | Ph | Ph | N-32 | N-32 | N-32 |
| 1247 | 1P | Ph | Ph | N-33 | N-33 | N-33 |
| 1248 | 1P | Ph | Ph | N-34 | N-34 | N-34 |

TABLE 1-continued

| Compound No. | Formula | $R_{11}$ | $R_{12}$ | $R_{31q}$ | $R_{32q}$ | $R_{33q}$ |
|---|---|---|---|---|---|---|
| 1249 | 1P | Ph | Ph | N-35 | N-35 | N-35 |
| 1250 | 1P | Ph | Ph | N-36 | N-36 | N-36 |
| 1251 | 1P | Ph | Ph | N-37 | N-37 | N-37 |
| 1252 | 1P | Ph | Ph | N-38 | N-38 | N-38 |
| 1253 | 1P | Me | Me | N-1 | N-15 | N-29 |
| 1254 | 1P | Me | Me | N-5 | N-30 | N-15 |
| 1255 | 1P | Ph | Ph | N-1 | N-15 | N-29 |
| 1256 | 1P | Ph | Ph | N-5 | N-30 | N-15 |
| 1257 | 1Q | Me | Me | N-5 | N-5 | N-5 |
| 1258 | 1Q | Me | Me | N-6 | N-6 | N-6 |
| 1259 | 1Q | Me | Me | N-7 | N-7 | N-7 |
| 1260 | 1Q | Me | Me | N-8 | N-8 | N-8 |
| 1261 | 1Q | Me | Me | N-1 | N-1 | N-1 |
| 1262 | 1Q | Me | Me | N-2 | N-2 | N-2 |
| 1263 | 1Q | Me | Me | N-3 | N-3 | N-3 |
| 1264 | 1Q | Me | Me | N-4 | N-4 | N-4 |
| 1265 | 1Q | Me | Me | N-5 | N-5 | N-5 |
| 1266 | 1Q | Me | Me | N-6 | N-6 | N-6 |
| 1267 | 1Q | Me | Me | N-7 | N-7 | N-7 |
| 1268 | 1Q | Me | Me | N-8 | N-8 | N-8 |
| 1269 | 1Q | Me | Me | N-9 | N-9 | N-9 |
| 1270 | 1Q | Me | Me | N-10 | N-10 | N-10 |
| 1271 | 1Q | Me | Me | N-11 | N-11 | N-11 |
| 1272 | 1Q | Me | Me | N-12 | N-12 | N-12 |
| 1273 | 1Q | Me | Me | N-13 | N-13 | N-13 |
| 1274 | 1Q | Me | Me | N-14 | N-14 | N-14 |
| 1275 | 1Q | Me | Me | N-15 | N-15 | N-15 |
| 1276 | 1Q | Me | Me | N-16 | N-16 | N-16 |
| 1277 | 1Q | Me | Me | N-17 | N-17 | N-17 |
| 1278 | 1Q | Me | Me | N-18 | N-18 | N-18 |
| 1279 | 1Q | Me | Me | N-19 | N-19 | N-19 |
| 1280 | 1Q | Me | Me | N-20 | N-20 | N-20 |
| 1281 | 1Q | Me | Me | N-21 | N-21 | N-21 |
| 1282 | 1Q | Me | Me | N-22 | N-22 | N-22 |
| 1283 | 1Q | Me | Me | N-23 | N-23 | N-23 |
| 1284 | 1Q | Me | Me | N-24 | N-24 | N-24 |
| 1285 | 1Q | Me | Me | N-25 | N-25 | N-25 |
| 1286 | 1Q | Me | Me | N-26 | N-26 | N-26 |
| 1287 | 1Q | Me | Me | N-27 | N-27 | N-27 |
| 1288 | 1Q | Me | Me | N-28 | N-28 | N-28 |
| 1289 | 1Q | Me | Me | N-29 | N-29 | N-29 |
| 1290 | 1Q | Me | Me | N-30 | N-30 | N-30 |
| 1291 | 1Q | Me | Me | N-31 | N-31 | N-31 |
| 1292 | 1Q | Me | Me | N-32 | N-32 | N-32 |
| 1293 | 1Q | Me | Me | N-33 | N-33 | N-33 |
| 1294 | 1Q | Me | Me | N-34 | N-34 | N-34 |
| 1295 | 1Q | Me | Me | N-35 | N-35 | N-35 |
| 1296 | 1Q | Me | Me | N-36 | N-36 | N-36 |
| 1297 | 1Q | Me | Me | N-37 | N-37 | N-37 |
| 1298 | 1Q | Me | Me | N-38 | N-38 | N-38 |
| 1299 | 1Q | Ph | Ph | N-1 | N-1 | N-1 |
| 1300 | 1Q | Ph | Ph | N-2 | N-2 | N-2 |
| 1301 | 1Q | Ph | Ph | N-3 | N-3 | N-3 |
| 1302 | 1Q | Ph | Ph | N-4 | N-4 | N-4 |
| 1303 | 1Q | Ph | Ph | N-5 | N-5 | N-5 |
| 1304 | 1Q | Ph | Ph | N-6 | N-6 | N-6 |
| 1305 | 1Q | Ph | Ph | N-7 | N-7 | N-7 |
| 1306 | 1Q | Ph | Ph | N-8 | N-8 | N-8 |
| 1307 | 1Q | Ph | Ph | N-9 | N-9 | N-9 |
| 1308 | 1Q | Ph | Ph | N-10 | N-10 | N-10 |
| 1309 | 1Q | Ph | Ph | N-11 | N-11 | N-11 |
| 1310 | 1Q | Ph | Ph | N-12 | N-12 | N-12 |
| 1311 | 1Q | Ph | Ph | N-13 | N-13 | N-13 |
| 1312 | 1Q | Ph | Ph | N-14 | N-14 | N-14 |
| 1313 | 1Q | Ph | Ph | N-15 | N-15 | N-15 |
| 1314 | 1Q | Ph | Ph | N-16 | N-16 | N-16 |
| 1315 | 1Q | Ph | Ph | N-17 | N-17 | N-17 |
| 1316 | 1Q | Ph | Ph | N-18 | N-18 | N-18 |
| 1317 | 1Q | Ph | Ph | N-19 | N-19 | N-19 |
| 1318 | 1Q | Ph | Ph | N-20 | N-20 | N-20 |
| 1319 | 1Q | Ph | Ph | N-21 | N-21 | N-21 |
| 1320 | 1Q | Ph | Ph | N-22 | N-22 | N-22 |
| 1321 | 1Q | Ph | Ph | N-23 | N-23 | N-23 |
| 1322 | 1Q | Ph | Ph | N-24 | N-24 | N-24 |
| 1323 | 1Q | Ph | Ph | N-25 | N-25 | N-25 |
| 1324 | 1Q | Ph | Ph | N-26 | N-26 | N-26 |
| 1325 | 1Q | Ph | Ph | N-27 | N-27 | N-27 |
| 1326 | 1Q | Ph | Ph | N-28 | N-28 | N-28 |
| 1327 | 1Q | Ph | Ph | N-29 | N-29 | N-29 |
| 1328 | 1Q | Ph | Ph | N-30 | N-30 | N-30 |
| 1329 | 1Q | Ph | Ph | N-31 | N-31 | N-31 |
| 1330 | 1Q | Ph | Ph | N-32 | N-32 | N-32 |
| 1331 | 1Q | Ph | Ph | N-33 | N-33 | N-33 |
| 1332 | 1Q | Ph | Ph | N-34 | N-34 | N-34 |
| 1333 | 1Q | Ph | Ph | N-35 | N-35 | N-35 |
| 1334 | 1Q | Ph | Ph | N-36 | N-36 | N-36 |
| 1335 | 1Q | Ph | Ph | N-37 | N-37 | N-37 |
| 1336 | 1Q | Ph | Ph | N-38 | N-38 | N-38 |
| 1337 | 1Q | Me | Me | N-38 | N-11 | N-31 |
| 1338 | 1Q | Me | Me | N-9 | N-10 | N-14 |
| 1339 | 1Q | Ph | Ph | N-38 | N-11 | N-31 |
| 1340 | 1Q | Ph | Ph | N-9 | N-10 | N-14 |

| Compound No. | Formula | $R_{11}$ | $R_{12}$ | $R_{31r}$ | $R_{32r}$ | $R_{33r}$ |
|---|---|---|---|---|---|---|
| 1341 | 1R | Me | Me | N-1 | N-1 | N-1 |
| 1342 | 1R | Me | Me | N-2 | N-2 | N-2 |
| 1343 | 1R | Me | Me | N-3 | N-3 | N-3 |
| 1344 | 1R | Me | Me | N-4 | N-4 | N-4 |
| 1345 | 1R | Me | Me | N-5 | N-5 | N-5 |
| 1346 | 1R | Me | Me | N-6 | N-6 | N-6 |
| 1347 | 1R | Me | Me | N-7 | N-7 | N-7 |
| 1348 | 1R | Me | Me | N-8 | N-8 | N-8 |
| 1349 | 1R | Me | Me | N-9 | N-9 | N-9 |
| 1350 | 1R | Me | Me | N-10 | N-10 | N-10 |
| 1351 | 1R | Me | Me | N-11 | N-11 | N-11 |
| 1352 | 1R | Me | Me | N-12 | N-12 | N-12 |
| 1353 | 1R | Me | Me | N-13 | N-13 | N-13 |
| 1354 | 1R | Me | Me | N-14 | N-14 | N-14 |
| 1355 | 1R | Me | Me | N-15 | N-15 | N-15 |
| 1356 | 1R | Me | Me | N-16 | N-16 | N-16 |
| 1357 | 1R | Me | Me | N-17 | N-17 | N-17 |
| 1358 | 1R | Me | Me | N-18 | N-18 | N-18 |
| 1359 | 1R | Me | Me | N-19 | N-19 | N-19 |
| 1360 | 1R | Me | Me | N-20 | N-20 | N-20 |
| 1361 | 1R | Me | Me | N-21 | N-21 | N-21 |
| 1362 | 1R | Me | Me | N-22 | N-22 | N-22 |
| 1363 | 1R | Me | Me | N-23 | N-23 | N-23 |
| 1364 | 1R | Me | Me | N-24 | N-24 | N-24 |
| 1365 | 1R | Me | Me | N-25 | N-25 | N-25 |
| 1366 | 1R | Me | Me | N-26 | N-26 | N-26 |
| 1367 | 1R | Me | Me | N-27 | N-27 | N-27 |
| 1368 | 1R | Me | Me | N-28 | N-28 | N-28 |
| 1369 | 1R | Me | Me | N-29 | N-29 | N-29 |
| 1370 | 1R | Me | Me | N-30 | N-30 | N-30 |
| 1371 | 1R | Me | Me | N-31 | N-31 | N-31 |
| 1372 | 1R | Me | Me | N-32 | N-32 | N-32 |
| 1373 | 1R | Me | Me | N-33 | N-33 | N-33 |
| 1374 | 1R | Me | Me | N-34 | N-34 | N-34 |
| 1375 | 1R | Me | Me | N-35 | N-35 | N-35 |
| 1376 | 1R | Me | Me | N-36 | N-36 | N-36 |
| 1377 | 1R | Me | Me | N-37 | N-37 | N-37 |
| 1378 | 1R | Me | Me | N-38 | N-38 | N-38 |
| 1379 | 1R | Ph | Ph | N-1 | N-1 | N-1 |
| 1380 | 1R | Ph | Ph | N-2 | N-2 | N-2 |
| 1381 | 1R | Ph | Ph | N-3 | N-3 | N-3 |
| 1382 | 1R | Ph | Ph | N-4 | N-4 | N-4 |
| 1383 | 1R | Ph | Ph | N-5 | N-5 | N-5 |
| 1384 | 1R | Ph | Ph | N-6 | N-6 | N-6 |
| 1385 | 1R | Ph | Ph | N-7 | N-7 | N-7 |
| 1386 | 1R | Ph | Ph | N-8 | N-8 | N-8 |
| 1387 | 1R | Ph | Ph | N-9 | N-9 | N-9 |
| 1388 | 1R | Ph | Ph | N-10 | N-10 | N-10 |
| 1389 | 1R | Ph | Ph | N-11 | N-11 | N-11 |
| 1390 | 1R | Ph | Ph | N-12 | N-12 | N-12 |
| 1391 | 1R | Ph | Ph | N-13 | N-13 | N-13 |
| 1392 | 1R | Ph | Ph | N-14 | N-14 | N-14 |
| 1393 | 1R | Ph | Ph | N-15 | N-15 | N-15 |
| 1394 | 1R | Ph | Ph | N-16 | N-16 | N-16 |
| 1395 | 1R | Ph | Ph | N-17 | N-17 | N-17 |
| 1396 | 1R | Ph | Ph | N-18 | N-18 | N-18 |
| 1397 | 1R | Ph | Ph | N-19 | N-19 | N-19 |
| 1398 | 1R | Ph | Ph | N-20 | N-20 | N-20 |
| 1399 | 1R | Ph | Ph | N-21 | N-21 | N-21 |
| 1400 | 1R | Ph | Ph | N-22 | N-22 | N-22 |
| 1401 | 1R | Ph | Ph | N-23 | N-23 | N-23 |
| 1402 | 1R | Ph | Ph | N-24 | N-24 | N-24 |

TABLE 1-continued

| | | | | | | |
|---|---|---|---|---|---|---|
| 1403 | 1R | Ph | Ph | N-25 | N-25 | N-25 |
| 1404 | 1R | Ph | Ph | N-26 | N-26 | N-26 |
| 1405 | 1R | Ph | Ph | N-27 | N-27 | N-27 |
| 1406 | 1R | Ph | Ph | N-28 | N-28 | N-28 |
| 1407 | 1R | Ph | Ph | N-29 | N-29 | N-29 |
| 1408 | 1R | Ph | Ph | N-30 | N-30 | N-30 |
| 1409 | 1R | Ph | Ph | N-31 | N-31 | N-31 |
| 1410 | 1R | Ph | Ph | N-32 | N-32 | N-32 |
| 1411 | 1R | Ph | Ph | N-33 | N-33 | N-33 |
| 1412 | 1R | Ph | Ph | N-34 | N-34 | N-34 |
| 1413 | 1R | Ph | Ph | N-35 | N-35 | N-35 |
| 1414 | 1R | Ph | Ph | N-36 | N-36 | N-36 |
| 1415 | 1R | Ph | Ph | N-37 | N-37 | N-37 |
| 1416 | 1R | Ph | Ph | N-38 | N-38 | N-38 | wherein, in Table 1, "Me" represents a methyl group, and "Ph" represents a phenyl group. [Please remove the Korean characters from the table above.]

The compound represented by Formula 1 may include core A (see Formula 1'). Ring A, ring B, and ring C of core A are respectively introduced to three sides of a silepin, i.e., a 7-membered ring including silicon. Accordingly, the structural stability thereof may improve, which may result in excellent light-emission effects. In addition, by varying the types of ring A, ring B, and ring C, the hole transportability and hole injectability of the condensed-cyclic compound may be controlled.

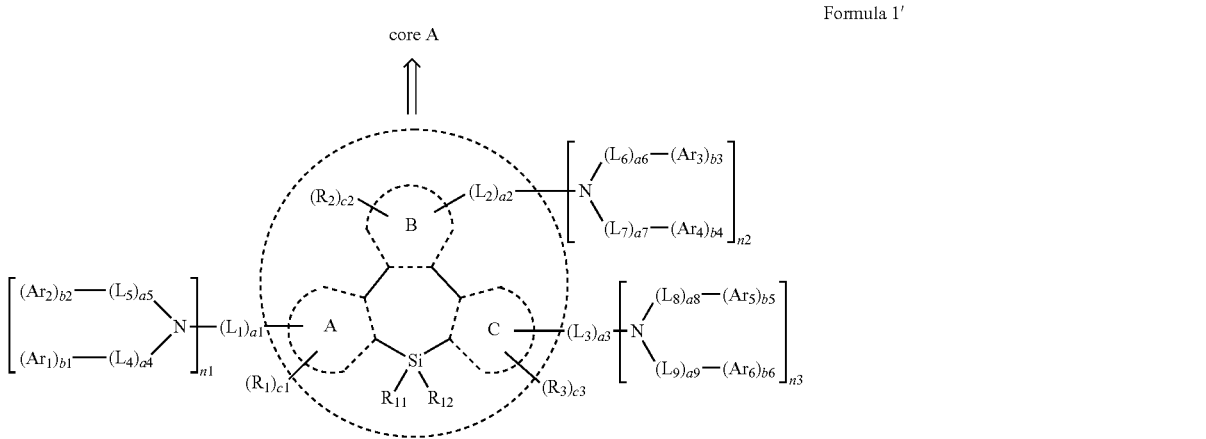

Formula 1'

In the condensed-cyclic compound represented by Formula 1, n1 to n3 may each independently be selected from 0, 1, 2, and 3, provided that the sum of n1, n2, and n3 may be 2 or greater. That is, the condensed-cyclic compound represented by Formula 1 may be a compound including at least two amino groups. Accordingly, the hole transportability and hole injectability of the condensed-cyclic compound may be further improved.

Therefore, an electronic device, e.g., an organic light-emitting device, employing the condensed-cyclic compound represented by Formula 1 may have a low driving voltage, high luminance, high efficiency, and long lifespan.

Methods of synthesizing the condensed-cyclic compound represented by Formula 1 should be readily apparent to those of ordinary skill in the art by referring to Examples described herein.

At least one of the condensed-cyclic compound represented by Formula 1 may be included between a pair of electrodes in an organic light-emitting device. In some embodiments, the condensed-cyclic compound may be included in at least one selected from a hole transport region and an emission layer.

Accordingly, there is provided an organic light-emitting device including a first electrode; a second electrode facing the first electrode; and an organic layer between the first electrode and the second electrode, the organic layer including an emission layer and at least one condensed-cyclic compound represented by Formula 1.

As used herein, the expression "(for example, the organic layer) including at least one condensed-cyclic compound" means that "(the organic layer) including a condensed-cyclic compound represented by Formula 1 (herein referred to as "Compound 1"), or at least two different condensed-cyclic compounds represented by Formula 1" (herein referred to as "Compound 1" and "Compound 2," which may be Compound 1 and Compound 2 of Table 1).

For example, the organic layer may include Compound 1 only as the condensed-cyclic compound. In this regard, Compound 1 may be included in a hole transport layer of the organic light-emitting device. In some embodiments, Compounds 1 and 2 may be included in the organic layer as the condensed-cyclic compounds. In this regard, Compounds 1 and 2 may be present in the same layer (for example, both Compounds 1 and 2 may be present in a hole transport layer), or in different layers (for example, Compound 1 may be present in a hole transport layer and Compound 2 may be present in an emission layer).

In one embodiment,
the first electrode may be an anode,
the second electrode may be a cathode,
the organic layer may include a hole transport region between the first electrode and the emission layer and an electron transport region between the emission layer and the second electrode,
the hole transport region may include at least one selected from a hole injection layer, a hole transport layer, a buffer layer, and an electron blocking layer, and
the electron transport region may include at least one selected from a hole blocking layer, an electron transport layer, and an electron injection layer.

In one embodiment, the hole transport region may include the condensed-cyclic compound represented by Formula 1. The hole transport region may include a hole transport layer, wherein the hole transport layer may include the condensed-cyclic compound represented by Formula 1. In some embodiments, the hole transport region may include a hole injection layer, wherein the hole injection layer may include the condensed-cyclic compound represented by Formula 1, but embodiments are not limited thereto.

In one or more embodiments, the emission layer may include the condensed-cyclic compound represented by Formula 1. The emission layer may further include a host (e.g., a fluorescent host), in addition to the condensed-cyclic compound represented by Formula 1, an amount of the host may be greater than that of the condensed-cyclic compound, but embodiments are not limited thereto.

The organic light-emitting device may further include at least one of a first capping layer disposed in a path of light extracted or emitted from the emission layer, allowing the light to pass through to the outside after passing the first electrode and a second capping layer disposed in a path of light extracted or emitted from the emission layer, allowing the light to pass through to the outside after passing the second electrode, wherein at least one of the first capping layer and the second capping layer may include at least one condensed-cyclic compound.

In some embodiments, the organic light-emitting device may have i) a first electrode/organic layer/second electrode/ second capping layer structure, ii) a first capping layer/first electrode/organic layer/second electrode structure, or iii) a first capping layer/first electrode/organic layer/second electrode/second capping layer structure, wherein layers of each structure are sequentially stacked in each stated order. At least one of the first capping layer and the second capping layer may include the condensed-cyclic compound.

The term "organic layer" as used herein refers to a single and/or a plurality of layers between the first electrode and the second electrode in an organic light-emitting device. A material included in the "organic layer" is not limited to an organic material.

Description of FIG. 1

Figure 1:
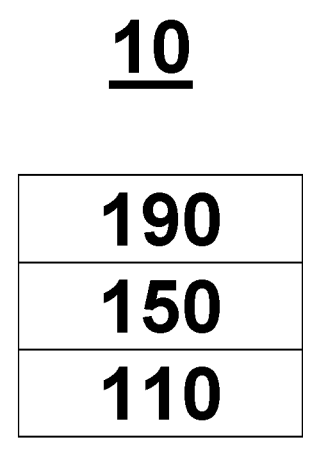

FIG. 1 illustrates a schematic cross-sectional view of an organic light-emitting device 10 according to an embodiment. The organic light-emitting device 10 may include the first electrode 110, the organic layer 150, and the second electrode 190.

Hereinafter, the structure of the organic light-emitting device 10 according to an embodiment and a method of manufacturing an organic light-emitting device according to an embodiment will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering, onto the substrate, a material for forming the first electrode 110. When the first electrode 110 is an anode, the material for forming the first electrode 110 may be selected from materials with a high work function that facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combinations thereof, but embodiments are not limited thereto. In some embodiments, when the first electrode 110 is a semi-transmissive electrode or a reflective electrode, as a material for forming the first electrode 110, at least one of magnesium (Mg), silver (Ag), aluminum (Al), aluminum-lithium (Al—Li), calcium (Ca), magnesium-indium (Mg—In), magnesium-silver (Mg—Ag), and any combination thereof may be used, but embodiments are not limited thereto.

The first electrode 110 may have a single-layered structure, or a multi-layered structure including two or more layers. In some embodiments, the first electrode 110 may have a triple-layered structure of ITO/Ag/ITO, but embodiments are not limited thereto.

Organic Layer 150

The organic layer 150 may be on the first electrode 110. The organic layer 150 may include an emission layer.

The organic layer 150 may further include a hole transport region between the first electrode 110 and the emission layer and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one selected from a hole injection layer, an emission auxiliary layer, and an electron blocking layer.

For example, the hole transport region may have a single-layered structure including a single layer including a plurality of different materials or a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein layers of each structure are sequentially stacked on the first electrode 110 in each stated order, but embodiments are not limited thereto.

The hole transport region may include the condensed-cyclic compound represented by Formula 1.

The hole transport region may include at least one selected from m-MTDATA, TDATA, 2-TNATA, NPB (NPD), β-NPB, TPD, a spiro-TPD, a spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), (polyaniline)/poly(4-styrenesulfonate) (PANI/PSS), a compound represented by Formula 201, and a compound represented by Formula 202:

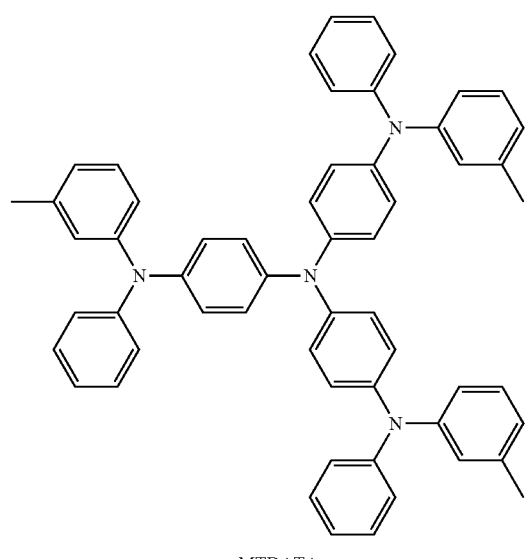

m-MTDATA

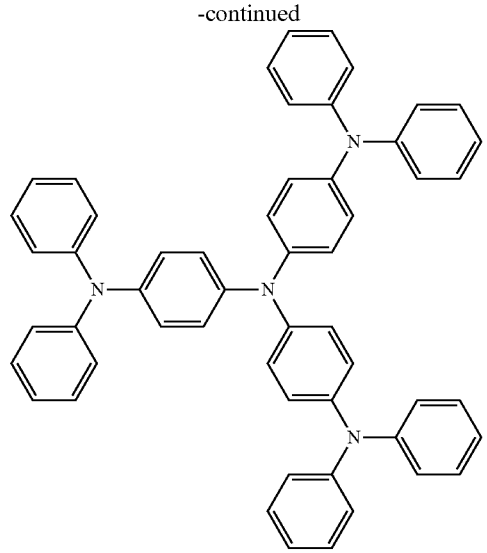
TDATA
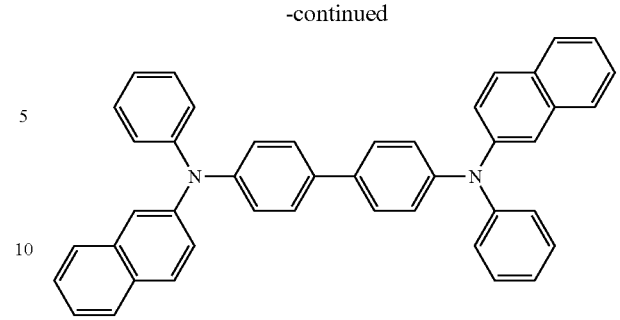
β-NPB
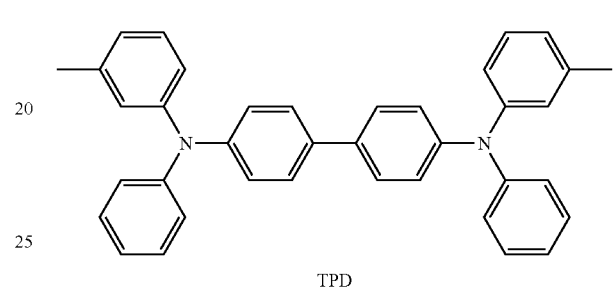
TPD
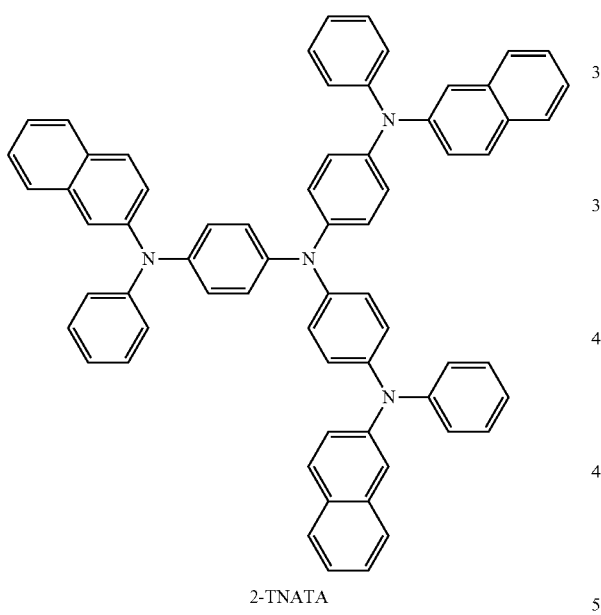
2-TNATA
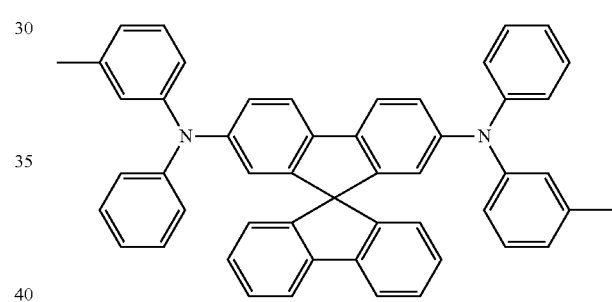
Spiro-TPD
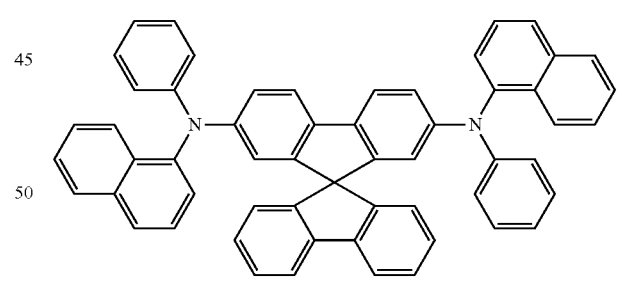
Spiro-NPB
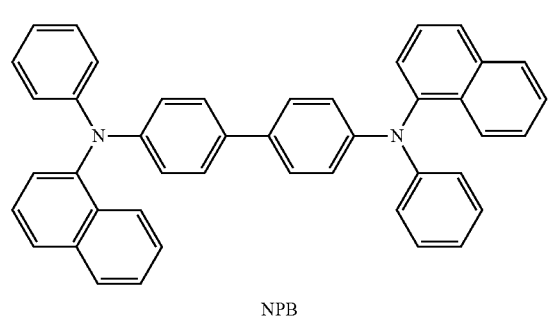
NPB
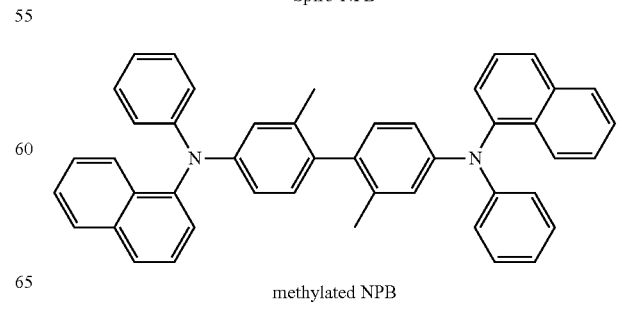
methylated NPB

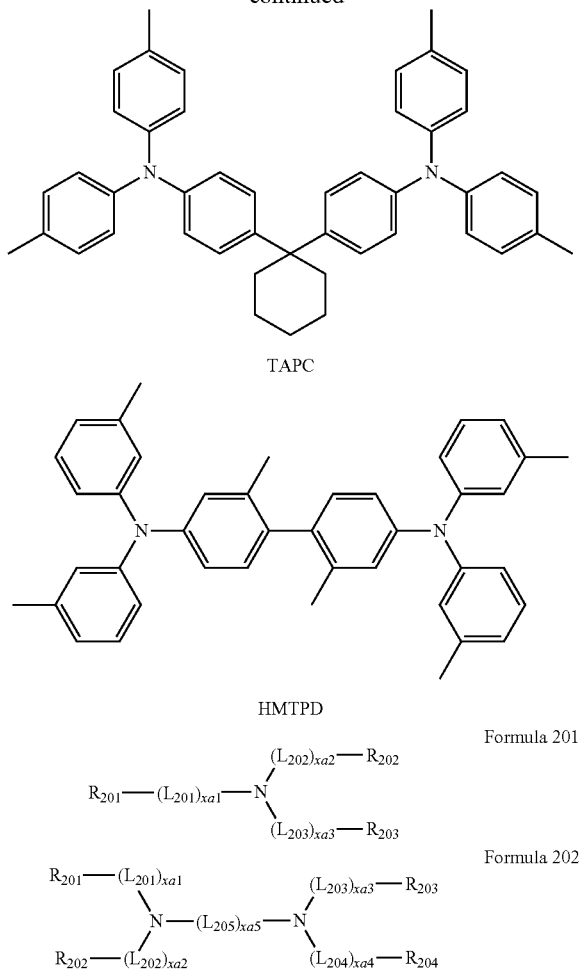

TAPC

HMTPD

Formula 201

$R_{201}$—$(L_{201})_{xa1}$—N$\begin{smallmatrix}(L_{202})_{xa2}\text{—}R_{202}\\(L_{203})_{xa3}\text{—}R_{203}\end{smallmatrix}$ Formula 202

$R_{201}$—$(L_{201})_{xa1}$
$R_{202}$—$(L_{202})_{xa2}$  N—$(L_{205})_{xa5}$—N  $(L_{203})_{xa3}$—$R_{203}$
$(L_{204})_{xa4}$—$R_{204}$ wherein, in Formulae 201 and 202, $L_{201}$ to $L_{204}$ may each independently be selected from a substituted or unsubstituted $C_{3-10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_{2-20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 202, $R_{201}$ and $R_{202}$ may optionally be bound via a single bond, a dimethyl-methylene group, or a diphenyl-methylene group, and $R_{203}$ and $R_{204}$ may optionally be bound via a single bond, a dimethyl-methylene group, or a diphenyl-methylene group.

In one embodiment, in Formulae 201 and 202, $L_{201}$ to $L_{205}$ may each independently be selected from a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may be the same as those described herein.

In one or more embodiments, in Formula 201, at least one of $R_{201}$ to $R_{203}$ may each independently be selected from a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

In one or more embodiments, in Formula 202, i) $R_{201}$ may be bound to $R_{202}$ via a single bond, and/or ii) $R_{203}$ may be bound to $R_{204}$ via a single bond.

In one or more embodiments, in Formula 202, at least one of $R_{201}$ to $R_{204}$ may be selected from a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

The compound represented by Formula 201 may be represented by Formula 201A:

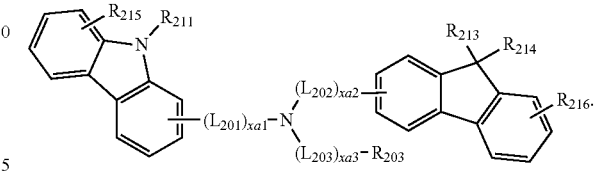

Formula 201A

In some embodiments, the compound represented by Formula 201 may be represented by Formula 201A(1), but embodiments are not limited thereto:

Formula 201A(1)

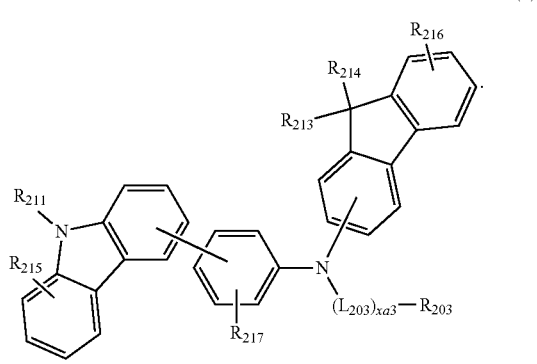

In some embodiments, the compound represented by Formula 201 may be represented by Formula 201A-1, but embodiments are not limited thereto:

Formula 201A-1

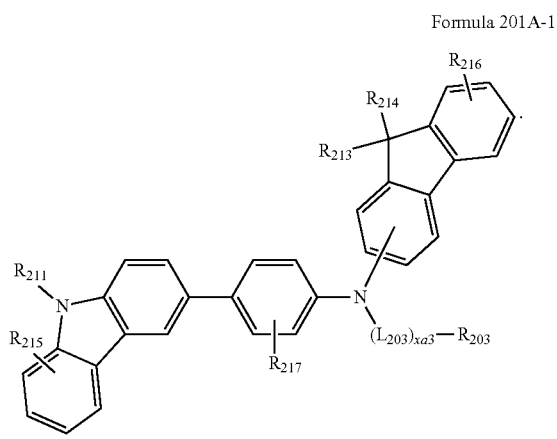

In some embodiments, the compound represented by Formula 202 may be represented by Formula 202A:

In some embodiments, the compound represented by Formula 202 may be represented by Formula 202A-1:

Formula 202A-1

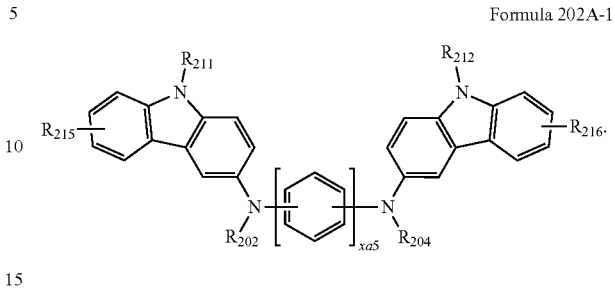

In Formulae 201A, 201A(1), 201A-1, 202A, and 202A-1, $L_{201}$ to $L_{203}$, xa1 to xa3, xa5, and $R_{202}$ to $R_{204}$ may each independently be the same as those described herein, $R_{211}$ and $R_{212}$ may each independently be substantially the same as $R_{203}$ described herein, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments are not limited thereto:

Formula 202A

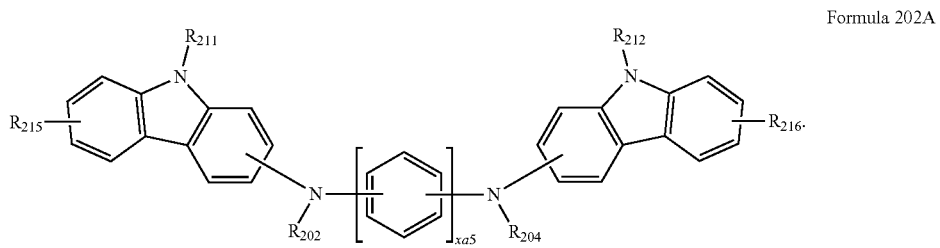

HT1
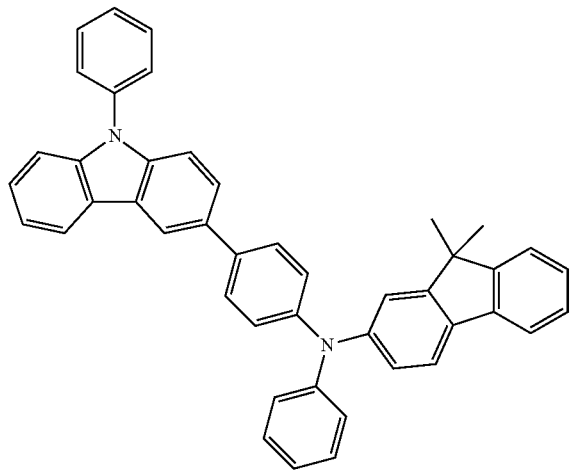
HT2
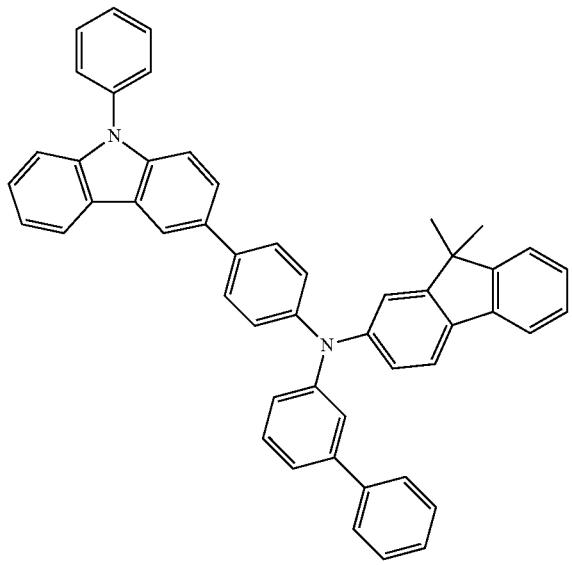
HT3
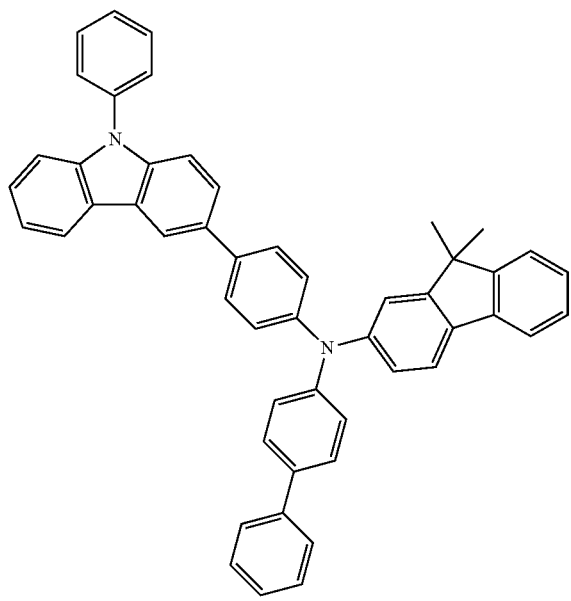
HT4
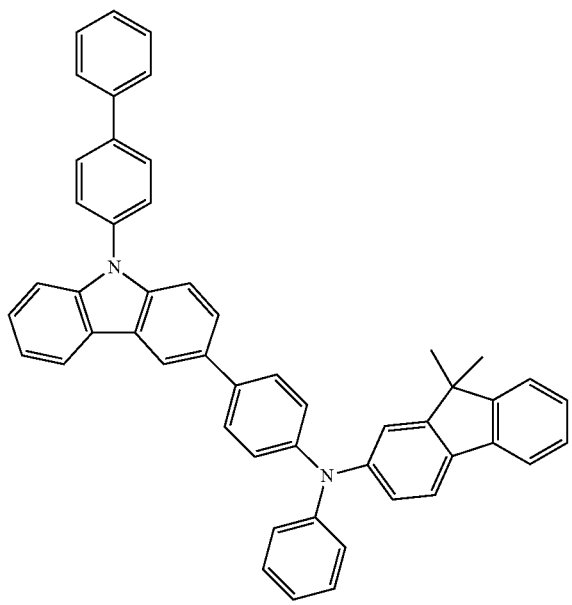

HT5
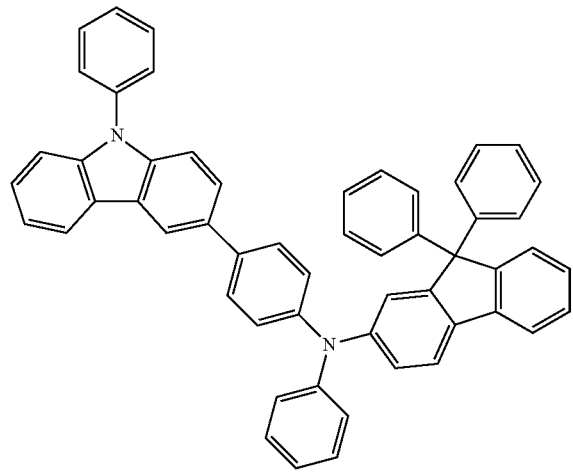
HT6
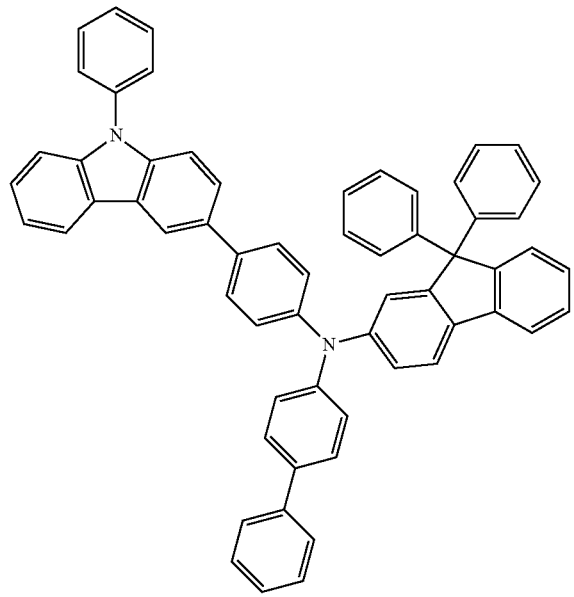
HT7
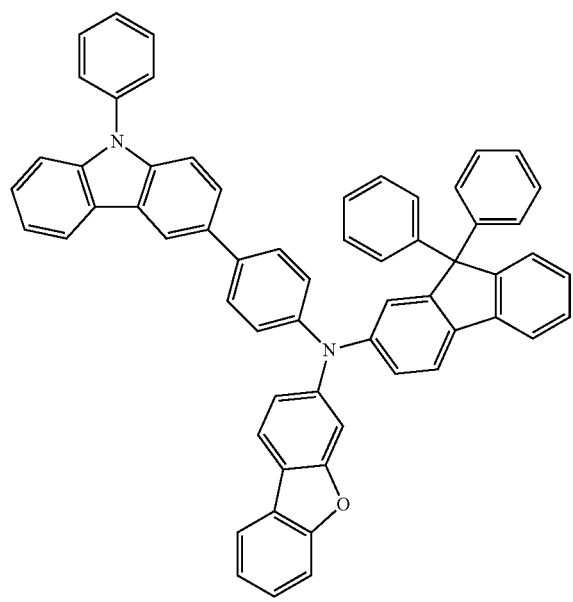
HT8
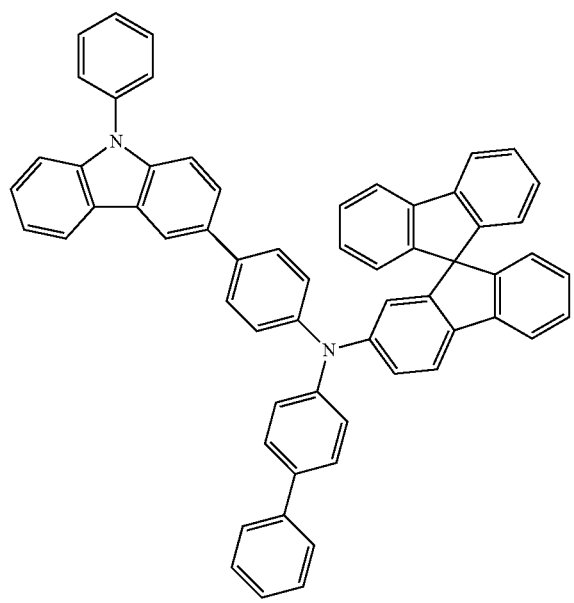

HT9
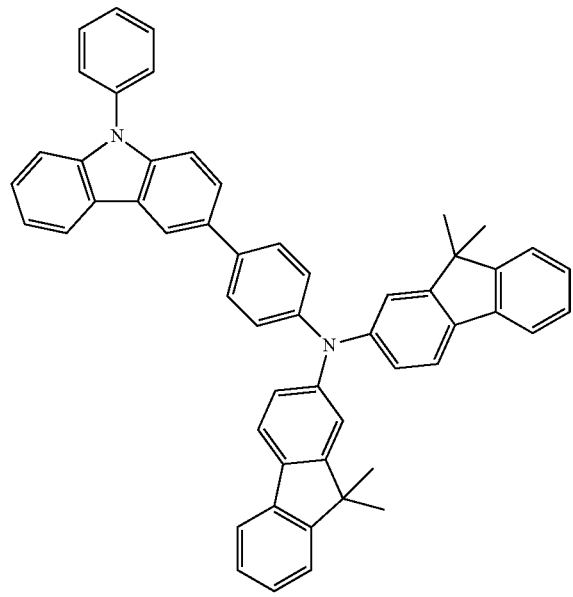
HT10
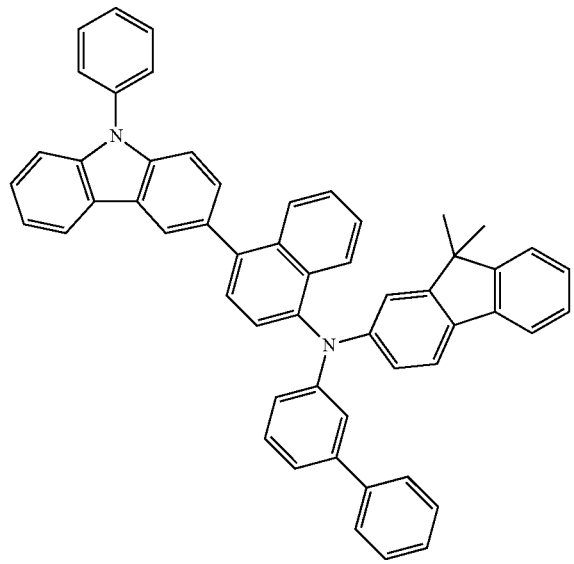
HT11
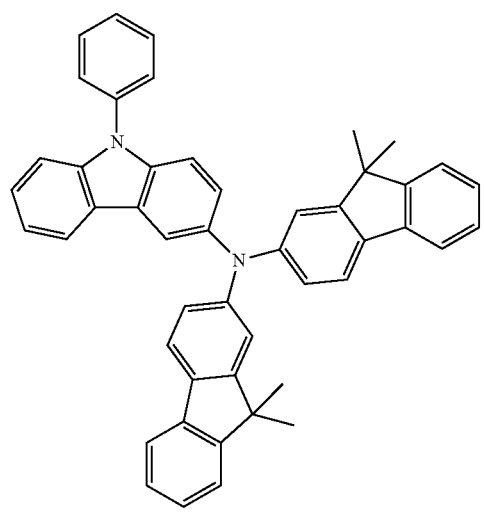
HT12
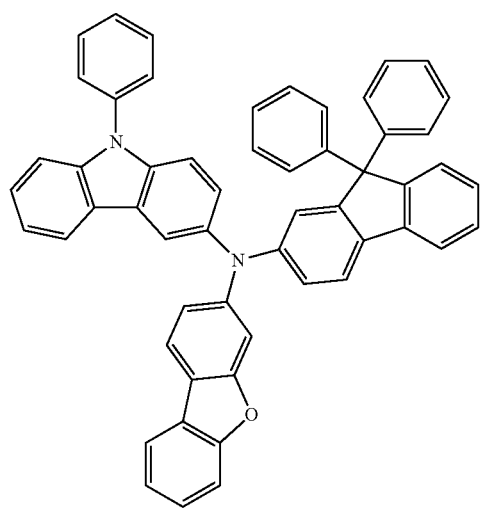

-continued
HT13
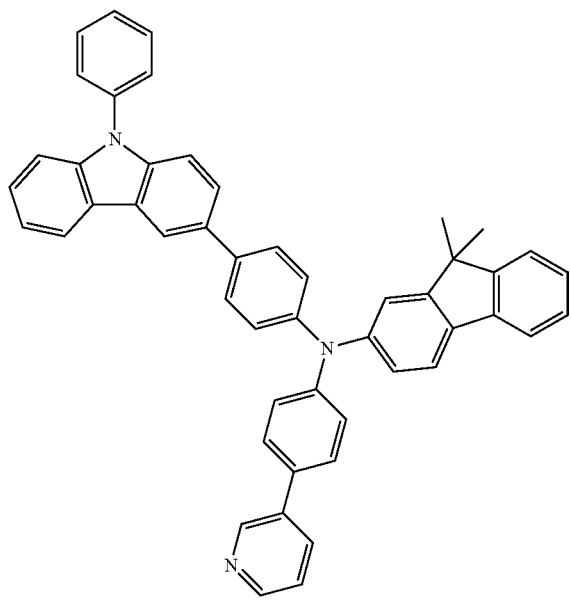
HT14
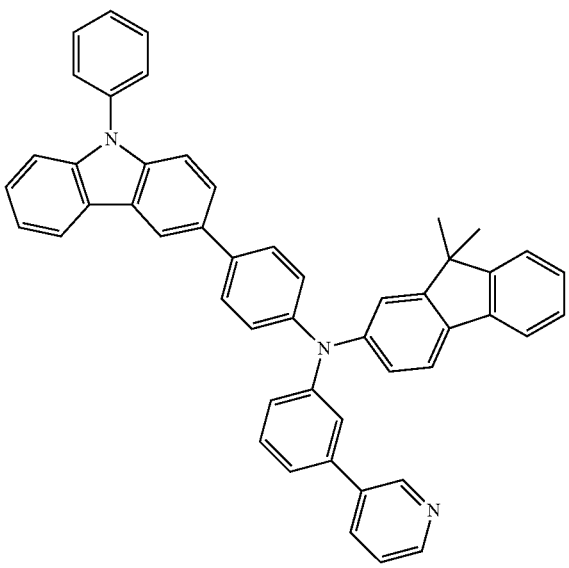
HT15
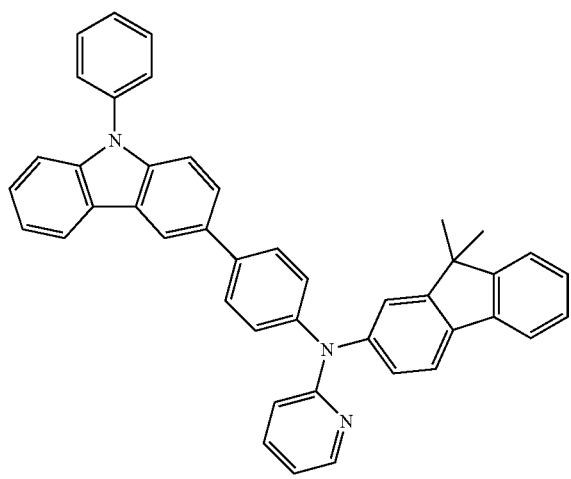
HT16
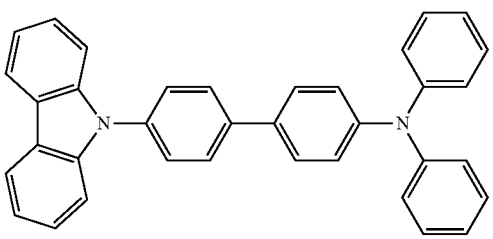
HT17
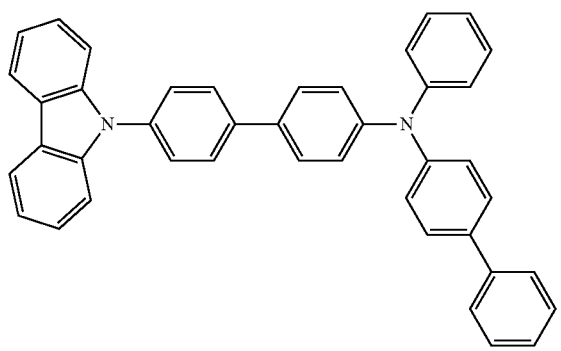
HT18
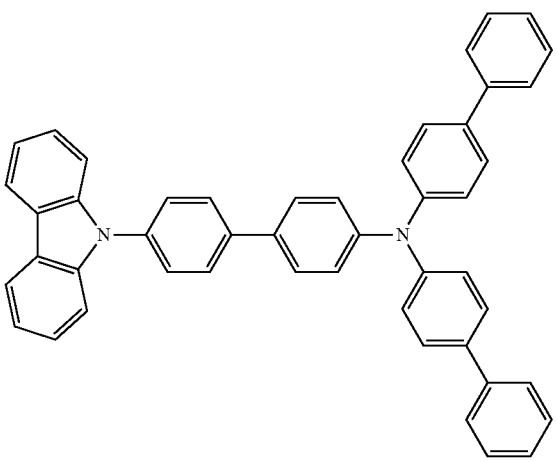

HT19 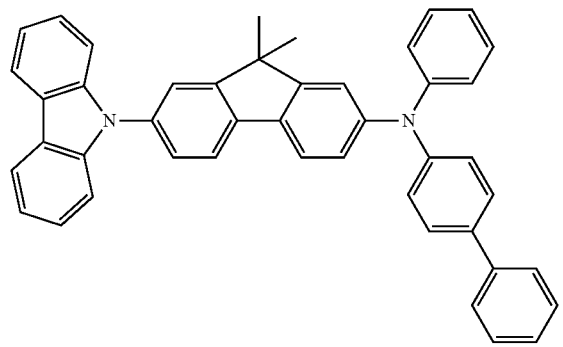
HT20 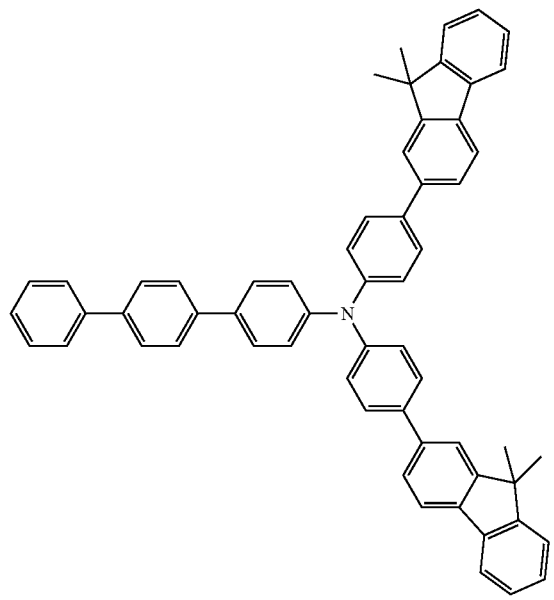
HT21 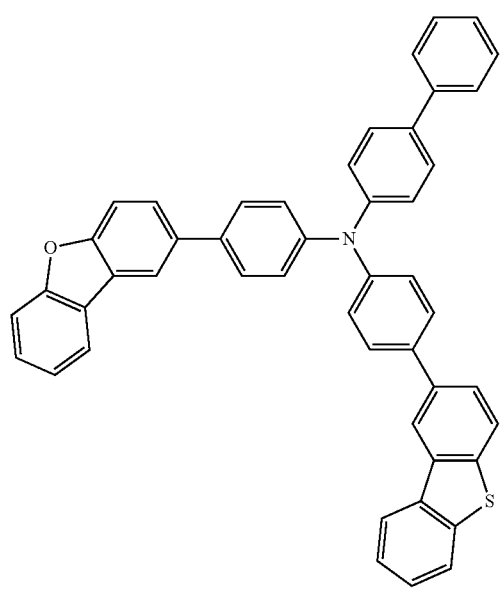
HT22 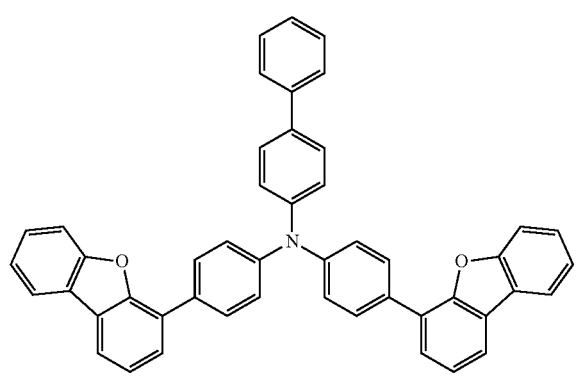

-continued
HT23
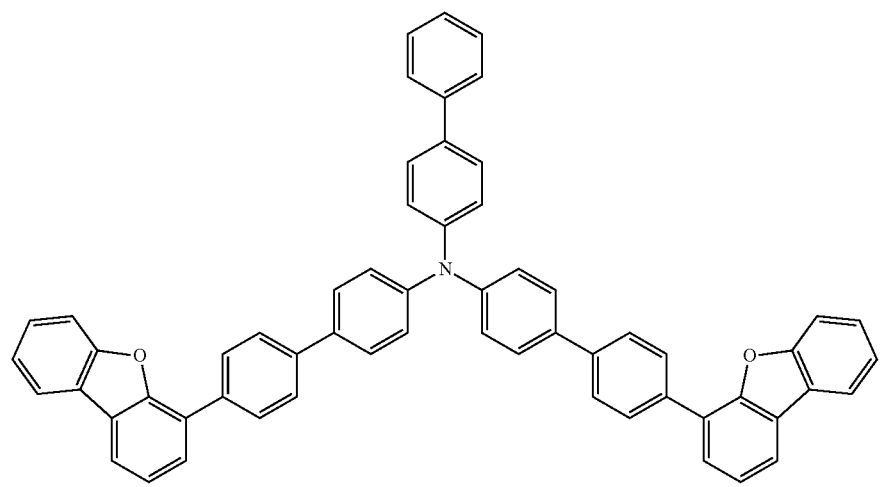
HT24
HT25
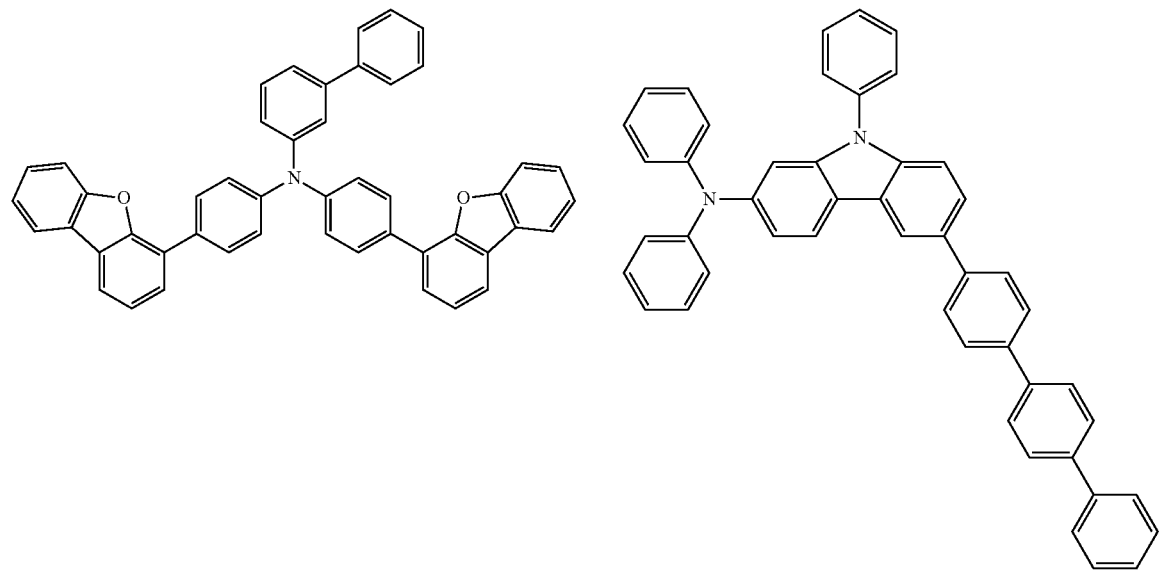
HT26
HT27
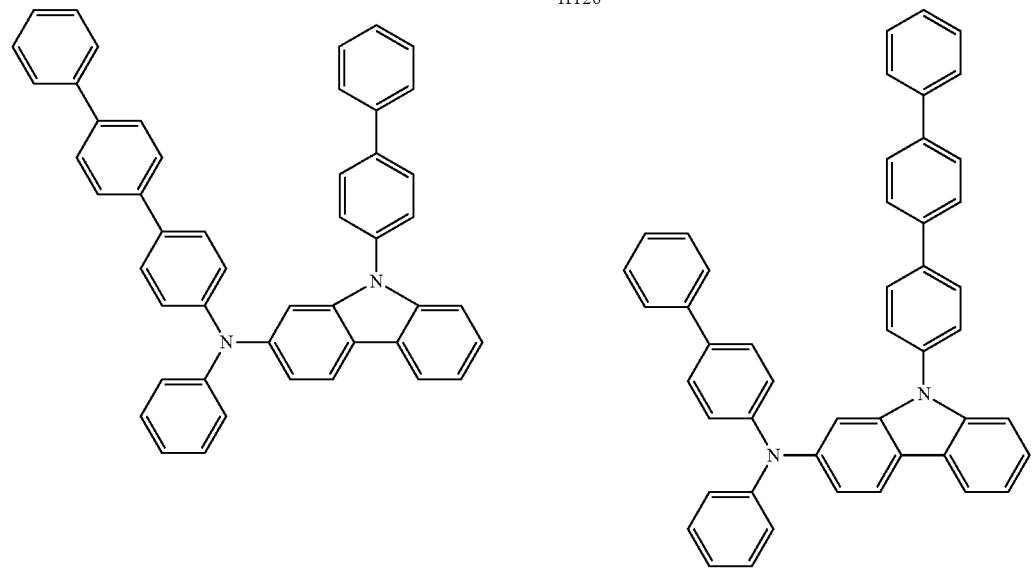

-continued
HT28
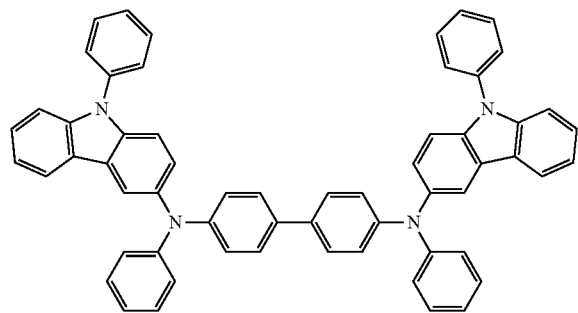
HT29
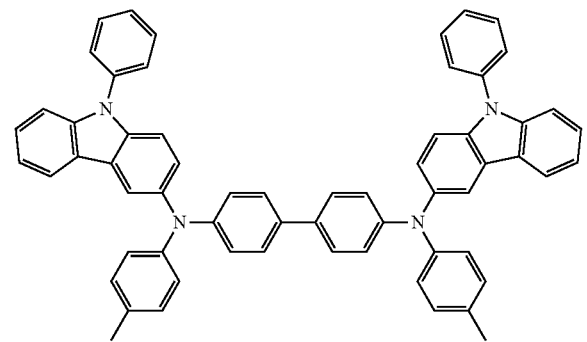
HT30
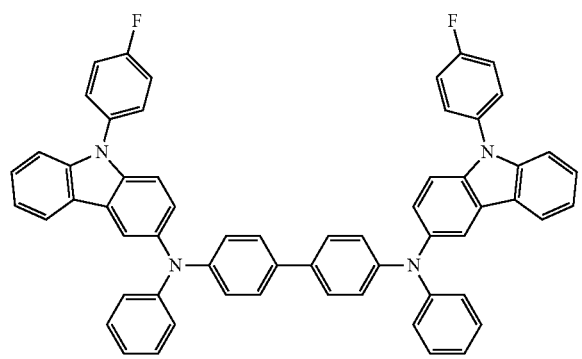
HT31
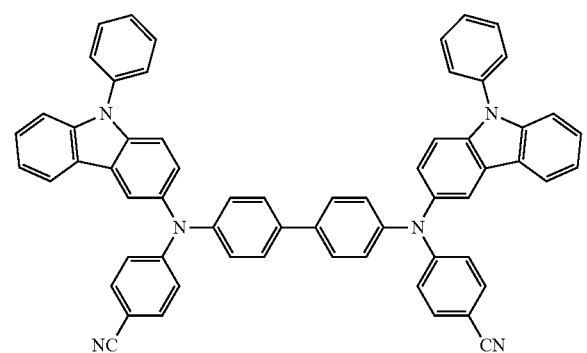
HT32
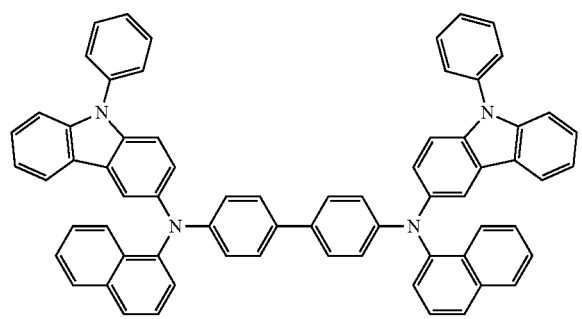
HT33
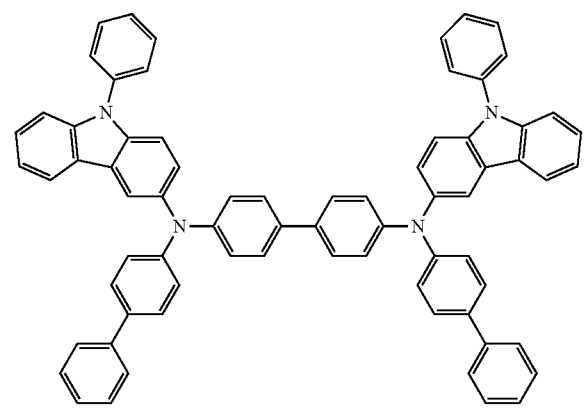

-continued
HT34
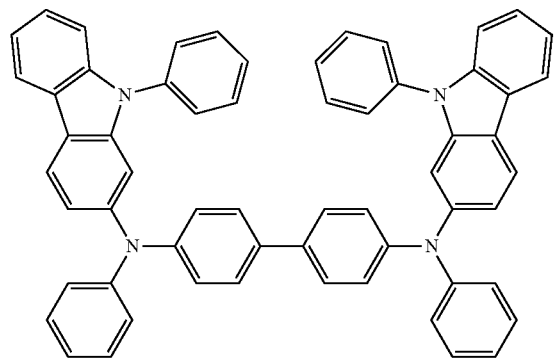
HT35
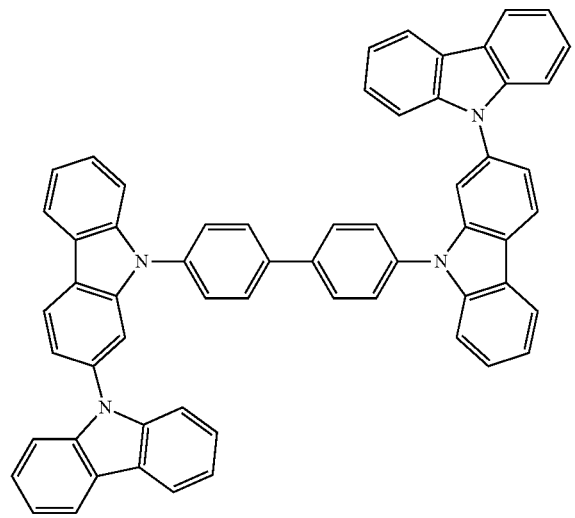
HT36
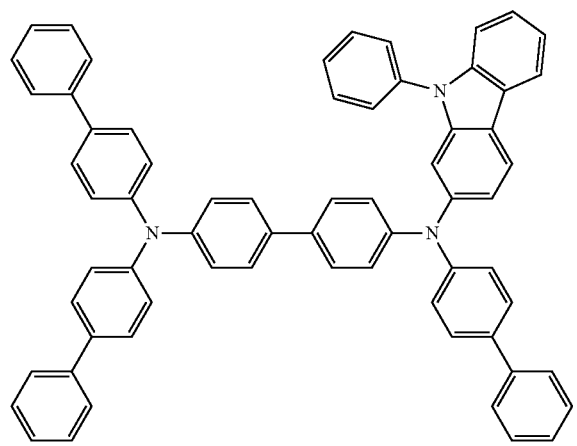
HT37
HT38
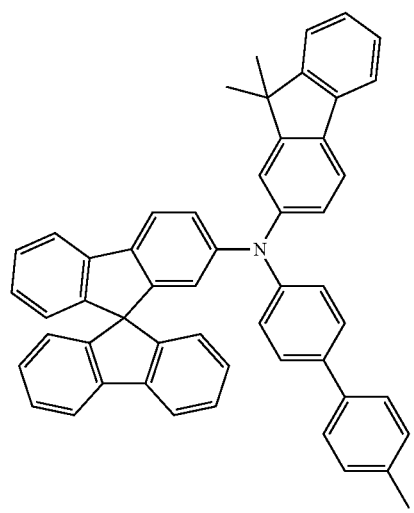
HT39
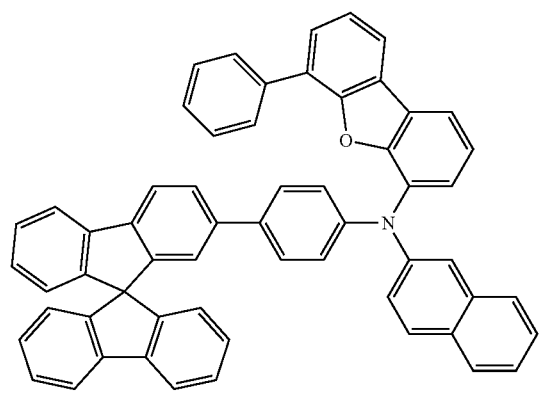

The thickness of the hole transport region may be in a range of about 100 (Angstroms) Å to about 10,000 Å, and in some embodiments, about 100 Å to about 1,000 Å. When the hole transport region includes at least one selected from a hole injection layer and a hole transport layer, the thickness of the hole injection layer may be in a range of about 100 Å to about 9,000 Å, and in some embodiments, about 100 Å to about 1,000 Å, and the thickness of the hole transport layer may be in a range of about 50 Å to about 2,000 Å, and in some embodiments, about 100 Å to about 1,500 Å. When the thicknesses of the hole transport region, the hole injection layer, and the hole transport layer are within any of these ranges, excellent hole transport characteristics may be obtained without a substantial increase in driving voltage.

The emission auxiliary layer may increase light emission efficiency by compensating for an optical resonance distance according to the wavelength of light emitted by an emission layer. The electron blocking layer may reduce or eliminate the flow of electrons from an electron transport region. The emission auxiliary layer and the electron blocking layer may include the aforementioned materials.

P-Dopant

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant.

In some embodiments, a lowest unoccupied molecular orbital (LUMO) of the β-dopant may be about −3.5 electron Volts (eV) or less.

The p-dopant may include at least one selected from a quinone derivative, a metal oxide, and a cyano group-containing compound, but embodiments are not limited thereto.

In some embodiments, the p-dopant may include at least one selected from a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221, but embodiments are not limited thereto:

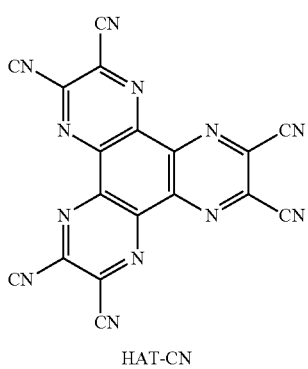

HAT-CN

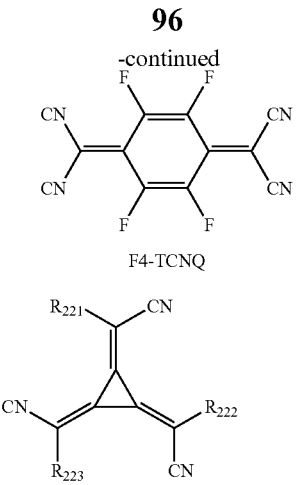

F4-TCNQ

Formula 221 wherein, in Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure. The stacked structure may include two or more layers selected from a red emission layer, a green emission layer, and a blue emission layer. The two or more layers may be in direct contact with each other. In some embodiments, the two or more layers may be separated from each other. In one or more embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light.

The emission layer may include a host and a dopant. The dopant may include at least one of a fluorescent dopant and a phosphorescent dopant.

The amount of the dopant in the emission layer may be, in general, in a range of about 0.01 parts to about 15 parts by weight based on 100 parts by weight of the host, but embodiments are not limited thereto.

The thickness of the emission layer may be in a range of about 100 Å to about 1,000 Å, and in some embodiments, about 200 Å to about 600 Å. When the thickness of the emission layer is within any of these ranges, improved light-emission characteristics may be obtained without a substantial increase in driving voltage.

The emission layer may include the condensed-cyclic compound represented by Formula 1.

Host in Emission Layer

The host may include a compound represented by Formula 301:

$[Ar_{301}]_{xb11}-[(L_{301})_{xb1}-R_{301}]_{xb21}$  Formula 301 wherein, in Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_{3-10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In some embodiments, $Ar_{301}$ in Formula 301 may be selected from a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

When xb11 in Formula 301 is two or greater, at least two $Ar_{301}$ groups may be bound via a single bond.

In one or more embodiments, the compound represented by Formula 301 may be represented by Formula 301-1 or 301-2:

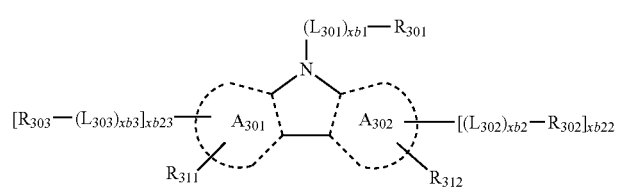

Formula 301-1

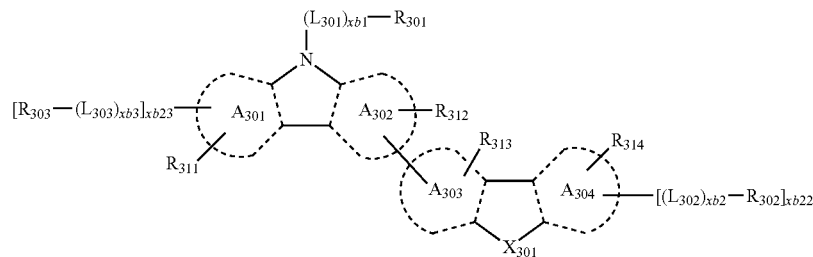

Formula 301-2 wherein, in Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonapthothiophene group, and a dinaphthothiophene group, $X_{301}$ may be O, S, or N-[$(L_{304})_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be the same as those described herein, $L_{302}$ to $L_{304}$ may each independently be substantially the same as $L_{301}$ described herein, xb2 to xb4 may each independently be substantially the same as xb1 described herein, and $R_{302}$ to $R_{304}$ may each independently be substantially the same as $R_{301}$ described herein.

In some embodiments, in Formulae 301, 301-1, and 301-2, $L_{301}$ to $L_{304}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be the same as those described herein.

In some embodiments, in Formulae 301, 301-1, and 301-2, $R_{301}$ to $R_{304}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be the same as those described herein.

In some embodiments, the host may include an alkaline earth metal complex. For example, the host may include a beryllium (Be) complex, e.g., Compound H55, a magnesium (Mg) complex, or a zinc (Zn) complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments are not limited thereto:

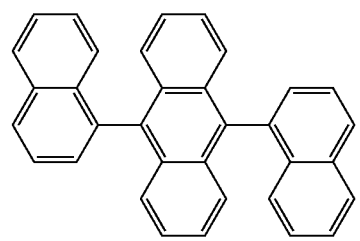

H1

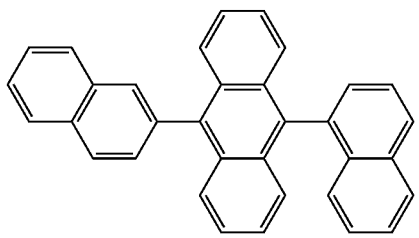

H2

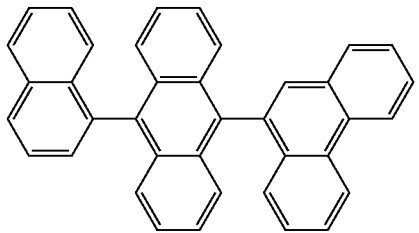

H3

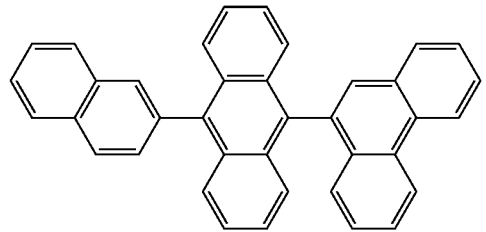

H4

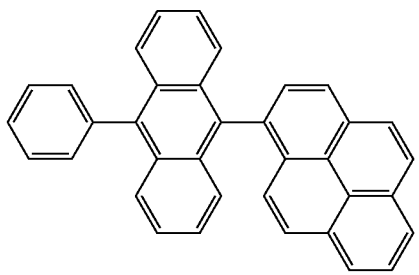

H5

H6 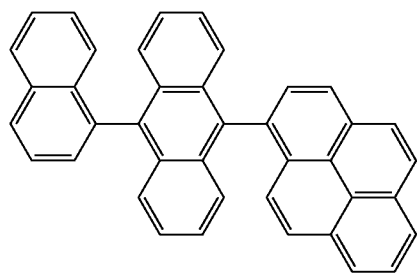
H7 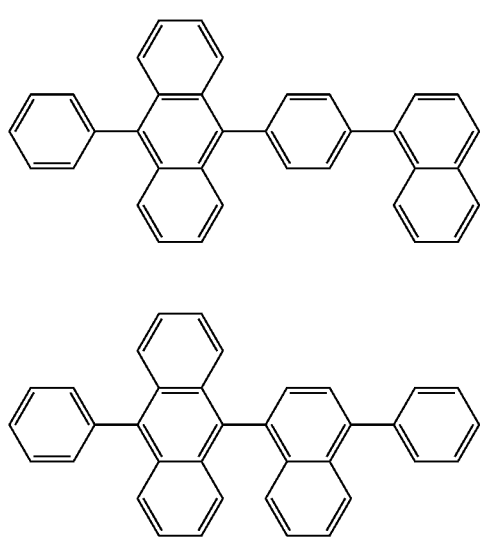
H8
H9
H10
H11 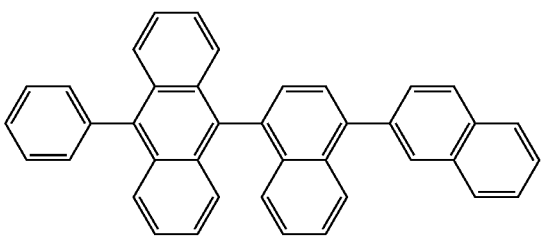 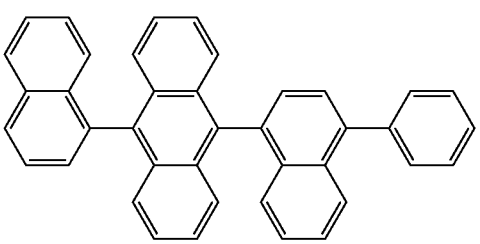 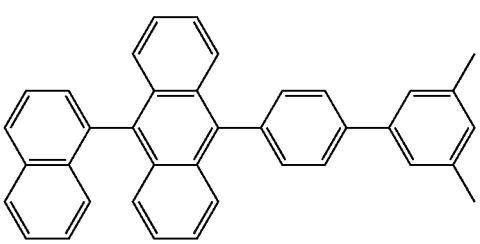
H12 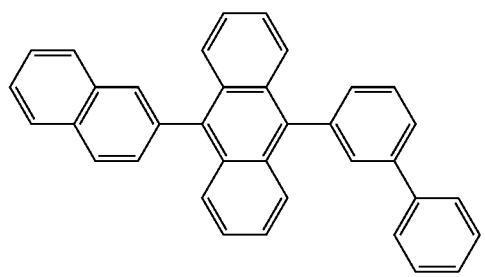
H13 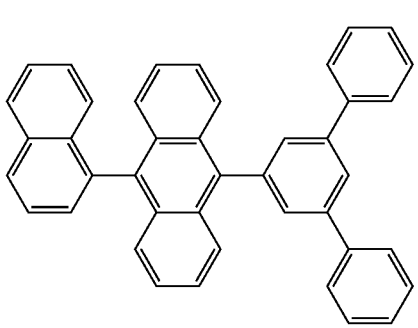
H14 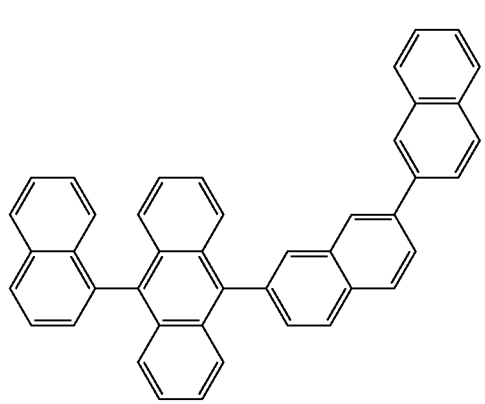
H15 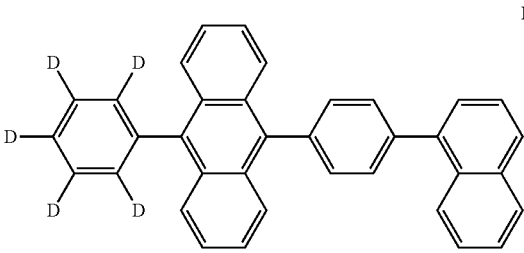
H16 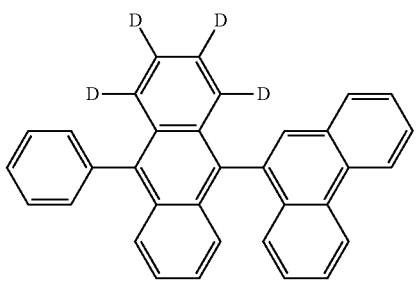

H17
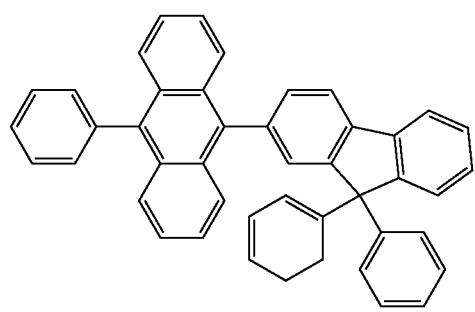
H18
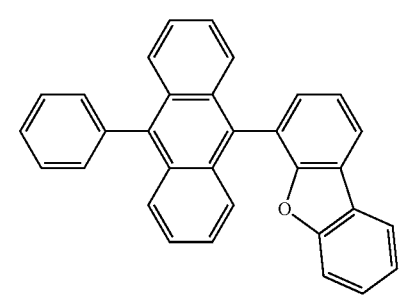
H19
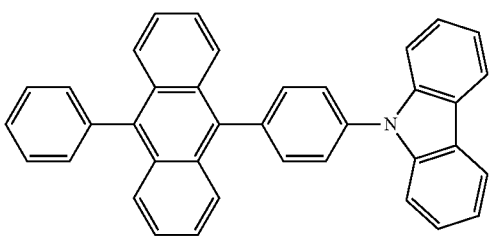
H20
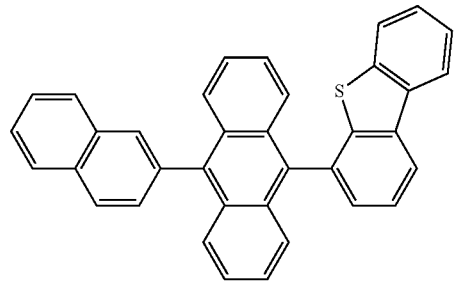
H21
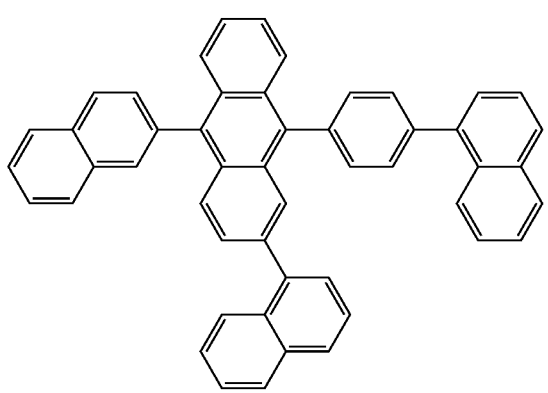
H22
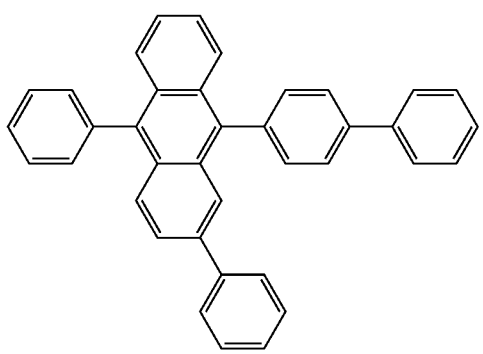
H23
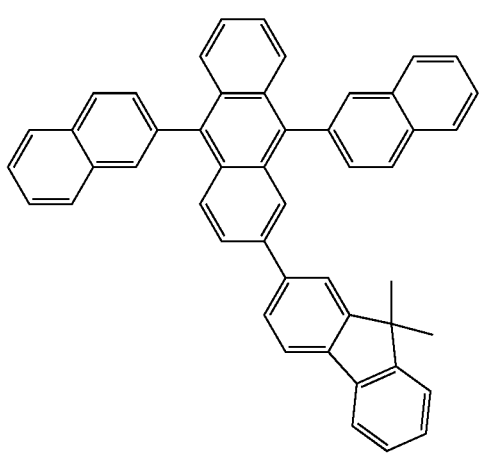
H24
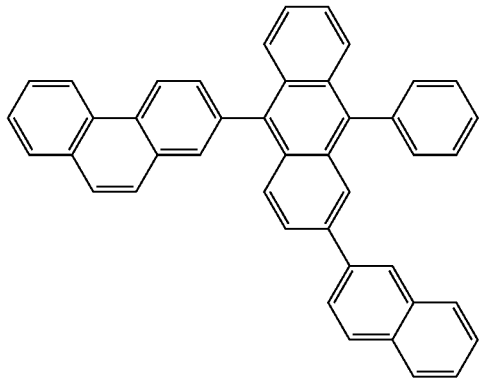

H25
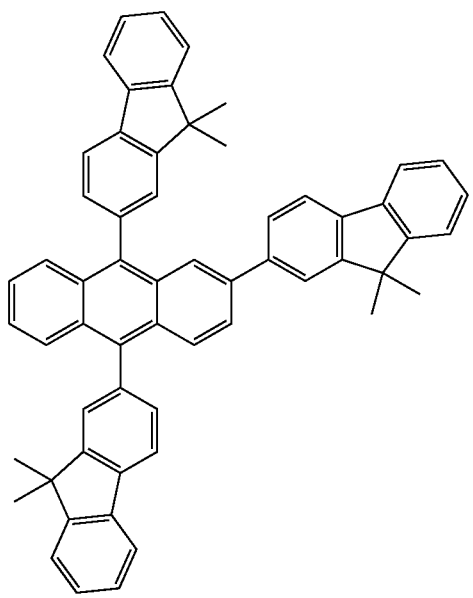
H26
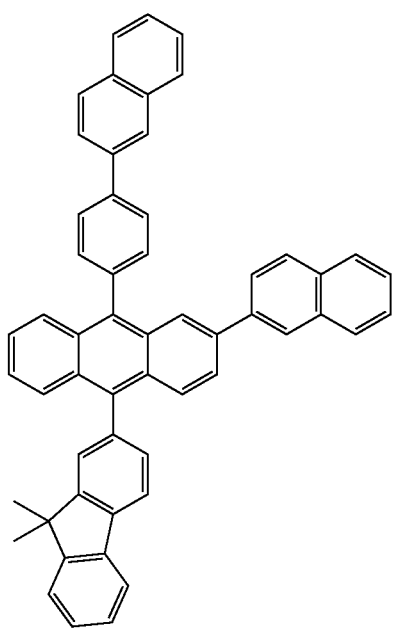
H27
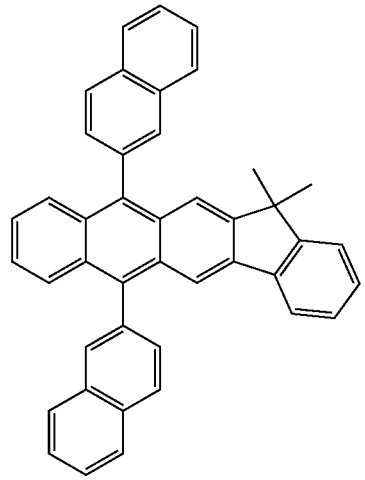
H28
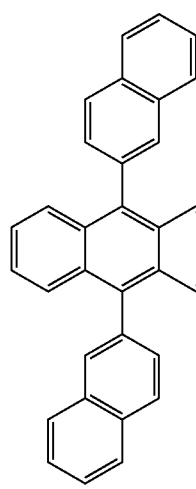
H29
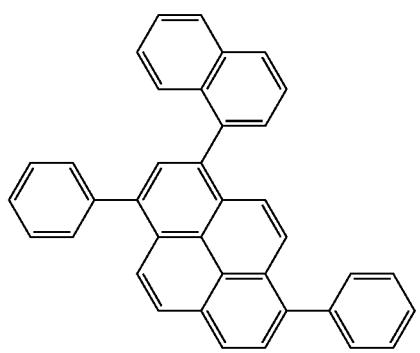

H30
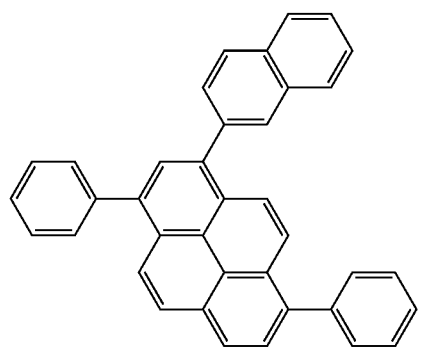
H31
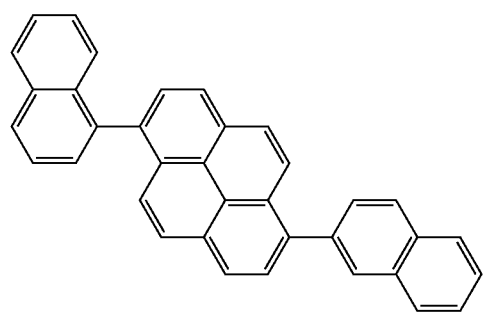
H32
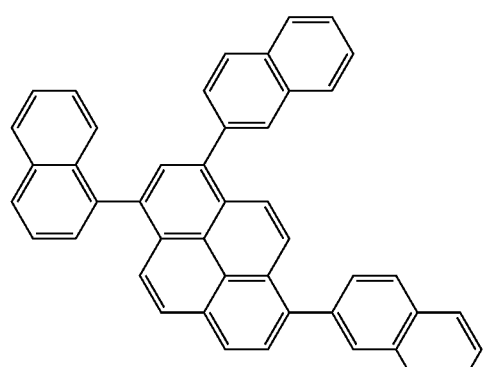
H33
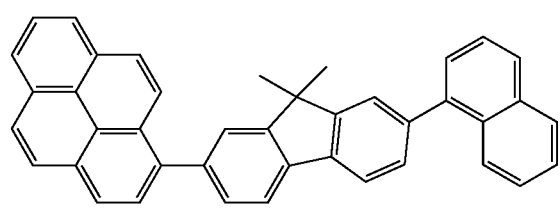
H34
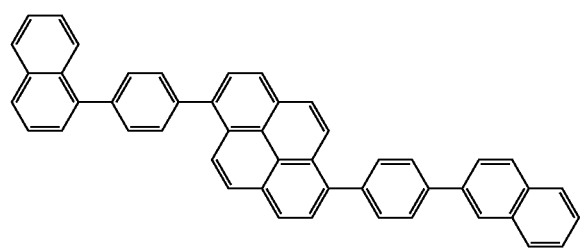
H35
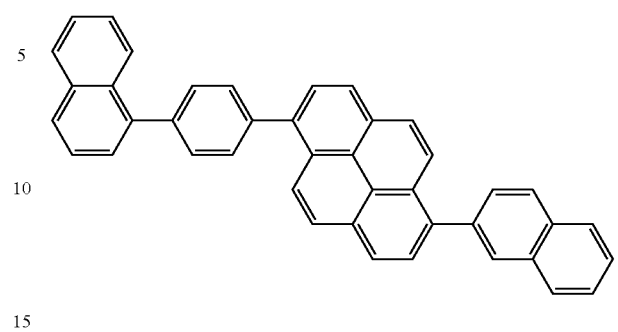
H36
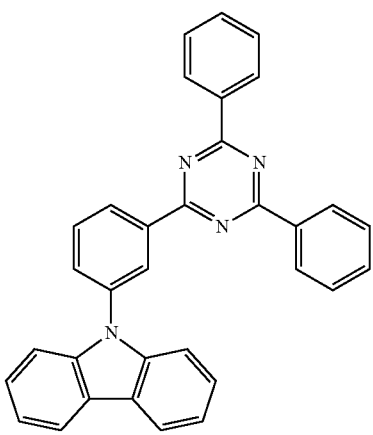
H37
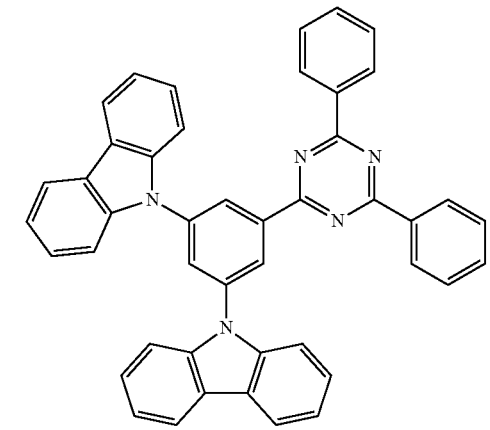
H38
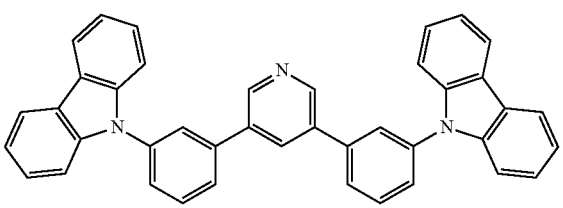

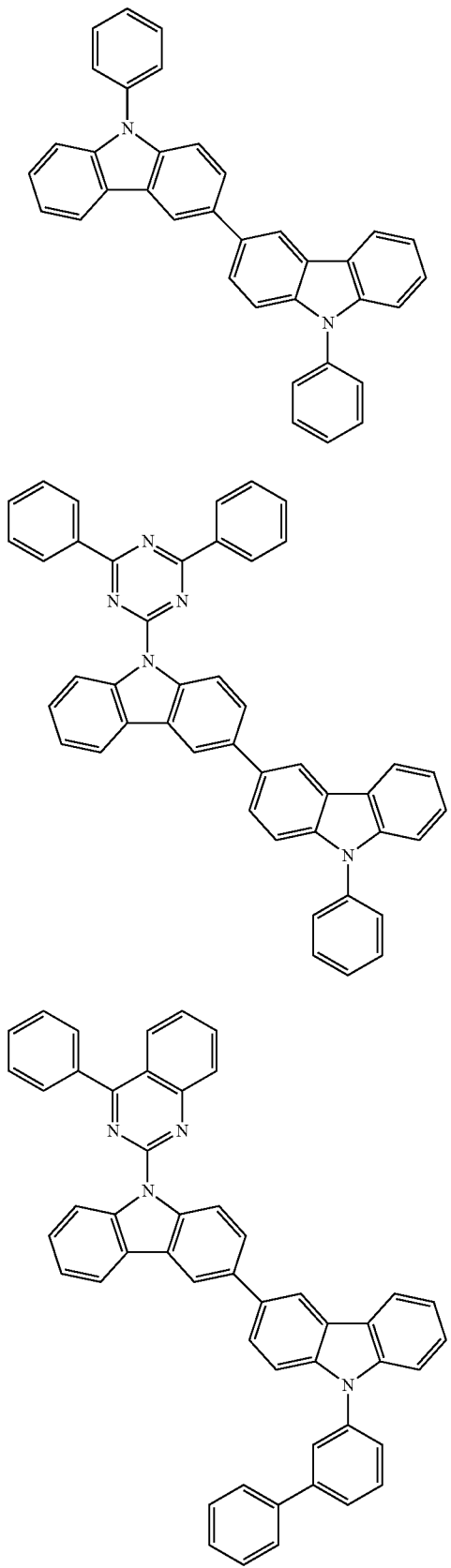
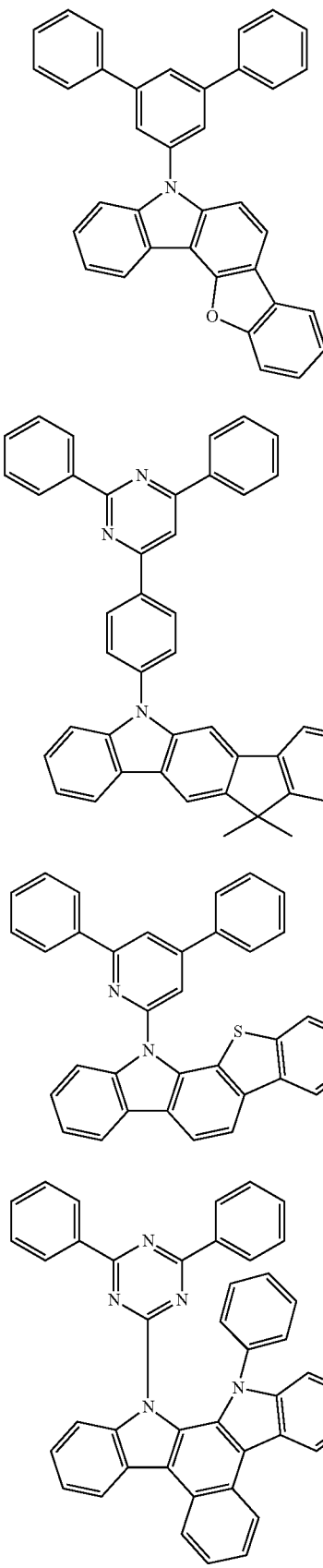

H46
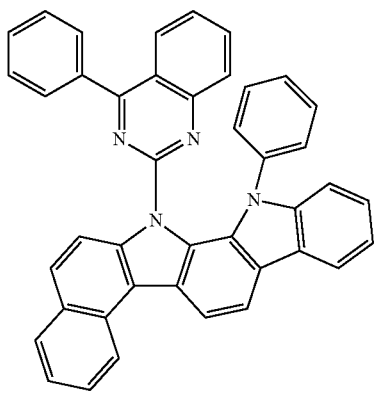
H47
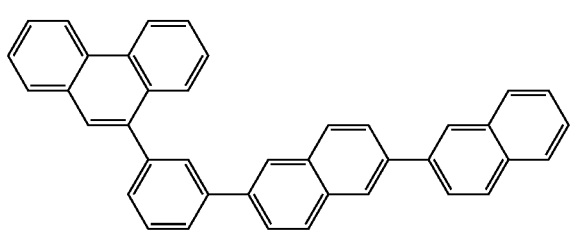
H48
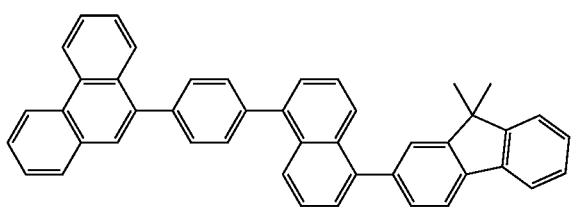
H49
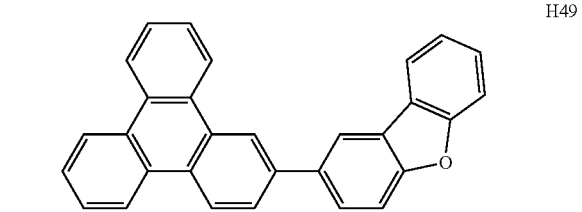
H50
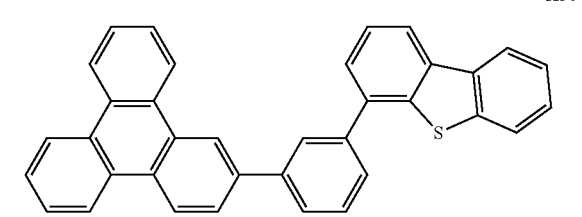
H51
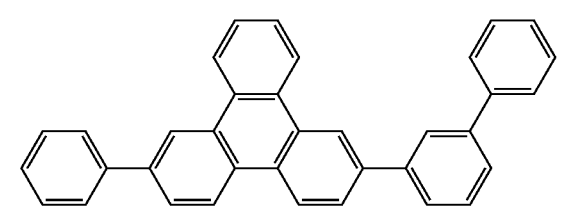
H52
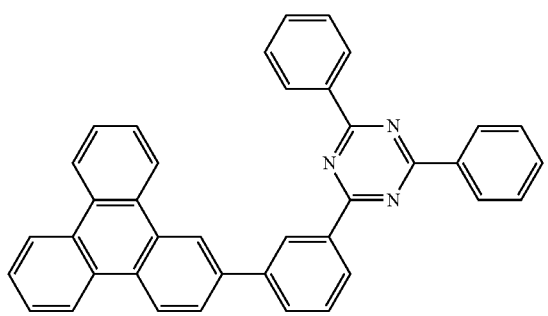
H53
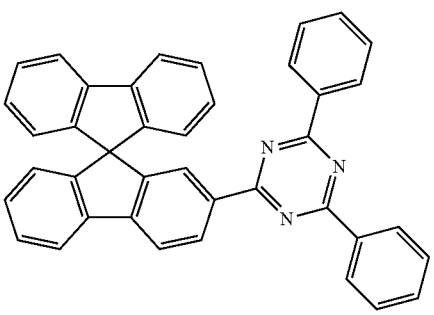
H54
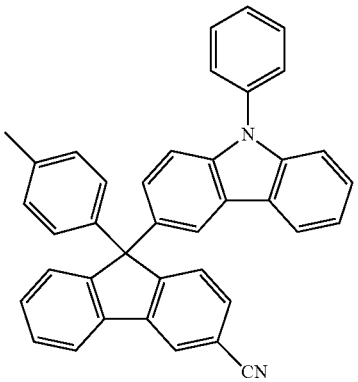
H55
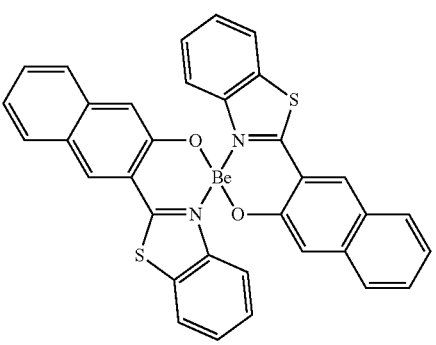

Phosphorescent Dopant Included in Emission Layer of Organic Layer 150

The phosphorescent dopant may include an organometallic complex represented by Formula 401:

$$M(L_{401})_{xc1}(L_{402})_{xc2} \quad \text{Formula 401}$$

Formula 2

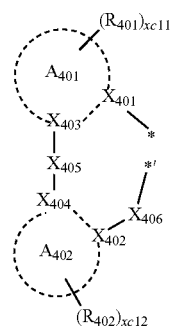

wherein, in Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, xc1 may be an integer from 1, 2, and 3; when xc1 is two or greater, at least two $L_{401}$ groups may be identical to or different from each other, $L_{402}$ may be an organic ligand, xc2 may be an integer from 0 to 4; when xc2 is two or greater, at least two $L_{402}$ groups may be identical to or different from each other, $X_{401}$ to $X_{404}$ may each independently be nitrogen (N) or carbon (C), $X_{401}$ and $X_{403}$ may be linked via a single bond or a double bond, $X_{402}$ and $X_{404}$ may be linked via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*', wherein $Q_{411}$ and $Q_{412}$ may each independently be selected from hydrogen, deuterium, a $C_1$-$C_{20}$ alkyl group, a $C_1$-$C_{20}$ alkoxy group, a phenyl group, a biphenyl group, a terphenyl group, and a naphthyl group, $X_{406}$ may be a single bond, 0, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 may each independently indicate a binding site to M in Formula 401.

In some embodiments, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen.

In one or more embodiments, in Formula 402, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanyl group, and a norbornenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments are not limited thereto.

In one or more embodiments, when xc1 in Formula 401 is two or greater, two $A_{401}$ groups of at least two $L_{401}$ groups may optionally be bound to each other via $X_{407}$ as a linking group; or two $A_{402}$ groups may optionally be bound to each other via $X_{408}$ as a linking group (see Compounds PD1 to PD4 and PD7). $X_{407}$ and $X_{408}$ may each independently be selected from a single bond, *—O—*', *—S—*', *—C(=O)—*', *—N($Q_{413}$)-*, *—C($Q_{413}$)($Q_{414}$)-*', and *—C($Q_{413}$)=C($Q_{414}$)-*', wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, but embodiments are not limited thereto.

$L_{402}$ in Formula 401 may be any suitable monovalent, divalent, or trivalent organic ligand. For example, $L_{402}$ may be selected from halogen, diketone (e.g., acetylacetonate), a carboxylic acid (e.g., picolinate), —C(=O), isonitrile, —CN, and phosphorus (e.g., phosphine or phosphite), but embodiments are not limited thereto.

In some embodiments, the phosphorescent dopant may include, for example, at least one selected from Compounds PD1 to PD25, but embodiments are not limited thereto:

PD1

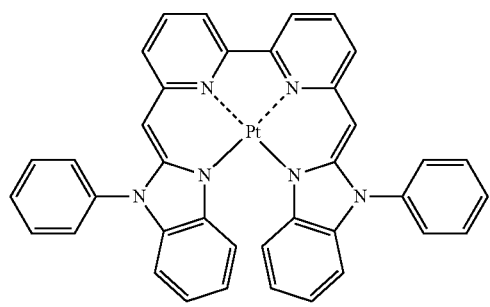

PD2

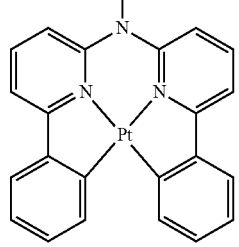

PD3

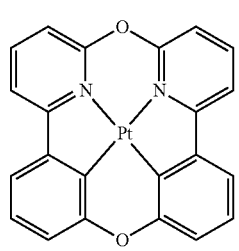

-continued

PD4

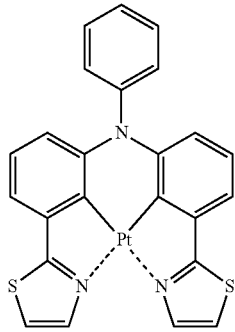

PD5

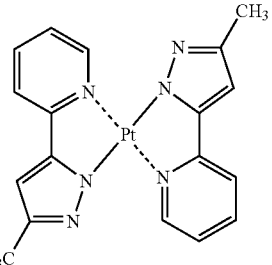

PD6

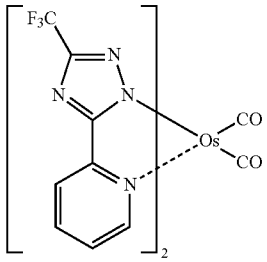

PD7

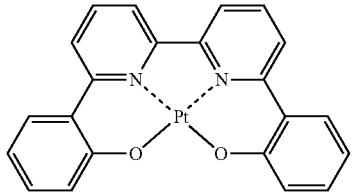

PD8

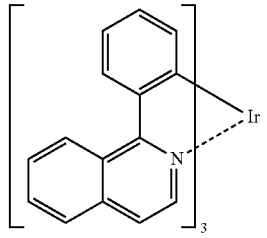

PD9

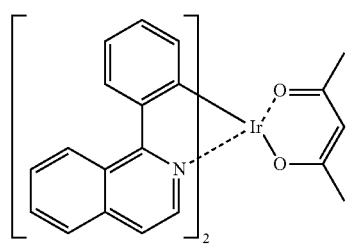

PD10
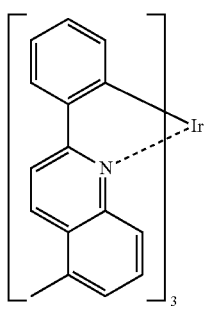
PD11
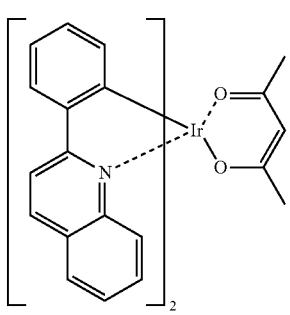
PD12
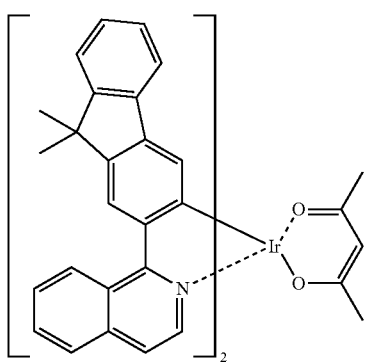
PD13
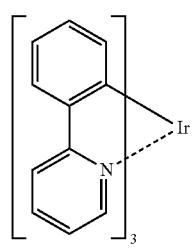
PD14
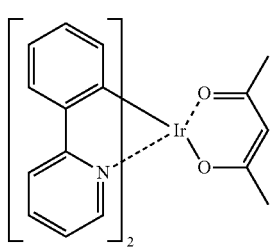
PD15
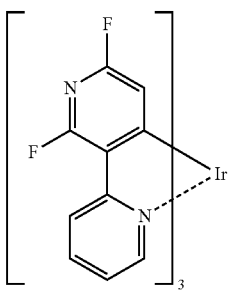
PD16
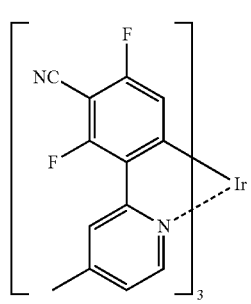
PD17
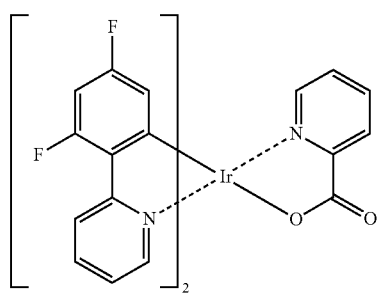
PD18
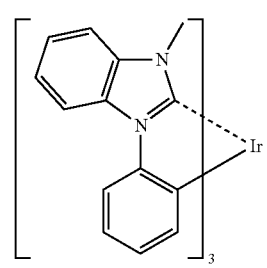
PD19
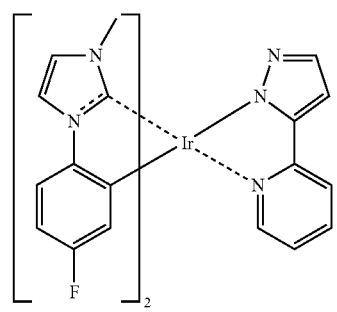

-continued

PD20
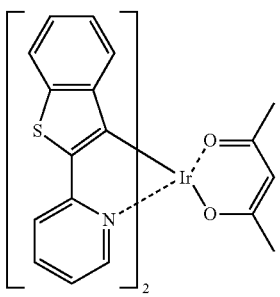

PD21
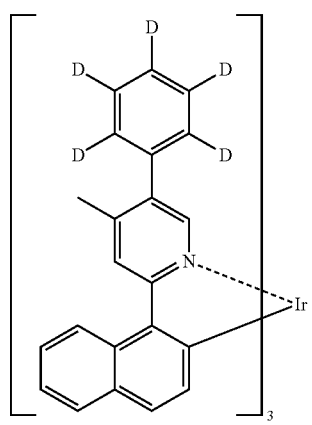

PD22
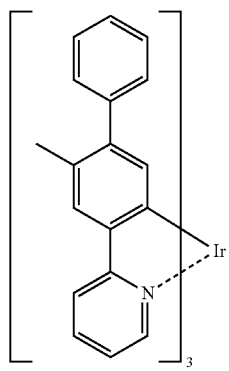

PD23
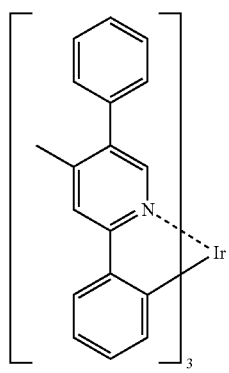

-continued

PD24
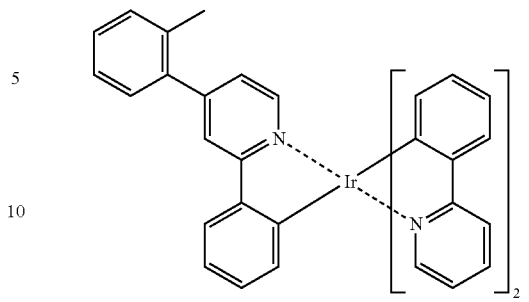

PD25
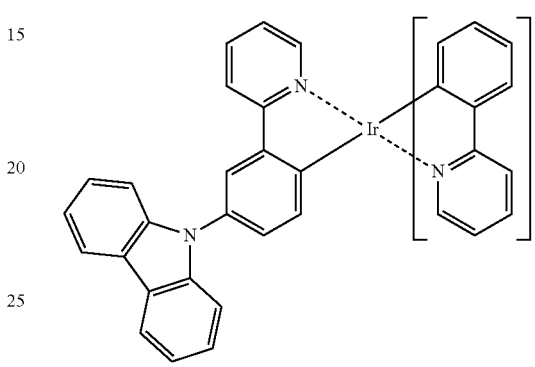

Fluorescent Dopant in Emission Layer

The fluorescent dopant may include an arylamine compound or a styrylamine compound.

In some embodiments, the fluorescent dopant may include a compound represented by Formula 501:

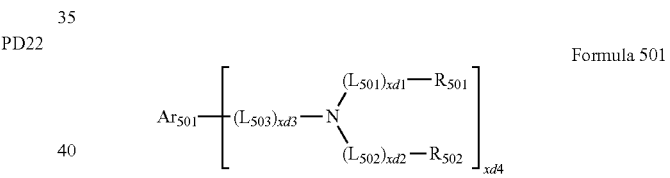

Formula 501 wherein, in Formula 501,

Ar$_{501}$ may be a substituted or unsubstituted C$_5$-C$_{60}$ carbocyclic group or a substituted or unsubstituted C$_1$-C$_{60}$ heterocyclic group, L$_{501}$ to L$_{503}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, R$_{501}$ and R$_{502}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In some embodiments, $Ar_{501}$ in Formula 501 may be selected from a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, in Formula 501, $L_{501}$ to $L_{503}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, in Formula 501, $R_{501}$ and $R_{502}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments are not limited thereto.

In some embodiments, the fluorescent dopant may be selected from Compounds FD1 to FD22:
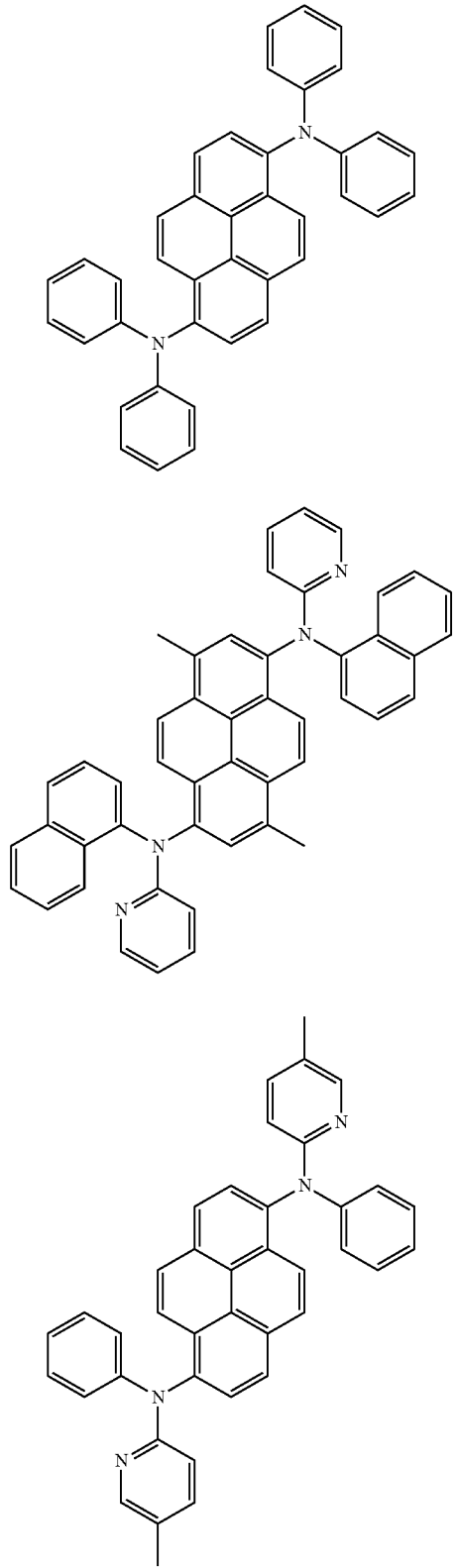
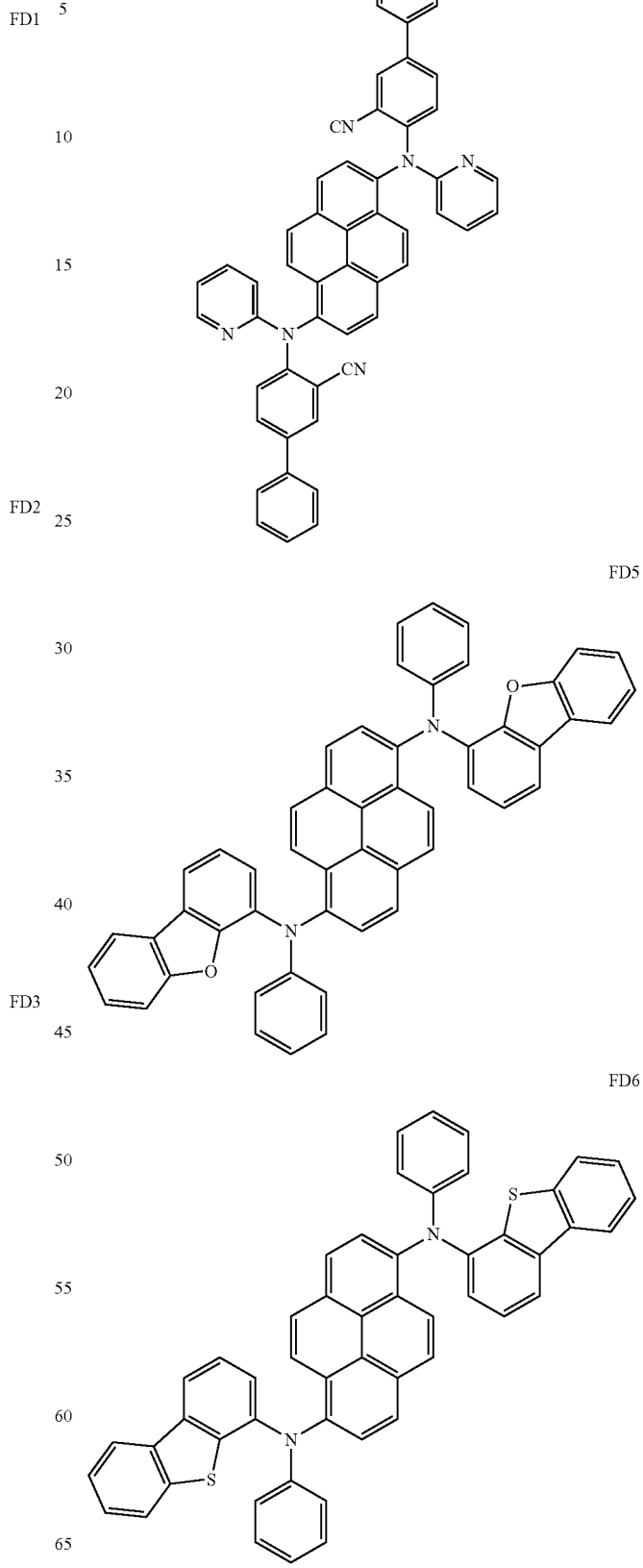

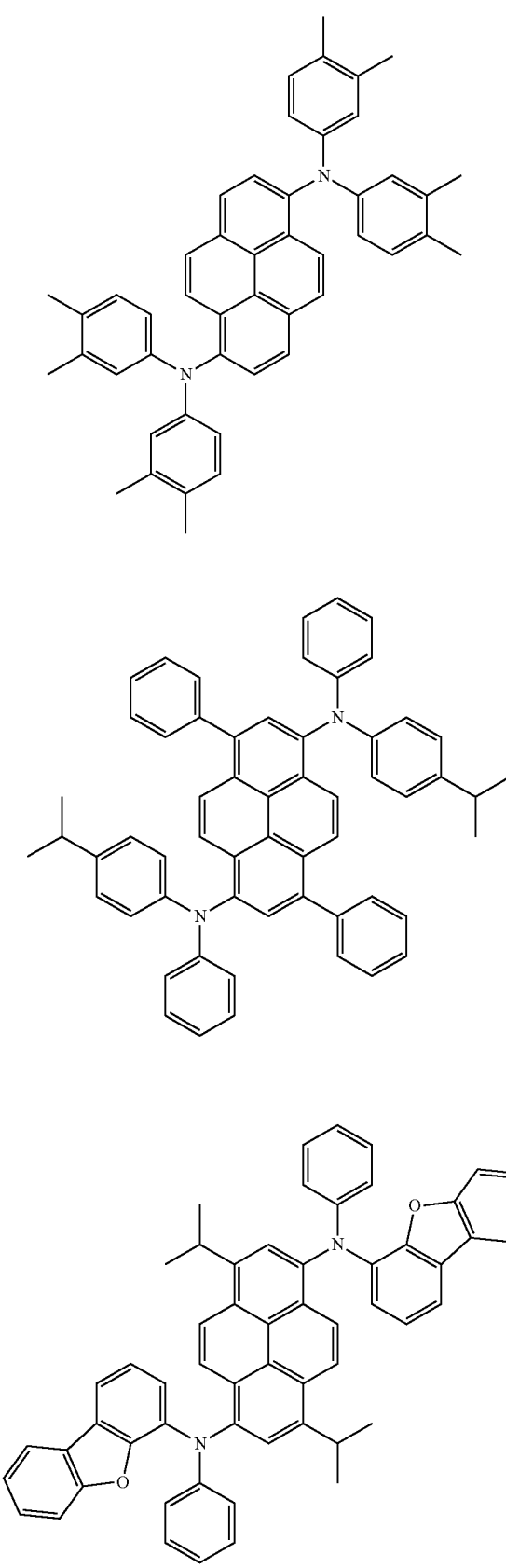
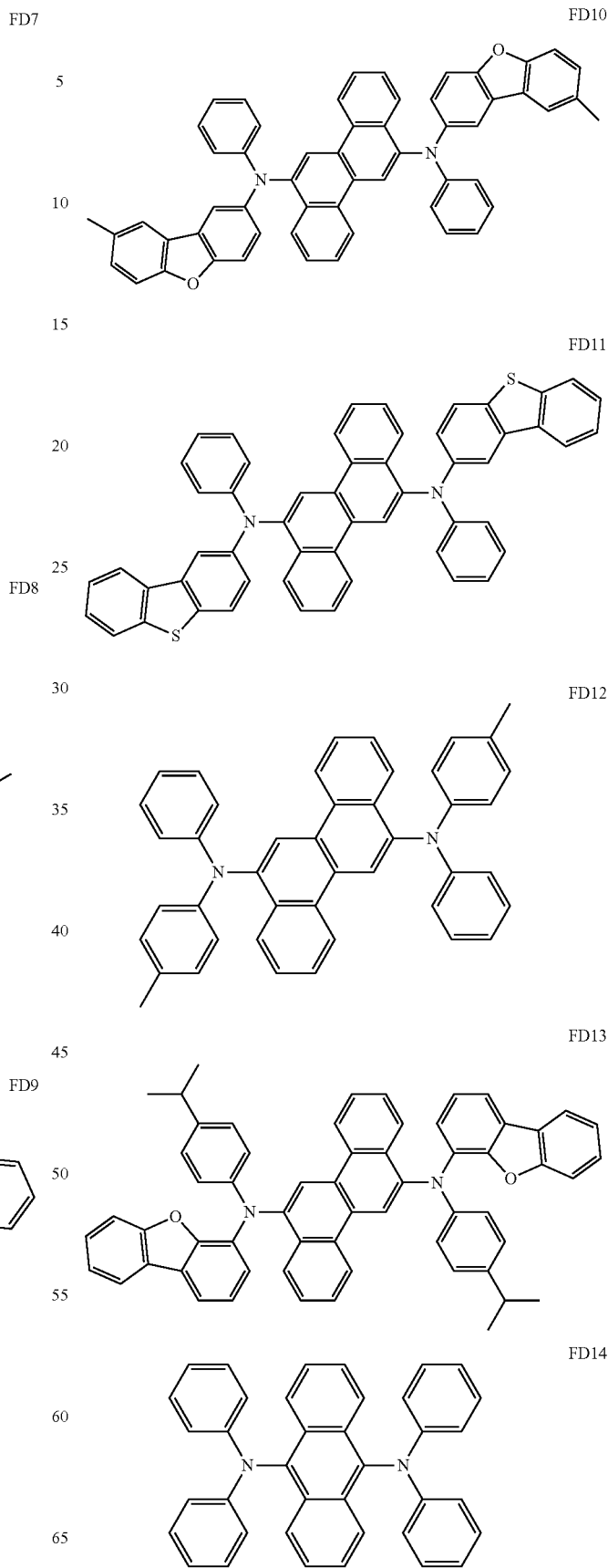

FD15
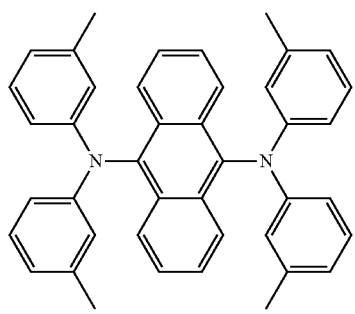
FD16
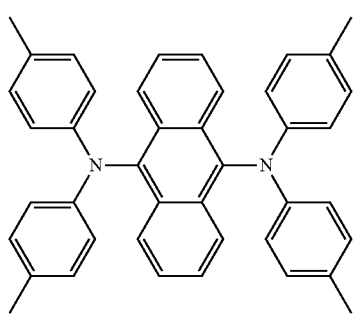
FD17
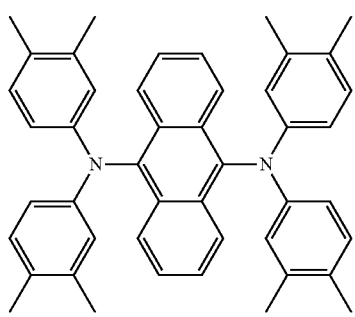
FD18
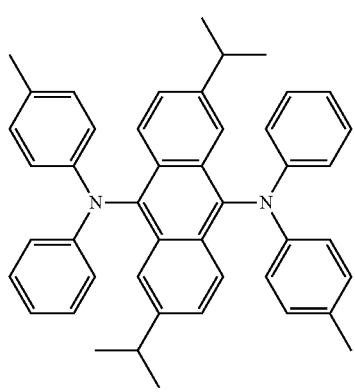
FD19
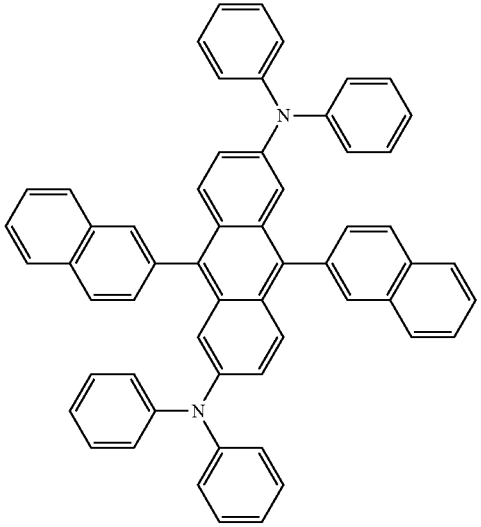
FD20
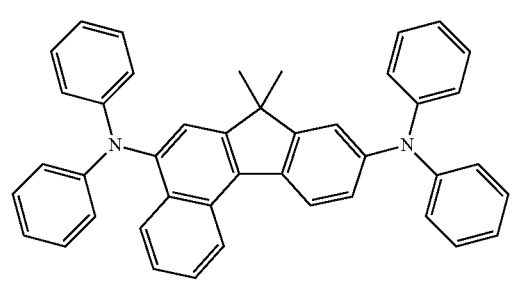
FD21
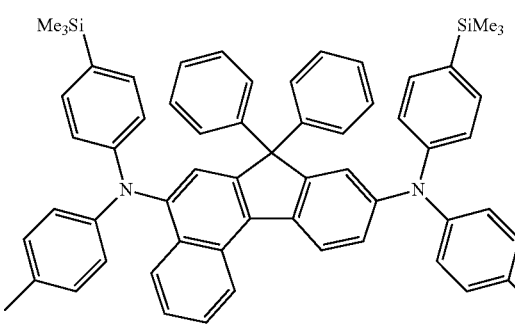
FD22
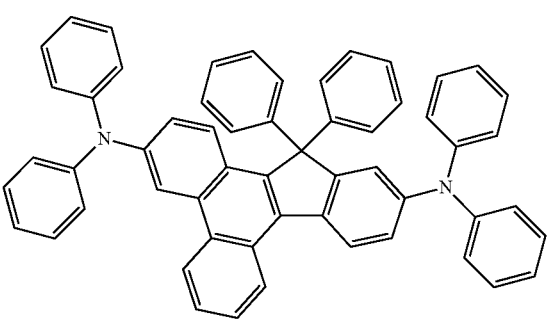
In some embodiments, the fluorescent dopant may be selected from the following compounds, but embodiments are not limited thereto:

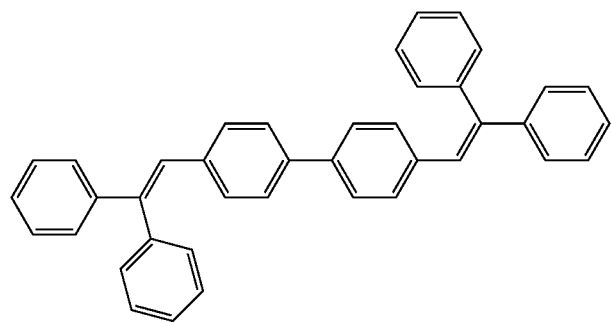

DPVBi

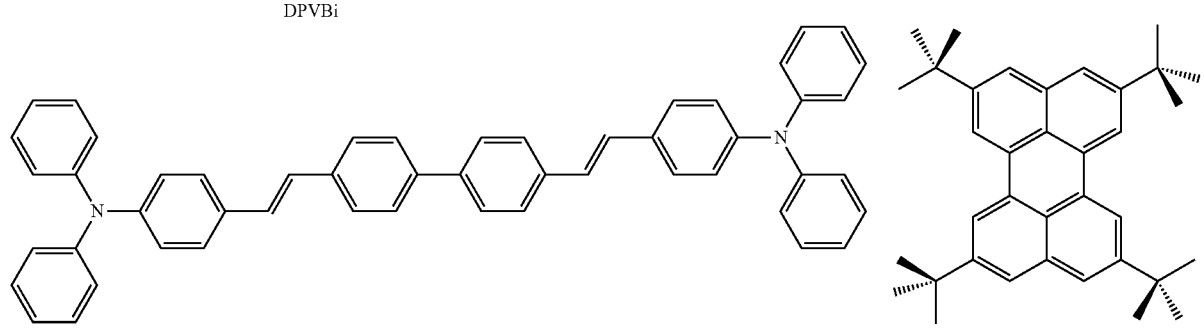

DPAVBi

TBPe

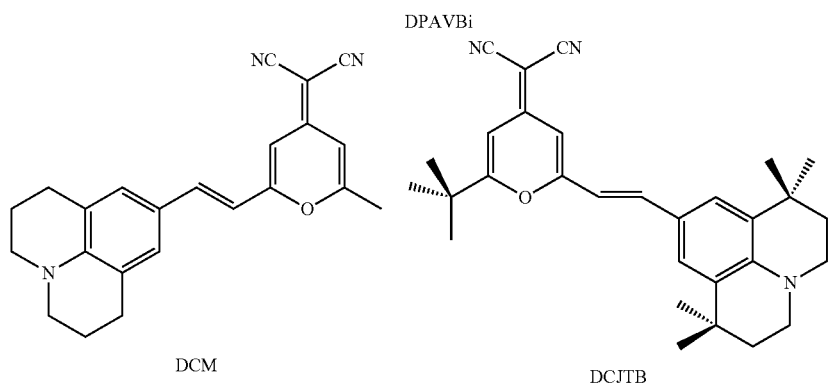

DCM

DCJTB

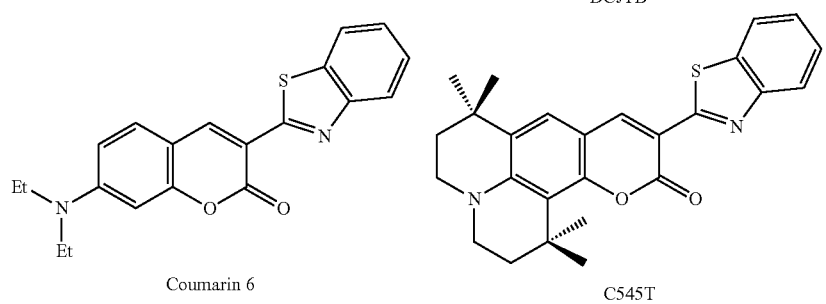

Coumarin 6

C545T

Electron Transport Region in Organic Layer 150

The electron transport region may have i) a single-layered structure including a single layer including a single material, ii) a single-layered structure including a single layer including a plurality of different materials, or iii) a multi-layered structure each having a plurality of layers, each having a plurality of different materials.

The electron transport region may include at least one selected from a buffer layer, a hole blocking layer, an electron control layer, an electron transport layer, and an electron injection layer, but embodiments are not limited thereto.

In some embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order, but embodiments are not limited thereto.

The electron transport region, e.g., a buffer layer, a hole blocking layer, an electron control layer, or an electron transport layer in the electron transport region, may include a metal-free compound. The metal-free compound may include at least one π electron-depleted nitrogen-containing ring.

The term "π electron-depleted nitrogen-containing ring" as used herein refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which at least two 5-membered to 7-membered heteromonocyclic groups, each having at least one *—N=*' moiety, are condensed, or iii) a heteropolycyclic group in which at least one of a 5-membered to 7-membered heteromonocyclic group, each having at least one *—N=*' moiety, is condensed with at least one $C_5$-$C_{60}$ carbocyclic group.

Examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an iso-benzothiazole, a benzoxazole, an isobenzoxazole, a triazole, a tetrazole, an oxadiazole, a triazine, a thiadiazole, an imidazopyridine, an imidazopyrimidine, and an azacarbazole, but embodiments are not limited thereto.

In some embodiments, the electron transport region may include a compound represented by Formula 601:

[Ar$_{601}$]$_{xe11}$-[(L$_{601}$)$_{xe1}$-R$_{601}$]$_{xe21}$      Formula 601 wherein, in Formula 601,

Ar$_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, L$_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_{3-10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, R$_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{601}$)(Q$_{602}$)(Q$_{603}$), —C(=O)(Q$_{601}$), —S(=O)$_2$(Q$_{601}$), and —P(=O)(Q$_{601}$)(Q$_{602}$), wherein Q$_{601}$ to Q$_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of Ar$_{601}$ groups in the number of xe11 and R$_{601}$ groups in the number of xe21 may include the π electron-depleted nitrogen-containing ring.

In some embodiments, Ar$_{601}$ in Formula 601 may be selected from a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si(Q$_{31}$)(Q$_{32}$)(Q$_{33}$), —S(=O)$_2$(Q$_{31}$), and —P(=O)(Q$_{31}$)(Q$_{32}$), wherein Q$_{31}$ to Q$_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or greater, at least two Ar$_{601}$ groups may be bound via a single bond.

In one or more embodiments, Ar$_{601}$ in Formula 601 may be an anthracene group.

In some embodiments, the compound represented by Formula 601 may be represented by Formula 601-1:

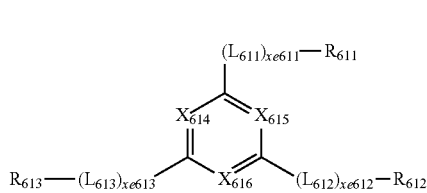

Formula 601-1 wherein, in Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be substantially the same as $L_{601}$ described herein, xe611 to xe613 may each independently be substantially the same as xe1 described herein, $R_{611}$ to $R_{613}$ may each independently be substantially the same as $R_{601}$ described herein, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{611}$ to $L_{613}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In one or more embodiments, in Formulae 601 and 601-1, xe1 and xe611 to xe613, may each independently be 0, 1, or 2.

In one or more embodiments, in Formulae 601 and 601-1, $R_{601}$ and $R_{611}$ to $R_{613}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$),
wherein Q$_{601}$ and Q$_{602}$ may each independently be substantially the same as those described herein.

The electron transport region may include at least one compound selected from Compounds ET1 to ET36, but embodiments are not limited thereto:

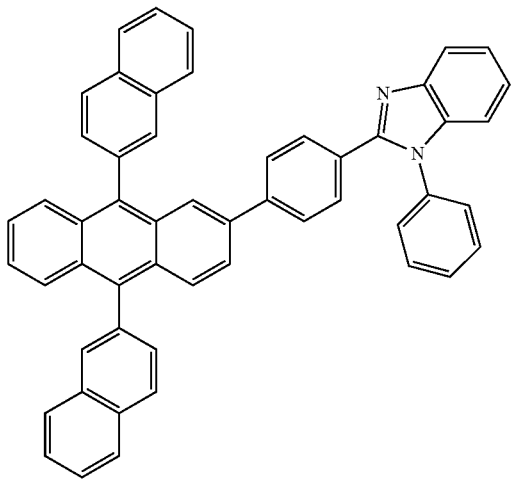

ET1

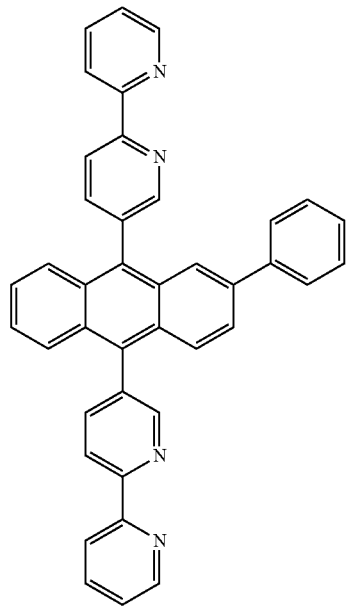

ET2

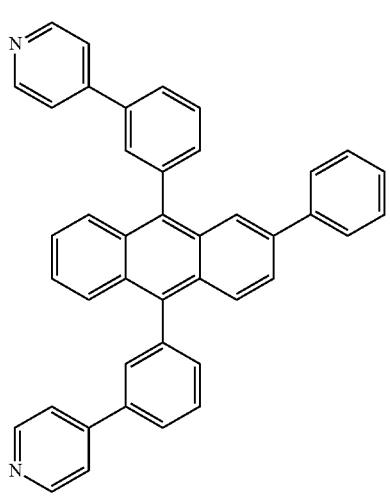

ET3

ET4
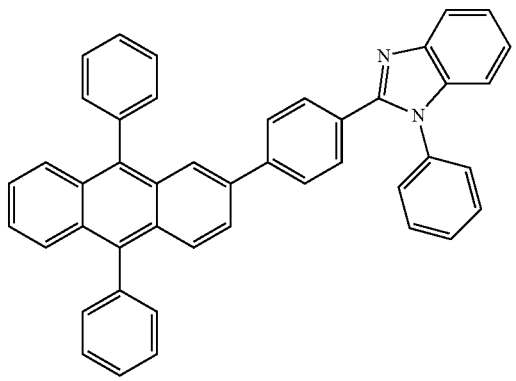
ET5
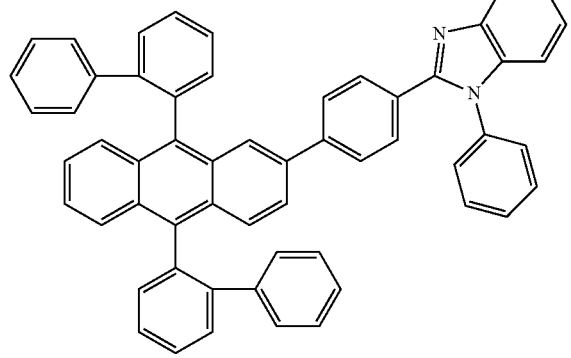
ET6
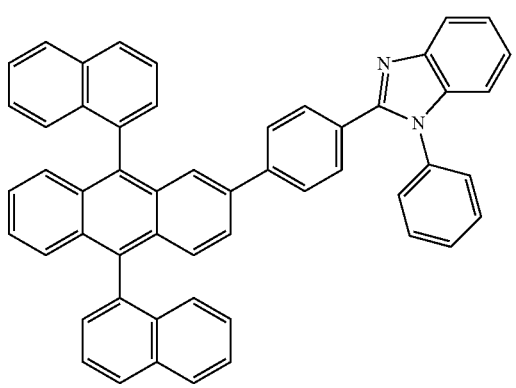
ET7
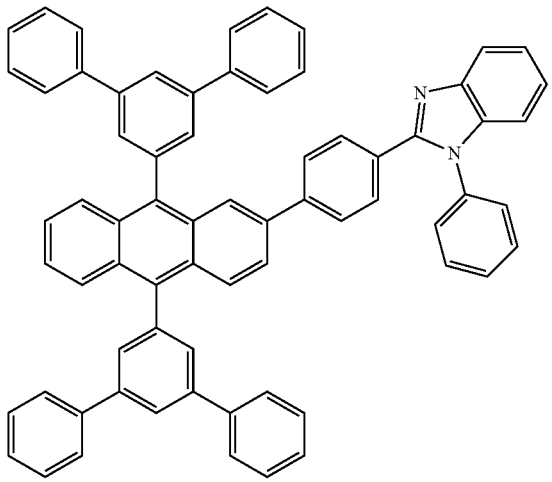
ET8
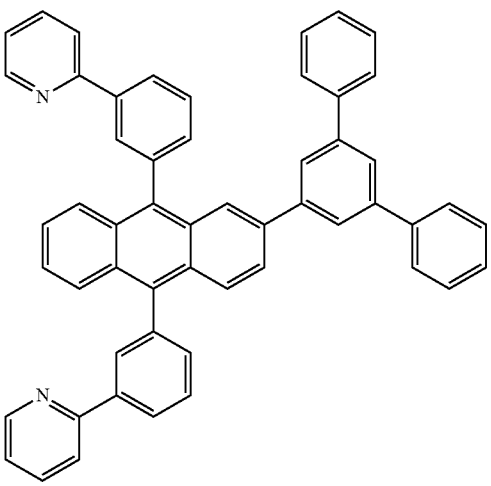
ET9

ET10
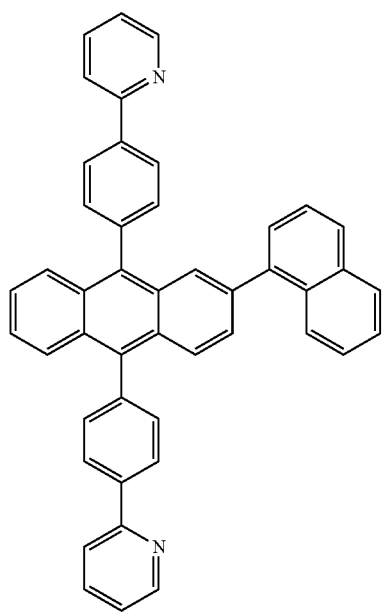
ET11
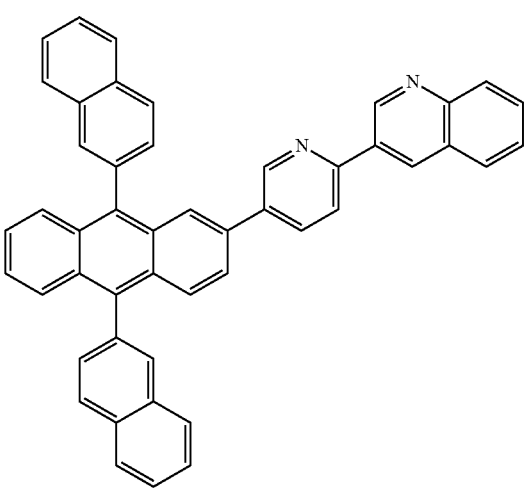
ET12
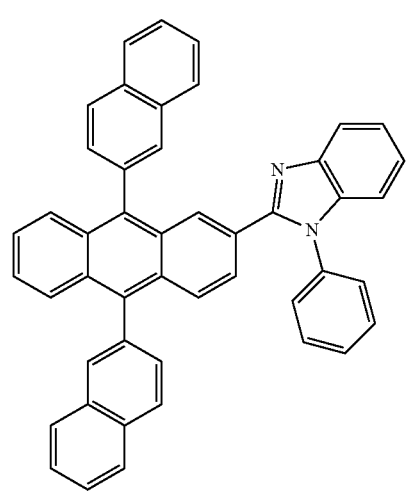
ET13
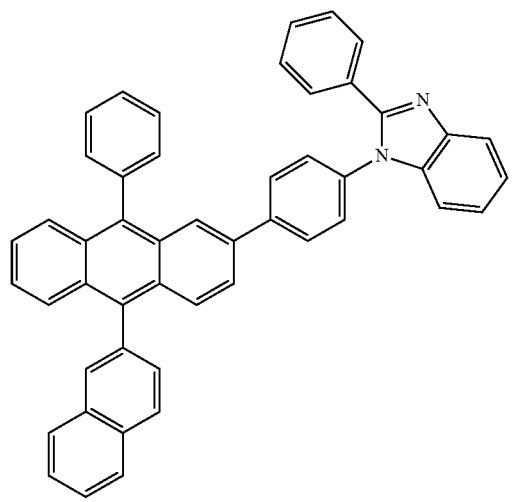
ET14
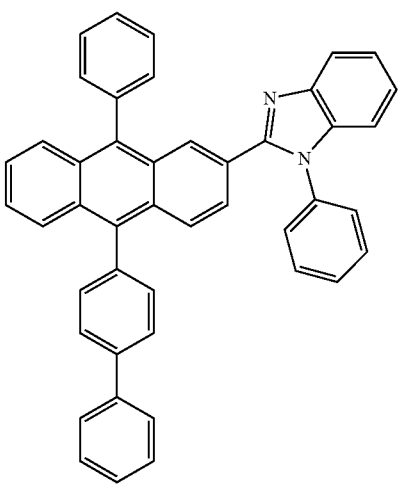
ET15

ET16
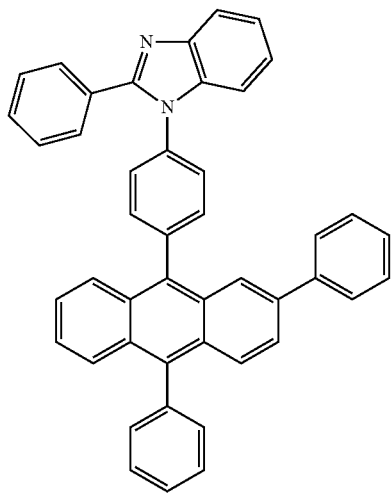
ET17
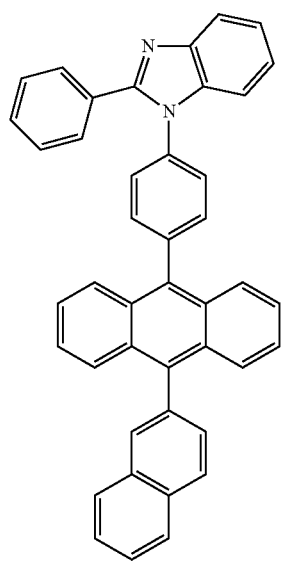
ET18
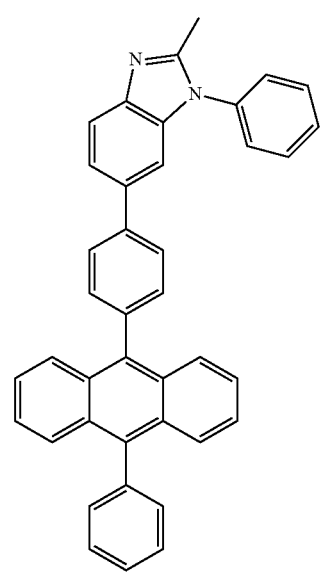
ET19
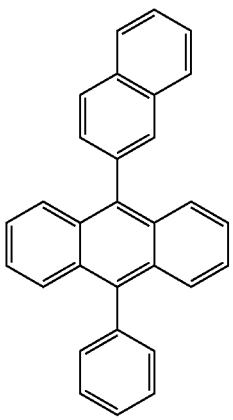
ET20
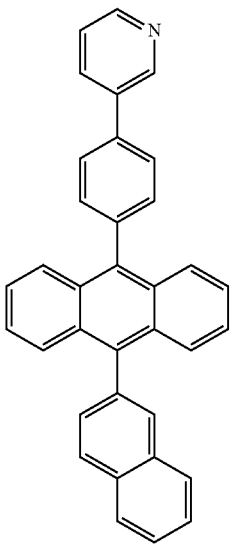
ET21
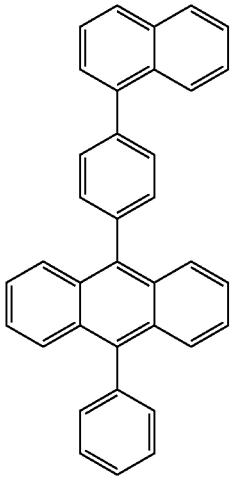

ET22
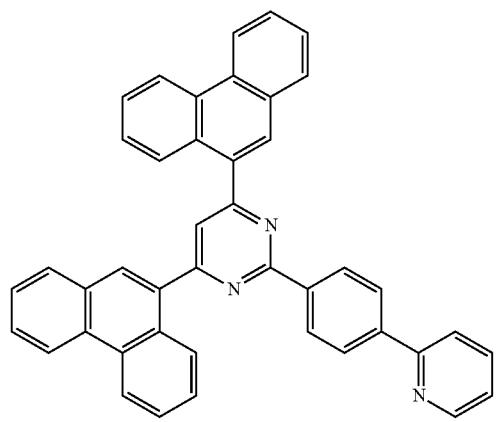
ET25
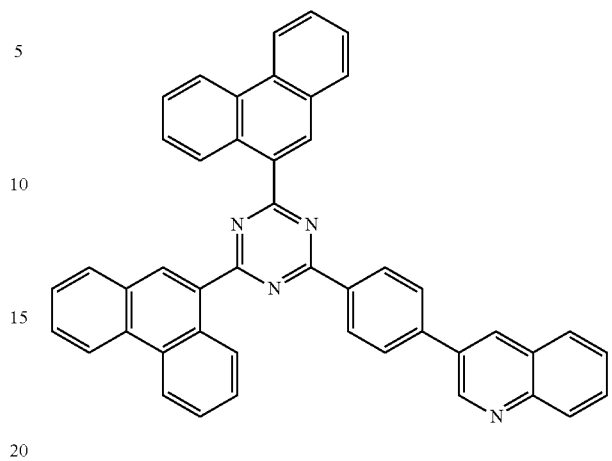
ET23
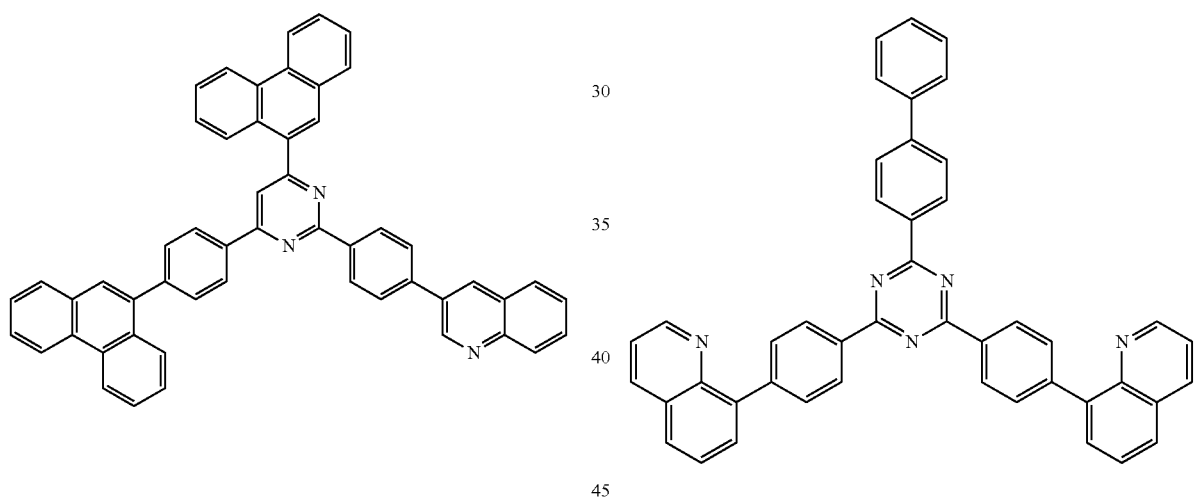
ET26
ET24
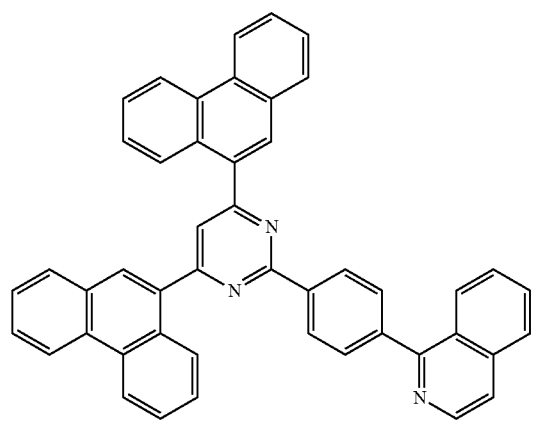
ET27
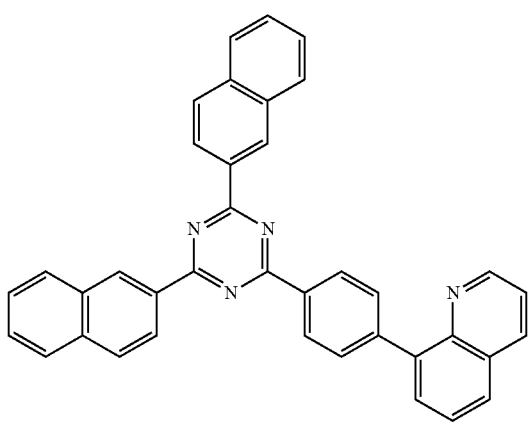

ET28
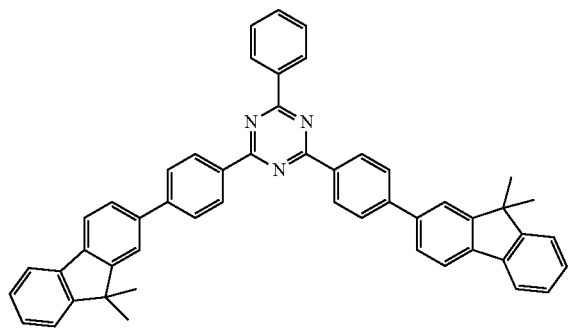
ET29
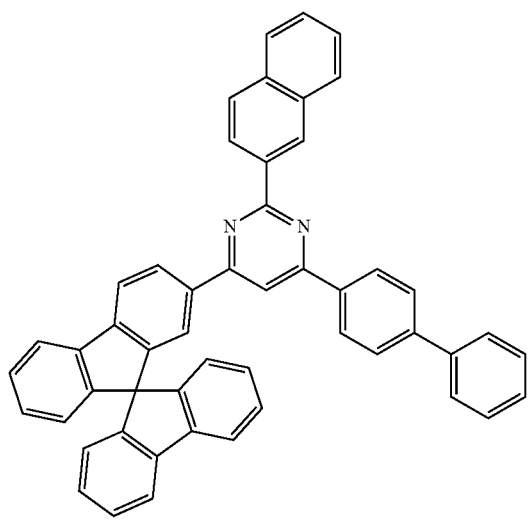
ET30
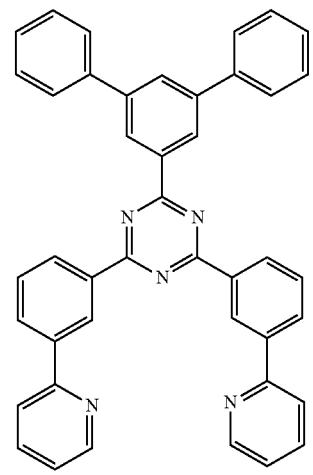
ET31
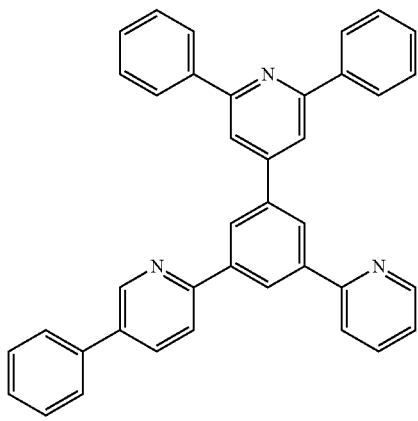
ET32
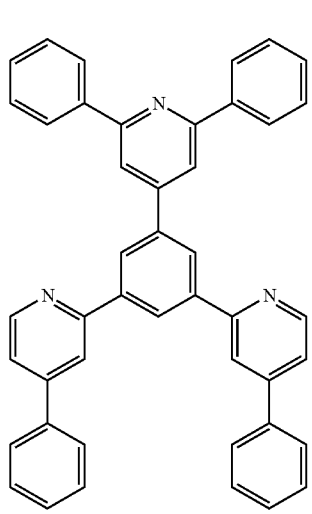
ET33
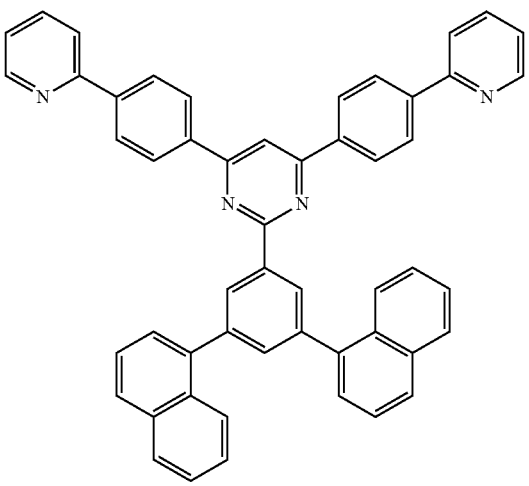

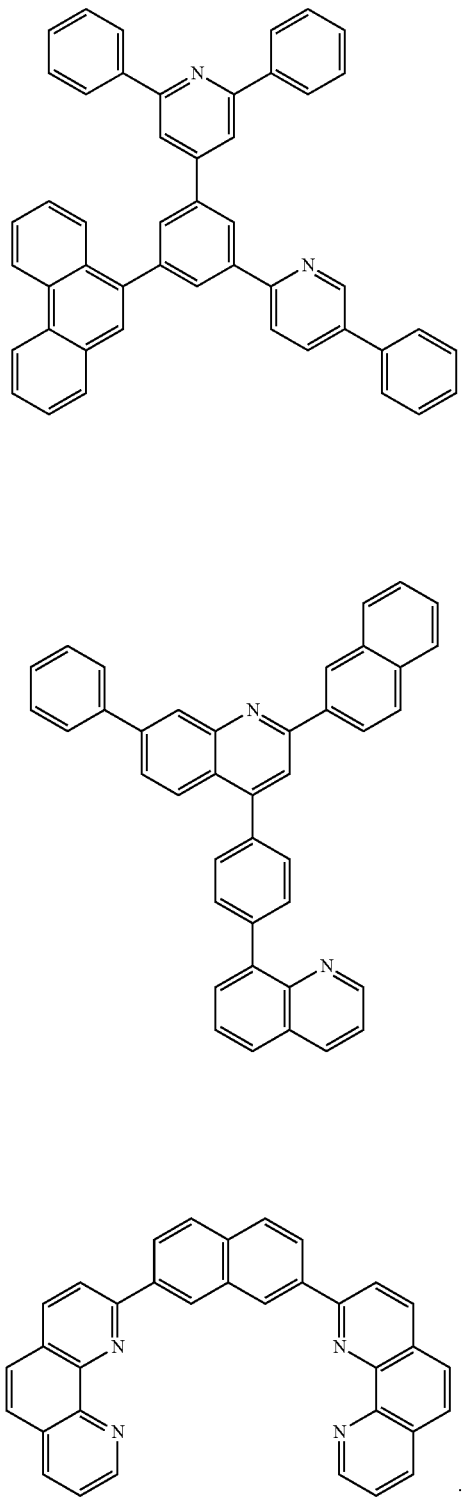

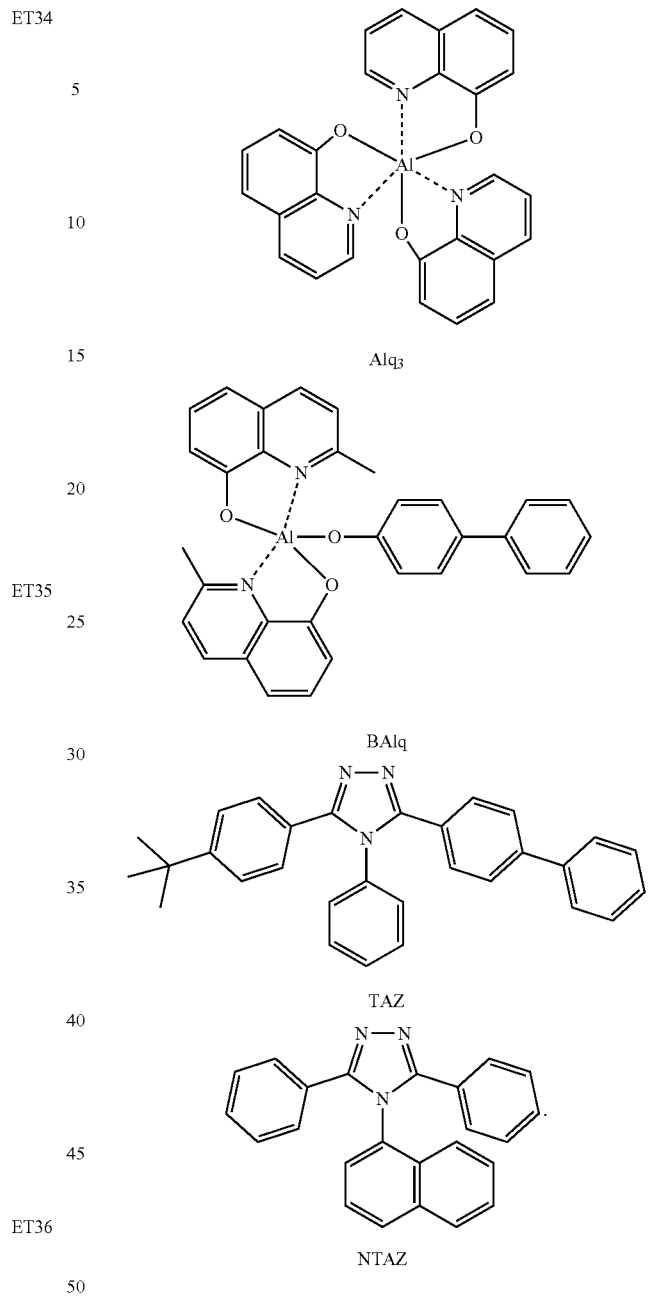

In some embodiments, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ:

The thickness of the buffer layer, the hole blocking layer, or the electron control layer may each independently be in a range of about 20 Å to about 1,000 Å, and in some embodiments, about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport region (e.g., the electron transport layer in the electron transport region) may further include, in addition to the materials described above, a material including metal.

The material including metal may include at least one selected from an alkali metal complex and an alkaline earth metal complex. The alkali metal complex may include a metal ion selected from a lithium (Li) ion, a sodium (Na) ion, a potassium (K) ion, a rubidium (Rb) ion, and a cesium (Cs) ion. The alkaline earth metal complex may include a metal ion selected from a beryllium (Be) ion, a magnesium (Mg) ion, a calcium (Ca) ion, an strontium (Sr) ion, and a barium (Ba) ion. Each ligand coordinated with the metal ion of the alkali metal complex and the alkaline earth metal complex may independently be selected from a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene, but embodiments are not limited thereto.

For example, the material including metal may include a Li complex. The Li complex may include, e.g., Compound ET-D1 (lithium quinolate, LiQ) or Compound ET-D2:

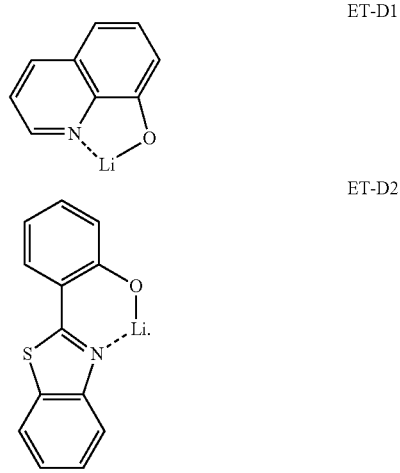

ET-D1

ET-D2

The electron transport region may include an electron injection layer that facilitates injection of electrons from the second electrode 190. The electron injection layer may be in direct contact with the second electrode 190.

The electron injection layer may have i) a single-layered structure including a single layer including a single material, ii) a single-layered structure including a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be selected from Li, Na, K, Rb, and Cs. In one embodiment, the alkali metal may be Li, Na, or Cs. In one or more embodiments, the alkali metal may be Li or Cs, but embodiments are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth metal compound, and the rare earth metal compound may each independently be selected from oxides and halides (e.g., fluorides, chlorides, bromides, or iodines) of the alkali metal, the alkaline earth metal, and the rare earth metal, respectively.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI, but embodiments are not limited thereto.

The alkaline earth metal compound may be selected from alkaline earth metal compounds such as BaO, SrO, CaO, $Ba_xSr_{1-x}O$ (where $0<x<1$), and $Ba_xCa_{1-x}O$ (where $0<x<1$). In one embodiment, the alkaline earth metal compound may be selected from BaO, SrO, and CaO, but embodiments are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments are not limited thereto.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene, but embodiments are not limited thereto.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

Second Electrode 190

The second electrode 190 may be disposed on the organic layer 150. The second electrode 190 may be a cathode that is an electron injection electrode. In this regard, a material for forming the second electrode 190 may be a material having a low work function, for example, a metal, an alloy, an electrically conductive compound, or a combination thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
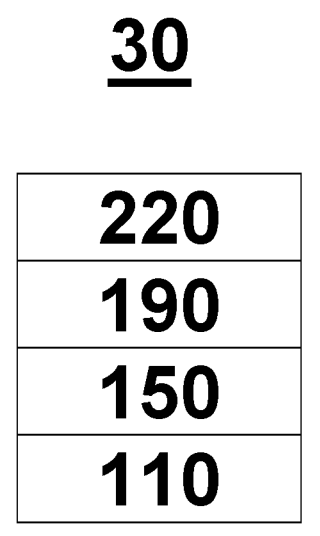
Figure 4:
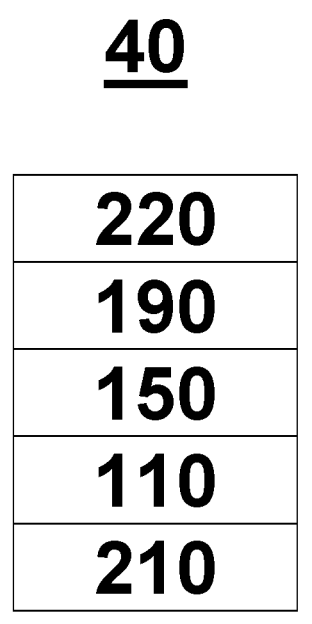

Description of FIGS. 2 to 4

Figure 2:
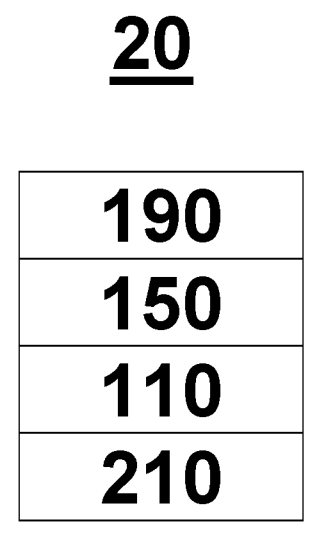

Referring to FIG. 2, an organic light-emitting device 20 has a first capping layer 210, the first electrode 110, the organic layer 150, and the second electrode 190 structure, wherein the layers are sequentially stacked in this stated order. Referring to FIG. 3, an organic light-emitting device 30 has the first electrode 110, the organic layer 150, the second electrode 190, and a second capping layer 220 structure, wherein the layers are sequentially stacked in this stated order. Referring to FIG. 4, an organic light-emitting device 40 has the first capping layer 210, the first electrode 110, the organic layer 150, the second electrode 190, and the second capping layer 220 structure, wherein the layers are stacked in this stated order.

The first electrode 110, the organic layer 150, and the second electrode 190 illustrated in FIGS. 2 to 4 may be substantially the same as those illustrated in FIG. 1.

In the organic light-emitting devices 20 and 40, light emitted from the emission layer in the organic layer 150 may pass through the first electrode 110 (which may be a semi-transmissive electrode or a transmissive electrode) and through the first capping layer 210 to the outside. In the organic light-emitting devices 30 and 40, light emitted from the emission layer in the organic layer 150 may pass through the second electrode 190 (which may be a semi-transmissive electrode or a transmissive electrode) and through the second capping layer 220 to the outside.

The first capping layer 210 and the second capping layer 220 may improve external light-emission efficiency based on the principle of constructive interference.

The first capping layer 210 and the second capping layer 220 may each independently be a capping layer including an organic material, an inorganic capping layer including an inorganic material, or a composite capping layer including an organic material and an inorganic material.

At least one of the first capping layer 210 and the second capping layer 220 may each independently include at least one material selected from carbocyclic compounds, heterocyclic compounds, amine-based compounds, porphine derivatives, phthalocyanine derivatives, naphthalocyanine derivatives, alkali metal complexes, and alkaline earth metal complexes. The carbocyclic compound, the heterocyclic compound, and the amine-based compound may optionally be substituted with a substituent containing at least one element selected from O, N, S, Se, Si, F, Cl, Br, and I. In one embodiment, at least one of the first capping layer 210 and the second capping layer 220 may each independently include an amine-based compound.

In one or more embodiments, at least one of the first capping layer 210 and the second capping layer 220 may each independently include a compound represented by Formula 201 or a compound represented by 202.

In one or more embodiments, at least one of the first capping layer 210 and the second capping layer 220 may each independently include a compound selected from Compounds HT28 to HT33 and Compound CP1 to CP5, but embodiments are not limited thereto:

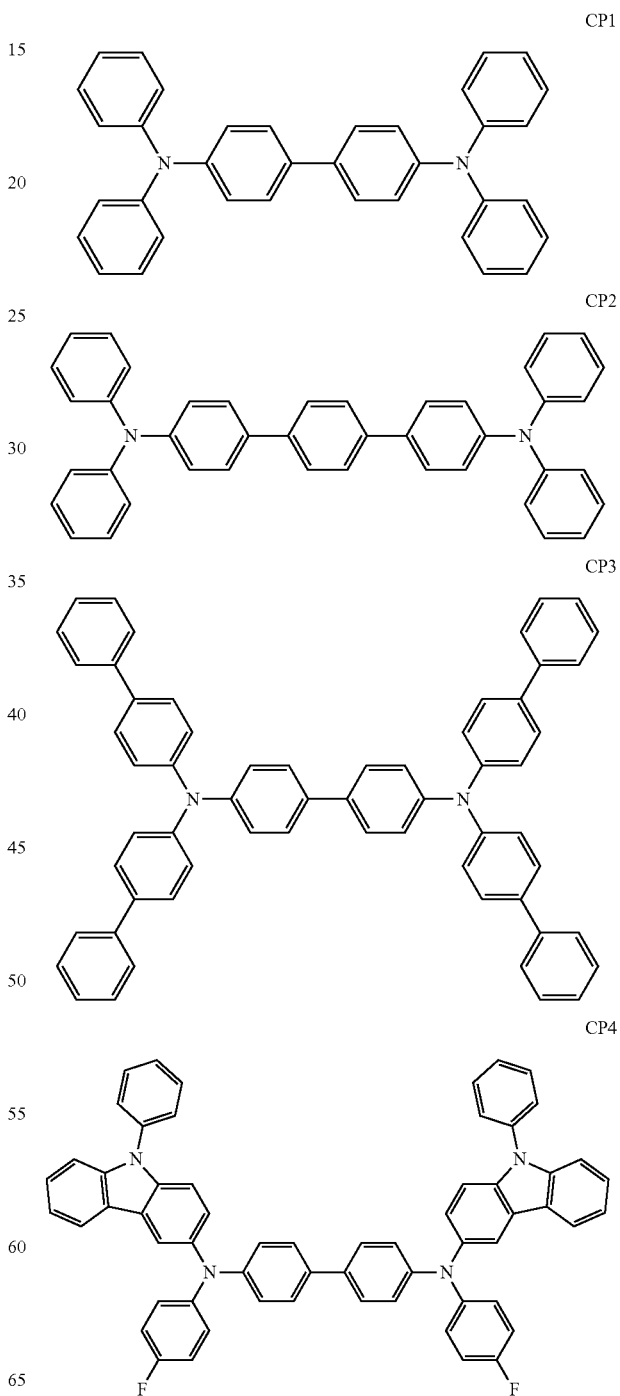

CP5

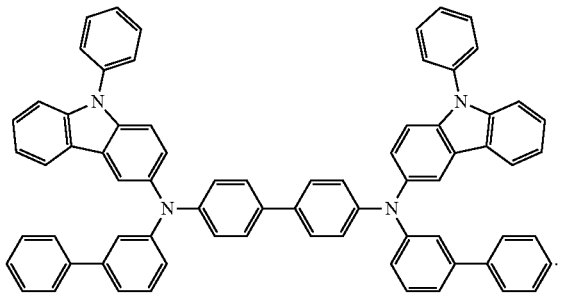

Hereinbefore, the organic light-emitting device has been described with reference to FIGS. 1 to 4, but embodiments are not limited thereto.

The layers constituting the hole transport region, the emission layer, and the layers constituting the electron transport region may be formed in a specific region by using one or more suitable methods such as vacuum deposition, spin coating, casting, Langmuir-Blodgett (LB) deposition, ink-jet printing, laser printing, and laser-induced thermal imaging.

When the layers constituting the hole transport region, the emission layer, and the layers constituting the electron transport region are each formed by vacuum deposition, the vacuum deposition may be performed at a deposition temperature in a range of about 100° C. to about 500° C. at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed.

When the layers constituting the hole transport region, the emission layer, and the layers constituting the electron transport region are each formed by spin coating, the spin coating may be performed at a coating rate of about 2,000 revolutions per minute (rpm) to about 5,000 rpm and at a heat treatment temperature of about 80° C. to about 200° C., depending on the material to be included in each layer and the structure of each layer to be formed.

General Definitions of Substituents

The term "$C_1$-$C_{60}$ alkyl group" as used herein refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having substantially the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is a $C_1$-$C_{60}$ alkyl group). Examples thereof include a methoxy group, an ethoxy group, and an isopropyloxy group.

The term "$C_3$-$C_{10}$ cycloalkyl group" as used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group including at least one heteroatom selected from N, O, Si, P, and S as a ring-forming atom and 1 to 10 carbon atoms. Examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Examples thereof include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, Si, P, and S as a ring-forming atom, 1 to 10 carbon atoms, and at least one double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein refers to a monovalent group having a heterocyclic aromatic system having at least one heteroatom selected from N, O, Si, P, and S as a ring-forming atom and 1 to 60 carbon atoms. The term "$C_1$-$C_{60}$ heteroarylene group" as used herein refers to a divalent group having a heterocyclic aromatic system having at least one heteroatom selected from N, O, Si, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused.

The term "$C_6$-$C_{60}$ aryloxy group" as used herein refers to a group represented by —$OA_{102}$ (where $A_{102}$ is a $C_6$-$C_{60}$ aryl group). The term "$C_6$-$C_{60}$ arylthio group" as used herein refers to a group represented by —$SA_{103}$ (where $A_{103}$ is a $C_6$-$C_{60}$ aryl group).

The term "monovalent non-aromatic condensed polycyclic group" as used herein refers to a monovalent group that has two or more rings condensed and only carbon atoms as ring forming atoms (e.g., 8 to 60 carbon atoms), wherein the entire molecular structure is non-aromatic. An example of the monovalent non-aromatic condensed polycyclic group may be a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings and at least one heteroatom selected from N, O, Si, P, and S, in addition to carbon atoms (e.g., 1 to 60 carbon atoms), as a ring-forming atom, wherein the entire molecular structure is non-aromatic. An example of the monovalent non-aromatic condensed heteropolycyclic group is a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{60}$ carbocyclic group" as used herein refers to a monocyclic or polycyclic group having 5 to 60 carbon atoms only as ring-forming atoms. The $C_5$-$C_{60}$ carbocyclic group may be an aromatic carbocyclic group or a non-aromatic carbocyclic group. The term "$C_5$-$C_{60}$ carbocyclic group" as used herein refers to a ring (such as, a benzene group), a monovalent group (e.g., a phenyl group), or a divalent group (e.g., a phenylene group). In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having substantially the same structure as the $C_1$-$C_{60}$ carbocyclic group, except that at least one heteroatom selected from N, O, Si, P, and S is used as a ring-forming atom, in addition to carbon atoms (e.g., 1 to 60 carbon atoms).

In the present specification, at least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein represents a phenyl group. The term "Me" as used herein represents a methyl group. The term "Et" as used herein represents an ethyl group. The term "ter-Bu" or "Bu$^t$" as used herein represents a tert-butyl group. The term "OMe" as used herein represents a methoxy group.

The term "biphenyl group" as used herein refers to a phenyl group substituted with a phenyl group. In other words, the "biphenyl group" may be a substituted phenyl group having a $C_6$-$C_{60}$ aryl group as a substituent.

The term "terphenyl group" as used herein refers to a phenyl group substituted with a biphenyl group. In other words, the "terphenyl group" may be a substituted phenyl group having a $C_6$-$C_{60}$ aryl group substituted with a $C_6$-$C_{60}$ aryl group as a substituent.

The symbols * and *' as used herein, unless defined otherwise, refer to a binding site to an adjacent atom in a corresponding formula.

Hereinafter, compounds and an organic light-emitting device according to one or more embodiments will be described in more detail with reference to Synthesis Examples and Examples. The wording "B was used instead of A" used in describing Synthesis Examples refers to that an identical number of molar equivalents of B was used in place of A.

EXAMPLES

Synthesis Example 1: Synthesis of Compound 1

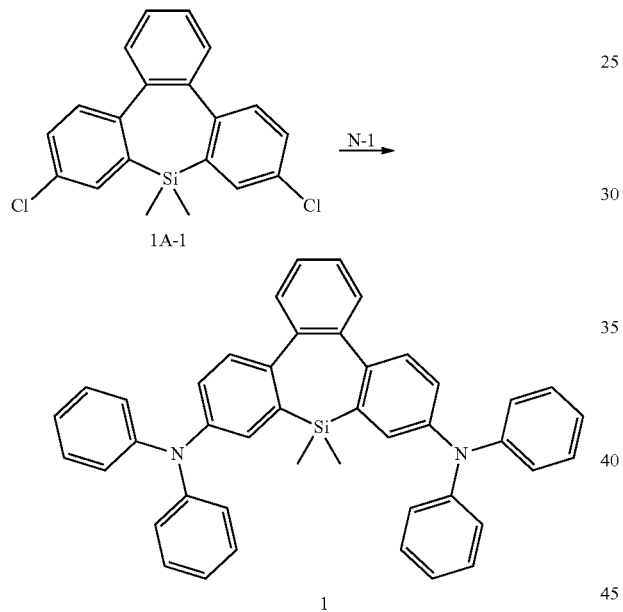

3.55 grams (g) of Compound 1A-1 (10.0 mmol), 3.55 g of amine compound N-1 (21.0 mmol), 0.15 g of $Pd_2(dba)_3$ (0.17 mmol), 0.03 g of $PtBu_3$ (0.17 mmol), and 1.2 g of NaOtBu (12.5 mmol) were dissolved in 70 mL of toluene. Then, the mixture was stirred at a temperature of 120° C. for 8 hours. The reaction solution was cooled to room temperature. Then, an organic layer was extracted therefrom three times using saline water, water, and diethylether. The obtained organic layer was dried by using magnesium sulfate ($MgSO_4$), and a solvent was removed therefrom by evaporation. The obtained residue was separated and purified through silica gel column chromatography to thereby obtain 4.59 g of Compound 1 (yield: 74%). The obtained compound was identified by using liquid chromatography-mass spectrometry (LC-MS) and $^1H$ nuclear magnetic resonance (NMR).

C44H36N2Si: M+1 620.3, $^1$H NMR (500 MHz, $CDCl_3$) δ=7.96 (d, 2H), 7.83 (d, 2H), 7.60 (d, 2H), 7.51-7.47 (m, 4H), 7.24-7.20 (m, 8H), 7.08-7.00 (m, 12H), 0.66 (s, 6H)

Synthesis Example 2: Synthesis of Compound 17

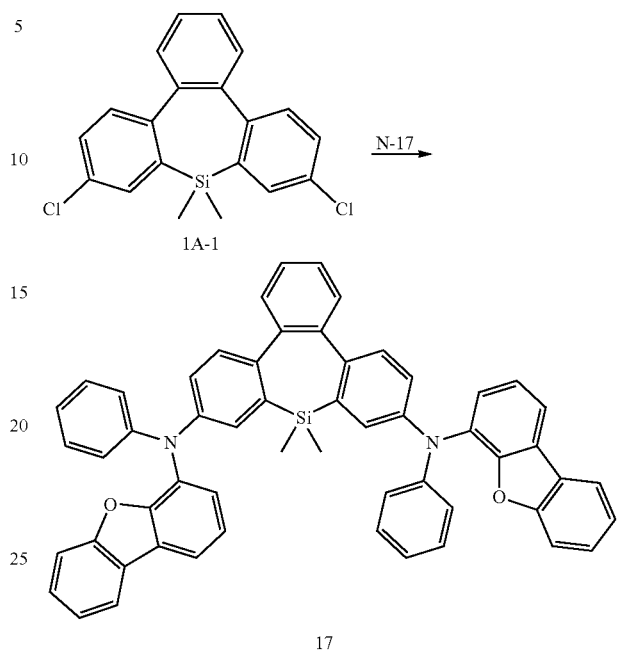

6.65 g of Compound 17 was obtained in substantially the same manner as in Synthesis Example 1, except that amine compound N-17 was used instead of amine compound N-1 (yield: 83%). The obtained compound was identified by using LC-MS and $^1$H NMR.

C56H40N2O2Si: M+1 800.3, $^1$H NMR (500 MHz, $CDCl_3$) δ=7.98-7.96 (m, 4H), 7.83 (d, 2H), 7.64-7.24 (m, 20H), 7.08-7.00 (m, 8H), 0.69 (s, 6H)

Synthesis Example 3: Synthesis of Compound 73

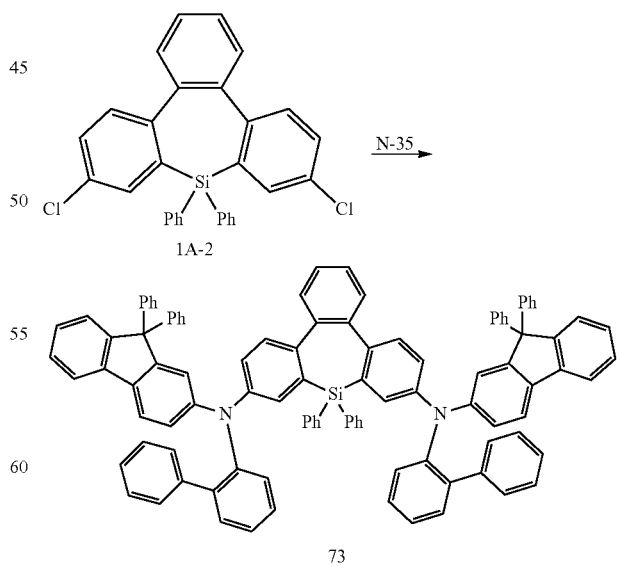

11.0 g of Compound 73 was obtained in substantially the same manner as in Synthesis Example 1, except that Compound 1A-2 was used instead of Compound 1A-1, and amine compound N-35 was used instead of amine compound N-1 (yield: 80%). The obtained compound was identified by using LC-MS and $^1$H NMR.

C104H72N2Si: M+1 1377.8, $^1$H NMR (500 MHz, CDCl$_3$) δ=8.1 (d, 2H), 7.96-7.90 (m, 4H), 7.83 (d, 2H), 7.56-7.08 (m, 64H)

Synthesis Example 4: Synthesis of Compound 172

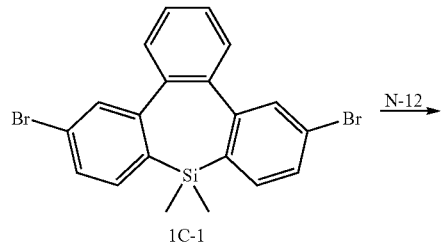

1C-1

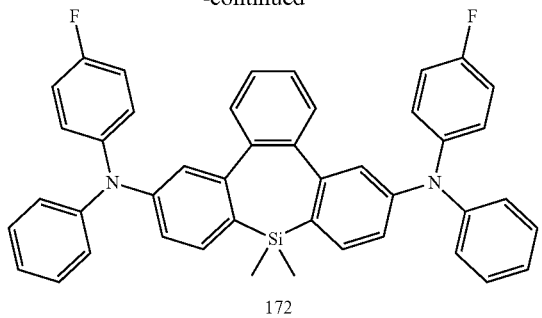

172

5.71 g of Compound 172 was obtained in substantially the same manner as in Synthesis Example 1, except that Compound 1C-1 was used instead of Compound 1A-1, and amine compound N-12 was used instead of amine compound N-1 (yield: 87%). The obtained compound was identified by using LC-MS and $^1$H NMR.

C44H34N2F2Si: M+1 656.3, $^1$H NMR (500 MHz, CDCl$_3$) δ=7.96 (d, 2H), 7.61-7.60 (m, 4H), 7.38-7.37 (m, 4H), 7.24-7.00 (m, 18H), 0.99 (s, 6H)

Synthesis Example 5: Synthesis of Compound 189

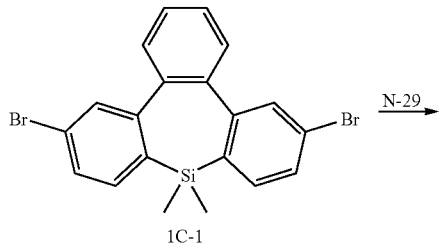

1C-1

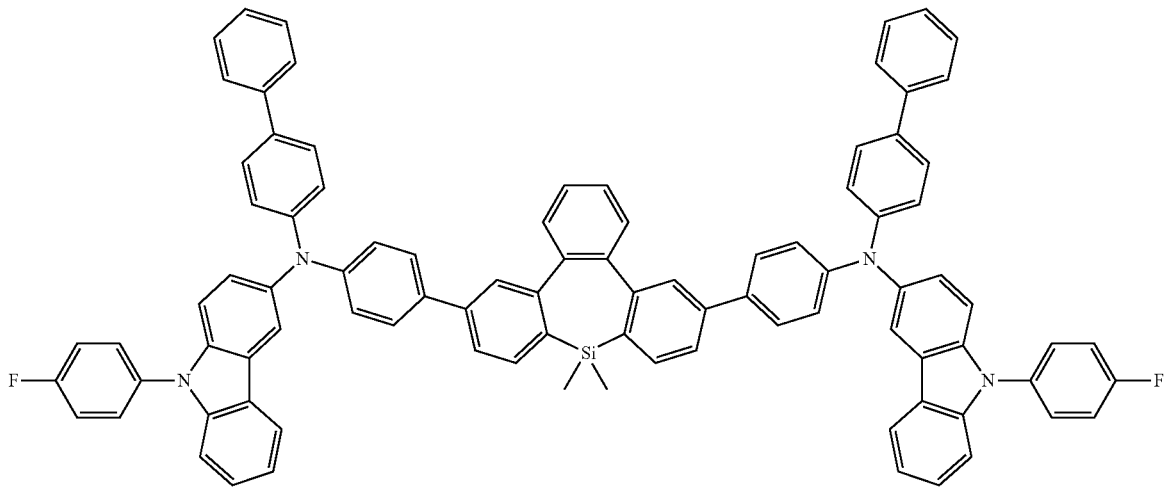

189

Compound 1C-1, boronic acid of amine compound N-29, Pd(PPh$_3$)$_4$, and K$_2$CO$_3$ were added to a mixture of tetrahydrofuran and water. Subsequently, the resulting mixture was stirred at a temperature of 100° C. for 4 hours. The reaction solution was cooled to room temperature, washed with saline water, and then, an organic layer was extracted therefrom three times using diethylether. The obtained organic layer was dried by using MgSO$_4$, and a solvent was removed therefrom by evaporation. The obtained residue was separated and purified through silica gel column chromatography to thereby obtain 10.5 g of Compound 189 (yield: 81%). The obtained compound was identified by using LC-MS and $^1$H NMR.

C92H64F2N4Si: M+1 1290.5, $^1$H NMR (500 MHz, CDCl$_3$) δ=8.55 (d, 1H), 8.19 (d, 1H), 8.04-7.84 (m, 10H), 7.75-7.71 (m, 8H), 7.58-7.34 (m, 34H), 7.20-7.16 (m, 2H), 6.48 (d, 2H), 0.84 (s, 6H)

Synthesis Example 6: Synthesis of Compound 671

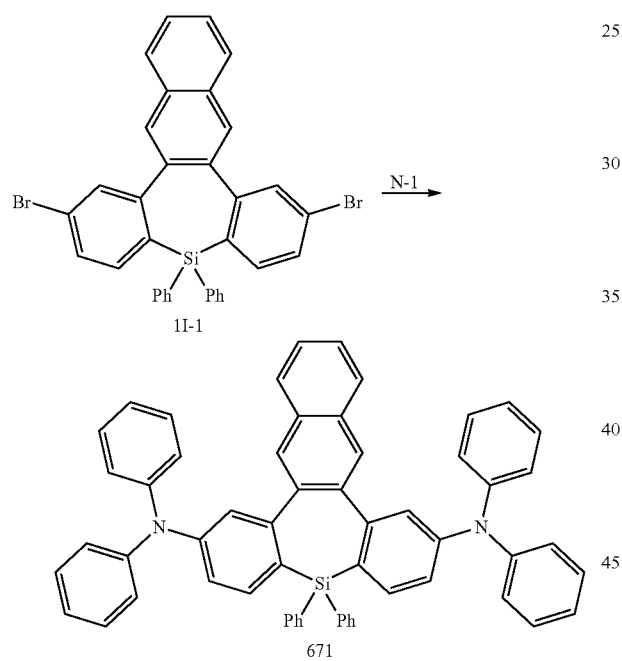

7.16 g of Compound 671 was obtained in substantially the same manner as in Synthesis Example 1, except that Compound 11-1 was used instead of amine compound 1A-1 (yield: 90%). The obtained compound was identified by using LC-MS and $^1$H NMR.

C58H42N2Si: M+1 794.3, $^1$H NMR (500 MHz, CDCl$_3$) δ=8.57 (s, 2H), 8.15 (d, 2H), 7.64-7.61 (m, 4H), 7.38-7.36 (m, 14H), 7.24-7.22 (m, 8H), 7.08-7.00 (m, 12H)

Example 1

A 15 Ohms per square centimeter (Ω/cm$_2$) (1,200 Å) ITO glass substrate (available from Corning Inc.) was cut to a size of 50 millimeters (mm)×50 mm×0.7 mm, sonicated in isopropyl alcohol and pure water for 5 minutes in each solvent, and cleaned by exposure to ultraviolet rays and ozone for 30 minutes so as to use the ITO glass substrate as a substrate and an anode. Then, the glass substrate was mounted on a vacuum-deposition device.

2-TNATA was vacuum-deposited on the ITO anode formed on the glass substrate to form a hole injection layer having a thickness of about 600 Å. Compound 1 was then vacuum-deposited on the hole injection layer to form a hole transport layer having a thickness of about 300 Å.

9,10-di-naphthalene-2-yl-anthracene (ADN), which is a host, and N,N,N',N'-tetraphenyl-pyrene-1,6-diamine (TPD), which is a dopant, were co-deposited on the hole transport layer at a weight ratio of about 98:2, thereby forming an emission layer having a thickness of about 300 Å.

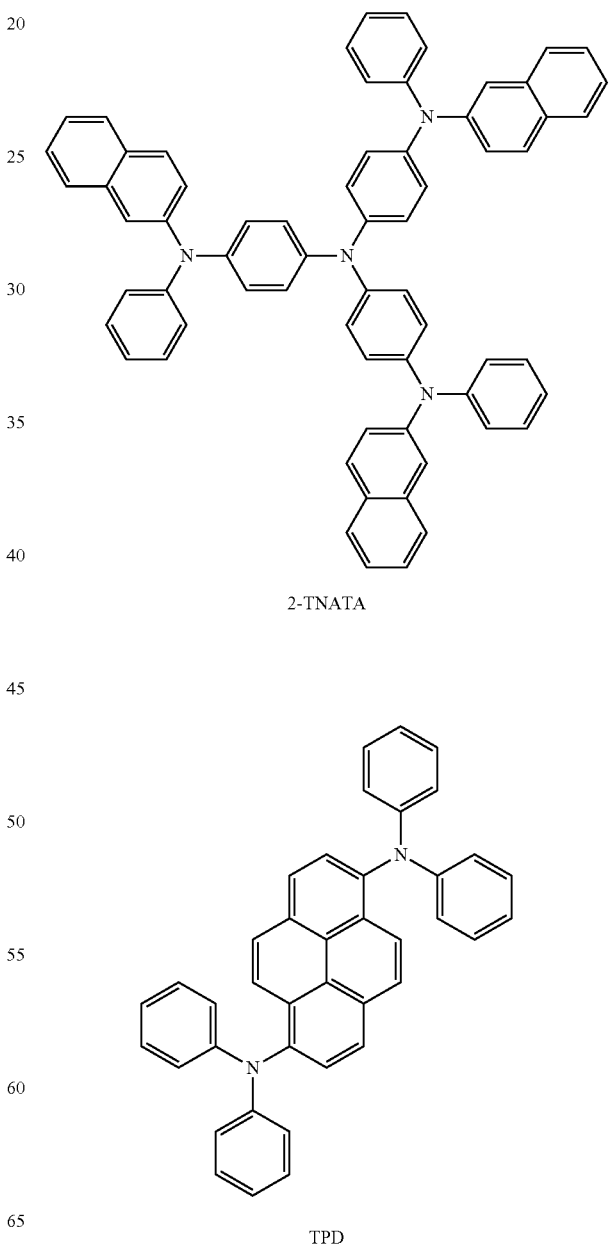

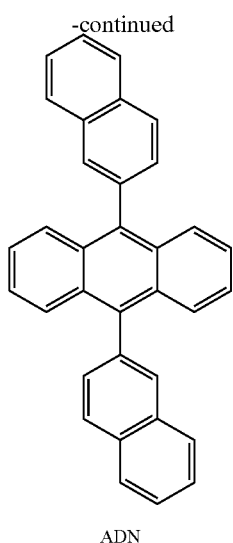

ADN $Alq_3$ was deposited on the emission layer to form an electron transport layer having a thickness of 300 Å, LiF was deposited on the electron transport layer to form an electron injection layer having a thickness of 10 Å, and Al was vacuum-deposited on the electron injection layer to form a LiF/Al electrode, i.e., a cathode, having a thickness of 3,000 Å, thereby completing the manufacture of an organic light-emitting device.

Examples 2 to 6 and Comparative Examples 1 to 3

Organic light-emitting devices were manufactured in substantially the same manner as in Example 1, except that the compounds shown in Table 2 were used instead of Compound 1 or TPD in forming each hole transport later and emission layer.

Evaluation Example 1

The efficiency and lifespan of the organic light-emitting devices manufactured in Examples 1 to 6 and Comparative Examples 1 to 3 were measured by using a Keithley 236 source-measure unit (SMU) and a PR650 luminance meter. The results thereof are shown in Table 2.

TABLE 2

| | Hole transport layer | Dopant in emission layer | Driving voltage (V) | Current density (mA/cm$^2$) | Luminance (cd/m$^2$) | Efficiency (cd/A) | Emission color | Half lifespan (hr @ 100 mA/cm$^2$) |
|---|---|---|---|---|---|---|---|---|
| Example 1 | Compound 1 | TPD | 5.39 | 50 | 3549 | 7.10 | blue | 327 |
| Example 2 | Compound 189 | TPD | 5.17 | 50 | 3544 | 7.09 | blue | 330 |
| Example 3 | Compound 671 | TPD | 5.55 | 50 | 3499 | 7.00 | blue | 311 |
| Example 4 | NPB | Compound 17 | 5.68 | 50 | 3611 | 7.22 | blue | 349 |
| Example 5 | NPB | Compound 172 | 5.79 | 50 | 3626 | 7.25 | blue | 351 |
| Example 6 | NPB | Compound 73 | 5.42 | 50 | 3105 | 6.21 | blue | 357 |
| Comparative Example 1 | NPB | TPD | 6.99 | 50 | 2755 | 5.51 | blue | 276 |
| Comparative Example 2 | NPB | Compound A | 6.65 | 50 | 2975 | 5.95 | blue | 255 |
| Comparative Example 3 | Compound B | TPD | 6.27 | 50 | 2880 | 5.76 | blue | 280 |

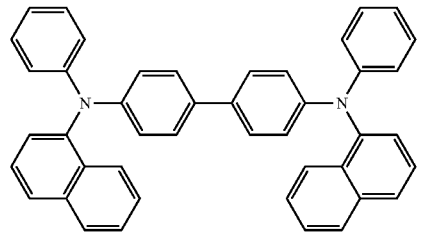

NPB

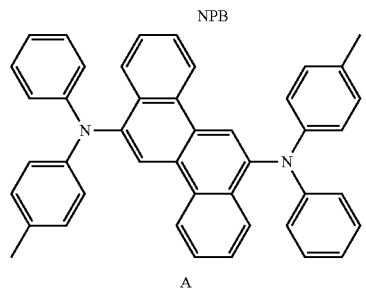

A

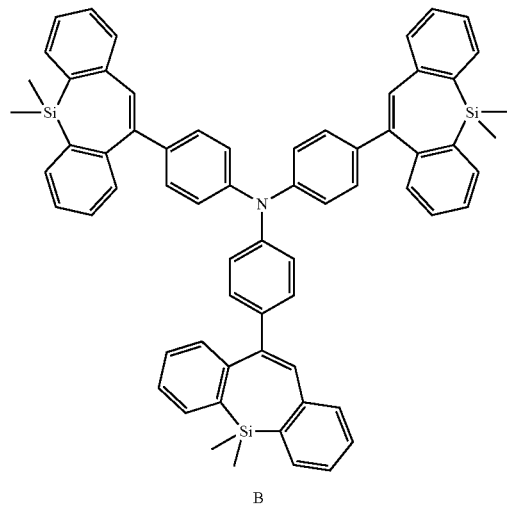

B

Referring to the results of Table 2, it was found that the organic light-emitting devices manufactured in Examples 1 to 6 had improved driving voltage, improved luminance, improved efficiency, and improved half-lifespan, as compared with those of the organic light-emitting devices manufactured in Comparative Examples 1 to 3.

As apparent from the foregoing description, an organic light-emitting device including the condensed-cyclic compound may have a low driving voltage, excellent luminance, excellent efficiency, and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A condensed-cyclic compound represented by Formula 1:

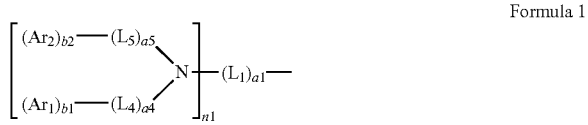

Formula 1

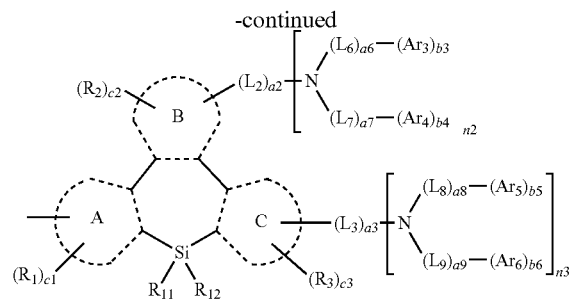

wherein, in Formula 1, ring A, ring B, and ring C are each independently selected from a $C_5$-$C_{30}$ carbocyclic group and a $C_1$-$C_{30}$ heterocyclic group, each of $L_1$ to $L_9$ is independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, each of a1 to a9 is independently an integer from 0 to 5, each of $Ar_1$ to $Ar_6$, $R_{11}$, and $R_{12}$ is independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, each of b1 to b6 is independently an integer from 1 to 5, each of n1 to n3 is independently selected from 0, 1, 2, and 3, provided that the sum of n1, n2, and n3 is 2 or greater, each of $R_1$ to $R_3$ is independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_{3-10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, each of c1 to c3 is independently an integer from 0 to 8, and at least one substituent of the substituted $C_{3-10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_{3-10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_{3-10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein each of $Q_1$ to $Q_3$, $Q_{11}$ to $Q_{13}$, $Q_{21}$ to $Q_{23}$, and $Q_{31}$ to $Q_{33}$ is independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a phenyl group, a biphenyl group, and a terphenyl group.

2. The condensed-cyclic compound of claim 1, wherein ring A, ring B, and ring C are each independently selected from a benzene group, a naphthalene group, an anthracene group, a phenanthrene group, a naphthacene group, a benzoanthracene group, a chrysene group, a pyridine group, a pyridazine group, a pyrimidine group, a pyrazine group, a quinoline group, an isoquinoline group, a quinazoline group, a quinoxaline group, and a naphthyridine group.

3. The condensed-cyclic compound of claim 1, wherein ring A, ring B, and ring C are each independently selected from a benzene group and a naphthalene group.

4. The condensed-cyclic compound of claim 1, wherein each of $L_1$ to $L_9$ is independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

5. The condensed-cyclic compound of claim 1, wherein each of $L_1$ to $L_9$ is independently selected from groups represented by Formulae 3-1 to 3-33:

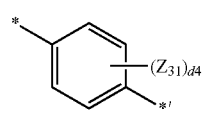

3-1

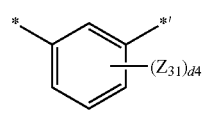

3-2

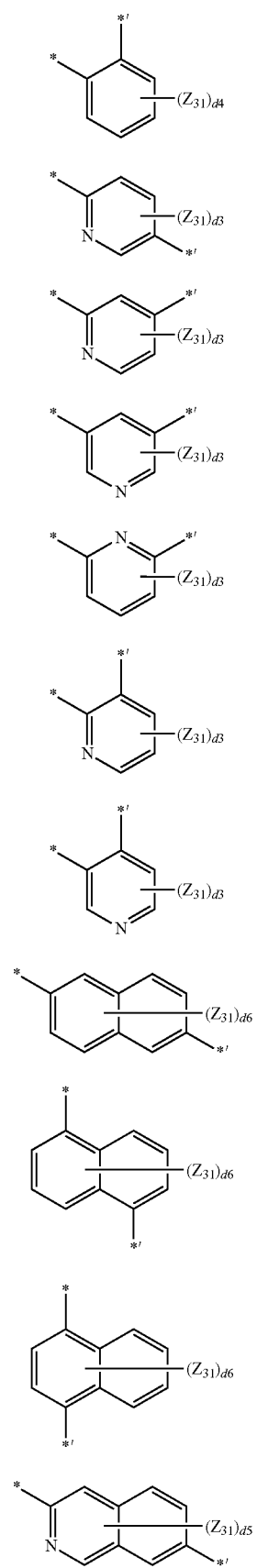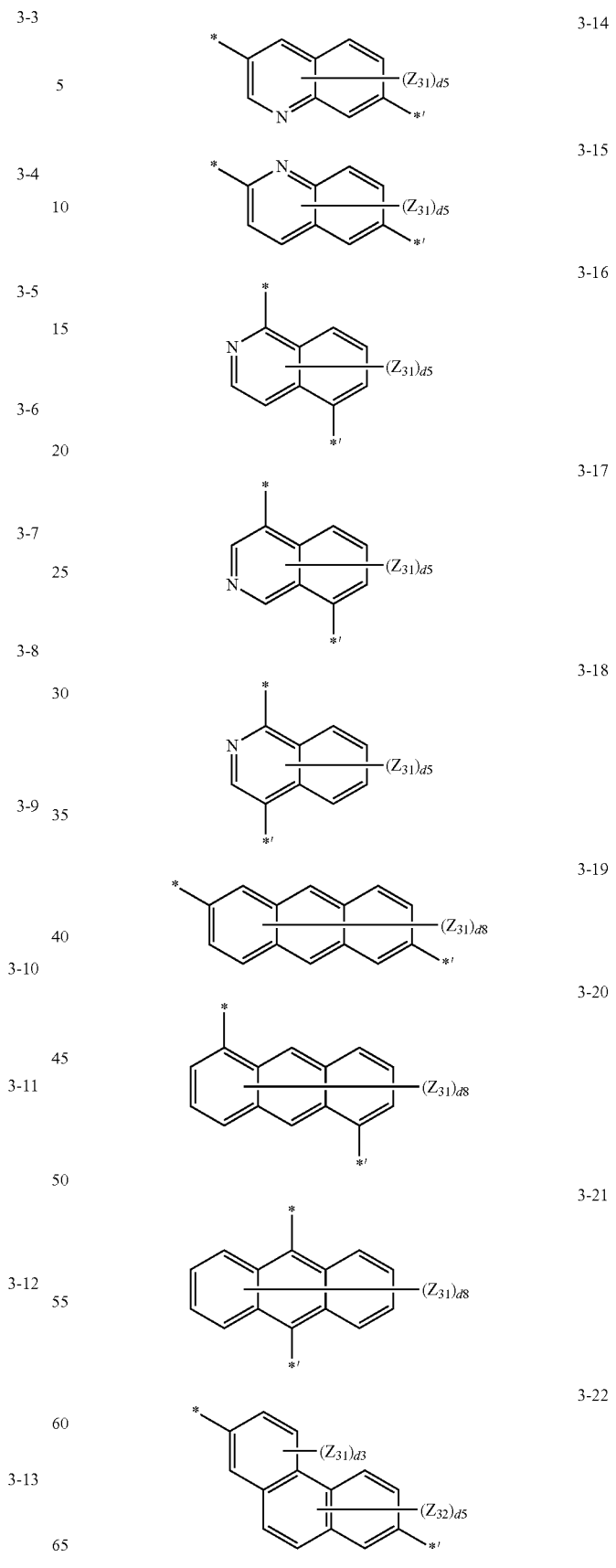

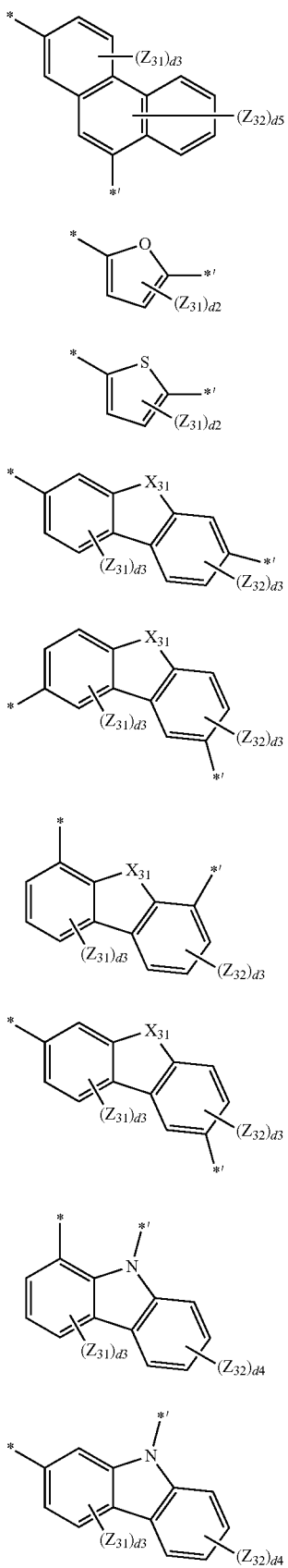

wherein, in Formulae 3-1 to 3-33, $X_{31}$ is selected from O, S, C($Z_{33}$)($Z_{34}$), N($Z_{33}$), and Si($Z_{33}$)($Z_{34}$), $Z_{31}$ to $Z_{34}$ are each independently selected from hydrogen, deuterium, —F, —CF$_3$, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —Si($Q_{31}$)($Q_{32}$)($Q_{33}$), wherein each of $Q_{31}$ to $Q_{33}$ is independently selected from a $C_1$-$C_{10}$ alkyl group, a $C_1$-$C_{10}$ alkoxy group, a phenyl group, a biphenyl group, a terphenyl group, and a naphthyl group, d2 is an integer selected from 1 and 2, d3 is an integer from 1 to 3, d4 is an integer from 1 to 4, d5 is an integer from 1 to 5, d6 is an integer from 1 to 6, d8 is an integer from 1 to 8, and

* and *' each indicate a binding site to an adjacent atom.

6. The condensed-cyclic compound of claim 1, wherein $L_1$ to $L_9$ are each independently selected from groups represented by Formulae 4-1 to 4-35:

-continued
4-4
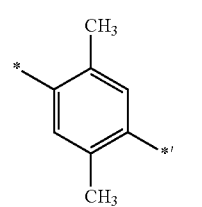
4-5
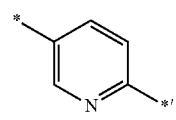
4-6
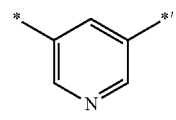
4-7
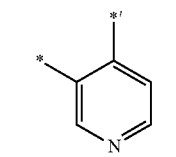
4-8
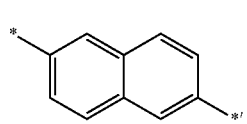
4-9
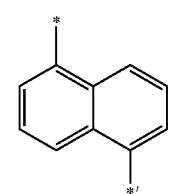
4-10
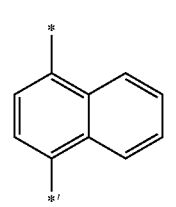
4-11
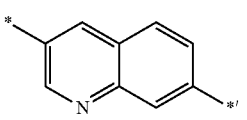
4-12
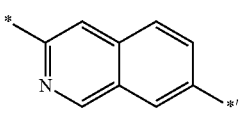
4-13
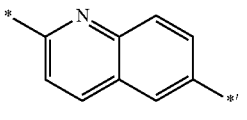
4-14
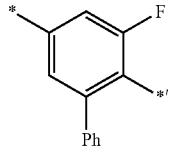
-continued
4-15
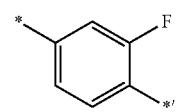
4-16
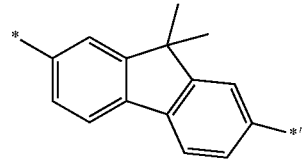
4-17
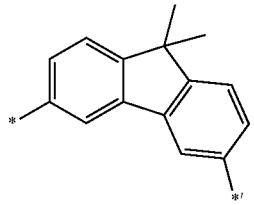
4-18
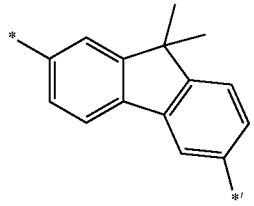
4-19
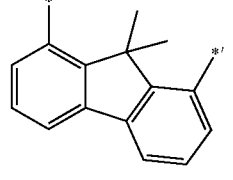
4-20
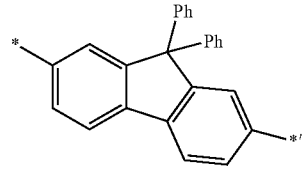
4-21
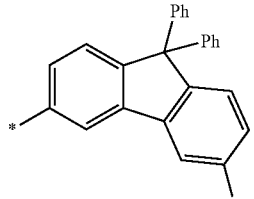
4-22
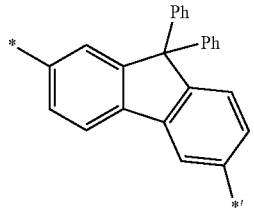

-continued 4-23 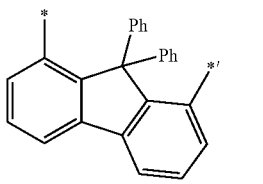

4-24 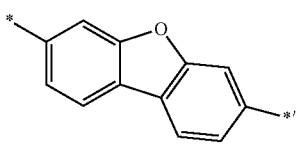

4-25 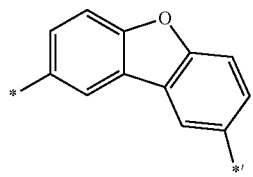

4-26 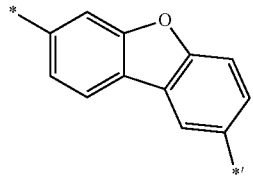

4-27 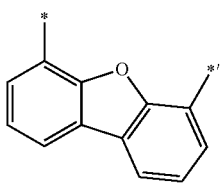

4-28 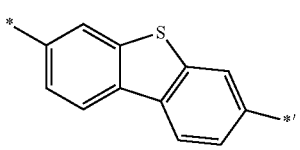

4-29 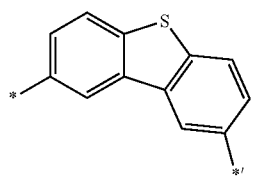

4-30 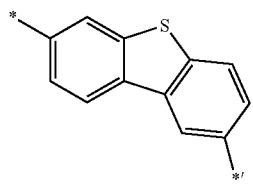

4-31 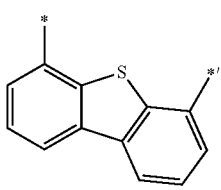

-continued 4-32 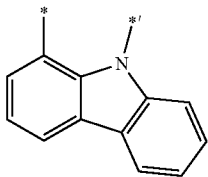

4-33 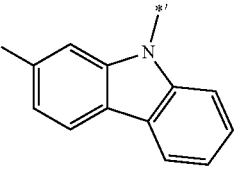

4-34

4-35 wherein, in Formulae 4-1 to 4-35, "Ph" represents a phenyl group, and * and *' each indicate a binding site to an adjacent atom.

7. The condensed-cyclic compound of claim 1, wherein $Ar_1$ to $Ar_6$ are each independently selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzosilolyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

8. The condensed-cyclic compound of claim 1, wherein $Ar_1$ to $Ar_6$ are each independently selected from groups represented by Formulae 5-1 to 5-37:

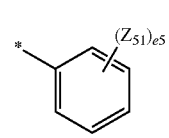

5-1

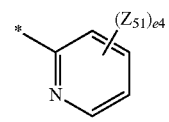

5-2

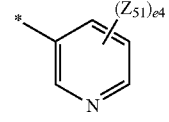

5-3

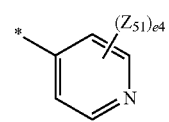

5-4

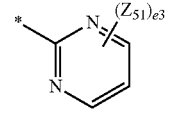

5-5

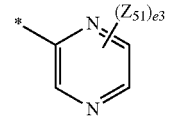

5-6

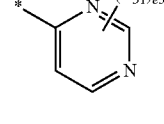

5-7

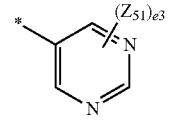

5-8

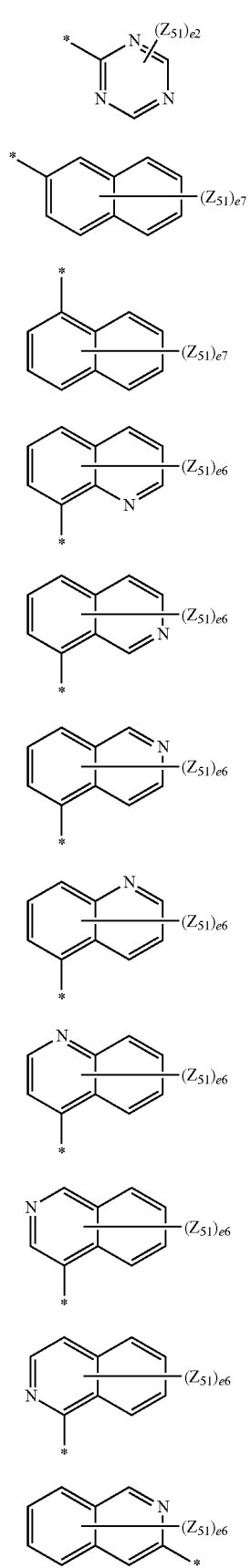
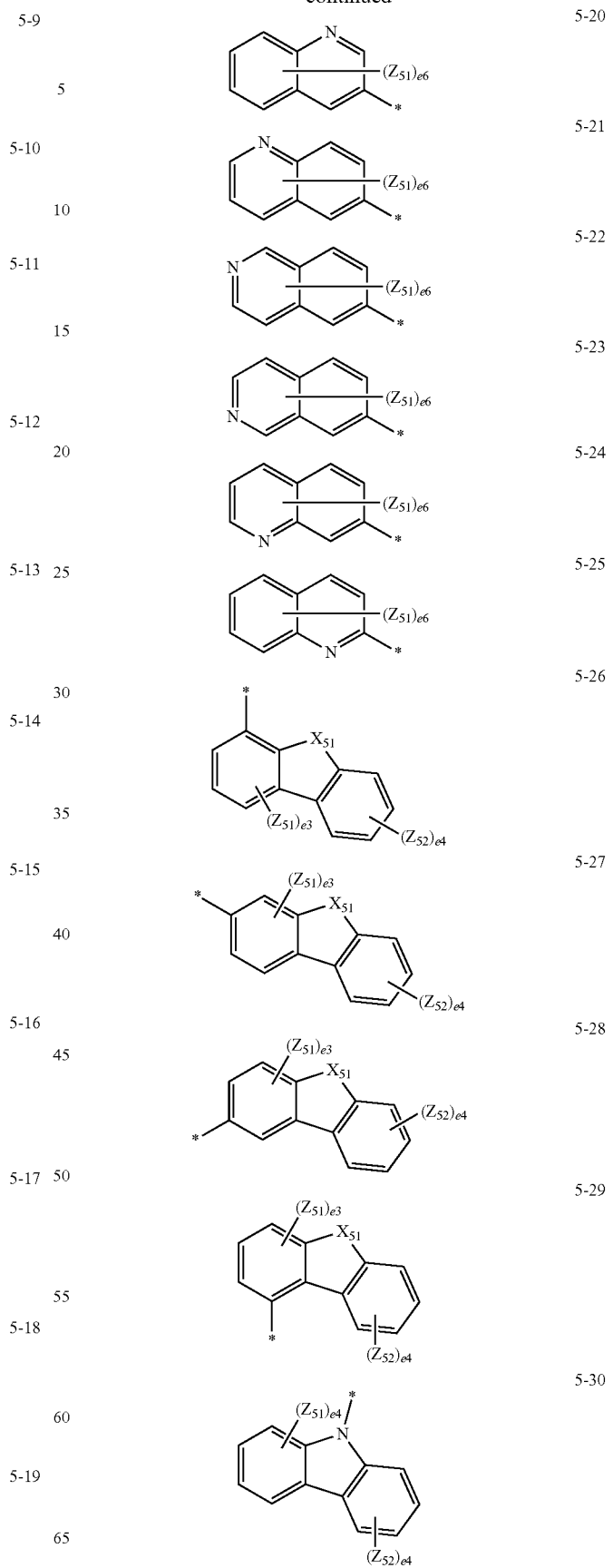

-continued

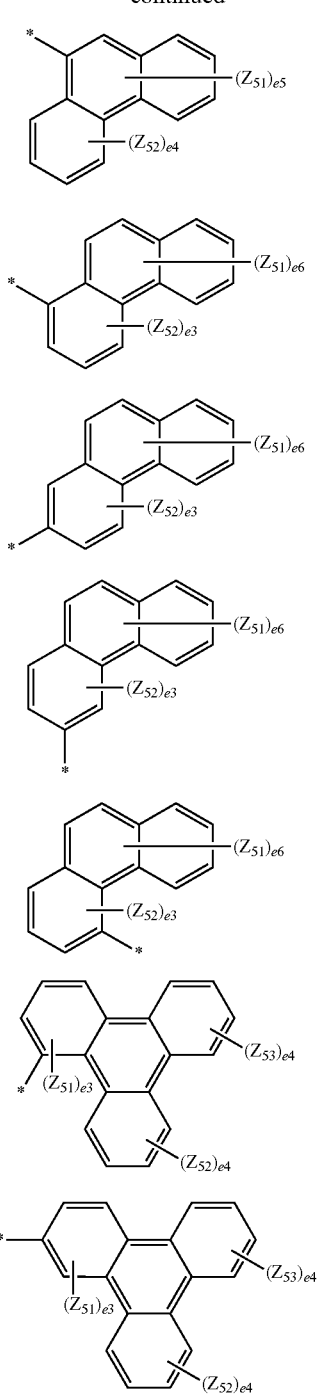

wherein, in Formulae 5-1 to 5-37,
$X_{51}$ is selected from O, S, $C(Z_{54})(Z_{55})$, $N(Z_{54})$, and $Si(Z_{54})(Z_{55})$,
each of $Z_{51}$ to $Z_{55}$ is independently selected from hydrogen, deuterium, —F, —CF$_3$, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —Si(Q$_{31}$)(Q$_{32}$)(Q$_{33}$),
wherein each of $Q_{31}$ to $Q_{33}$ is independently selected from a C$_1$-C$_{10}$ alkyl group, a C$_1$-C$_{10}$ alkoxy group, a phenyl group, a biphenyl group, a terphenyl group, and a naphthyl group,
e2 is an integer selected from 1 and 2,
e3 is an integer from 1 to 3,
e4 is an integer from 1 to 4,
e5 is an integer from 1 to 5,
e6 is an integer from 1 to 6,
e7 is an integer from 1 to 7, and
* indicates a binding site to an adjacent atom.

9. The condensed-cyclic compound of claim 1, wherein each of Ar$_1$ to Ar$_6$ is independently selected from groups represented by Formulae 6-1 to 6-40:

6-1
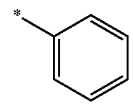

6-2
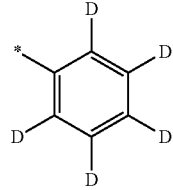

6-3
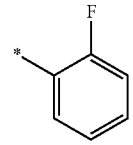

6-4
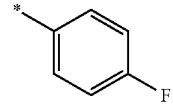

6-5
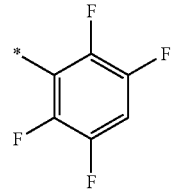

6-6
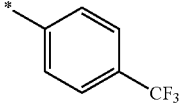

6-7
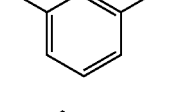

6-8
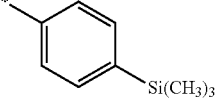

-continued
6-9
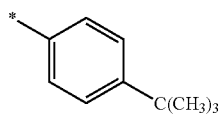
6-10
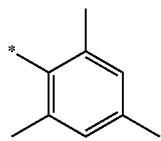
6-11
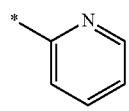
6-12
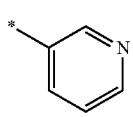
6-13
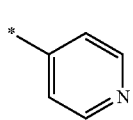
6-14
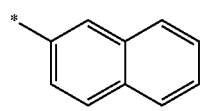
6-15
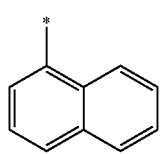
6-16
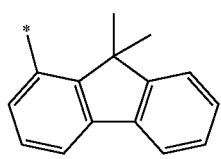
6-17
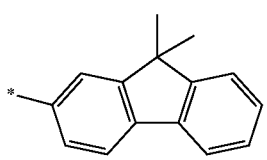
6-18
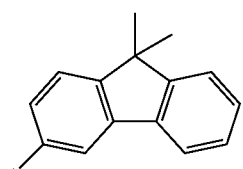
6-19
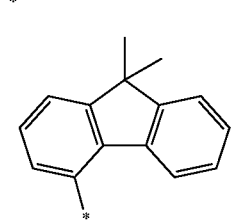
-continued
6-20
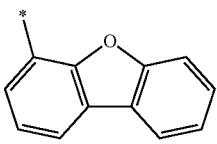
6-21
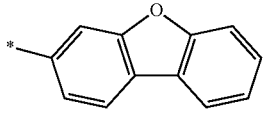
6-22
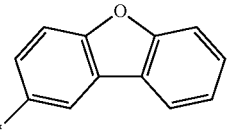
6-23
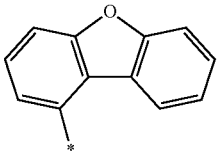
6-24
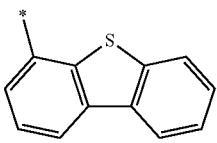
6-25
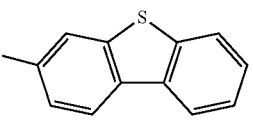
6-26
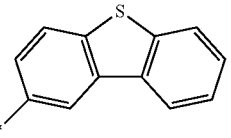
6-27
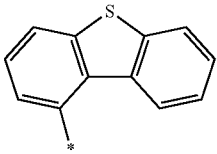
6-28
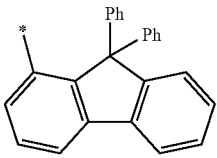
6-29
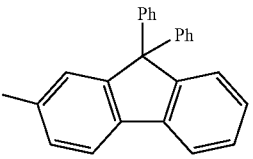

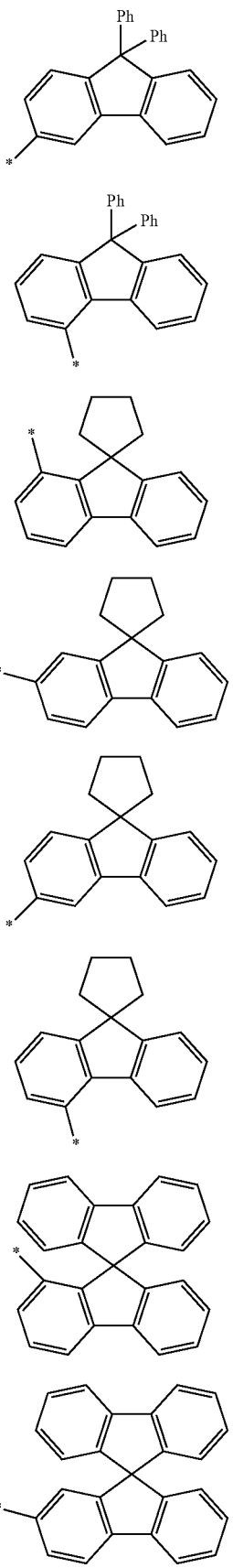
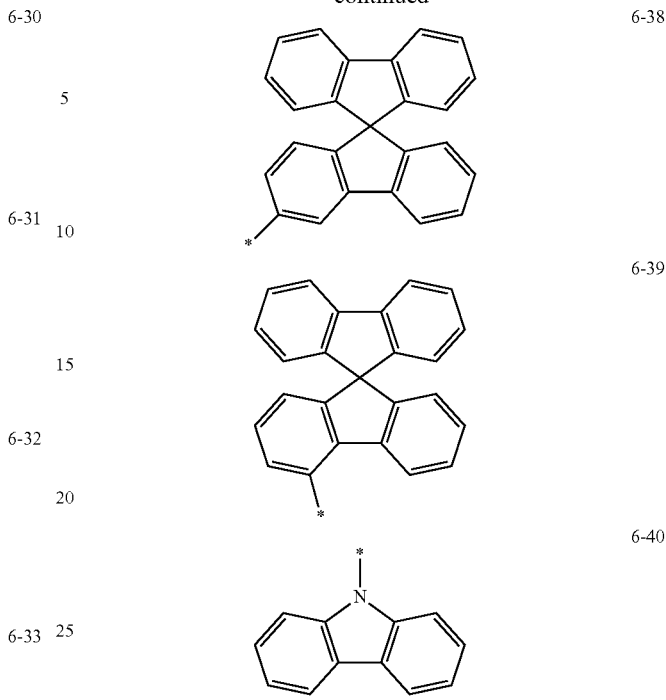

wherein, in Formulae 6-1 to 6-40, "Ph" represents a phenyl group, and * indicates a binding site to an adjacent atom.

10. The condensed-cyclic compound of claim 1 wherein, in Formula 1,
n1 is 1, n2 is 1, and n3 is 0;
n1 is 1, n2 is 0, and n3 is 1;
n1 is 0, n2 is 1, and n3 is 1; or
n1 is 1, n2 is 1, and n3 is 1.

11. The condensed-cyclic compound of claim 1, wherein each of $R_1$ to $R_3$ is independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, and —Si($Q_1$)($Q_2$)($Q_3$),
wherein each of $Q_1$ to $Q_3$ is independently selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

12. The condensed-cyclic compound of claim 1, wherein each of $R_{11}$ and $R_{12}$ is independently selected from
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and —Si($Q_{31}$)($Q_{32}$)($Q_{33}$);

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, and a chrysenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and —Si($Q_{31}$)($Q_{32}$)($Q_{33}$), wherein each of $Q_{31}$ to $Q_{33}$ is independently selected from a $C_1$-$C_{10}$ alkyl group, a $C_1$-$C_{10}$ alkoxy group, a phenyl group, a biphenyl group, a terphenyl group, and a naphthyl group.

13. The condensed-cyclic compound of claim 1, represented by one of Formulae 1-1 to 1-18:

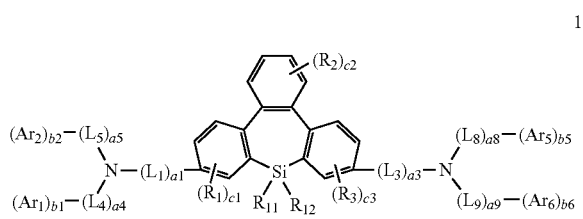

1-1

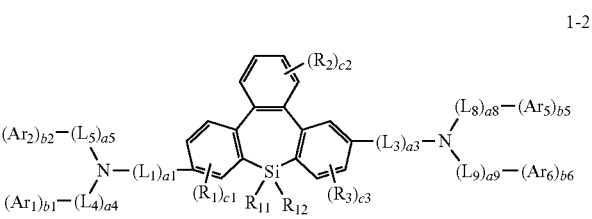

1-2

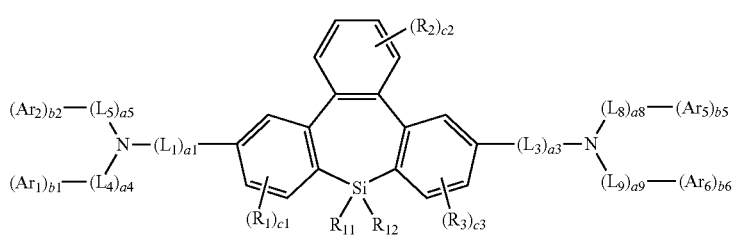

1-3

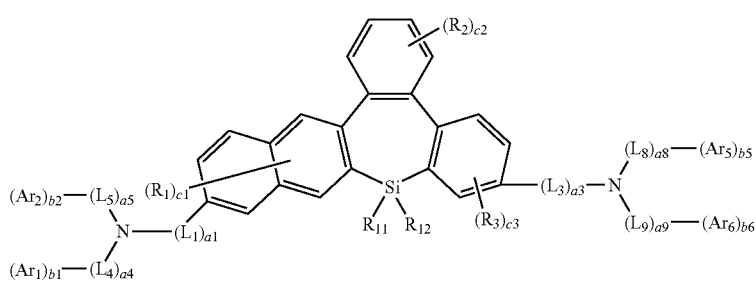

1-4

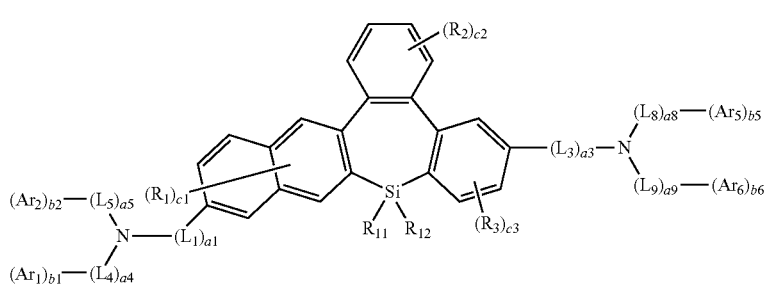

1-5

-continued
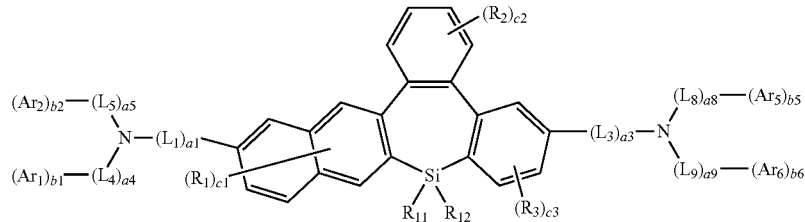
1-6
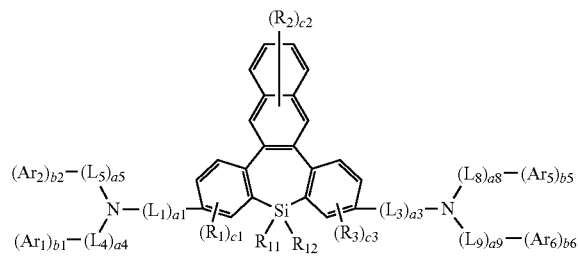
1-7 1-8
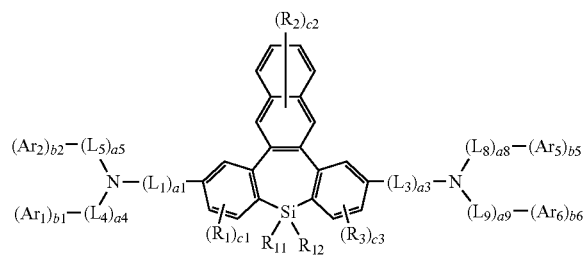
1-9 1-10
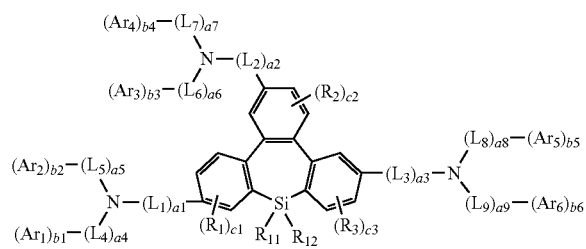
1-11
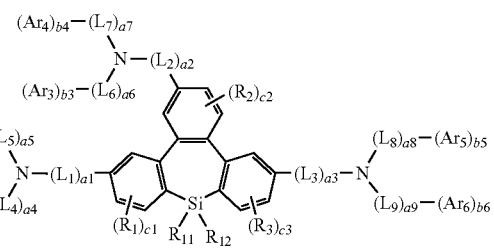
1-12
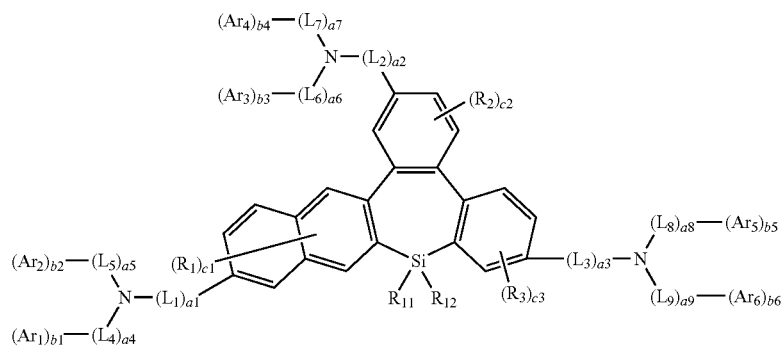
1-13

1-14
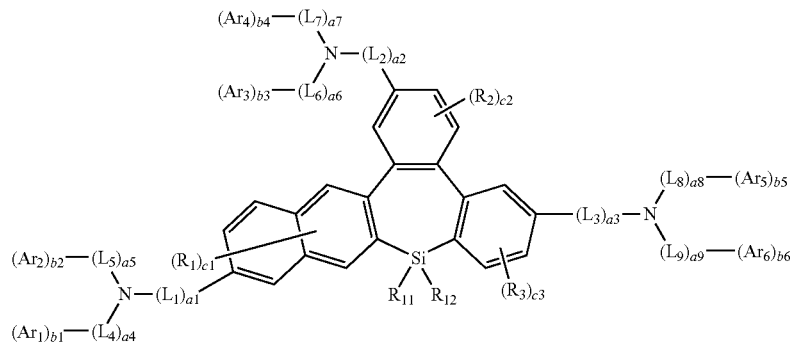
1-15
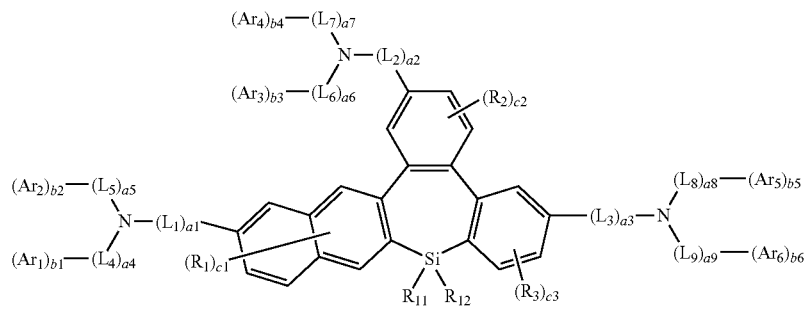
1-16
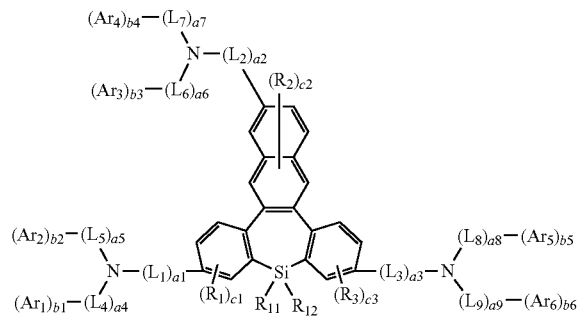
1-17
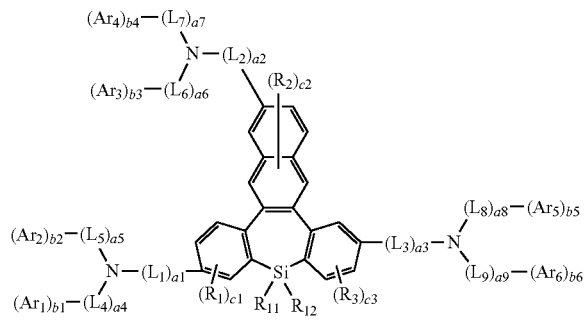
1-18
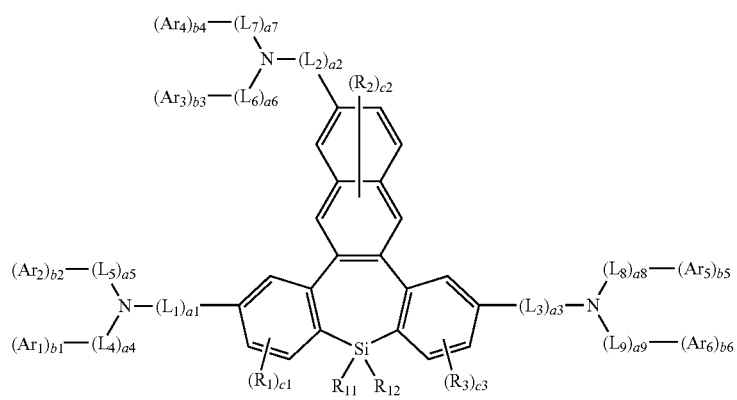

wherein, in Formulae 1-1 and 1-18,
$L_1$ to $L_9$, a1 to a9, $Ar_1$ to $Ar_6$, b1 to b6, $R_1$ to $R_3$, c1 to c3, $R_{11}$, and $R_{12}$ are the same as those defined in claim 1.
14. The condensed-cyclic compound of claim 13, wherein each of $R_1$ to $R_3$ is hydrogen.
15. The condensed-cyclic compound of claim 1, represented by one of Formulae 1A to 1R:
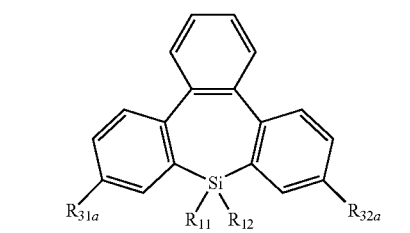
1A
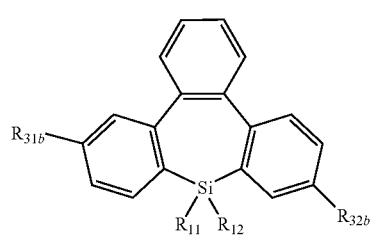
1B
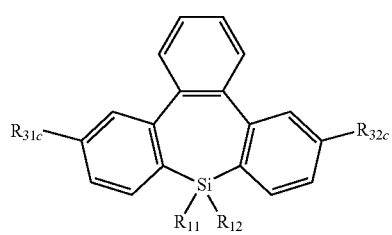
1C
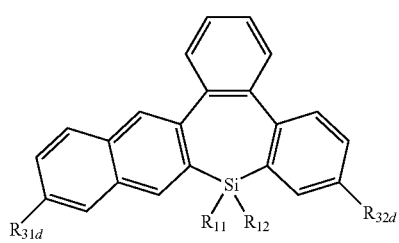
1D
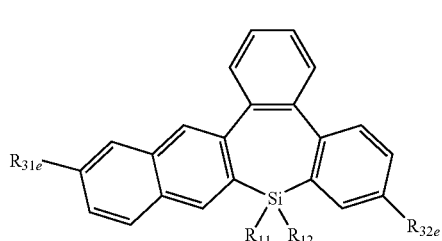
1E
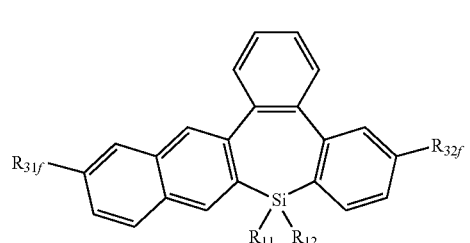
1F
-continued
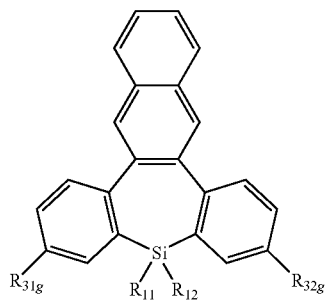
1G
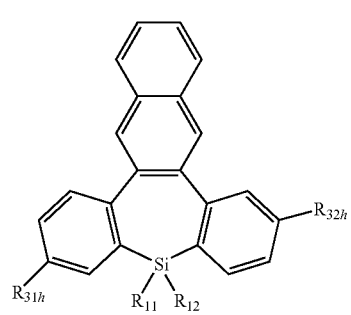
1H
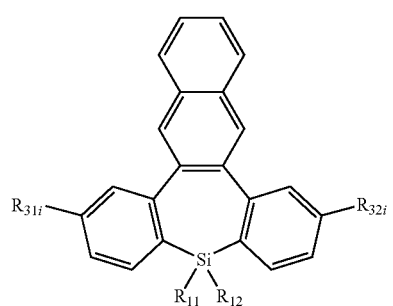
1I
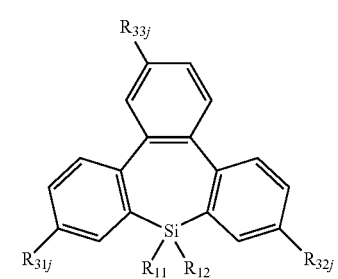
1J
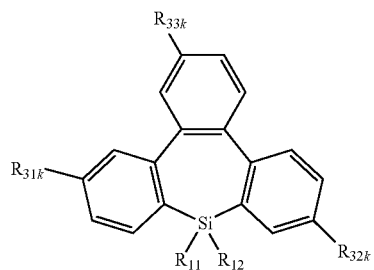
1K -continued
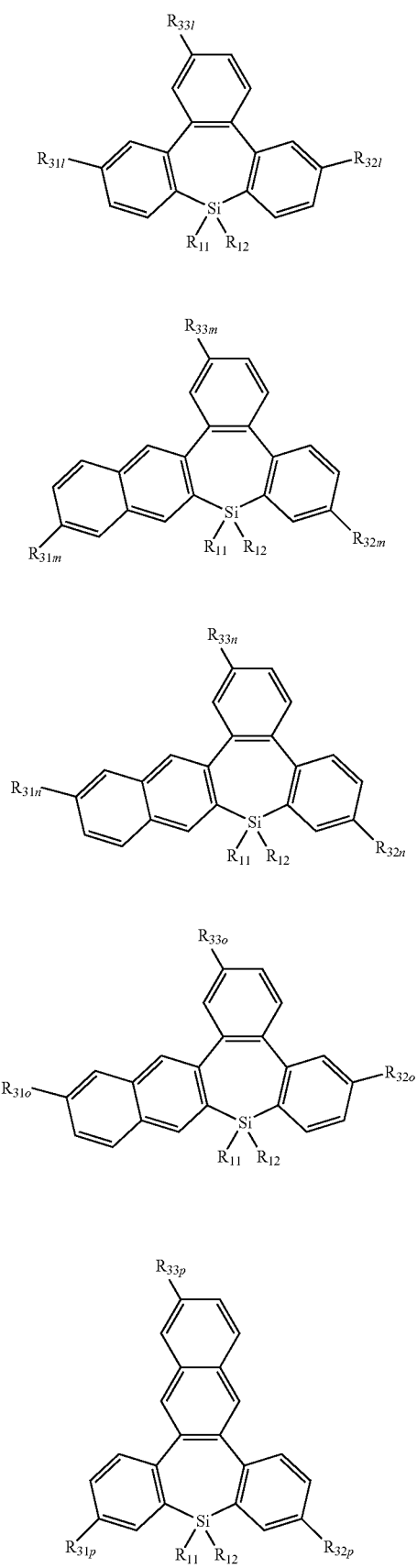
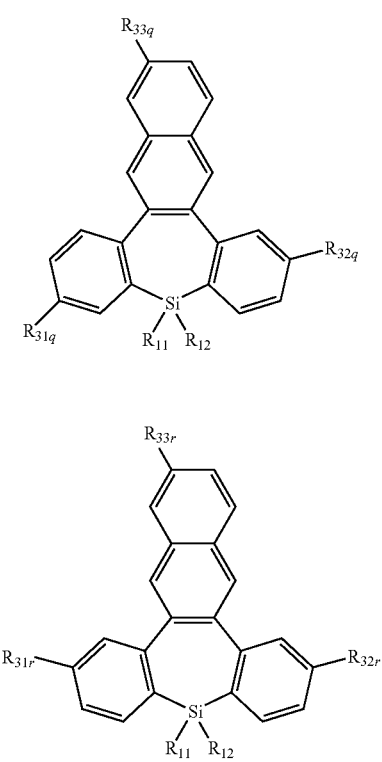
wherein, in Formulae 1A to 1R,
$R_{11}$ and $R_{12}$ are each the same as those defined in claim 1,
$R_{31a}$ to $R_{31r}$, $R_{32a}$ to $R_{32r}$, and $R_{33j}$ to $R_{33r}$ are each independently selected from groups represented by Formulae N-1 to N-38:
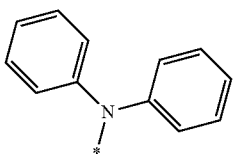
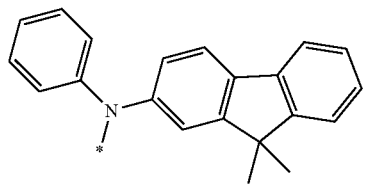
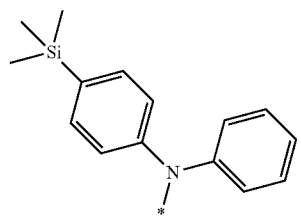

-continued
N-4
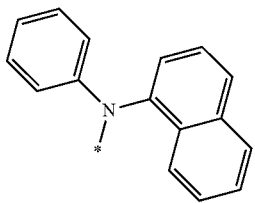
N-5
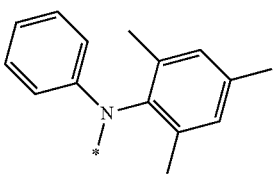
N-6
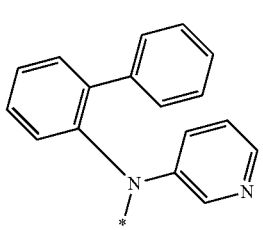
N-7
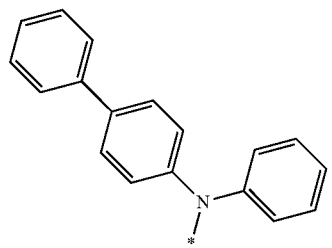
N-8
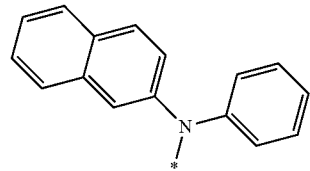
N-9
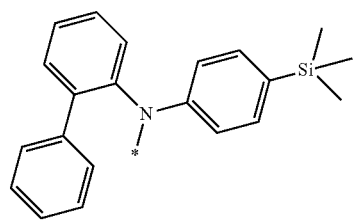
N-10
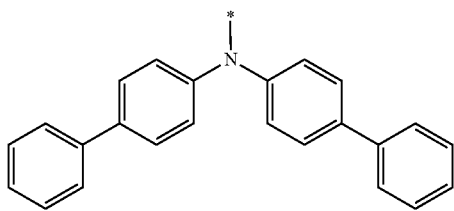
-continued
N-11
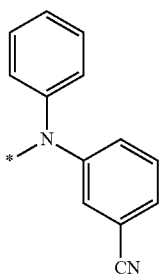
N-12
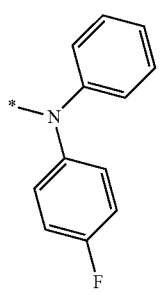
N-13
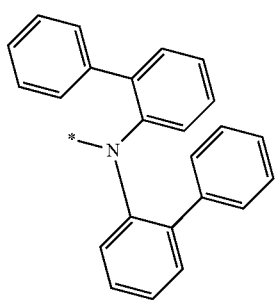
N-14
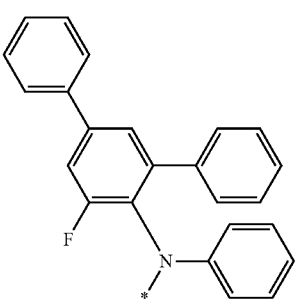
N-15
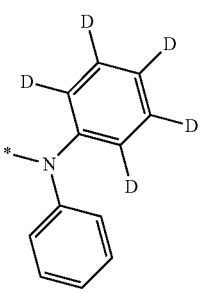

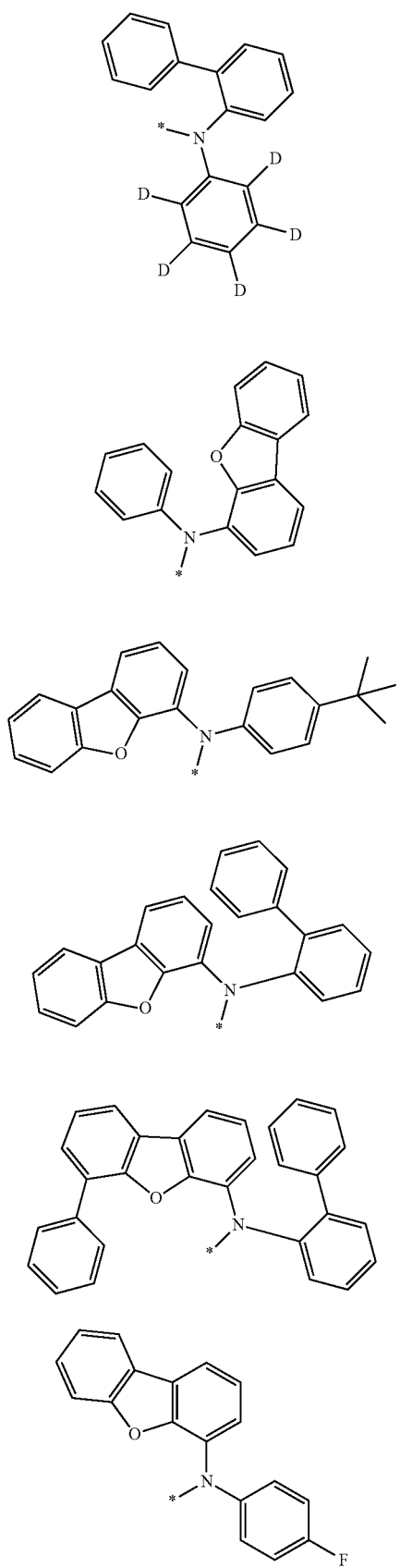
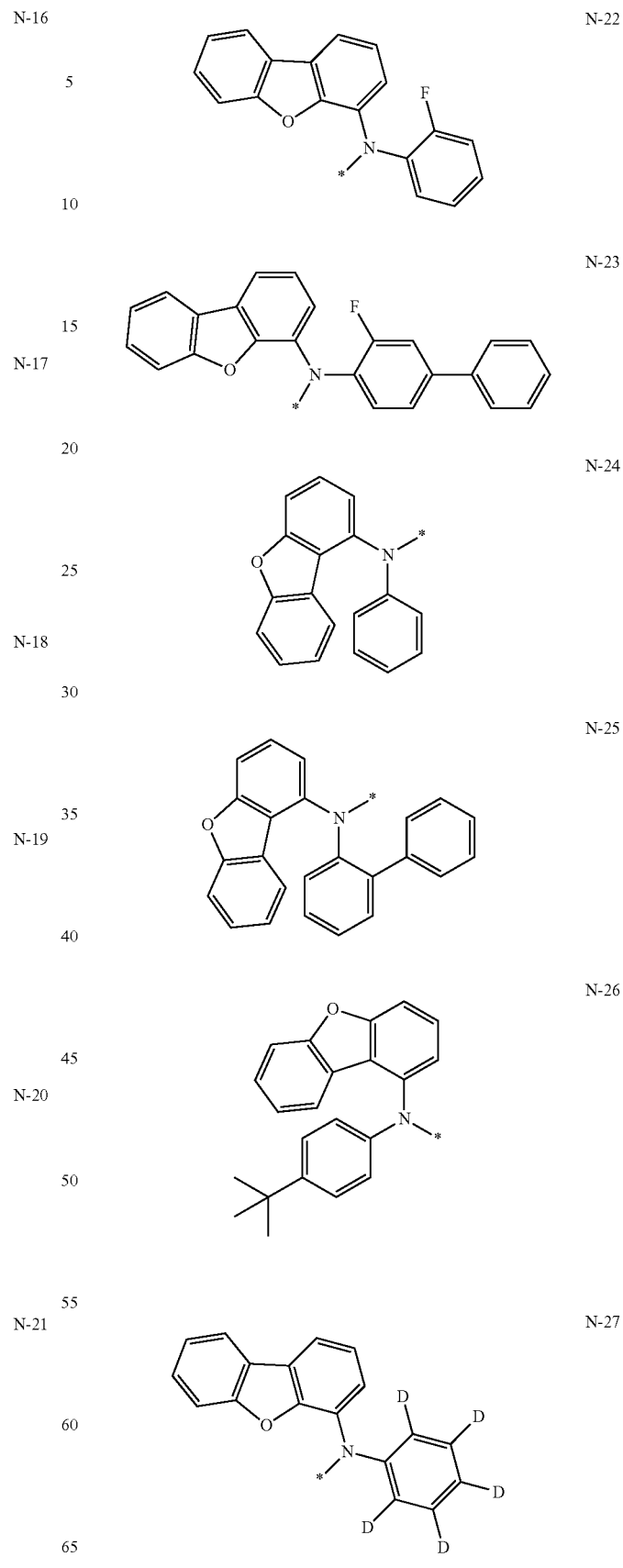

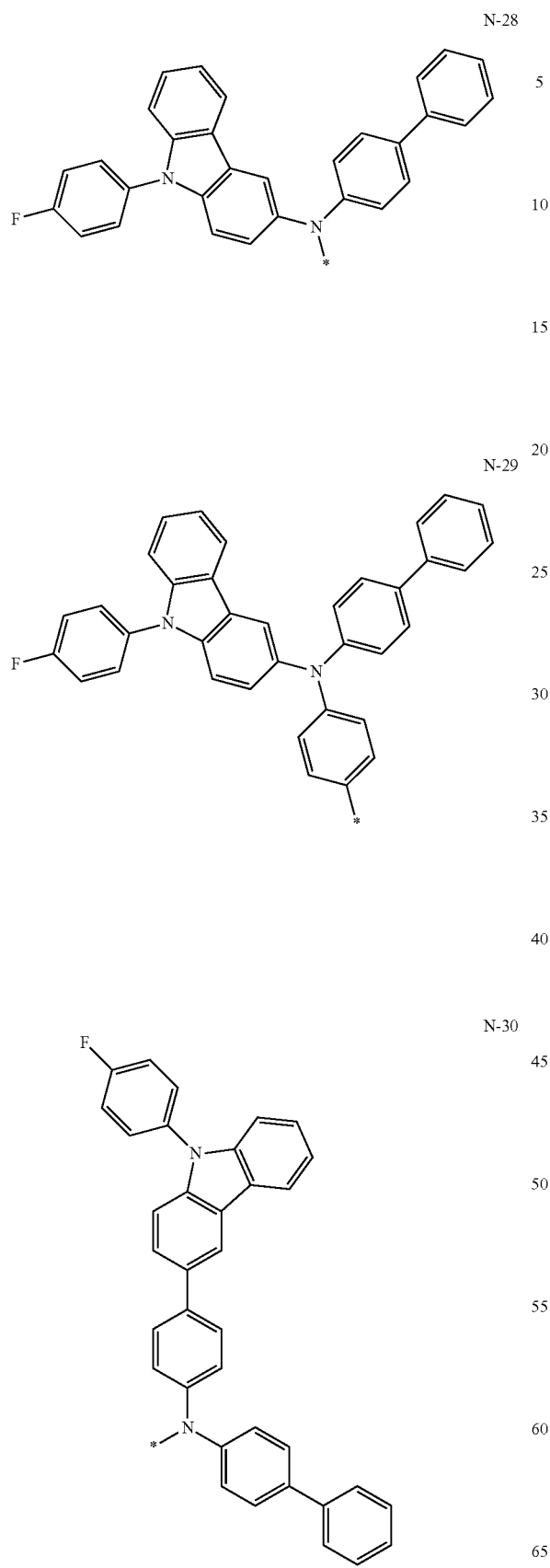
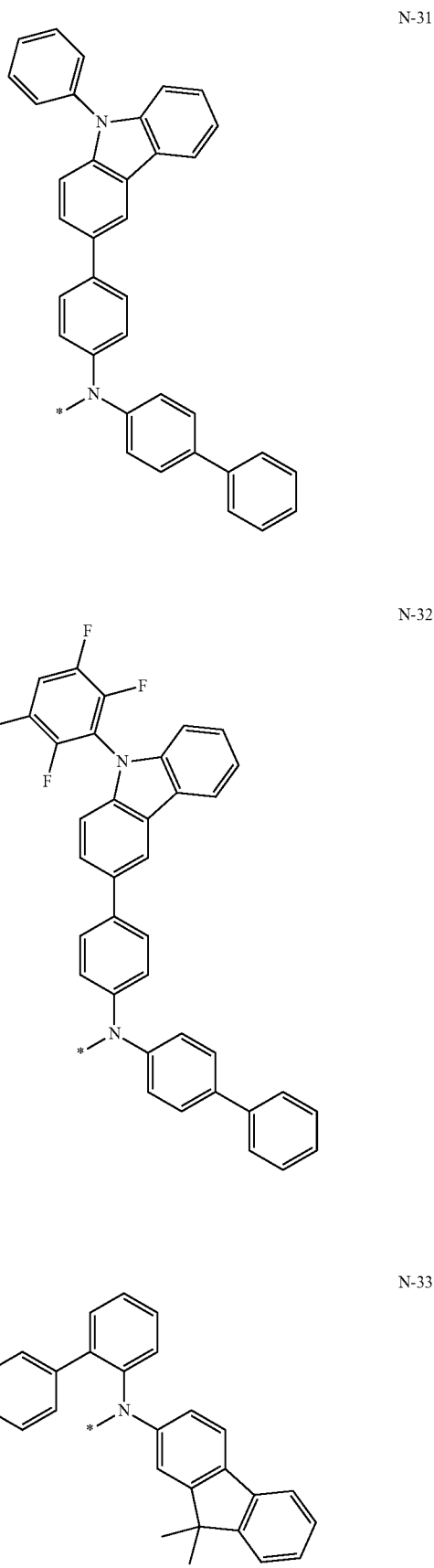

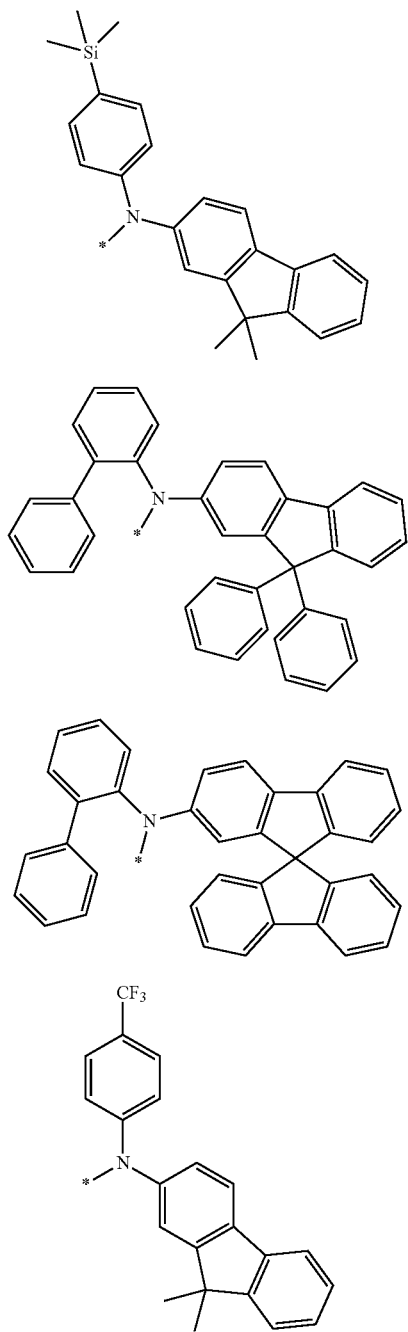

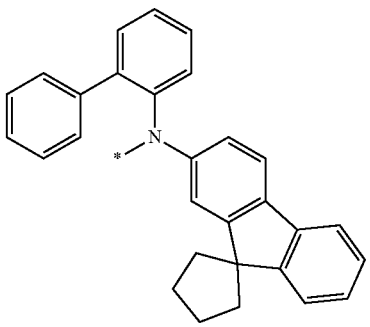

wherein, in Formulae N-1 to N-38, * indicates a binding site to an adjacent atom.

16. An organic light-emitting device comprising: a first electrode; a second electrode facing the first electrode; and an organic layer between the first electrode and the second electrode, the organic layer comprising an emission layer and at least one condensed-cyclic compound represented by Formula 1 of claim 1.

17. The organic light-emitting device of claim 16, wherein the emission layer comprises the at least one condensed-cyclic compound.

18. The organic light-emitting device of claim 17, wherein the emission layer further comprises a host, and an amount of the host is greater than that of the condensed-cyclic compound.

19. The organic light-emitting device of claim 16, wherein the first electrode is an anode, the second electrode is a cathode, the organic layer comprises a hole transport region disposed between the first electrode and the emission layer and an electron transport region disposed between the emission layer and the second electrode, the hole transport region comprises at least one selected from a hole injection layer, a hole transport layer, a buffer layer, and an electron blocking layer, and the electron transport region comprises at least one selected from a hole blocking layer, an electron transport layer, and an electron injection layer.

20. The organic light-emitting device of claim 19, wherein the hole transport region comprises a hole transport layer, and the hole transport layer comprises the at least one condensed-cyclic compound.

* * * * *